United States Patent
Zhang et al.

(10) Patent No.: US 9,181,277 B2
(45) Date of Patent: Nov. 10, 2015

(54) AMINOQUINAZOLINE DERIVATIVES AND THEIR SALTS AND METHODS OF USE

(71) Applicant: SUNSHINE LAKE PHARMA CO., LTD., Dongguan, Guangdong (CN)

(72) Inventors: Jiancun Zhang, San Mateo, CA (US); Yingjun Zhang, Dongguan (CN); Weihong Zhang, Dongguan (CN); Bing Liu, Dongguan (CN); Jiquan Zhang, Dongguan (CN); Jinlei Liu, Dongguan (CN); Lu Zhang, Dongguan (CN)

(73) Assignee: SUNSHINE LAKE PHARMA CO., LTD., Dongguan, Guangdong (CN)

( * ) Notice: Subject to any disclaimer, the term of this patent is extended or adjusted under 35 U.S.C. 154(b) by 0 days.

(21) Appl. No.: 14/346,741

(22) PCT Filed: Nov. 14, 2012

(86) PCT No.: PCT/CN2012/001545
§ 371 (c)(1),
(2) Date: Mar. 24, 2014

(87) PCT Pub. No.: WO2013/071697
PCT Pub. Date: May 23, 2013

(65) Prior Publication Data
US 2014/0228361 A1  Aug. 14, 2014

(30) Foreign Application Priority Data
Nov. 14, 2011  (CN) .......................... 2011 1 0359739

(51) Int. Cl.
| | | |
|---|---|---|
| A61K 31/517 | (2006.01) | |
| A61K 31/5383 | (2006.01) | |
| C07D 403/12 | (2006.01) | |
| C07D 487/04 | (2006.01) | |
| C07D 491/052 | (2006.01) | |
| C07D 491/056 | (2006.01) | |
| C07D 491/048 | (2006.01) | |
| C07D 513/04 | (2006.01) | |
| C07D 498/04 | (2006.01) | |
| C07D 401/12 | (2006.01) | |
| C07D 471/04 | (2006.01) | |
| C07D 495/04 | (2006.01) | |
| A61K 45/06 | (2006.01) | |
| A61K 31/519 | (2006.01) | |

(52) U.S. Cl.
CPC ............ *C07D 513/04* (2013.01); *A61K 31/517* (2013.01); *A61K 31/519* (2013.01); *A61K 31/5383* (2013.01); *A61K 45/06* (2013.01); *C07D 401/12* (2013.01); *C07D 403/12* (2013.01); *C07D 471/04* (2013.01); *C07D 487/04* (2013.01); *C07D 491/048* (2013.01); *C07D 491/052* (2013.01); *C07D 491/056* (2013.01); *C07D 495/04* (2013.01); *C07D 498/04* (2013.01)

(58) Field of Classification Search
None
See application file for complete search history.

(56) References Cited

U.S. PATENT DOCUMENTS

| | | | |
|---|---|---|---|
| 5,770,599 A | 6/1998 | Gibson | |
| 6,617,329 B2 | 9/2003 | Himmelsbach et al. | |
| 7,462,623 B2 | 12/2008 | Ple | |
| 7,504,408 B2 | 3/2009 | Hennequin et al. | |
| 7,560,558 B2 | 7/2009 | Shimizu et al. | |
| 7,838,530 B2 | 11/2010 | Barlaam et al. | |
| 8,143,250 B2 | 3/2012 | Jyothi Prasad et al. | |
| 8,318,752 B2 | 11/2012 | Barlaam | |
| 8,343,982 B2 | 1/2013 | Himmelsbach et al. | |
| 8,426,430 B2 | 4/2013 | Zhang et al. | |
| 8,476,298 B2 | 7/2013 | Bannen et al. | |
| 8,658,654 B2 | 2/2014 | Rice et al. | |
| 2002/0049197 A1 | 4/2002 | Himmelsbach | |
| 2006/0063752 A1 | 3/2006 | Himmelsbach et al. | |
| 2006/0122199 A1* | 6/2006 | Ple .......................... 514/266.21 | |
| 2006/0142297 A1 | 6/2006 | Barge | |
| 2007/0027145 A1* | 2/2007 | Hennequin ................ 514/227.8 | |
| 2013/0035350 A1 | 2/2013 | Zhang | |
| 2013/0172373 A1 | 7/2013 | Zhang et al. | |
| 2013/0225811 A1 | 8/2013 | Wang et al. | |
| 2014/0206664 A1* | 7/2014 | Qian ......................... 514/210.21 | |

FOREIGN PATENT DOCUMENTS

| | | |
|---|---|---|
| CN | 101367793 A | 2/2009 |
| CN | 101619043 A | 1/2010 |
| WO | 2006081741 A | 8/2006 |
| WO | 2010037339 A | 4/2010 |

OTHER PUBLICATIONS

Zukin Rev.Assoc.Med. Bras. vol. 58, pp. 263-268 (2012).*
Galvani et al. Current Pharmaceutical Design vol. 19, pp. 818-832 (2013).*
Cancer Drug Design and Discovery, Neidle, Stephen,ed. (Elsevier/Academic Press), pp. 427-431 (2008).*
Eng. translation of the abstract of CN101619043.
Eng. translation of the abstract of CN101367793.

* cited by examiner

*Primary Examiner* — Emily Bernhardt
(74) *Attorney, Agent, or Firm* — Kam. W. Law; Squire Patton Boggs

(57) ABSTRACT

The present invention relates to the field of medicine. Provided herein are aminoquinazoline derivatives, their salts and pharmaceutical formulations useful in modulating the protein tyrosine kinase activity, and in modulating inter- and/or intracellular signaling. Also provided herein are pharmaceutically acceptable compositions comprising the aminoquinazoline compounds and methods of using the compositions in the treatment of hyperproliferative disorders in mammals, especially humans.

8 Claims, 1 Drawing Sheet

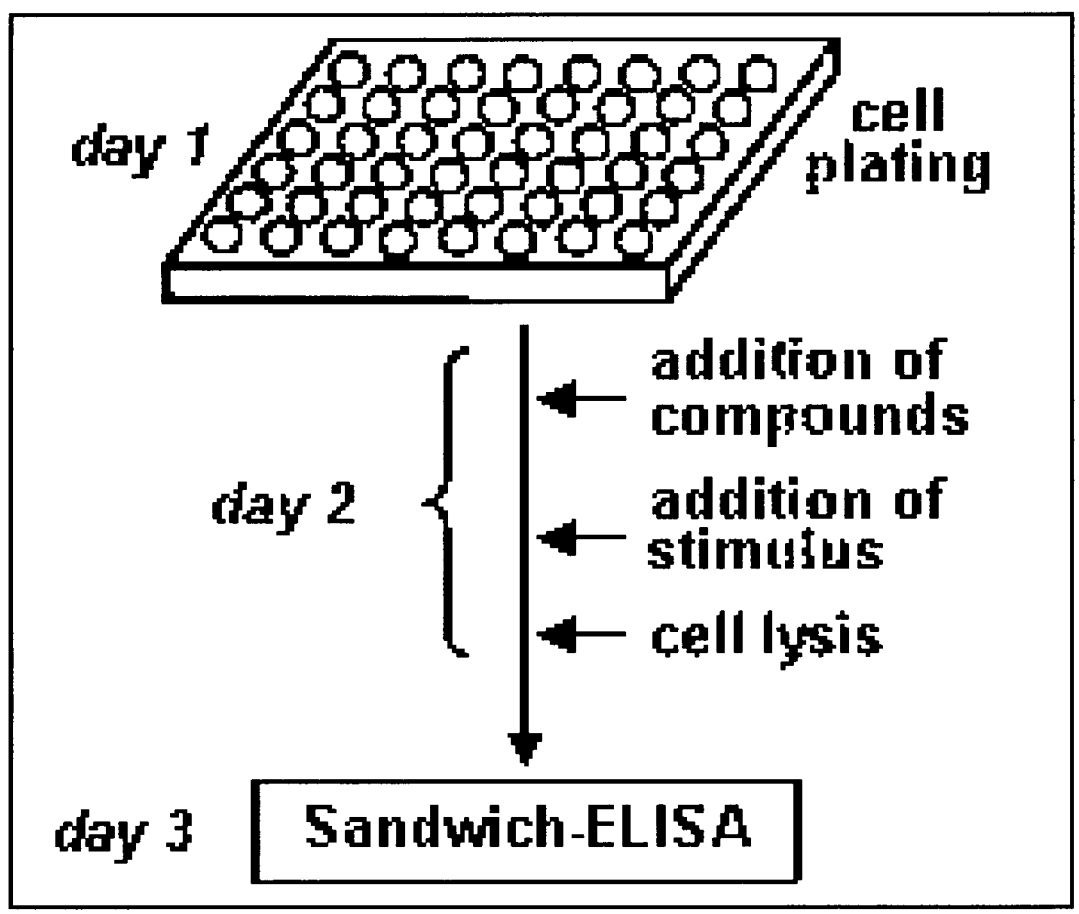

AMINOQUINAZOLINE DERIVATIVES AND THEIR SALTS AND METHODS OF USE

CROSS-REFERENCE TO RELATED APPLICATIONS

This is a U.S. national stage application of the International Patent Application No. PCT/CN2012/001545, filed Nov. 14, 2012, which claims priority to Chinese Patent Application No. 201110359739.8, filed Nov. 14, 2011, both of which are incorporated herein by reference in their entireties.

FIELD OF THE INVENTION

Provided herein are novel aminoquinazoline derivatives and their salts that are useful in treatment of hyperproliferative diseases, such as cancers, in mammals. In particular, this invention relates to the compounds that inhibit the activity of protein tyrosine kinase, resulting in the inhibition of intra- or inter-cellular signaling. Provided also herein are methods of using compounds or pharmaceutical compositions containing the compounds in the treatment of hyperproliferative diseases in mammals, especially those of humans.

BACKGROUND OF THE INVENTION

Protein kinases represent a large family of proteins, which play an important role in the regulation of a wide variety of cellular processes, maintaining control over cellular functions. Protein tyrosine kinases may be classified as growth factor receptor (e.g. VEGFR, EGFR, PDGFR, FGFR and erbB2) or non-receptor (e.g. c-src and bcr-abl) kinases. The receptor type tyrosine kinases make up about 20 different subfamilies. The non-receptor type tyrosine kinases make up numerous subfamilies. Receptor tyrosine kinases are large enzymes that span the cell membrane and possess an extracellular binding domain for growth factors, a transmembrane domain, and an intracellular portion that functions as a kinase to phosphorylate a specific tyrosine residue in proteins and hence to influence cell proliferation. Aberrant or inappropriate protein kinase activity can contribute to the rise of disease states associated with such aberrant kinase activity.

A partial list of such kinases include abl, AATK, ALK, Akt, axl, bmx, bcr-abl, Blk, Brk, Btk, csk, c-kit, c-Met, c-src, c-fms, CDK1, CDK2, CDK3, CDK4, CDK5, CDK6, CDK7, CDK8, CDK9, CDK10, cRaf1, CSF1R, CSK, DDR1, DDR2, EPHA, EPHB, EGFR, ErbB2, ErbB3, ErbB4, Erk, Fak, fes, FER, FGFR1, FGFR2, FGFR3, FGFR4, FGFR5, Fgr, flt-1, Fps, Frk, Fyn, GSG2, GSK, Hck, ILK, INSRR, IRAK4, ITK, IGF-1R, INS-R, Jak, KSR1, KDR, LMTK2, LMTK3, LTK, Lck, Lyn, MATK, MERTK, MLTK, MST1R, MUSK, NPR1, NTRK, MEK, PLK4, PTK, p38, PDGFR, PIK, PKC, PYK2, RET, ROR1, ROR2, RYK, ros, Ron, SGK493, SRC, SRMS, STYK1, SYK, TEC, TEK, TEX14, TNK1, TNK2, TNNI3K, TXK, TYK2, TYRO3, tie, tie2, TRK, Yes, and Zap70. Inhibition of such kinases has become an important therapeutic target.

Epidermal growth factor receptor (EGFR), a kind of receptor tyrosine kinases, is over expressed and/or mutated in most tumors. It can control the tumor growth by signal transduction and is closely related to the angiogenesis, invasion and metastasis of tumor. EGFR is an important regulatory factor in cell growth, differentiation and survival, members of which include erbB-1 (EGFR, HER1), erbB-2 (EGFR, HER2), erbB-3 (EGFR, HER3) and erbB-4 (EGFR, HER4), and they have similar structure consisting of extracellular receptor ligand domain, single-strand transmembrane domain and highly conserved protein tyrosine kinase domain, with the function of the receptor as well as the ability of converting extracellular signal into intracellular effect directly as a novel transmembrane transit mode. Once combined with specific ligand, EGFR is activated by autophosphorylation of relative tyrosine kinase, resulting in activation of intracellular signal transduction pathways. These pathways of signal transduction include: activation of Ras protein kinase and mitogen-activated protein kinase leads to activation of multiple proteins in the nucleus involving cyclin D1, thereby leading to DNA synthesis, cell growth and differentiation. Excessive activation of the growth factor receptors makes cell proliferation out of control, therefore, induces various types of excess proliferative diseases, such as non-small cell lung cancer, cancer of breast and head, etc. Since inhibition of epidermal growth factor receptor tyrosine kinases has been proved to be of value in regulating cell replication out of control, it becomes the therapeutic target for novel antitumor drugs.

SUMMARY OF THE INVENTION

Provided herein are new aminoquinazoline compounds and methods for treating cell proliferative diseases. The compounds disclosed herein are useful in inhibiting the protein tyrosine kinase activity. To be satisfying, the compounds disclosed herein are multiple function inhibitors, capable of inhibiting, for example, such as EGFR signaling.

Specifically, it has been found that compounds disclosed herein, and pharmaceutically acceptable compositions thereof, are effective as EGFR inhibitors.

In one aspect, provided herein are compounds having Formula (I) as shown below:

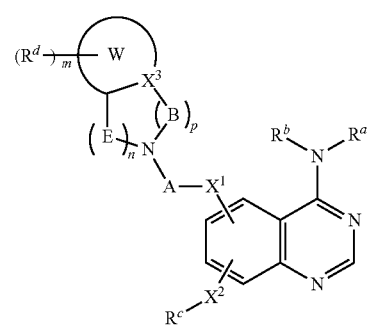

I or a racemic mixture, a diastereoisomer, an enantiomer, a geometric isomer, a tautomer, an N-oxide, a hydrate, a solvate, a metabolite, a pharmaceutically acceptable salt or a prodrug thereof, wherein each of $R^a$, $R^b$, $R^c$, $R^d$, A, B, E, $X^1$, $X^2$, $X^3$, W, n, m and p is as defined herein.

In some embodiments, IV is aryl, heteroaryl or unsaturated heterocyclyl;

$R^b$ is alkyl or H;

$R^c$ is H, alkyl, haloalkyl, ether alkyl, heteroalkyl, cycloalkyl, heterocyclylalkyl, aryl, aralkyl, heteroaryl or heteroarylalkyl;

each of $X^1$ and $X^2$ is independently S, O, $CH_2$ or NH;

A is $(CH_2)_q$—$X^4$—$(CH_2)_k$— or —$(CH_2)_q$—;

each of B and E is independently a bond or $CH_2$;

$X^3$ is N, C, CH or $CR^x$;

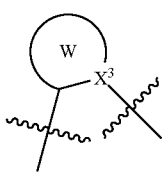

is carbocyclyl, heterocyclyl, aryl or heteroaryl;

$X^4$ is O, S or NH;

$R^d$ can be the same or different, and each $R^d$ is independently —CH=CHC(=O)NR$^1$R$^2$, R$^1$—S(=O)$_g$—, R$^1$—S(=O)$_g$—, R$^1$—OS(=O)$_g$—, R$^1$—C(=S)—, R$^1$O(CH$_2$)$_i$—O—(CH$_2$)$_j$—, —(CH$_2$)$_i$NR$^1$R$^2$, oxo, ether alkyl, H, F, Cl, Br, I, hydroxy, mercapto, amino, nitro, carboxy, cyano, alkyl, alkylamino, hydroxy-substituted alkyl, haloalkyl, heteroalkyl, alkoxy, alkenyl, alkynyl, cycloalkyl, heterocyclyl, aryl, heteroaryl, aralkyl, heteroarylalkyl, aminosulfonyl, carbamoyl, arylamino, heteroarylamino, arylalkylamino, heteroarylalkylamino, heterocyclylamino, heterocyclylalkylamino, aryloxy, heteroaryloxy, arylalkoxy, heteroarylalkoxy, heterocyclyloxy or heterocyclylalkoxy;

$R^x$ is —CH=CHC(=O)NR$^1$R$^2$, R$^1$—S(=O)$_g$O—, R$^1$—OS(=O)$_g$—, R$^1$—C(=O)—, R$^1$—C(=S)—, R$^1$O(CH$_2$)$_i$—O—(CH$_2$)$_j$—, —(CH$_2$)$_i$—NR$^1$R$^2$, ether alkyl, F, Cl, Br, I, hydroxy, mercapto, amino, nitro, carboxy, cyano, alkyl, alkylamino, hydroxy-substituted alkyl, haloalkyl, heteroalkyl, alkoxy, alkenyl, alkynyl, cycloalkyl, heterocyclyl, aryl, heteroaryl, aralkyl, heteroarylalkyl, aminosulfonyl, carbamoyl, arylamino, heteroarylamino, arylalkylamino, heteroarylalkylamino, heterocyclylamino, heterocyclylalkylamino, aryloxy, heteroaryloxy, arylalkoxy, heteroarylalkoxy, heterocyclyloxy or heterocyclylalkoxy;

each of n, m, i, j, k, p and q is independently 1, 2, 3, 4 or 5;

each g is independently 0, 1 or 2;

each of $R^1$ and $R^2$ is independently H, alkyl, cycloalkyl, aralkyl, heteroarylalkyl or haloalkyl; and wherein each of —CH=CHC(=O)NR$^1$R$^2$, R$^1$—S(=O)$_g$—, R$^1$—S(=O)$_g$O—, R$^1$—OS(=O)$_g$—, R$^1$—C(=O)—, R$^1$—C(=S)—, R$^1$O(CH$_2$)$_i$—O—(CH$_2$)$_j$—, —(CH$_2$)$_i$—NR$^1$R$^2$, ether alkyl, unsaturated heterocyclyl, amino, carboxy, alkyl, alkylamino, hydroxy-substituted alkyl, haloalkyl, heteroalkyl, alkoxy, alkenyl, alkynyl, cycloalkyl, heterocyclyl, aryl, heteroaryl, aralkyl, heteroarylalkyl, aminosulfonyl, carbamoyl, arylamino, heteroarylamino, arylalkylamino, heteroarylalkylamino, heterocyclylamino, heterocyclylalkylamino, aryloxy, heteroaryloxy, arylalkoxy, heteroarylalkoxy, heterocyclyloxy or heterocyclylalkoxy is substituted or unsubstituted, wherein the substitutent is hydroxy, hydroxyalkyl, amino, halo, cyano, oxo, aryl, heteroaryl, alkoxy, alkyl, haloalkyl, aminoalkyl, alkenyl, alkynyl, heterocyclyl, mercapto, nitro, aryloxy or aralkyl.

In certain embodiments,

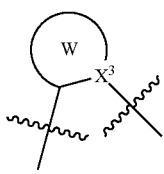

is $C_{3-10}$ carbocyclyl or $C_{2-10}$ heterocyclyl, wherein $X^3$ is as defined herein.

In certain embodiments,

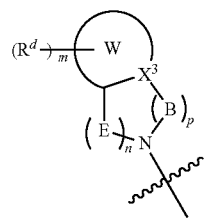

is:

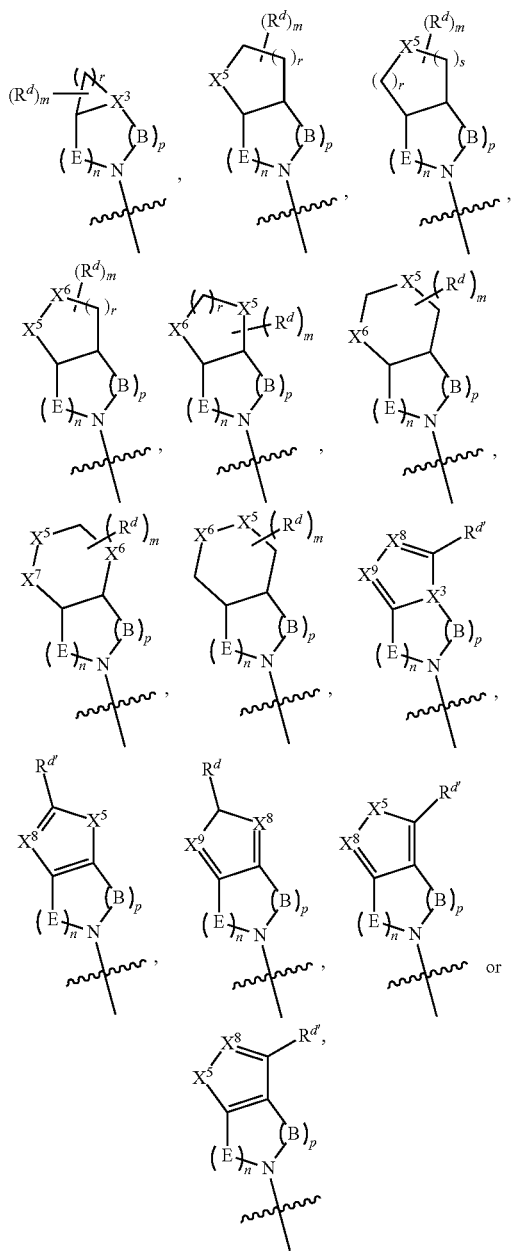

wherein each of $X^5$, $X^6$ and $X^7$ is independently O, NH, NR$^y$ or S;

each of $X^8$ and $X^9$ is independently N or CH;

each of n, m, p, r and s is independently 1, 2, 3, 4 or 5;

$R^{d'}$ is —CH=CHC(=O)$NR^1R^2$, $R^1$—S(=O)$_g$—, $R^1$—S(=O)$_g$O—, $R^1$—OS(=O)$_g$—, $R^1$—C(=O)—, $R^1$—C(=S)—, $R^1$O(CH$_2$)$_i$—O—(CH$_2$)$_j$—, —(CH$_2$)$_i$—$NR^1R^2$, ether alkyl, H, F, Cl, Br, I, hydroxy, mercapto, amino, nitro, carboxy, cyano, alkyl, alkylamino, hydroxy-substituted alkyl, haloalkyl, heteroalkyl, alkoxy, alkenyl, alkynyl, cycloalkyl, heterocyclyl, aryl, heteroaryl, aralkyl, heteroarylalkyl, aminosulfonyl, carbamoyl, arylamino, heteroarylamino, arylalkylamino, heteroarylalkylamino, heterocyclylamino, heterocyclylalkylamino, aryloxy, heteroaryloxy, arylalkoxy, heteroarylalkoxy, heterocyclyloxy or heterocyclylalkoxy;

$R^y$ is CH=CHC(=O)$NR^1R^2$, $R^1$—C(=O)—, $R^1$—C(=S)—, $R^1$O(CH$_2$)$_i$—O—(CH$_2$)$_j$—, —(CH$_2$)$_i$—$NR^1R^2$, ether alkyl, H, F, Cl, Br, I, hydroxy, mercapto, nitro, carboxy, cyano, alkyl, hydroxy-substituted alkyl, haloalkyl, heteroalkyl, alkoxy, alkenyl, alkynyl, cycloalkyl, heterocyclyl, aryl, heteroaryl, aralkyl, heteroarylalkyl, aryloxy, heteroaryloxy, arylalkoxy, heteroarylalkoxy, heterocyclyloxy or heterocyclylalkoxy;

$R^d$ can be the same or different, and each $R^d$ is independently —CH=CHC(=O)$NR^1R^2$, $R^1$—S(=O)$_g$—, $R^1$—S(=O)$_g$O—, $R^1$—OS(=O)$_g$—, $R^1$—C(=O)—, $R^1$—C(=S)—, $R^1$O(CH$_2$)$_i$—O—(CH$_2$)$_j$—, —(CH$_2$)$_i$—$NR^1R^2$, oxo, ether alkyl, H, F, Cl, Br, I, hydroxy, mercapto, amino, nitro, carboxy, cyano, alkyl, alkylamino, hydroxy-substituted alkyl, haloalkyl, heteroalkyl, alkoxy, alkenyl, alkynyl, cycloalkyl, heterocyclyl, aryl, heteroaryl, aralkyl or heteroarylalkyl; and each of $R^1$ and $R^2$ is independently H, alkyl, cycloalkyl, aralkyl, heteroarylalkyl or haloalkyl.

In other embodiments, $X^3$ is N, C or CH.

In other embodiments, $R^{d'}$ is —CH=CHC(=O)$NR^1R^2$, $R^1$O(CH$_2$)$_i$—O—(CH$_2$)$_j$—, —(CH$_2$)$_j$—$NR^1R^2$, $C_{2-10}$ ether alkyl, H, F, Cl, Br, I, hydroxy, mercapto, amino, nitro, carboxy, cyano, $C_{1-6}$ alkyl, $C_{1-6}$ alkylamino, hydroxy-substituted $C_{1-10}$ alkyl, $C_{1-6}$ haloalkyl, $C_{1-6}$ heteroalkyl, $C_{1-6}$ alkoxy, $C_{2-6}$ alkenyl, $C_{2-6}$ alkynyl, $C_{3-8}$ cycloalkyl, $C_{2-10}$ heterocyclyl, $C_{6-10}$ aryl, $C_{1-9}$ heteroaryl, $C_{6-10}$ aryl-$C_{1-6}$-alkyl or $C_{1-9}$ heteroaryl-$C_{1-6}$-alkyl;

each of i and j is independently 1, 2, 3, 4 or 5; and each of $R^1$ and $R^2$ is independently H, $C_{1-6}$ alkyl, $C_{3-8}$ cycloalkyl, $C_{6-10}$ aryl-$C_{1-6}$-alkyl, $C_{1-9}$ heteroaryl-$C_{1-6}$-alkyl or $C_{1-6}$ haloalkyl.

In other embodiments, $R^d$ can be the same or different, and each $R^d$ is independently —CH=CHC(=O)$NR^1R^2$, $R^1$—S(=O)$_g$—, $R^1$—OS(=O)$_g$—, $R^1$—C(=O)—, $R^1$—C(=S)—, $R^1$O(CH$_2$)$_i$—O—(CH$_2$)$_j$—, —(CH$_2$)$_i$—$NR^1R^2$, oxo, $C_{2-10}$ ether alkyl, H, F, Cl, Br, I, hydroxy, mercapto, amino, nitro, carboxy, cyano, $C_{1-6}$ alkyl, $C_{1-6}$ alkylamino, hydroxy-substituted $C_{1-10}$ alkyl, $C_{1-6}$ haloalkyl, $C_{1-6}$ heteroalkyl, $C_{1-6}$ alkoxy, $C_{2-6}$ alkenyl, $C_{2-6}$ alkynyl, $C_{3-8}$ cycloalkyl, $C_{2-10}$ heterocyclyl, $C_{6-10}$ aryl, $C_{1-9}$ heteroaryl, $C_{6-10}$ aryl-$C_{1-6}$-alkyl or $C_{1-9}$ heteroaryl-$C_{1-6}$-alkyl;

each of i and j is independently 1, 2, 3, 4 or 5;

each g is independently 0, 1 or 2; and each of $R^1$ and $R^2$ is independently H, $C_{1-6}$ alkyl, $C_{3-8}$ cycloalkyl, $C_{6-10}$ aryl-$C_{1-6}$-alkyl, $C_{1-9}$ heteroaryl-$C_{1-6}$-alkyl or $C_{1-6}$ haloalkyl.

In other embodiments, $R^d$ can be the same or different, and each $R^d$ is independently $R^1$—C(=O)—, oxo, methoxymethyl, ethoxymethyl, methoxyethoxymethyl, H, hydroxy, methyl, ethyl, propyl, butyl, isopropyl, pentyl, N,N-dimethylamino, N,N-diethylamino, trifluoromethyl or benzyl; and $R^1$ is H, methyl, ethyl, propyl, isopropyl, butyl or pentyl.

In other embodiments, $R^y$ is —CH=CHC(=O)$NR^1R^2$, $R^1$O(CH$_2$)$_i$—O—(CH$_2$)$_j$—, —(CH$_2$)$_j$—$NR^1R^2$, $C_{2-10}$ ether alkyl, H, F, Cl, Br, I, hydroxy, mercapto, nitro, carboxy, cyano, $C_{1-6}$ alkyl, hydroxy-substituted $C_{1-6}$ alkyl, $C_{1-6}$ haloalkyl, $C_{1-6}$ heteroalkyl, $C_{2-6}$ alkenyl, $C_{2-6}$ alkynyl, $C_{3-8}$ cycloalkyl, $C_{2-10}$ heterocyclyl, $C_{6-10}$ aryl, $C_{1-9}$ heteroaryl, $C_{6-10}$ aryl-$C_{1-6}$-alkyl or $C_{1-9}$ heteroaryl-$C_{1-6}$-alkyl;

each of i and j is independently 1, 2, 3, 4 or 5; and each of $R^1$ and $R^2$ is independently H, $C_{1-6}$ alkyl, $C_{3-8}$ cycloalkyl, $C_{6-10}$ aryl-$C_{1-6}$-alkyl, $C_{1-9}$ heteroaryl-$C_{1-6}$-alkyl or $C_{1-6}$ haloalkyl.

In certain embodiments, $R^d$ can be the same or different, and each $R^d$ is independently —CH=CHC(=O)$NR^1R^2$, $R^1$—S(=O)$_g$—, $R^1$—OS(=O)$_g$—, $R^1$—C(=O)—, $R^1$—C(=S)—, $R^1$O(CH$_2$)$_i$—O—(CH$_2$)$_j$—, —(CH$_2$)$_1$—$NR^1R^2$, oxo, $C_{2-10}$ ether alkyl, H, F, Cl, Br, I, hydroxy, mercapto, amino, nitro, carboxy, cyano, $C_{1-6}$ alkyl, $C_{1-6}$ alkylamino, hydroxy-substituted $C_{1-10}$ alkyl, $C_{1-6}$ haloalkyl, $C_{1-6}$ heteroalkyl, $C_{1-6}$ alkoxy, $C_{2-6}$ alkenyl, $C_{2-6}$ alkynyl, $C_{3-8}$ cycloalkyl, $C_{2-10}$ heterocyclyl, $C_{6-10}$ aryl, $C_{1-9}$ heteroaryl, $C_{6-10}$ aryl-$C_{1-6}$-alkyl, $C_{1-9}$ heteroaryl-$C_{1-6}$-alkyl, $C_{6-10}$ arylamino, $C_{1-9}$ heteroarylamino, $C_{6-10}$ aryl-$C_{1-6}$-alkylamino, $C_{1-9}$ heteroaryl-$C_{1-6}$-alkylamino, $C_{2-10}$ heterocyclylamino, $C_{2-10}$ heterocyclyl-$C_{1-6}$-alkylamino, $C_{6-10}$ aryloxy, $C_{1-9}$ heteroaryloxy, $C_{6-10}$ aryl-$C_{1-6}$-alkoxy, $C_{1-9}$ heteroaryl-$C_{1-6}$-alkoxy, $C_{2-10}$ heterocyclyloxy or $C_{2-10}$ heterocyclyl-$C_{1-6}$-alkoxy; and each of $R^1$ and $R^2$ is independently H, $C_{1-6}$ alkyl, $C_{3-8}$ cycloalkyl, $C_{6-10}$ aryl-$C_{1-6}$-alkyl, $C_{1-9}$ heteroaryl-$C_{1-6}$-alkyl or $C_{1-6}$ haloalkyl.

In certain embodiments, $R^x$ is —CH=CHC(=O)$NR^1R^2$, $R^1$O(CH$_2$)$_i$—O—(CH$_2$)$_j$—, —(CH$_2$)$_i$—$NR^1R^2$, $C_{2-10}$ ether alkyl, F, Cl, Br, I, hydroxy, mercapto, amino, nitro, carboxy, cyano, $C_{1-6}$ alkyl, $C_{1-6}$ alkylamino, hydroxy-substituted $C_{1-10}$ alkyl, $C_{1-6}$ haloalkyl, $C_{1-6}$ heteroalkyl, $C_{1-6}$ alkoxy, $C_{2-6}$ alkenyl, $C_{2-6}$ alkynyl, $C_{3-8}$ cycloalkyl, $C_{2-10}$ heterocyclyl, $C_{6-10}$ aryl, $C_{1-9}$ heteroaryl, $C_{6-10}$ arylamino, $C_{1-9}$ heteroarylamino, $C_{2-10}$ heterocyclylamino, $C_{6-10}$ aryloxy, $C_{1-9}$ heteroaryloxy or $C_{2-10}$ heterocyclyloxy; and each of $R^1$ and $R^2$ is independently H, $C_{1-6}$ alkyl, $C_{3-8}$ cycloalkyl, $C_{6-10}$ aryl-$C_{1-6}$-alkyl, $C_{1-9}$ heteroaryl-$C_{1-6}$-alkyl or $C_{1-6}$ haloalkyl.

In certain embodiments,

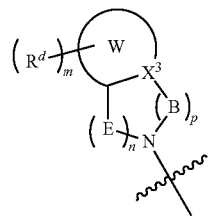

is:

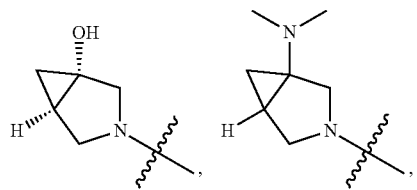

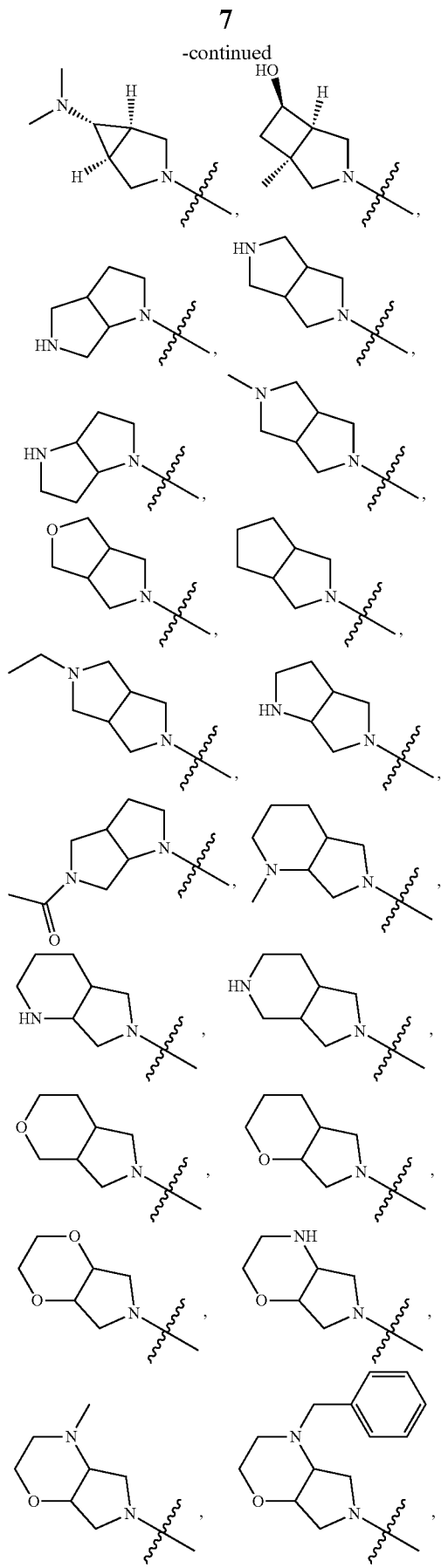
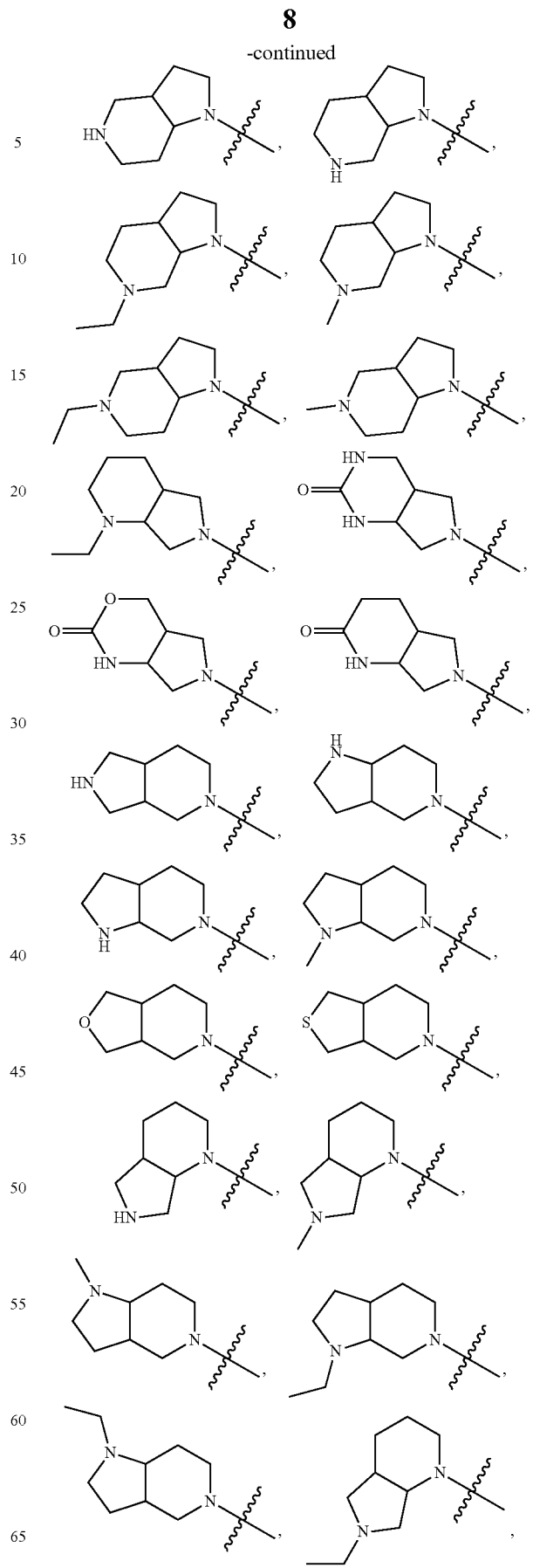

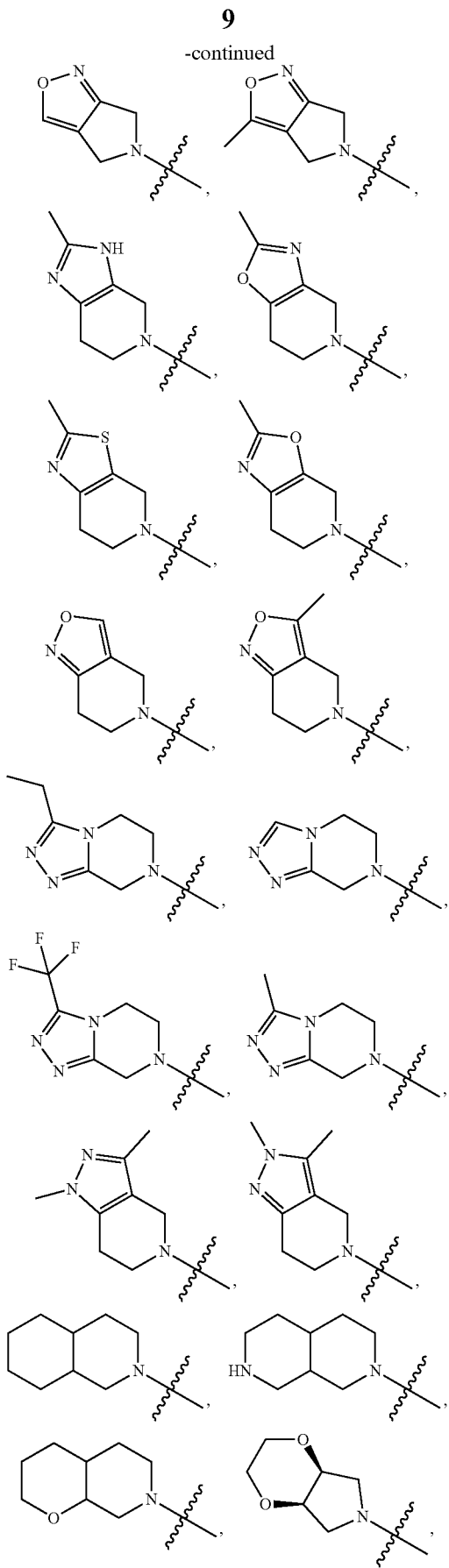
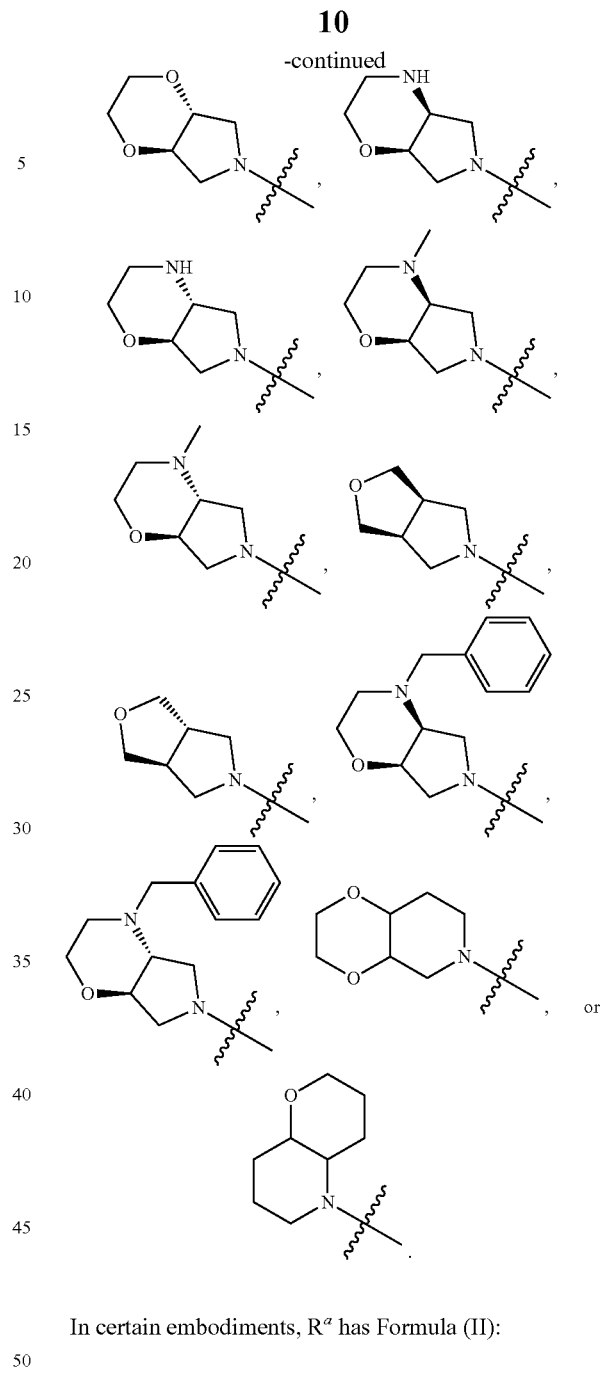

In certain embodiments, $R^a$ has Formula (II):

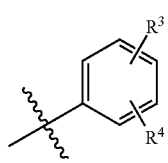

II wherein each of $R^3$ and $R^4$ is independently H, F, Cl, Br, I, alkenyl, alkynyl, alkyl, cycloalkyl, haloalkyl, heteroalkyl, alkoxy, alkylamino, heterocyclyl, hydroxy, amino, nitro, carboxy, cyano, aryl, heteroaryl, aralkyl, heteroarylalkyl, aminosulfonyl, carbamoyl, arylamino, heteroarylamino, arylalkylamino, heteroarylalkylamino, heterocyclylamino, heterocyclylalkylamino, heteroaryloxy, arylalkoxy, heteroarylalkoxy, heterocyclyloxy or heterocyclylalkoxy.

In other embodiments, each of $R^3$ and $R^4$ is independently H, F, Cl, Br, I, $C_{2-6}$ alkenyl, $C_{2-6}$ alkynyl, $C_{1-6}$ alkyl, $C_{1-6}$ haloalkyl, hydroxy, amino, nitro, carboxy, cyano, $C_{6-10}$ aryl or $C_{1-9}$ heteroaryl.

In other embodiments, $R^b$ is:

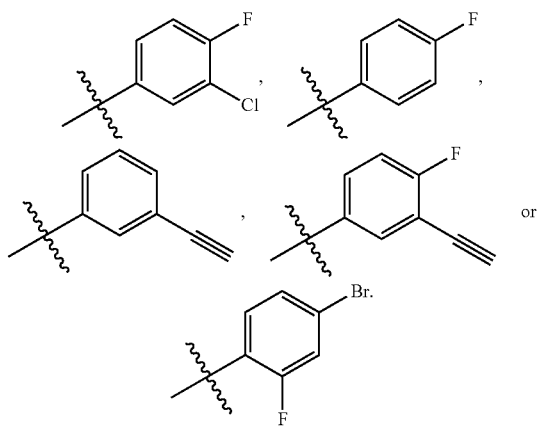

In certain embodiments, $R^b$ is H or $C_{1-6}$ alkyl.

In certain embodiments, $R^c$ is H, $C_{1-6}$ alkyl, $C_{1-6}$ haloalkyl, $C_{2-10}$ ether alkyl, $C_{1-6}$ heteroalkyl, $C_{3-8}$ cycloalkyl, $C_{2-10}$ heterocycloalkyl, $C_{6-10}$ aryl, $C_{6-10}$ aryl-$C_{1-6}$-alkyl, $C_{1-9}$ heteroaryl or $C_{1-9}$ heteroaryl-$C_{1-6}$-alkyl.

In certain embodiments, $R^c$ is methyl, ethyl, propyl, isopropyl, trifluoromethyl, methoxyethyl, cyclopropyl, cyclopentyl, phenyl or phenylmethyl.

In certain embodiments, provided herein are compounds having Formula (III) as shown below:

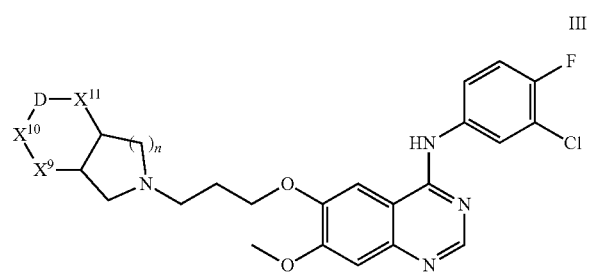

wherein each of $X^9$, $X^{10}$ and $X^{11}$ is independently $CR^eR^f$, $NR^e$, O or S, with the proviso that at least one of $X^9$, $X^{10}$ and $X^{11}$ is $CR^eR^f$;

D is a bond, methylene or ethylene;

each of $R^e$ and $R^f$ is independently H, $C_{1-6}$ alkyl, $C_{1-6}$ alkylacyl, $C_{3-8}$ cycloalkyl, $C_{6-10}$ aryl-$C_{1-6}$-alkyl, $C_{1-9}$ heteroaryl-$C_{1-6}$-alkyl or $C_{1-6}$ haloalkyl; and n is 1 or 2.

In another aspect, provided herein are pharmaceutical compositions comprising a compound disclosed herein, or a stereoisomer, geometric isomer, tautomer, solvate, metabolite, pharmaceutically acceptable salt or prodrug thereof, and an optional pharmaceutically acceptable carrier, excipient, diluent, adjuvant, vehicle or a combination thereof. In certain embodiments, the compound is an inhibitor of protein tyrosine kinase. In other embodiments, the compound is an inhibitor of EGFR receptor signaling.

In some embodiments, the pharmaceutical composition disclosed herein further comprises an additional therapeutic agent. In other embodiments, the therapeutic agent is a chemotherapeutic agent, an anti-proliferative agent, an agent for treating non-small cell lung cancer or epidermoid carcinoma, and combinations thereof.

In further embodiments, the therapeutic agent is adriamycin, rapamycin, temsirolimus, everolimus, ixabepilone, gemcitabine, cyclophosphamide, dexamethasone, etoposide, fluorouracil, imatinib mesylate, dasatinib, nilotinib, erlotinib, lapatinib, gefitinib, sorafenib, sunitinib, an interferon, carboplatin, topotecan, taxol, vinblastine, vincristine, temozolomide, tositumomab, trabectedin, bevacizumab (AVASTIN®), trastuzumab (HERCEPTIN®), cetuximab (ERBITUX®), panitumumab (VECTIBIX®) or a combination thereof.

In another aspect, provided herein are methods for preventing, managing, treating or lessening the severity of a proliferative disorder in a patient infected with the proliferative disorder, which comprises administrating a pharmaceutically effective amount of a compound or a pharmaceutical composition comprising the compounds disclosed herein to the patient.

In another aspect, provided herein is use of the compound or the pharmaceutical composition comprising the compounds disclosed herein in the manufacture of a medicament for preventing, managing, treating a proliferative disorder in a patient, as well as lessening the severity of a proliferative disorder in a patient.

In some embodiments, the proliferative disorder is metastatic cancer. In other embodiments, the proliferative disorder is epidermoid carcinoma, colon cancer, gastric adenocarcinoma, bladder cancer, breast cancer, kidney cancer, liver cancer, lung cancer, thyroid cancer, cerebroma, neck cancer, prostate cancer, pancreatic cancer, cancer of the CNS, glioblastoma, or a myeloproliferative disorder. In further embodiments, the proliferative disorder is atherosclerosis or lung fibrosis.

In another aspect, provided herein is a method of inhibiting or modulating protein kinase activity in a biological sample comprises contacting a biological sample with the compound or the pharmaceutical composition disclosed herein.

In some embodiments, the protein kinases are receptor tyrosine kinases. In other embodiments, the receptor tyrosine kinase is EGFR.

In another aspect, provided herein is a method of inhibiting protein tyrosine kinase, the method comprises contacting the kinase with a compound disclosed herein, or with a composition disclosed herein. In other embodiments, provided herein is a method of inhibiting EGFR receptor signaling, the method comprises contacting the receptor with a compound disclosed herein, or with a composition disclosed herein. Inhibition of receptor protein kinase activity, in some embodiments, EGFR receptor signaling, can be in a cell or a multicellular organism. If in a multicellular organism, the method disclosed herein comprises administering to the organism a compound disclosed herein, or a composition disclosed herein. In some embodiments, the organism is a mammal; in other embodiments, the organism is a human. In still other embodiments, the method further comprises contacting the kinase with an additional therapeutic agent.

In another aspect, provided herein is a method of inhibiting proliferative activity of a cell, the method comprises contacting the cell with an effective proliferative inhibiting amount of a compound disclosed herein or a composition thereof. In other embodiments, the method further comprises contacting the cell with an additional therapeutic agent.

In another aspect, provided herein is a method of treating a cell proliferative disease in a patient, the method comprises administering to the patient in need of such treatment an effective therapeutic amount of a compound disclosed herein or a composition thereof. In other embodiments, the method further comprises administering an additional therapeutic agent.

In another aspect, provided herein is a method of inhibiting tumor growth in a patient, the method comprises administering to the patient in need of such treatment an effective therapeutic amount of a compound disclosed herein or a composition thereof. In other embodiments, the method further comprises administering an additional therapeutic agent.

In another aspect, provided herein include methods of preparing, methods of separating, and methods of purifying compounds of Formula (I).

The foregoing merely summarizes certain aspects disclosed herein and is not intended to be limiting in nature. These aspects and other aspects and embodiments are described more fully below.

DESCRIPTION OF THE DRAWING

FIG. 1 depicts the procedures of kinase assay in Example C.

DETAILED DESCRIPTION OF THE INVENTION

Definitions and General Terminology

Reference will now be made in detail to certain embodiments disclosed herein, examples of which are illustrated in the accompanying structures and formulas. The invention is intended to cover all alternatives, modifications, and equivalents that may be included within the scope disclosed herein as defined by the claims. One skilled in the art will recognize many methods and materials similar or equivalent to those described herein, which could be used in the practice disclosed herein. Described herein is in no way limited to the methods and materials. In the event that one or more of the incorporated literature, patents, and similar materials differ from or contradict this application, including but not limited to defined terms, term usage, described techniques, or the like, this application controls.

As used herein, the following definitions shall be applied unless otherwise indicated. For purposes disclosed herein, the chemical elements are identified in accordance with the Periodic Table of the Elements, CAS version, and *the Handbook of Chemistry and Physics*, 75th Ed. 19094. Additionally, general principles of organic chemistry are described in "*Organic Chemistry*", Thomas Sorrell, University Science Books, Sausalito: 1999, and "*March's Advanced Organic Chemistry*" by Michael B. Smith and Jerry March, John Wiley & Sons, New York: 2007, the entire contents of which are hereby incorporated by reference.

As described herein, compounds may optionally be substituted with one or more substituents, such as are illustrated generally above, or as exemplified by particular classes, subclasses, and species disclosed herein. It will be appreciated that the phrase "optionally substituted" is used interchangeably with the phrase "substituted or unsubstituted". In general, the term "substituted" whether preceded by the term "optionally" or not, refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position. Examples of substituents include, but are not limited to, hydroxy, cyano, hydroxy-substituted alkyl, haloalkyl, aminoalkyl, amino, halogen, oxo, aryl, heteroaryl, alkoxy, alkyl, alkenyl, alkynyl, heterocyclyl, sulphydryl, nitro, aryloxy, aralkyl, and the like.

The term "aliphatic" or "aliphatic group" as used herein, refers to a straight chain (i.e., unbranched) or branched, substituted or unsubstituted hydrocarbon chain that is completely saturated or that contains one or more units of unsaturation. Unless otherwise specified, aliphatic groups contain 1-20 carbon atoms. In some embodiments, aliphatic groups contain 1-10 carbon atoms. In other embodiments, aliphatic groups contain 1-8 carbon atoms. In still other embodiments, aliphatic groups contain 1-6 carbon atoms. In yet other embodiments, aliphatic groups contain 1-4 carbon atoms. In other embodiments, aliphatic groups contain 1-3 carbon atoms. Suitable aliphatic groups include, but are not limited to, linear or branched, substituted or unsubstituted alkyl, alkylene, alkenyl, or alkynyl groups, such as methyl, ethyl, propyl, vinyl, etc.

The term "alkyl" as used herein refers to a saturated linear or branched-chain monovalent hydrocarbon radical of one to twenty carbon atoms, wherein the alkyl radical may be optionally substituted independently with one or more substituents described below. In some embodiments, alkyl groups contain 1-10 carbon atoms. In other embodiments, alkyl groups contain 1-8 carbon atoms. In still other embodiments, alkyl groups contain 1-6 carbon atoms. In yet other embodiments, alkyl groups contain 1-4 carbon atoms. In other embodiments, alkyl groups contain 1-3 carbon atoms. Further examples of alkyl groups include, but are not limited to, methyl (Me, $-CH_3$), ethyl (Et, $-CH_2CH_3$), 1-propyl (n-Pr, n-propyl, $-CH_2CH_2CH_3$), 2-propyl (i-Pr, i-propyl, $-CH(CH_3)_2$), 1-butyl (n-Bu, n-butyl, $-CH_2CH_2CH_2CH_3$), 2-methyl-1-propyl (i-Bu, i-butyl, $-CH_2CH(CH_3)_2$), 2-butyl (s-Bu, s-butyl, $-CH(CH_3)CH_2CH_3$), 2-methyl-2-propyl (t-Bu, t-butyl, $-C(CH_3)_3$), 1-pentyl (n-pentyl, $-CH_2CH_2CH_2CH_2CH_3$), 2-pentyl ($-CH(CH_3)CH_2CH_2CH_3$), 3-pentyl ($-CH(CH_2CH_3)_2$), 2-methyl-2-butyl ($-C(CH_3)_2CH_2CH_3$), 3-methyl-2-butyl ($-CH(CH_3)CH(CH_3)_2$), 3-methyl-1-butyl ($-CH_2CH_2CH(CH_3)_2$), 2-methyl-1-butyl ($-CH_2CH(CH_3)CH_2CH_3$), 1-hexyl ($-CH_2CH_2CH_2CH_2CH_2CH_3$), 2-hexyl ($-CH(CH_3)CH_2CH_2CH_2CH_3$), 3-hexyl ($-CH(CH_2CH_3)(CH_2CH_2CH_3)$), 2-methyl-2-pentyl ($-C(CH_3)_2CH_2CH_2CH_3$), 3-methyl-2-pentyl ($-CH(CH_3)CH(CH_3)CH_2CH_3$), 4-methyl-2-pentyl ($-CH(CH_3)CH_2CH(CH_3)_2$), 3-methyl-3-pentyl ($-C(CH_3)(CH_2CH_3)_2$), 2-methyl-3-pentyl ($-CH(CH_2CH_3)CH(CH_3)_2$), 2,3-dimethyl-2-butyl ($-C(CH_3)_2CH(CH_3)_2$), 3,3-dimethyl-2-butyl ($-CH(CH_3)C(CH_3)_3$), 1-heptyl, 1-octyl, and the like. The terms "alkyl" and the prefix "alk-" as used herein, are inclusive of both straight chain and branched saturated carbon chain.

The term "haloalkyl" as used herein, refers to alkyl as described herein, as the case may be, substituted with one or more halogen atoms. Halogen atoms refer to F, Cl, Br or I. Some non-limiting examples include trifluoromethyl and trifluoroethyl.

The term "hydroxy-substituted alkyl" as used herein, refers to alkyl as described herein, as the case may be, substituted with one or more hydroxy groups. Some non-limiting examples of hydroxy-substituted alkyl include hydroxymethyl, (R)-hydroxyethyl, (S)-hydroxyethyl, (R)-hydroxypropyl, (S)-hydroxypropyl, 2-hydroxypropyl, 2-hydroxy-2-propyl, 3-hydroxy-3-pentyl, and the like.

The term "ether alkyl" as used herein, refers to alkyl radical containing one or more of O or S, wherein carbon atom serves as the attaching point to the rest of the molecule. Some examples of ether alkyl include, but are not limited to, methoxymethyl, ethoxyethyl, propoxypropyl, ethoxyethoxyethyl, and the like.

The term "alkenyl" refers to linear or branched-chain monovalent hydrocarbon radical of two to twelve carbon atoms with at least one site of unsaturation, i.e., a carbon-carbon, sp$^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—CH═CH$_2$), allyl (—CH$_2$CH═CH$_2$), propenyl (CH$_3$CH═CH—), and the like.

The term "alkynyl" refers to a linear or branched-chain monovalent hydrocarbon radical of two to twelve carbon atoms with at least one site of unsaturation, i.e., a carbon-carbon, sp triple bond, wherein the alkynyl radical may be optionally substituted independently with one or more substituents described herein. Examples include, but are not limited to, ethynyl (—C≡CH), propynyl (propargyl, —CH$_2$C≡CH), and the like.

The term "carbocyclyl" or "cycloalkyl" refers to a monovalent or multivalent non-aromatic, saturated or partially unsaturated ring having 3 to 12 carbon atoms as a monocyclic ring or 7 to 12 carbon atoms as a bicyclic ring. Bicyclic carbocycles having 7 to 12 atoms can be arranged, for example, as a bicyclo [4,5], [5,5], [5,6] or [6,6] system, and bicyclic carbocycles having 9 or 10 ring atoms can be arranged as a bicyclo [5,6] or [6,6] system. Suitable carbocyclyl groups include, but are not limited to, cycloalkyl, cycloalkenyl and cycloalkynyl. Further examples of carbocyclyl groups include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like. The term "carbocyclyl" or "cycloalkyl" described herein can be substituted or unsubstituted, wherein the substituents include, but are not limited to, hydroxy, amino, halogen, cyano, aryl, heteroaryl, alkoxy, alkyl, alkenyl, alkynyl, heterocyclyl, sulphydryl, nitro, aryloxy, aralkyl, and the like.

The term "cycloalkoxy" or "carbocyclyloxy" refers to optionally substituted cycloalkyl radicals, as defined herein, attached to an oxygen atom, wherein oxygen atom serves as the attaching point to the rest of the molecule. Some non-limiting examples include cyclopropoxy, cyclopentoxy, cyclohexoxy, hydroxy-substituted cyclopropoxy, and the like.

The term "alkoxy" as used herein, refers to optionally substituted alkyl radicals, as defined herein, attached to an oxygen atom, wherein oxygen atom serves as the attaching point to the rest of the molecule. Some non-limiting examples include methoxy, ethoxy, propoxy, and the like.

The term "alkylamino" refers to "N-alkylamino" and "N,N-dialkylamino" wherein amino groups are independently substituted with one alkyl radical or with two alkyl radicals, respectively. In other embodiments, alkylamino radicals are "lower alkylamino" radicals having one or two alkyl radicals of one to six carbon atoms, attached to a nitrogen atom. In still other embodiments, alkylamino radicals are lower alkylamino radicals having one to three carbon atoms. Some non-limiting examples of suitable alkylamino radicals include mono or dialkylamino such as N-methylamino, N-ethylamino, N,N-dimethylamino, N,N-diethylamino, and the like.

The term "heteroalkyl" refers to alkyl radical, as defined herein, in which one or more atoms are optionally substituted with heteroatoms, wherein the carbon serves as attaching point to the rest of the molecule. In some embodiments, the "heteroalkyl" is a linear or branched-chain having one to ten atoms (e.g., 1 to 9 carbon atoms and 1 to 3 heteroatoms selected from N, O, P or S, wherein the S or P is optionally substituted with one or more oxo to provide the group SO or SO$_2$, PO or PO$_2$). Some non-limiting examples of heteroalkyl include aminomethyl, methoxyethyl, and the like.

The term "heterocycle" or "heterocyclyl" as used interchangeably herein refers to a monocyclic, bicyclic, or tricyclic ring system in which one or more ring members are an independently selected heteroatom and that is completely saturated or that contains one or more units of unsaturation, but which is not aromatic, that has one or more points of attachment to the rest of the molecule. One or more ring atoms are optionally substituted independently with one or more substituents described below. In some embodiments, the "heterocycle" or "heterocyclyl" group is a monocycle having 3 to 7 ring members (e.g., 1 to 6 carbon atoms and 1 to 3 heteroatoms selected from N, O, P or S, wherein the S or P is optionally substituted with one or more oxo to provide the group SO or SO$_2$, PO or PO$_2$, with the proviso that when the ring is a 3-membered ring, there is only one heteroatom) or a bicycle having 7 to 10 ring members (e.g., 4 to 9 carbon atoms and 1 to 3 heteroatoms selected from N, O, P or S, wherein the S or P is optionally substituted with one or more oxo to provide the group SO or SO$_2$, PO or PO$_2$).

The heterocyclyl may be a carbon radical or heteroatom radical. "Heterocyclyl" also includes radicals where heterocycle radicals are fused with a saturated, partially unsaturated ring, or heterocyclic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, epoxypropyl, azepanyl, oxepanyl, thiepanyl, oxazepinyl, diazepinyl, thiazepinyl, 2-pyrrolinyl, 3-pyrrolinyl, dihydroindolinyl, 2H-pyranyl, 4H-pyranyl, dioxanyl, 1,3-dioxolanyl, pyrazolinyl, dithianyl, dithiolanyl, dihydrothienyl, pyrazolidinylimidazolinyl, imidazolidinyl, 1,2,3,4-tetrahydroisoquinolinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Some non-limiting examples of a heterocyclic ring include 1,1-dioxo-thiomorpholinyl and heterocyclic group wherein 2 carbon atoms on the ring are substituted with oxo moieties are pyrimidindionyl. The heterocyclic groups herein are optionally substituted independently with one or more substituents described herein, wherein the substituents include, but are not limited to hydroxy, amino, halogen, cyano, aryl, heteroaryl, alkoxy, alkyl, alkenyl, alkynyl, heterocyclyl, sulphydryl, nitro, aryloxy, and the like.

The term "unsaturated heterocyclyl" refers to heterocyclyl radical as described herein, containing one or more units of unsaturation, but which is not aromatic, that has one or more points of attachment to the rest of the molecule. Some non-limiting examples include 2H-pyranyl, 4H-pyranyl, and the like.

The term "heterocyclyloxy" refers to optionally substituted heterocyclyl radicals, as defined herein, attached to an oxygen atom, wherein oxygen atom serves as the attaching point to the rest of the molecule. Some non-limiting examples of heterocyclyloxy include (pyrrol-2-yl)oxy, (pyrrol-3-yl)

oxy, (piperidin-2-yl)oxy, (piperidin-3-yl)oxy, (piperazin-2-yl)oxy, (piperidin-4-yl)oxy, and the like.

The terms "heterocyclylamino" refers to amino group substituted with one or two heterocyclyl radicals as described herein, wherein nitrogen atom serves as the attaching point to the rest of the molecule. Some non-limiting examples of heterocyclylamino include (pyrrol-2-yl)amino, (pyrrol-3-yl)amino, (piperidin-2-yl)amino, (piperidin-3-yl)amino, (piperidin-4-yl)amino, (piperazin-2-yl)amino, (dipyrrol-2-yl)amino, and the like.

The term "heterocyclylalkyl" refers to heterocyclyl-substituted alkyl radical. The term "heterocyclylalkoxy" refers to hetercyclyl-substituted alkoxy radical wherein oxygen atom serves as the attaching point to the rest of the molecule; and the term "heterocyclylalkylamino" refers to heterocyclyl-substituted alkylamino radical wherein nitrogen atom serves as the attaching point to the rest of the molecule, wherein the heterocyclyl, alkyl, alkoxy and alkylamino groups are described herein. Some non-limiting examples include (pyrrol-2-yl)methyl, (morpholin-4-yl)methyl, (pyrrol-2-yl)methoxy, (piperidin-2-yl)ethoxy, (piperazin-2-yl)ethylamino, (morpholin-4-yl)propoxy, (morpholin-4-yl)ethylamino, and the like.

The term "heteroatom" refers to one or more of oxygen, sulfur, nitrogen, phosphorus or silicon, including any oxidized form of nitrogen, sulfur or phosphorus; the quaternized form of any basic nitrogen; or a substitutable nitrogen of a heterocyclic ring, for example, N (as in 3,4-dihydro-2H-pyrrolyl), NH (as in pyrrolidinyl) or NR (as in N-substituted pyrrolidinyl).

The term "halogen" refers to F, Cl, Br or I.

The term "unsaturated" as used herein, refers to that a moiety has one or more units of unsaturation.

The term "aryl" used alone or as part of a larger moiety as in "aralkyl", "arylalkoxy" or "aryloxyalkyl" refers to monocyclic, bicyclic, and tricyclic carbocyclic ring systems having a total of six to fourteen ring members, wherein at least one ring in the system is aromatic, wherein each ring in the system contains 3 to 7 ring members and that has a single point of attachment to the rest of the molecule. The term "aryl" may be used interchangeably with the term "aryl ring". Some non-limiting examples of aryl rings include phenyl, naphthyl and anthracene. And aryl as described herein, is substituted or unsubstituted, wherein the substituents include, but are not limited to, hydroxy, amino, halogen, cyano, aryl, heteroaryl, alkoxy, alkyl, alkenyl, alkynyl, heterocyclyl, sulphydryl, nitro, aryloxy, and the like.

The term "aralkyl" refers alkyl radical substituted with one or more aryl radicals, wherein alkyl and aryl groups are described herein. Some examples of aralkyl include, but are not limited to, benzyl, phenylethyl, p-tolylethyl, phenylethenyl, and the like.

The term "aryloxy" refers to optionally substituted aryl radicals, as defined herein, attached to an oxygen atom, wherein oxygen atom serves as the attaching point to the rest of the molecule. Some non-limiting examples of such radicals include phenoxy, p-tolyloxy, p-ethylphenyloxy, and the like.

The term "arylamino" refers to amino groups, which have been substituted with one or two aryl radicals. Some non-limiting examples of arylamino include phenylamino, diphenylamino, ditolylamino, and the like.

The term "arylalkoxy" refers to alkoxy radical substituted with one or more aryl radicals, wherein aryl and alkoxy groups are described herein, and oxygen atom serves as the attaching point to the rest of the molecule. Some non-limiting examples of such radicals include phenylmethoxy, p-tolylethoxy, p-ethylbenzyloxy, and the like.

The term "arylalkylamino" refers to alkylamino groups substituted with one or more aryl radicals, wherein aryl and alkylamino groups are described herein, and nitrogen atom serves as the attaching point to the rest of the molecule. Some non-limiting examples of arylalkylamino include phenylmethylamino, diphenylethylamino, and the like.

The term "heteroaryl" used alone or as part of a larger moiety as in "heteroarylalkyl" or "heteroarylalkoxy" refers to monocyclic, bicyclic, and tricyclic ring systems having a total of five to fourteen ring members, wherein at least one ring in the system is aromatic, at least one ring in the system contains one or more heteroatoms, wherein each ring in the system contains 3 to 7 ring members and that has a single point of attachment to the rest of the molecule. The term "heteroaryl" may be used interchangeably with the term "heteroaryl ring" or the term "heteroaromatic". And heteroaryl described herein, is substituted or unsubstituted, wherein the substituents include, but are not limited to, hydroxy, amino, halogen, cyano, aryl, heteroaryl, alkoxy, alkyl, alkenyl, alkynyl, heterocyclyl, sulphydryl, nitro, aryloxy, and the like.

Some non-limiting examples of suitable heteroaryl rings include the following monocycles: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridinyl, 3-pyridinyl, 4-pyridinyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the following bicycles: benzimidazolyl, benzofuryl, benzothiophenyl, indolyl (e.g., 2-indolyl), purinyl, quinolinyl (e.g., 2-quinolinyl, 3-quinolinyl, 4-quinolinyl), or isoquinolinyl (e.g., 1-isoquinolinyl, 3-isoquinolinyl, or 4-isoquinolinyl), and the like.

The term "heteroarylalkyl" refers to alkyl, which have been substituted with one or more heteroaryl radicals. Some non-limiting examples of heteroarylalkyl include (pyridin-2-yl)ethyl, (thiazol-2-yl)methyl, (imidazol-2-yl)ethyl, (pyrimid-2-yl) propyl, and the like.

The term "heteroaryloxy" refers to optionally substituted heteroaryl radicals, as defined herein, attached to an oxygen atom, wherein oxygen atom serves as the attaching point to the rest of the molecule. Some non-limiting examples of such radicals include (pyridin-2-yl)oxy, (thiazol-2-yl)oxy, (imidazol-2-yl)oxy, (pyrimidin-2-yl)oxy, and the like.

The term "heteroarylamino" refers to amino groups, which have been substituted with one or two heteroaryl radicals, wherein heteroaryl is described herein. Some non-limiting examples of heteroarylamino include (pyridin-2-yl)amino, (thiazol-2-yl)amino, (imidazol-2-yl)amino, (pyrimidin-2-yl)amino, and the like.

The term "heteroarylalkoxy" refers to oxy-containing heteroarylalkyl radicals attached through an oxygen atom to other radicals, wherein heteroaryl and alkoxy groups are described herein. Some non-limiting examples include (pyridin-2-yl)methoxy, (pyridin-4-yl)ethoxy, (thiazol-2-yl)ethoxy, (imidazol-3-yl)propoxy, and the like.

The term "heteroarylalkylamino" refers to alkylamino groups, which have been substituted with one or more heteroaryl radicals, wherein heteroaryl and alkylamino groups are described herein, and nitrogen atom serves as the attaching point to the rest of the molecule. Some non-limiting examples include (pyridin-2-yl)methylamino, (pyridin-4-yl)ethylamino, (thiazol-2-yl)ethylamino, (imidazol-3-yl)propylamino, and the like.

The term "aminosulfonyl" refers to a sulfonyl radical substituted with an amine radical, forming a sulfonamide (—SO$_2$NH$_2$).

The term "carbamoyl" refers to a formyl radical substituted with an amine radical, forming a carbamoyl(—CONH$_2$).

The term "carboxy", whether used alone or with other terms, such as "carboxyalkyl", refers to —CO$_2$H.

As described herein, two bonds drawn from two substituents to the center of one ring within a ring system (as shown in Figure a and Figure b) represents substitution of the two substituents at any substitutable position on the rings to which it is attached. For example, Figure a represents possible substitution in any of the positions on the A ring shown in Figure b (b1-b12).

Figure a

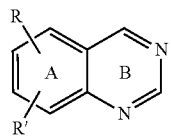

Figure b

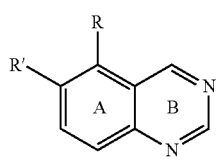
b1

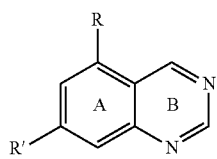
b2

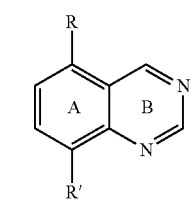
b3

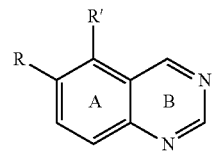
b4

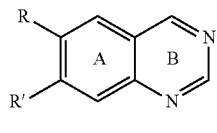
b5

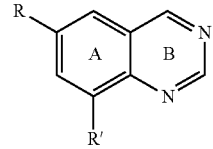
b6

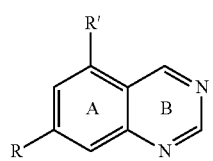
b7

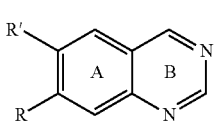
b8

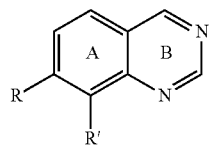
b9

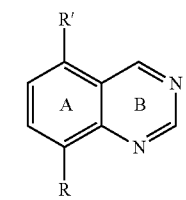
b10

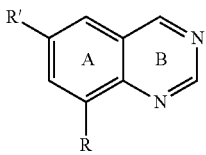
b11

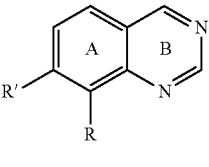
b12

As described herein, a bond drawn from a substituent to the center of one ring within a ring system (as shown in Figure c) represents substitution of R$^d$ at any substitutable position on the rings to which it is attached. For example, structure in Figure c represents possible substitution of R$^d$ in any of the positions on the W ring.

Figure c

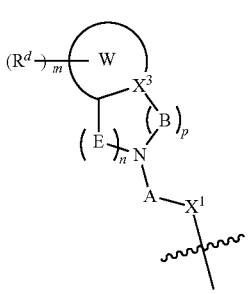

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, or geometric (or conformational) mixtures of the present compounds are within the scope disclosed herein.

The term "prodrug" as used herein, represents a compound that is transformed in vivo into a compound of Formula (I). Such a transformation can be affected, for example, by hydrolysis in blood or enzymatic transformation of the prodrug form to the parent form in blood or tissue. Prodrugs of the compounds disclosed herein may be, for example, esters. Esters that may be utilized as prodrugs in the present invention are phenyl esters, aliphatic ($C_1$-$C_{24}$) esters, acyloxymethyl esters, carbonates, carbamates, and amino acid esters. For example, a compound disclosed herein that contains an OH group may be acylated at this position in its prodrug form. Other prodrug forms include phosphates, such as, for example those phosphates resulting from the phosphonation of an OH group on the parent compound. A thorough discussion of prodrugs is provided in T. Higuchi and V. Stella, *Pro-drugs as Novel Delivery Systems*, Vol. 14 of the A.C.S. Symposium Series, Edward B. Roche, ed., *Bioreversible Carriers in Drug Design*, American Pharmaceutical Association and Pergamon Press, 1987, J. Rautio et al, Prodrugs: Design and Clinical Applications, *Nature Review Drug Discovery*, 2008, 7, 255-270, and S. J. Hecker et al, Prodrugs of Phosphates and Phosphonates, *Journal of Medicinal Chemistry*, 2008, 51, 2328-2345, each of which is incorporated herein by reference.

Unless otherwise stated, all tautomeric forms of the compounds disclosed herein are within the scope of the invention. Additionally, unless otherwise stated, structures depicted herein are also meant to include compounds that differ only in the presence of one or more isotopically enriched atoms.

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds disclosed herein, including compounds produced by a process comprising contacting a compound disclosed herein with a mammal for a period of time sufficient to yield a metabolic product thereof.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "*Stereochemistry of Organic Compounds*", John Wiley & Sons, Inc., New York, 1994. The compounds disclosed herein may contain asymmetric or chiral centers, and therefore exist in different stereoisomeric forms. It is intended that all stereoisomeric forms of the compounds disclosed herein, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. Some non-limiting examples of proton tautomers (also known as prototropic tautomers) include interconversions via migration of a proton, such as keto-enol and imine-enamine isomerizations. Valence tautomers include interconversions by reorganization of some of the bonding electrons.

A "pharmaceutically acceptable salt" \s used herein, refers to organic or inorganic salts of a compound disclosed herein. Pharmaceutically acceptable salts are well known in the art. For example, S. M. Berge et al., describe pharmaceutically acceptable salts in detail in *J. Pharmaceutical Sciences*, 66: 1-19, 1977, which is incorporated herein by reference. Examples of pharmaceutically acceptable, nontoxic acid addition salts include, but are not limited to, salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, malic acid, 2-hydracrylic acid, alginate, ascorbate, aspartate, benzenesulfonate, benzoate, bisulfate, borate, butyrate, camphorate, camphorsulfonate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, malonate, methanesulfonate, 2-naphthalenesulfonate, nicotinate, nitrate, oleate, palmitate, pamoate, pectinate, persulfate, 3-phenylpropionate, picrate, pivalate, propionate, stearate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. This invention also envisions the quaternization of any basic nitrogen-containing groups of the compounds disclosed herein. Water or oil soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate or aryl sulfonate.

A "solvate" refers to an association or complex of one or more solvent molecules and a compound disclosed herein. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

The term "protecting group" or "Pg" refers to a substituent that is commonly employed to block or protect a particular functionality while reacting with other functional groups on the compound. For example, an "amino-protecting group" is a substituent attached to an amino group that blocks or protects the amino functionality in the compound. Some non-limiting examples of suitable amino-protecting groups include acetyl, trifluoroacetyl, t-butoxycarbonyl (Boc), benzyloxycarbonyl (Cbz) and 9-fluorenylmethylenoxycarbonyl (Fmoc). Similarly, a "hydroxy-protecting group" refers to a substituent of a hydroxy group that blocks or protects the hydroxy functionality. Some non-limiting examples of suitable hydroxy-protecting groups include acetyl and silyl. A "carboxy-protecting group" refers to a substituent of the carboxy group that blocks or protects the carboxy functionality. Some non-limiting examples of common carboxy-protecting groups include —CH$_2$CH$_2$SO$_2$Ph, cyanoethyl, 2-(trimethylsilyl)ethyl, 2-(trimethylsilyl) ethoxymethyl, 2-(p-toluenesulfonyl)ethyl, 2-(p-nitrophenylsulfonyl)ethyl, 2-(diphenyl phosphino)-ethyl, nitroethyl, and the like. For a general description of protecting groups and their use, see T. W. Greene, *Protective Groups in Organic Synthesis*, John Wiley & Sons, New York, 1991; and P. J. Kocienski, *Protecting Groups*, Thieme, Stuttgart, 2005.

DESCRIPTION OF COMPOUNDS OF THE INVENTION

Disclosed herein are aminoquinazoline compounds, and pharmaceutical formulations thereof, that are potentially useful in the treatment of diseases, conditions and/or disorders modulated by protein kinases, especially EGFR. In one aspect, provided herein include compounds of Formula (I):

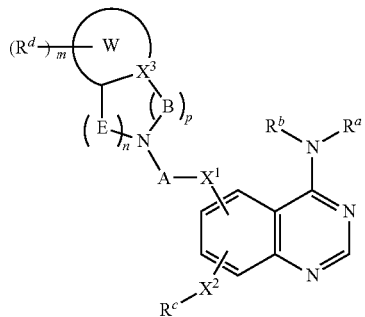

I or a racemic mixture, a diastereoisomer, an enantiomer, a geometric isomer, a tautomer, an N-oxide, a hydrate, a solvate, a metabolite, or a pharmaceutically acceptable salt thereof, wherein each of R$^a$, R$^b$, R$^c$, R$^d$, A, B, E, X$^1$, X$^2$, X$^3$, W, n, m and p is as defined herein.

In some embodiments, R$^a$ is aryl, heteroaryl or unsaturated heterocyclyl;

R$^b$ is alkyl or H;

R$^c$ is H, alkyl, haloalkyl, ether alkyl, heteroalkyl, cycloalkyl, heterocyclylalkyl, aryl, aralkyl, heteroaryl or heteroarylalkyl;

each of X$^1$ and X$^2$ is independently S, O, CH$_2$ or NH;

A is —(CH$_2$)$_q$—X$^4$—(CH$_2$)$_k$— or —(CH$_2$)$_q$—;

each of B and E is independently a bond or CH$_2$;

X$^3$ is N, C, CH or CR$^x$;

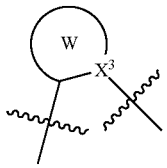

is carbocyclyl, heterocyclyl, aryl or heteroaryl;

X$^4$ is O, S or NH;

R$^d$ can be the same or different, and each R$^d$ is independently —CH=CHC(=O)NR$^1$R$^2$, R$^1$—S(=O)$_g$—, R$^1$—S(=O)$_g$O—, R$^1$—OS(=O)$_g$—, R$^1$—C(=O)—, R$^1$—C(=S)—, R$^1$O(CH$_2$)$_i$—O—(CH$_2$)$_j$—, —(CH$_2$)$_i$—NR$^1$R$^2$, oxo, ether alkyl, H, F, Cl, Br, I, hydroxy, mercapto, amino, nitro, carboxy, cyano, alkyl, alkylamino, hydroxy-substituted alkyl, haloalkyl, heteroalkyl, alkoxy, alkenyl, alkynyl, cycloalkyl, heterocyclyl, aryl, heteroaryl, aralkyl, heteroarylalkyl, aminosulfonyl, carbamoyl, arylamino, heteroarylamino, arylalkylamino, heteroarylalkylamino, heterocyclylamino, heterocyclylalkylamino, aryloxy, heteroaryloxy, arylalkoxy, heteroarylalkoxy, heterocyclyloxy or heterocyclylalkoxy;

R$^x$ is —CH=CHC(=O)NR$^1$R$^2$, R$^1$—S(=O)$_g$—, R$^1$—S(=O)$_g$O—, R$^1$—OS(=O)$_g$—, R$^1$—C(=O)—, R$^1$—C(=S)—, R$^1$O(CH$_2$)$_i$—O—(CH$_2$)$_j$—, —(CH$_2$)$_i$—NR$^1$R$^2$, ether alkyl, F, Cl, Br, I, hydroxy, mercapto, amino, nitro, carboxy, cyano, alkyl, alkylamino, hydroxy-substituted alkyl, haloalkyl, heteroalkyl, alkoxy, alkenyl, alkynyl, cycloalkyl, heterocyclyl, aryl, heteroaryl, aralkyl, heteroarylalkyl, aminosulfonyl, carbamoyl, arylamino, heteroarylamino, arylalkylamino, heteroarylalkylamino, heterocyclylamino, heterocyclylalkylamino, aryloxy, heteroaryloxy, arylalkoxy, heteroarylalkoxy, heterocyclyloxy or heterocyclylalkoxy;

each of n, m, i, j, k, p and q is independently 1, 2, 3, 4 or 5;

each g is independently 0, 1 or 2; and each of R$^1$ and R$^2$ is independently H, alkyl, cycloalkyl, aralkyl, heteroarylalkyl or haloalkyl;

wherein each of —CH=CHC(=O)NR$^1$R$^2$, R$^1$—S(=O)$_g$—, R$^1$—S(=O)$_g$O—, R$^1$—OS(=O)$_g$—, R$^1$—C(=O)—, R$^1$—C(=S)—, R$^1$O(CH$_2$)$_i$—O—(CH$_2$)$_j$—, —(CH$_2$)$_i$—NR$^1$R$^2$, ether alkyl, unsaturated heterocyclyl, amino, carboxy, alkyl, alkylamino, hydroxy-substituted alkyl, haloalkyl, heteroalkyl, alkoxy, alkenyl, alkynyl, cycloalkyl, heterocyclyl, aryl, heteroaryl, aralkyl, heteroarylalkyl, aminosulfonyl, carbamoyl, arylamino, heteroarylamino, arylalkylamino, heteroarylalkylamino, heterocyclylamino, heterocyclylalkylamino, aryloxy, heteroaryloxy, arylalkoxy, heteroarylalkoxy, heterocyclyloxy or heterocyclylalkoxy is substituted or unsubstituted, wherein the substitutent is hydroxy, hydroxyalkyl, amino, halo, cyano, oxo, aryl, heteroaryl, alkoxy, alkyl, haloalkyl, aminoalkyl, alkenyl, alkynyl, heterocyclyl, mercapto, nitro, aryloxy or aralkyl.

In certain embodiments,

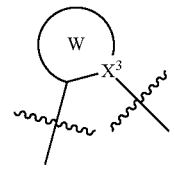

is C$_{3-10}$ carbocyclyl or C$_{2-10}$ heterocyclyl.

In certain embodiments,

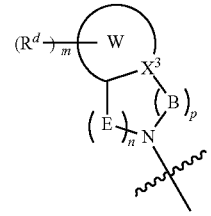

is:

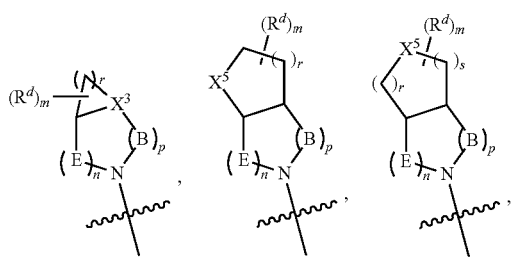

wherein each of $X^5$, $X^6$ and $X^7$ is independently O, NH, $NR^y$ or S;

each of $X^8$ and $X^9$ is independently N or CH;

each of n, m, p, r and s is independently 1, 2, 3, 4 or 5;

$R^{d'}$ is —CH═CHC(═O)$NR^1R^2$, $R^1$—S(═O)$_g$—, $R^1$—OS(═O)$_g$—, $R^1$—C(═O)—, $R^1$—C(═S)—, $R^1$O(CH$_2$)$_i$—O—(CH$_2$)$_j$—, —(CH$_2$)$_i$—$NR^1R^2$, ether alkyl, H, F, Cl, Br, I, hydroxy, mercapto, amino, nitro, carboxy, cyano, alkyl, alkylamino, hydroxy-substituted alkyl, haloalkyl, heteroalkyl, alkoxy, alkenyl, alkynyl, cycloalkyl, heterocyclyl, aryl, heteroaryl, aralkyl, heteroarylalkyl, aminosulfonyl, carbamoyl, arylamino, heteroarylamino, arylalkylamino, heteroarylalkylamino, heterocyclylamino, heterocyclylalkylamino, aryloxy, heteroaryloxy, arylalkoxy, heteroarylalkoxy, heterocyclyloxy or heterocyclylalkoxy;

$R^y$ is CH═CHC(═O)$NR^1R^2$, $R^1$—C(═O)—, $R^1$—C(═S)—, $R^1$O(CH$_2$)$_i$—O—(CH$_2$)$_j$—, —(CH$_2$)$_i$—$NR^1R^2$, ether alkyl, H, F, Cl, Br, I, hydroxy, mercapto, nitro, carboxy, cyano, alkyl, hydroxy-substituted alkyl, haloalkyl, heteroalkyl, alkoxy, alkenyl, alkynyl, cycloalkyl, heterocyclyl, aryl, heteroaryl, aralkyl, heteroarylalkyl, aryloxy, heteroaryloxy, arylalkoxy, heteroarylalkoxy, heterocyclyloxy or heterocyclylalkoxy;

$R^d$ can be the same or different, and each $R^d$ is independently —CH═CHC(═O)$NR^1R^2$, $R^1$—S(═O)$_g$—, $R^1$—S(═O)$_g$O—, $R^1$—OS(═O)$_g$—, $R^1$—C(═O)—, $R^1$—C(═S)—, $R^1$O(CH$_2$)$_i$—O—(CH$_2$)$_j$—, —(CH$_2$)$_i$—$NR^1R^2$, oxo, ether alkyl, H, F, Cl, Br, I, hydroxy, mercapto, amino, nitro, carboxy, cyano, alkyl, alkylamino, hydroxy-substituted alkyl, haloalkyl, heteroalkyl, alkoxy, alkenyl, alkynyl, cycloalkyl, heterocyclyl, aryl, heteroaryl, aralkyl or heteroarylalkyl; and each of $R^1$ and $R^2$ is independently H, alkyl, cycloalkyl, aralkyl, heteroarylalkyl or haloalkyl.

In other embodiments, $X^3$ is N, C or CH.

In other embodiments, $R^{d'}$ is —CH═CHC(═O)$NR^1R^2$, $R^1$O(CH$_2$)$_i$—O—(CH$_2$)$_j$—, —(CH$_2$)$_i$—$NR^1R^2$, $C_{2-10}$ ether alkyl, H, F, Cl, Br, I, hydroxy, mercapto, amino, nitro, carboxy, cyano, $C_{1-6}$ alkyl, $C_{1-6}$ alkylamino, hydroxy-substituted $C_{1-10}$ alkyl, $C_{1-6}$ haloalkyl, $C_{1-6}$ heteroalkyl, $C_{1-6}$ alkoxy, $C_{2-6}$ alkenyl, $C_{2-6}$ alkynyl, $C_{3-8}$ cycloalkyl, $C_{2-10}$ heterocyclyl, $C_{6-10}$ aryl, $C_{1-9}$ heteroaryl, $C_{6-10}$ aryl-$C_{1-6}$-alkyl or $C_{1-9}$ heteroaryl-$C_{1-6}$-alkyl;

each of i and j is independently 1, 2, 3, 4 or 5; and each of $R^1$ and $R^2$ is independently H, $C_{1-6}$ alkyl, $C_{3-8}$ cycloalkyl, $C_{6-10}$ aryl-$C_{1-6}$-alkyl, $C_{1-9}$ heteroaryl-$C_{1-6}$-alkyl or $C_{1-6}$ haloalkyl.

In other embodiments, $R^d$ can be the same or different, and each $R^d$ is independently —CH═CHC(═O)$NR^1R^2$, $R^1$—S(═O)$_g$—, $R^1$—OS(═O)$_g$—, $R^1$—C(═O)—, $R^1$—C(═S)—, $R^1$O(CH$_2$)$_i$—O—(CH$_2$)$_j$—, —(CH$_2$)$_i$—$NR^1R^2$, oxo, $C_{2-10}$ ether alkyl, H, F, Cl, Br, I, hydroxy, mercapto, amino, nitro, carboxy, cyano, $C_{1-6}$ alkyl, $C_{1-6}$ alkylamino, hydroxy-substituted $C_{1-10}$ alkyl, $C_{1-6}$ haloalkyl, $C_{1-6}$ heteroalkyl, $C_{1-6}$ alkoxy, $C_{2-6}$ alkenyl, $C_{2-6}$ alkynyl, $C_{3-8}$ cycloalkyl, $C_{2-10}$ heterocyclyl, $C_{6-10}$ aryl, $C_{1-9}$ heteroaryl, $C_{6-10}$ aryl-$C_{1-6}$-alkyl or $C_{1-9}$ heteroaryl-$C_{1-6}$-alkyl;

each of i and j is independently 1, 2, 3, 4 or 5;

each g is independently 0, 1 or 2; and each of $R^1$ and $R^2$ is independently H, $C_{1-6}$ alkyl, $C_{3-8}$ cycloalkyl, $C_{6-10}$ aryl-$C_{1-6}$-alkyl, $C_{1-9}$ heteroaryl-$C_{1-6}$-alkyl or $C_{1-6}$ haloalkyl.

In other embodiments, $R^d$ can be the same or different, and each $R^d$ is independently $R^1$—C(═O)—, oxo, methoxymethyl, ethoxymethyl, methoxyethoxymethyl, H, hydroxy, methyl, ethyl, propyl, butyl, isopropyl, pentyl, N,N-dimethylamino, N,N-diethylamino, trifluoromethyl or benzyl; and $R^1$ is H, methyl, ethyl, propyl, isopropyl, butyl or pentyl.

In other embodiments, $R^y$ is —CH═CHC(═O)$NR^1R^2$, $R^1$O(CH$_2$)$_i$—O—(CH$_2$)$_j$—, —(CH$_2$)$_i$—$NR^1R^2$, $C_{2-10}$ ether alkyl, H, F, Cl, Br, I, hydroxy, mercapto, nitro, carboxy, cyano, $C_{1-6}$ alkyl, hydroxy-substituted $C_{1-6}$ alkyl, $C_{1-6}$ haloalkyl, $C_{1-6}$ heteroalkyl, $C_{2-6}$ alkenyl, $C_{2-6}$ alkynyl, $C_{3-8}$ cycloalkyl, $C_{2-10}$ heterocyclyl, $C_{6-10}$ aryl, $C_{1-9}$ heteroaryl, $C_{6-10}$ aryl-$C_{1-6}$-alkyl or $C_{1-9}$ heteroaryl-$C_{1-6}$-alkyl;

each of i and j is independently 1, 2, 3, 4 or 5; and each of $R^1$ and $R^2$ is independently H, $C_{1-6}$ alkyl, $C_{3-8}$ cycloalkyl, $C_{6-10}$ aryl-$C_{1-6}$-alkyl, $C_{1-9}$ heteroaryl-$C_{1-6}$-alkyl or $C_{1-6}$ haloalkyl.

In certain embodiments, $R^d$ can be the same or different, and each $R^d$ is independently —CH═CHC(═O)$NR^1R^2$, $R^1$—S(═O)$_g$—, $R^1$—S(═O)$_g$O—, $R^1$—OS(═O)$_g$—, $R^1$—C(═O)—, $R^1$—C(═S)—, $R^1$O(CH$_2$)$_i$O—(CH$_2$)$_j$—, —(CH$_2$)$_1$—$NR^1R^2$, oxo, $C_{2-10}$ ether alkyl, H, F, Cl, Br, I, hydroxy, mercapto, amino, nitro, carboxy, cyano, $C_{1-6}$ alkyl, $C_{1-6}$ alkylamino, hydroxy-substituted $C_{1-10}$ alkyl, $C_{1-6}$ haloalkyl, $C_{1-6}$ heteroalkyl, $C_{1-6}$ alkoxy, $C_{2-6}$ alkenyl, $C_{2-6}$ alkynyl, $C_{3-8}$ cycloalkyl, $C_{2-10}$ heterocyclyl, $C_{6-10}$ aryl, $C_{1-9}$ heteroaryl, $C_{6-10}$ aryl-$C_{1-6}$-alkyl, $C_{1-9}$ heteroaryl-$C_{1-6}$-alkyl, $C_{6-10}$ arylamino, $C_{1-9}$ heteroarylamino, $C_{6-10}$ aryl-$C_{1-6}$-alkylamino, $C_{1-9}$ heteroaryl-$C_{1-6}$-alkylamino, $C_{2-10}$ heterocyclylamino, $C_{2-10}$ heterocyclyl $C_{1-6}$ alkylamino, $C_{6-10}$ aryloxy, $C_{1-9}$ heteroaryloxy, $C_{6-10}$ aryl-$C_{1-6}$-alkoxy, $C_{1-9}$ heteroaryl-$C_{1-6}$-alkoxy, $C_{2-10}$ heterocyclyloxy or $C_{2-10}$ heterocyclyl-$C_{1-6}$-alkoxy; and each of $R^1$ and $R^2$ is independently H, $C_{1-6}$ alkyl, $C_{3-8}$ cycloalkyl, $C_{6-10}$ aryl-$C_{1-6}$-alkyl, $C_{1-9}$ heteroaryl-$C_{1-6}$-alkyl or $C_{1-6}$ haloalkyl.

In certain embodiments, $R^x$ is —CH=CHC(=O)NR$^1$R$^2$, R$^1$O(CH$_2$)$_i$—O—(CH$_2$)$_j$—, —(CH$_2$)$_i$—NR$^1$R$^2$, C$_{2-10}$ ether alkyl, F, Cl, Br, I, hydroxy, mercapto, amino, nitro, carboxy, cyano, C$_{1-6}$ alkyl, C$_{1-6}$ alkylamino, hydroxy-substituted C$_{1-10}$ alkyl, C$_{1-6}$ haloalkyl, C$_{1-6}$ heteroalkyl, C$_{1-6}$ alkoxy, C$_{2-6}$ alkenyl, C$_{2-6}$ alkynyl, C$_{3-8}$ cycloalkyl, C$_{2-10}$ heterocyclyl, C$_{6-10}$ aryl, C$_{1-9}$ heteroaryl, C$_{6-10}$ arylamino, C$_{1-9}$ heteroarylamino, C$_{2-10}$ heterocyclylamino, C$_{6-10}$ aryloxy, C$_{1-9}$ heteroaryloxy or C$_{2-10}$ heterocyclyloxy; and each of R$^1$ and R$^2$ is independently H, C$_{1-6}$ alkyl, C$_{3-8}$ cycloalkyl, C$_{6-19}$ aryl-C$_{1-6}$-alkyl, C$_{1-9}$ heteroaryl-C$_{1-6}$-alkyl or C$_{1-6}$ haloalkyl.

In certain embodiments,

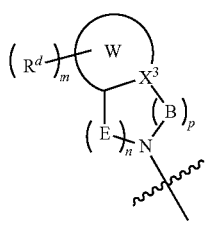

is:

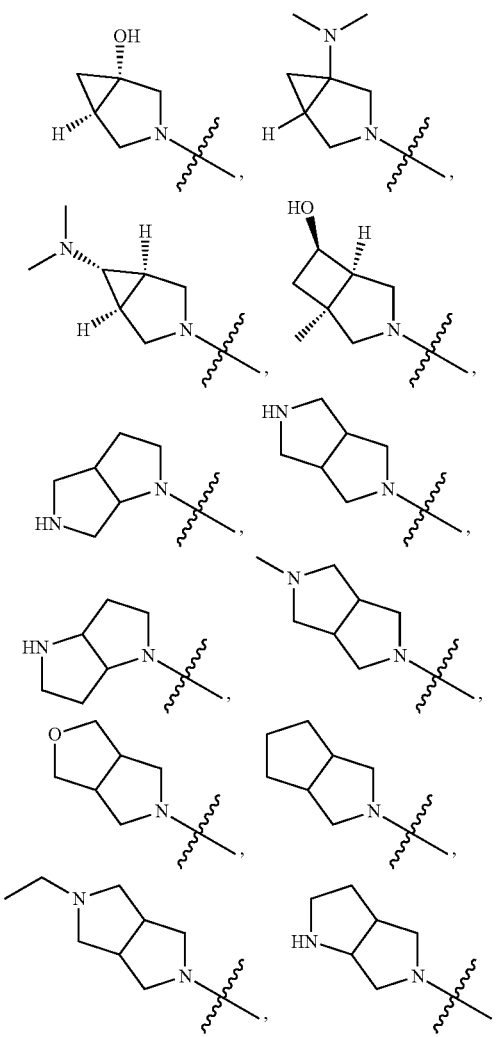
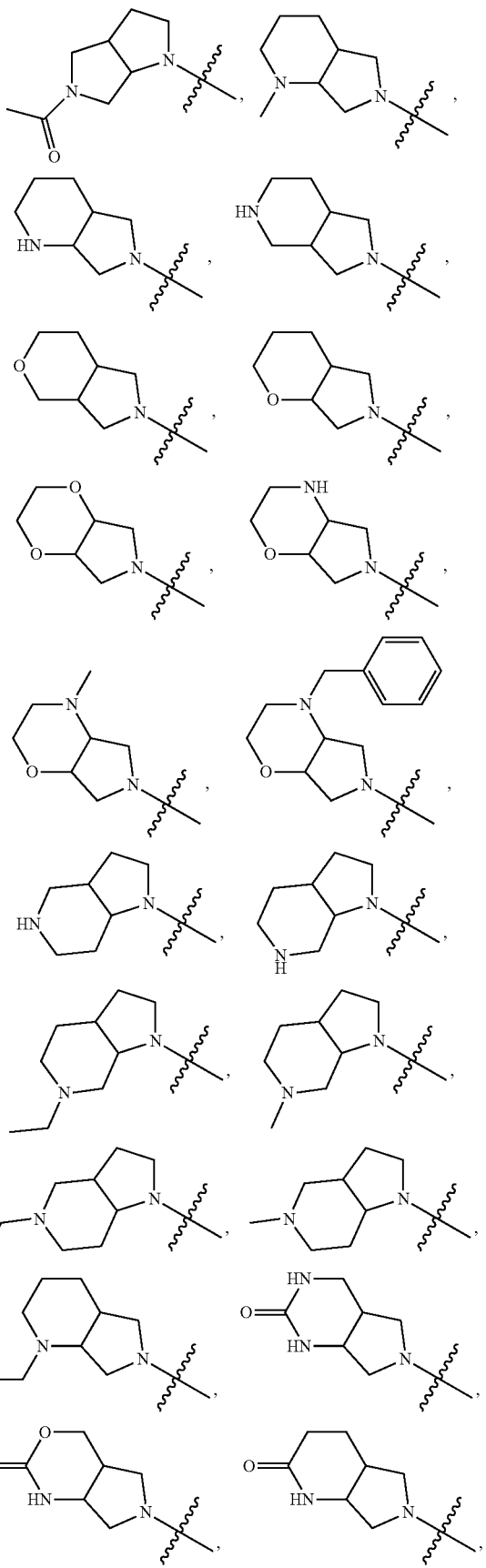

-continued
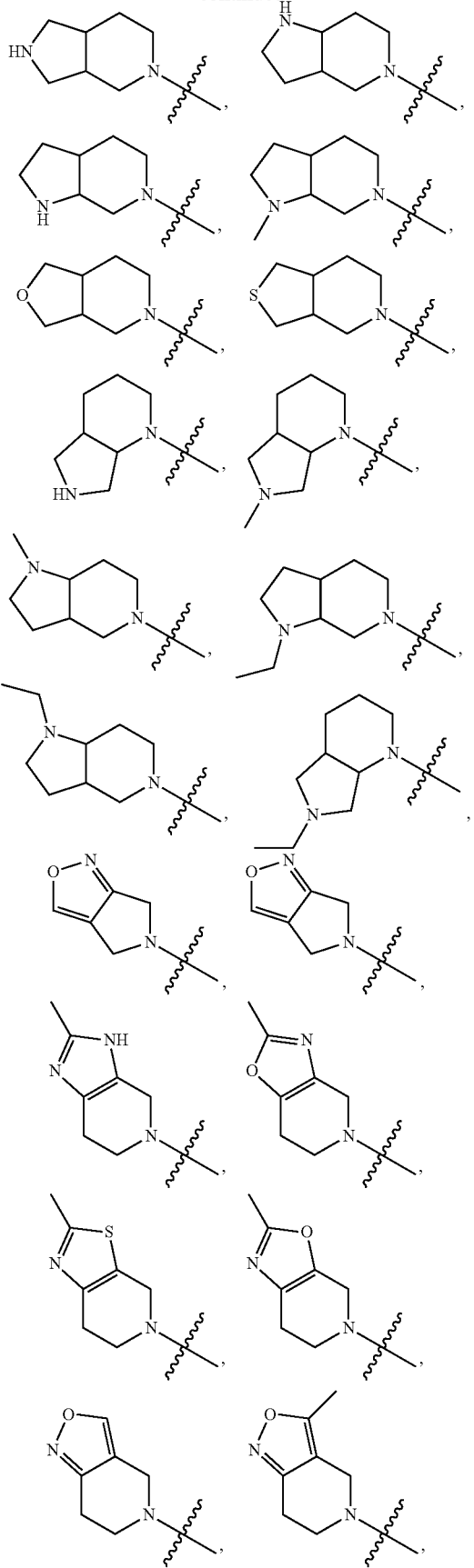
-continued
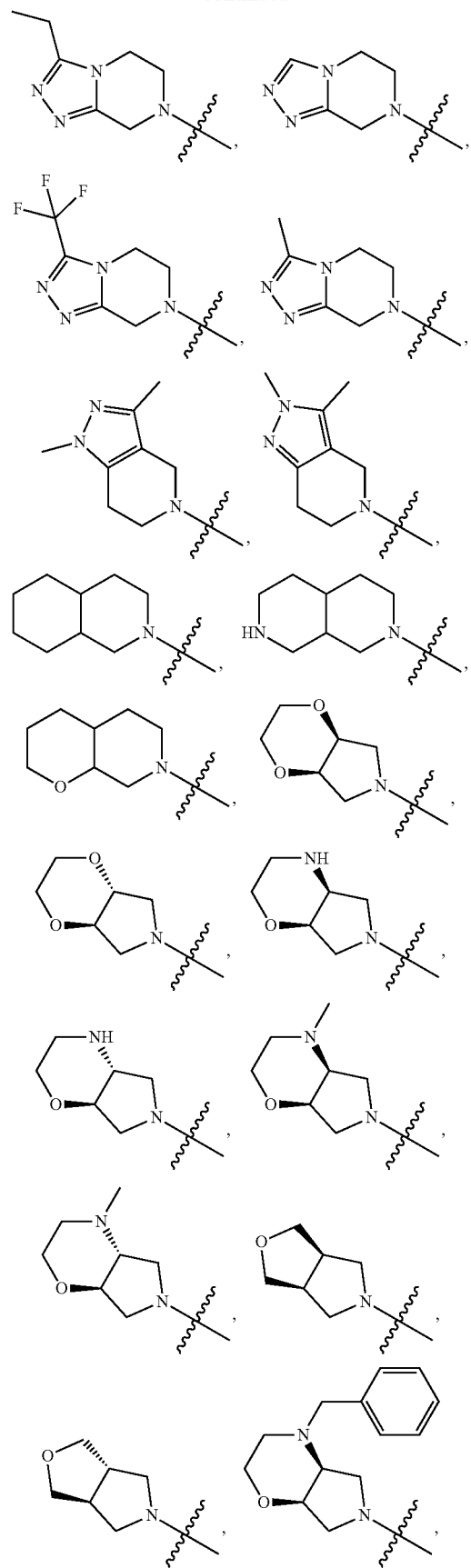

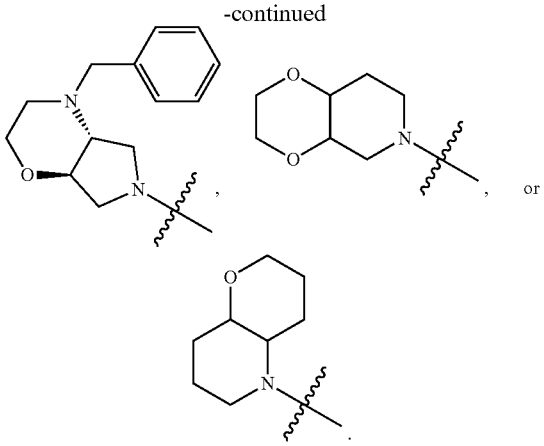

In certain embodiments, R" has Formula (II):

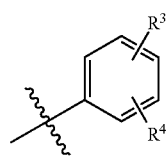

II wherein each of $R^3$ and $R^4$ is independently H, F, Cl, Br, I, alkenyl, alkynyl, alkyl, cycloalkyl, haloalkyl, heteroalkyl, alkoxy, alkylamino, heterocyclyl, hydroxy, amino, nitro, carboxy, cyano, aryl, heteroaryl, aralkyl, heteroarylalkyl, aminosulfonyl, carbamoyl, arylamino, heteroarylamino, arylalkylamino, heteroarylalkylamino, heterocyclylamino, heterocyclylalkylamino, heteroaryloxy, arylalkoxy, heteroarylalkoxy, heterocyclyloxy or heterocyclylalkoxy.

In other embodiments, each of $R^3$ and $R^4$ is independently H, F, Cl, Br, I, $C_{2-6}$ alkenyl, $C_{2-6}$ alkynyl, $C_{1-6}$ alkyl, $C_{1-6}$ haloalkyl, hydroxy, amino, nitro, carboxy, cyano, $C_{6-10}$ aryl or $C_{1-9}$ heteroaryl.

In other embodiments, $R^a$ is:

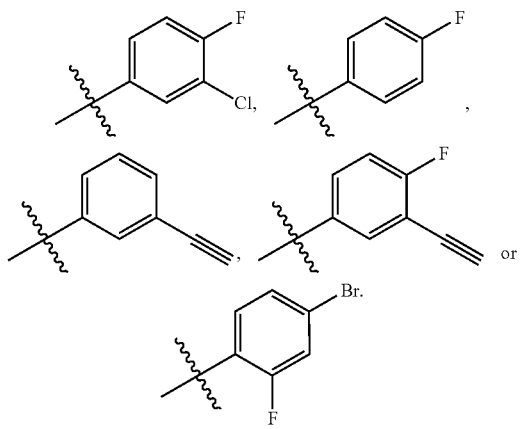

In certain embodiments, $R^b$ is H or $C_{1-6}$ alkyl.

In certain embodiments, $R^c$ is H, $C_{1-6}$ alkyl, $C_{1-6}$ haloalkyl, $C_{2-10}$ ether alkyl, $C_{1-6}$ heteroalkyl, $C_{3-8}$ cycloalkyl, $C_{2-10}$ heterocycloalkyl, $C_{6-10}$ aryl, $C_{6-10}$ aryl-$C_{1-6}$-alkyl, $C_{1-9}$ heteroaryl or $C_{1-9}$ heteroaryl-$C_{1-6}$-alkyl.

In certain embodiments, $R^c$ is methyl, ethyl, propyl, isopropyl, trifluoromethyl, methoxyethyl, cyclopropyl, cyclopentyl, phenyl or phenylmethyl.

In certain embodiments, provided herein are compounds having Formula (III) as shown below:

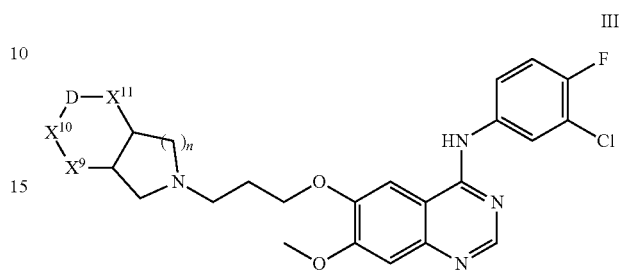

III wherein each of $X^9$, $X^{10}$ and $X^{11}$ is independently $CR^eR^f$, $NR^e$, O or S, with the proviso that at least one of $X^9$, $X^{10}$ and $X^{11}$ is $CR^eR^f$;

D is a bond, methylene or ethylene;

each of $R^e$ and $R^f$ is independently H, $C_{1-6}$ alkyl, $C_{1-6}$ alkylacyl, $C_{3-8}$ cycloalkyl, $C_{6-10}$ aryl-$C_{1-6}$-alkyl, $C_{1-9}$ heteroaryl-$C_{1-6}$-alkyl or $C_{1-6}$ haloalkyl; and n is 1 or 2.

In other embodiments, non-limiting examples of compounds disclosed herein, and their pharmaceutically acceptable salts and solvates thereof, include:

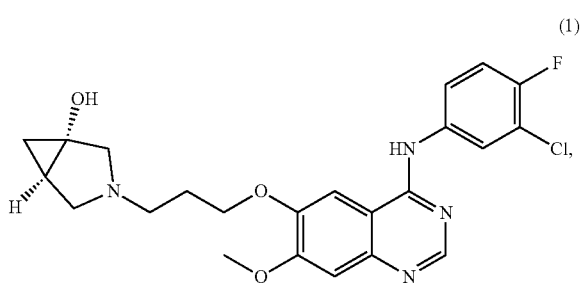

(1)

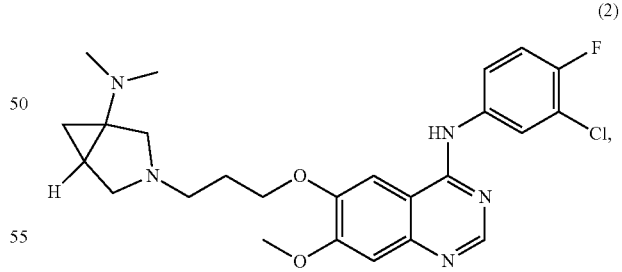

(2)

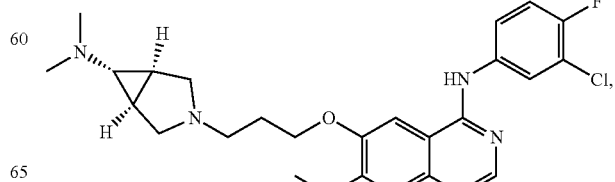

(3)

(4)
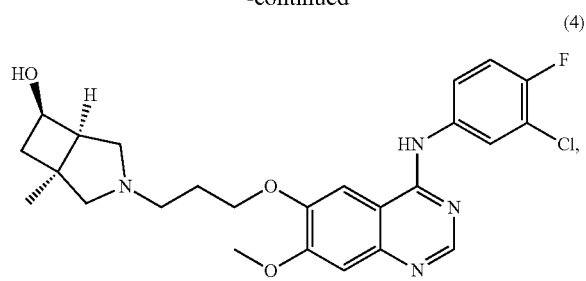
(10)
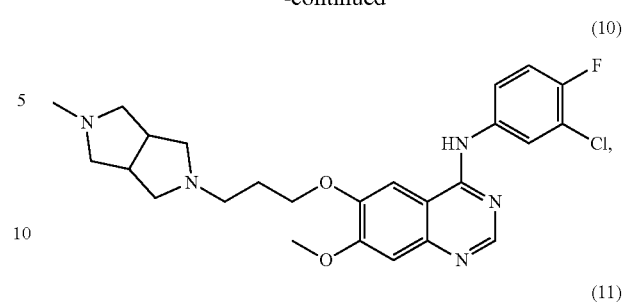
(5)
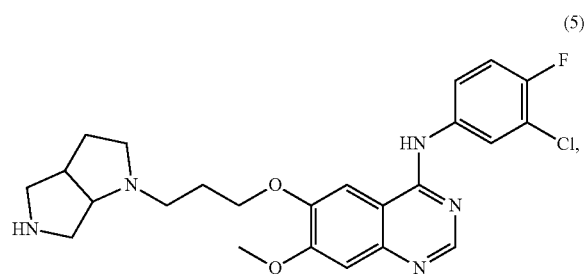
(11)
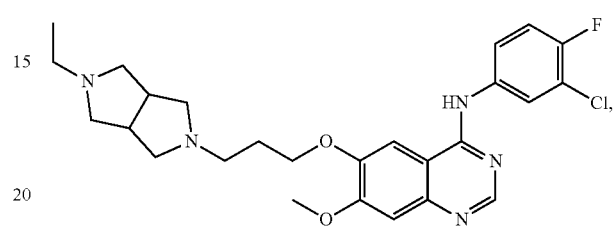
(6)
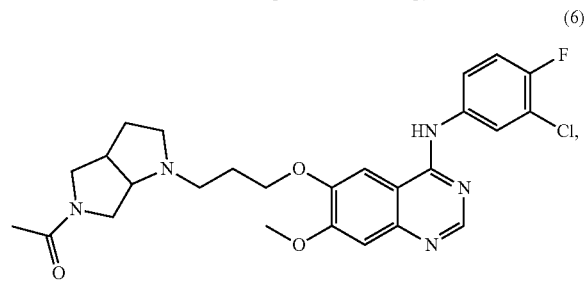
(12)
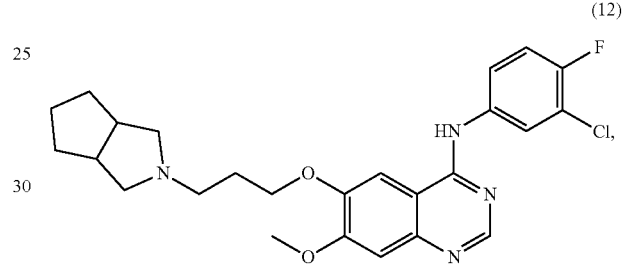
(7)
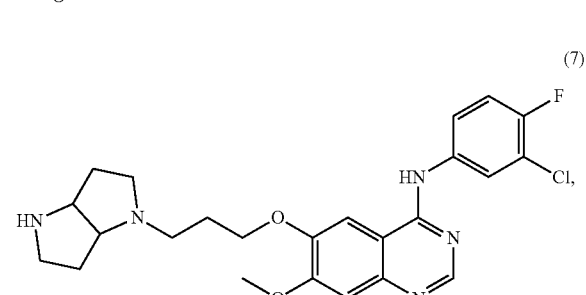
(13)
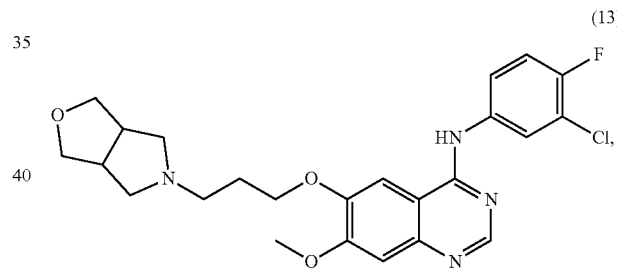
(8)
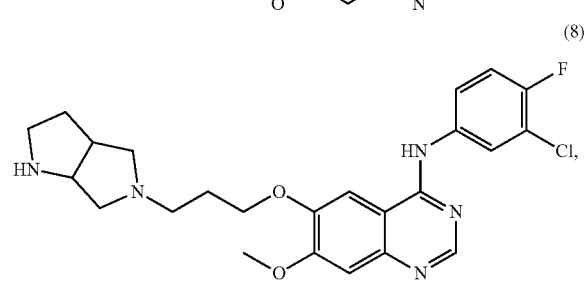
(14)
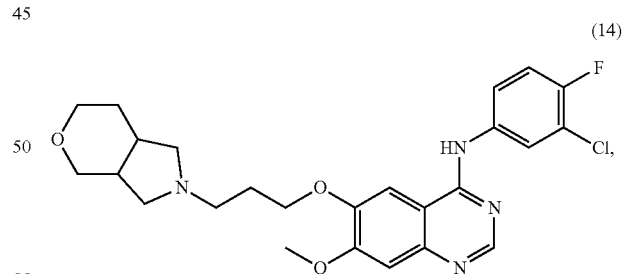
(9)
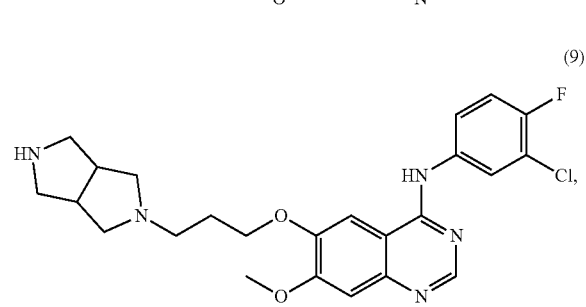
(15)
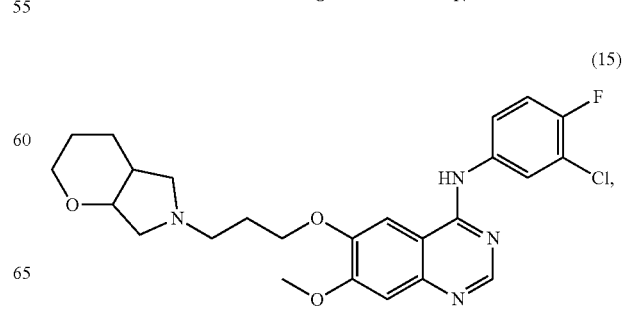

(16)
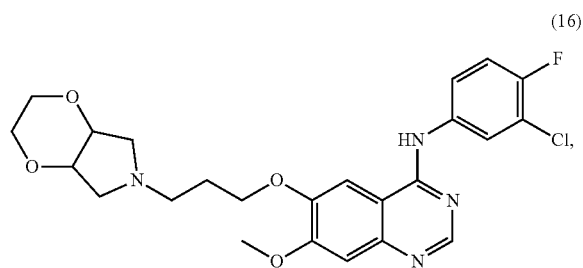
(22)
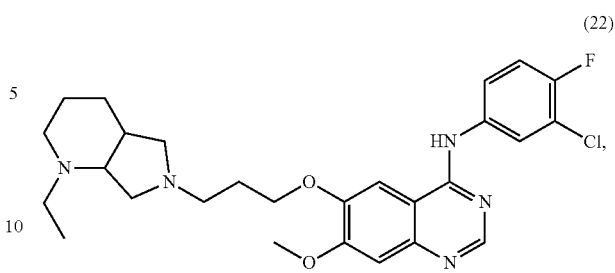
(17)
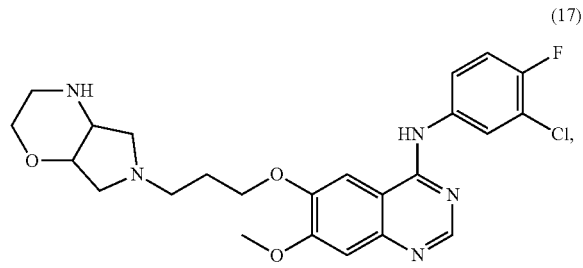
(23)
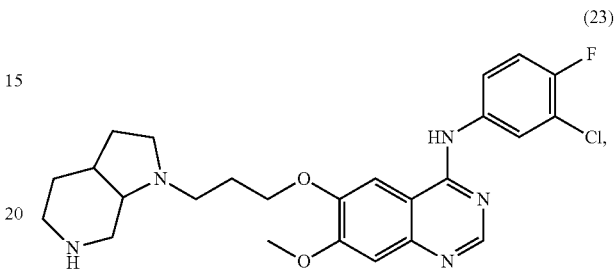
(18)
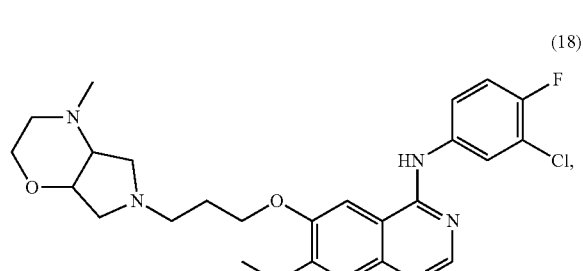
(24)
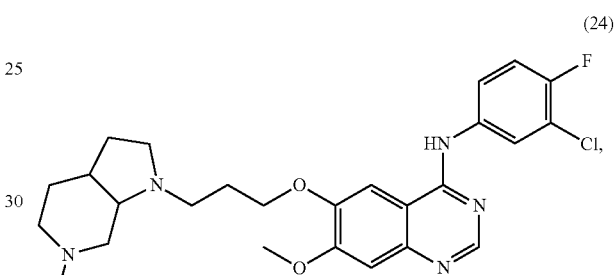
(19)
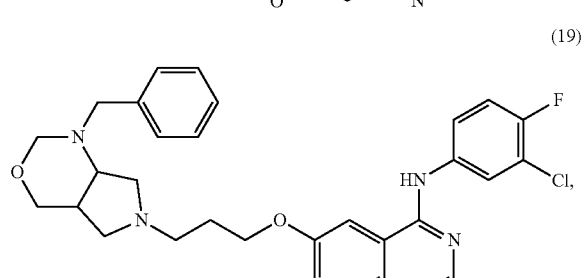
(25)
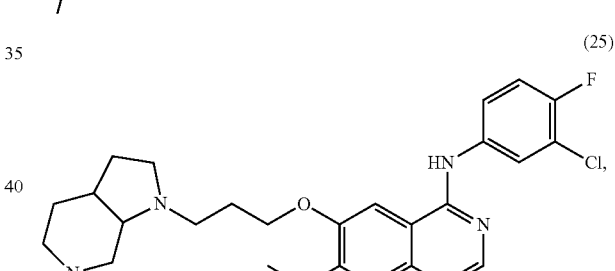
(20)
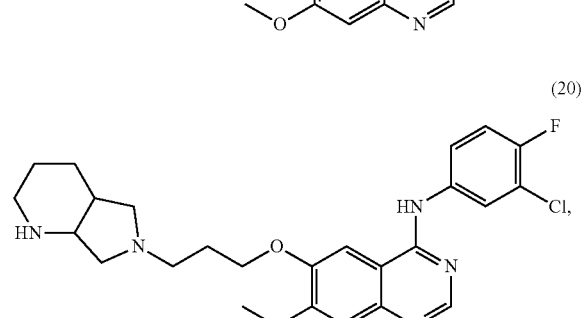
(26)
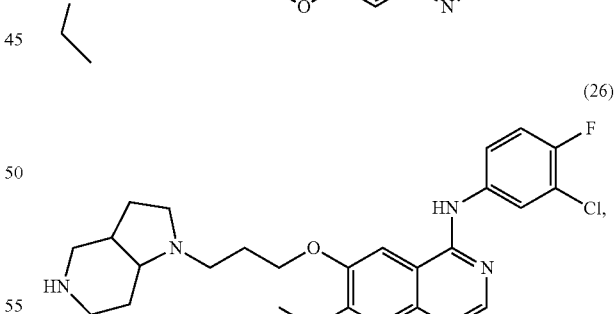
(21)
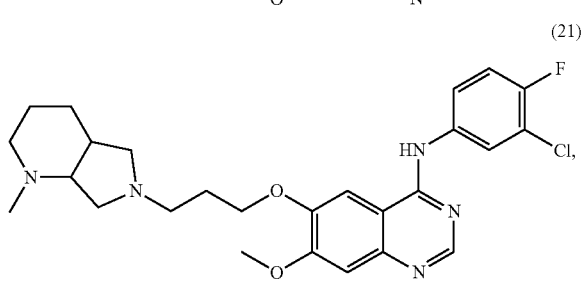
(27)
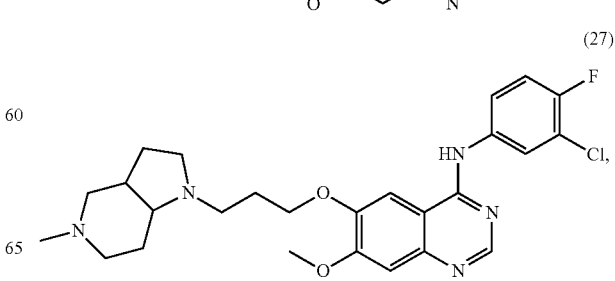

(28)
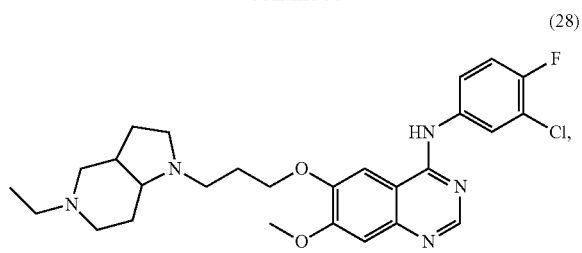
(34)
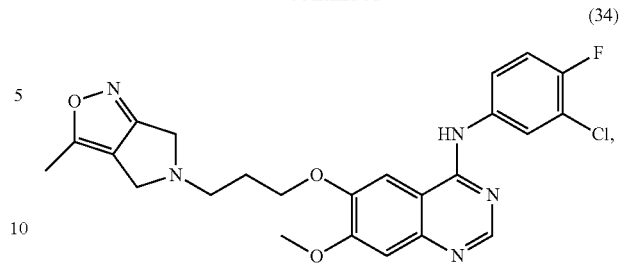
(29)
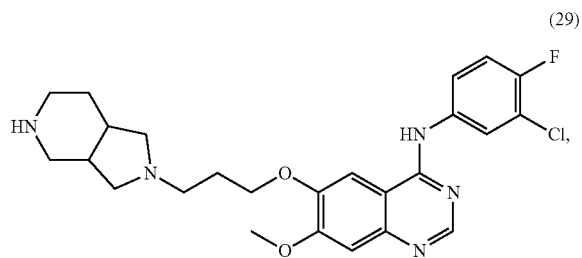
(35)
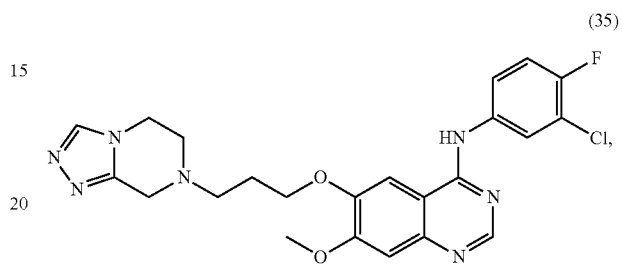
(30)
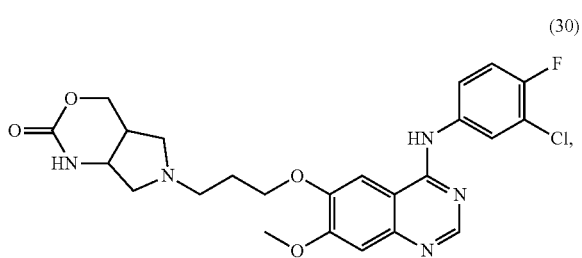
(36)
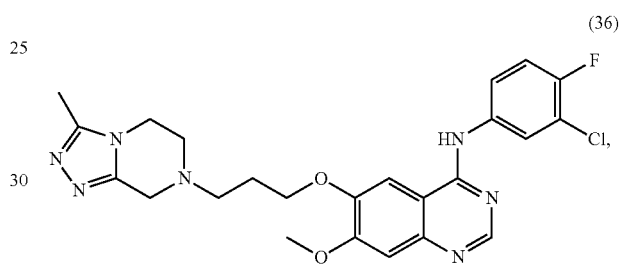
(31)
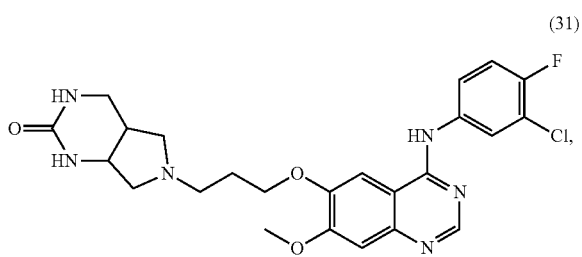
(37)
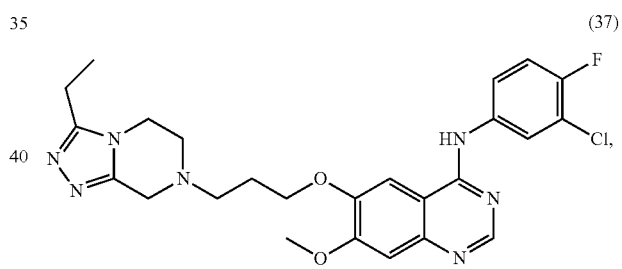
(32)
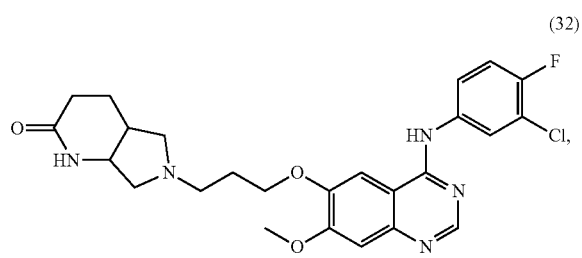
(38)
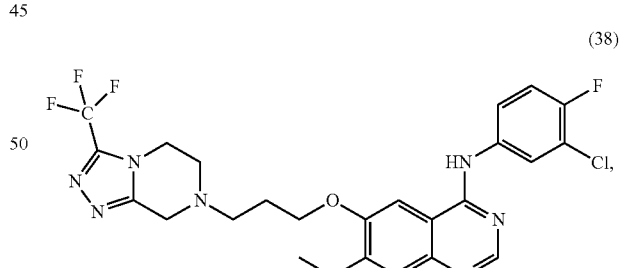
(33)
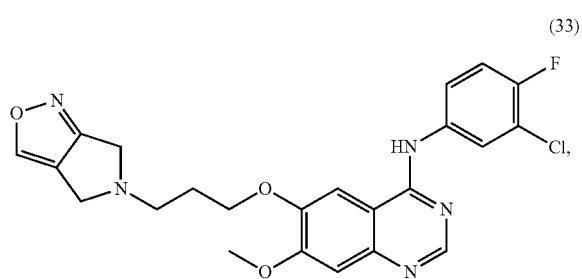
(39)
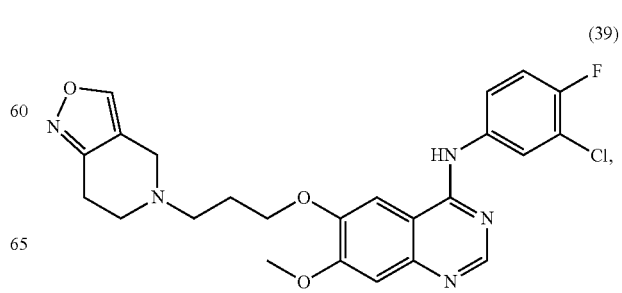

(40) 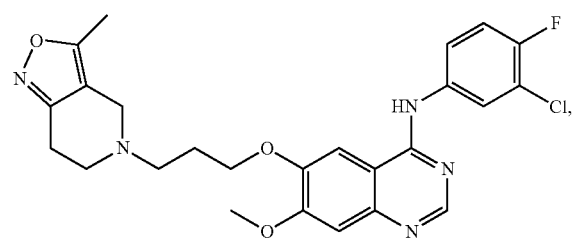
(41) 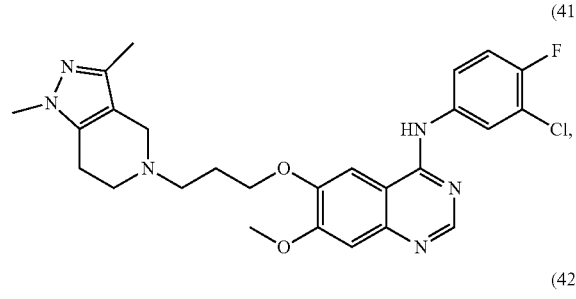
(42)
(43) 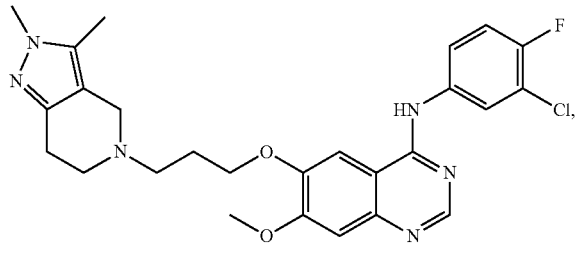
(44) 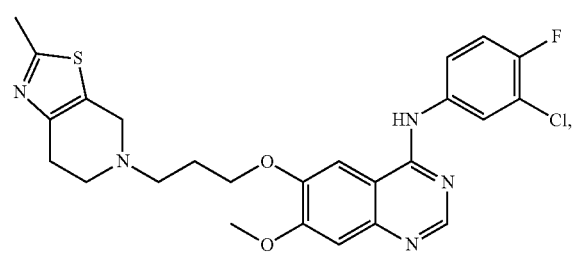
(45) 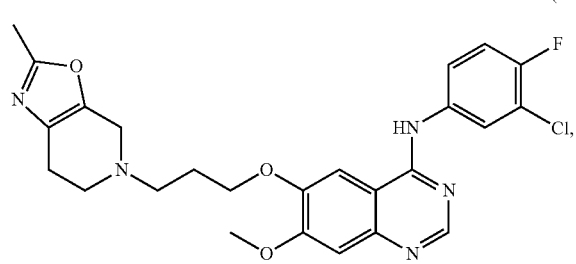
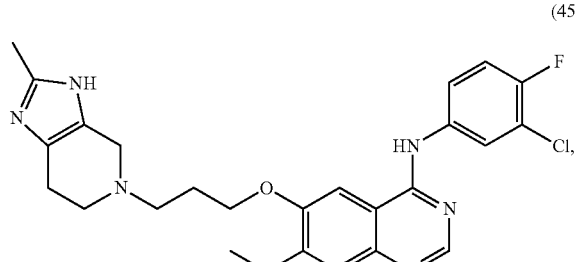
(46) 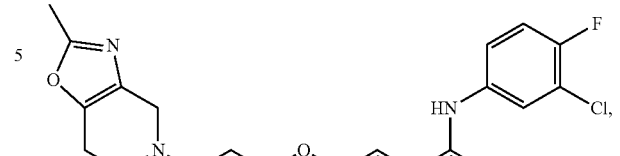
(47) 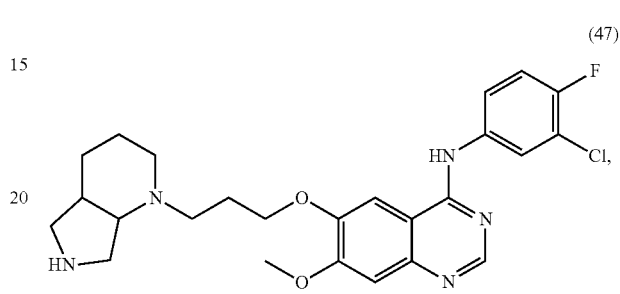
(48)
(49) 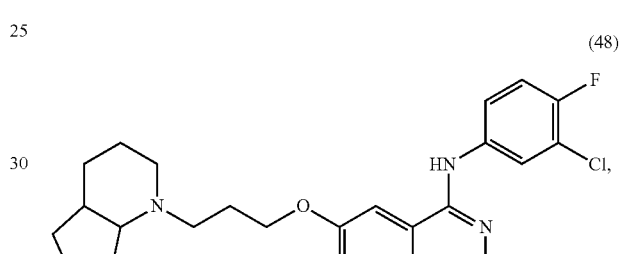
(50) 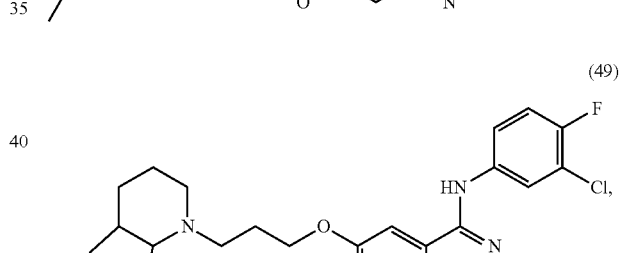
(51) 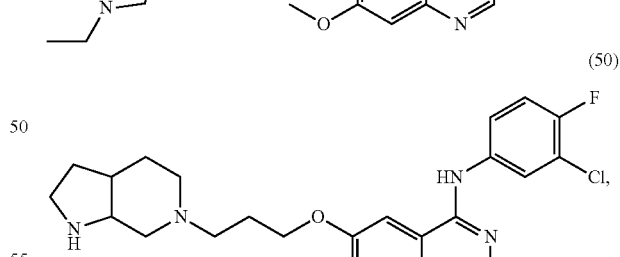
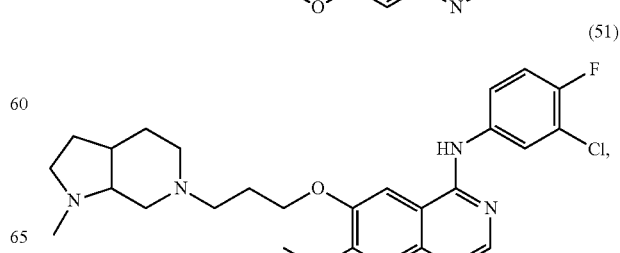

(52)
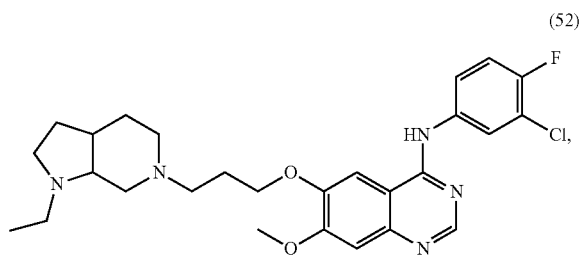
(58)
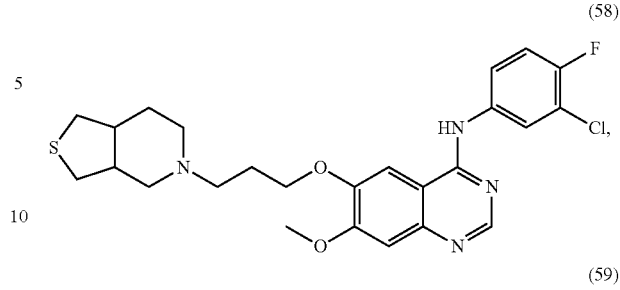
(53)
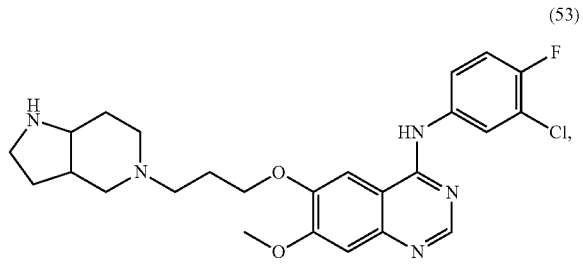
(59)
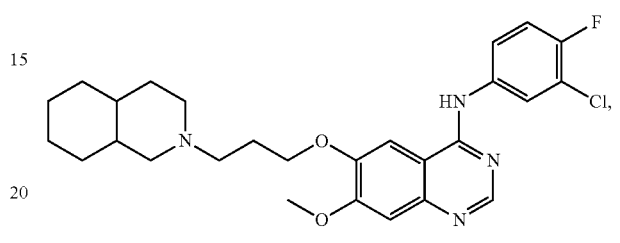
(54)
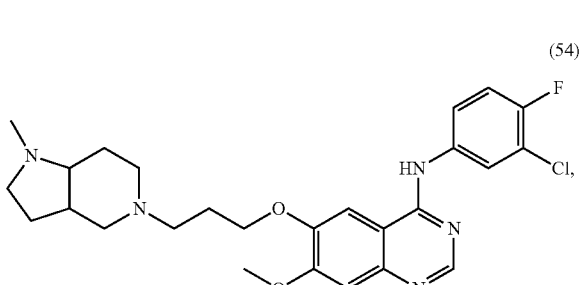
(60)
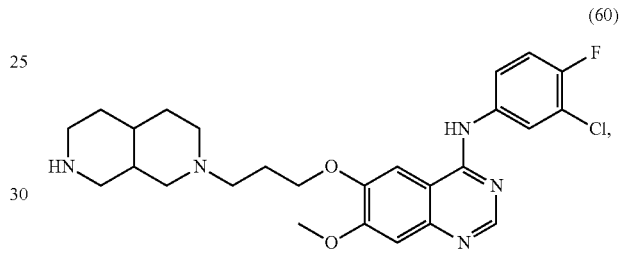
(55)
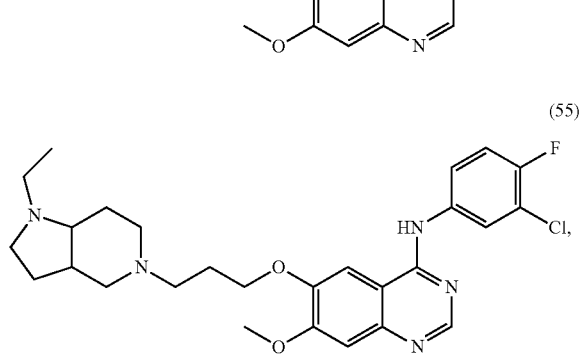
(61)
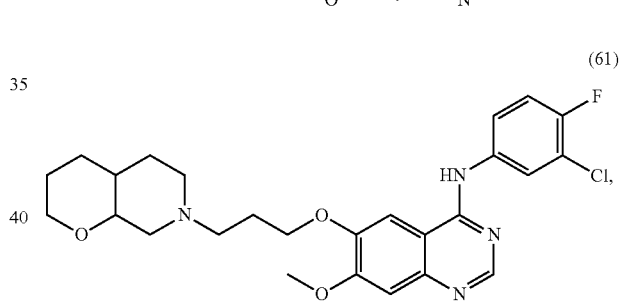
(56)
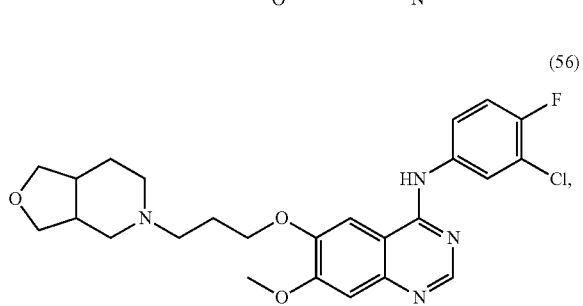
(62)
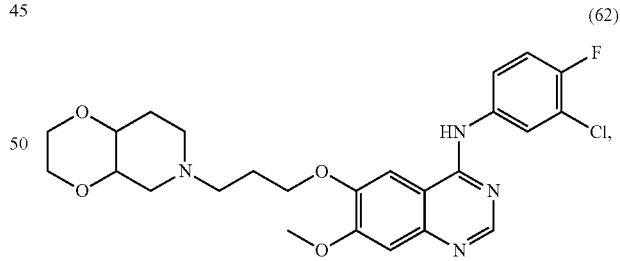
(57)
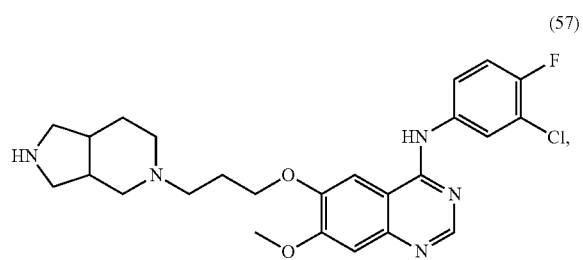
(63)
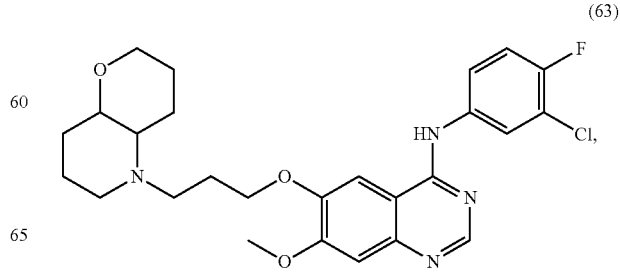

-continued
(64)
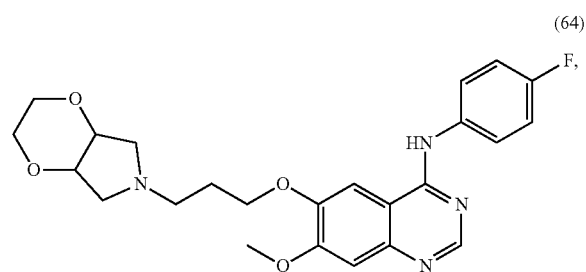
(65)
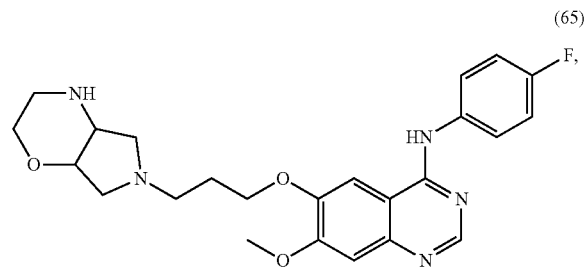
(66)
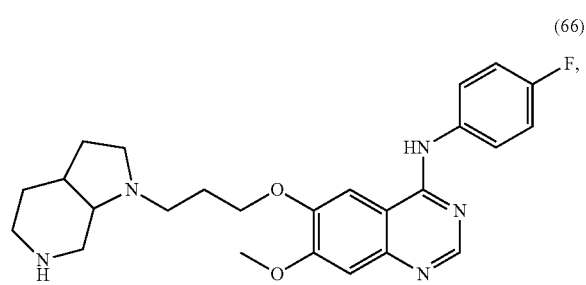
(67)
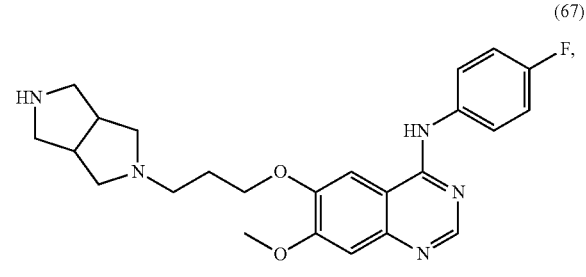
(68)
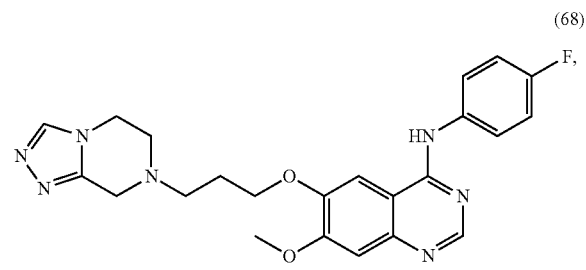
(69)
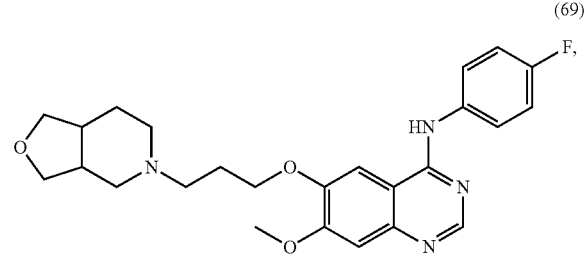
-continued
(70)
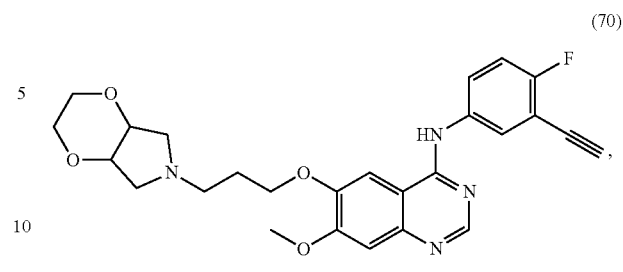
(71)
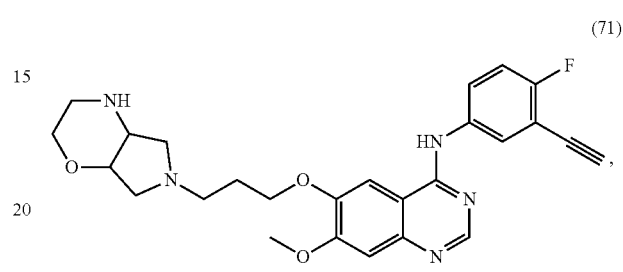
(72)
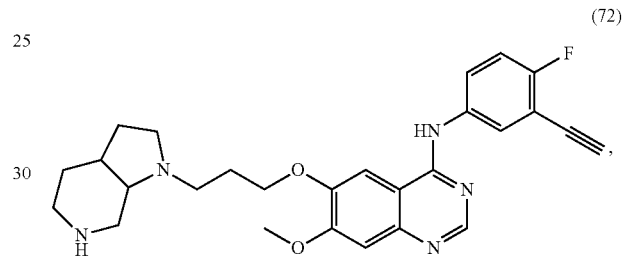
(73)
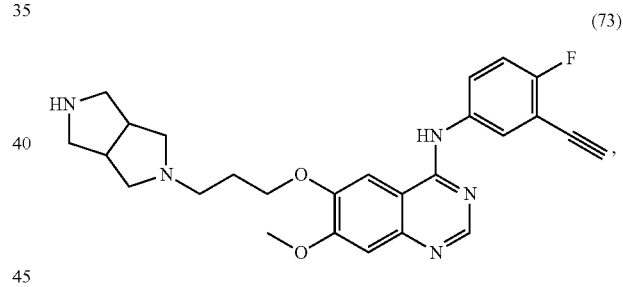
(74)
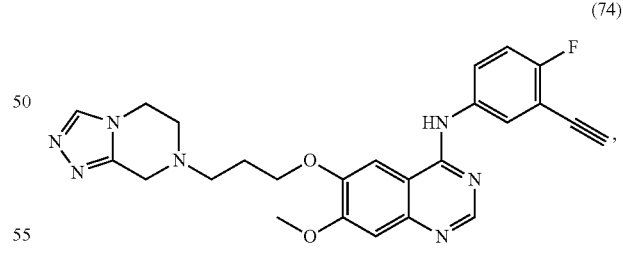
(75)
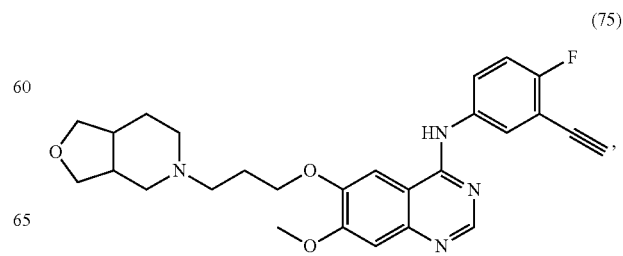

(76)
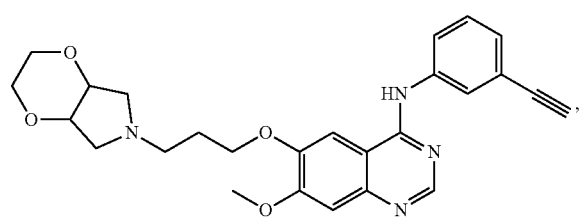
(77)
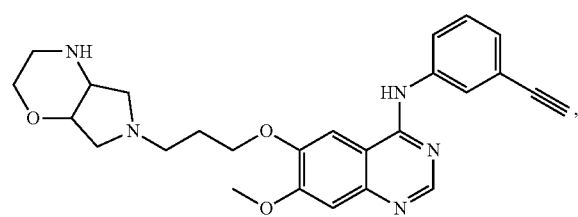
(78)
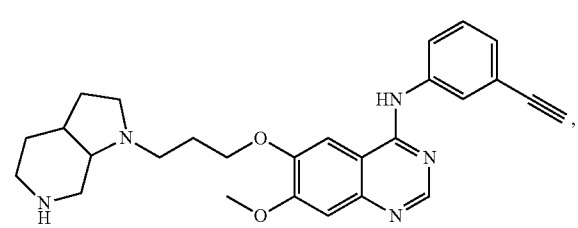
(79)
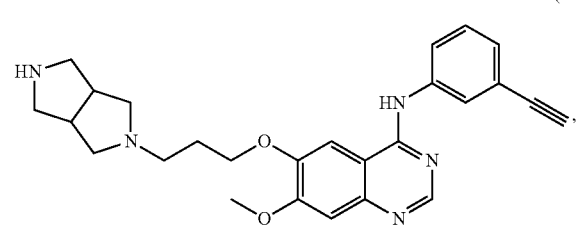
(80)
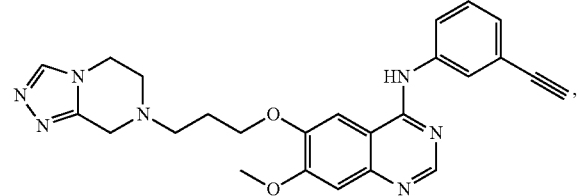
(81)
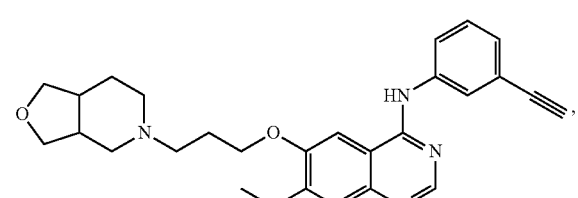
(82)
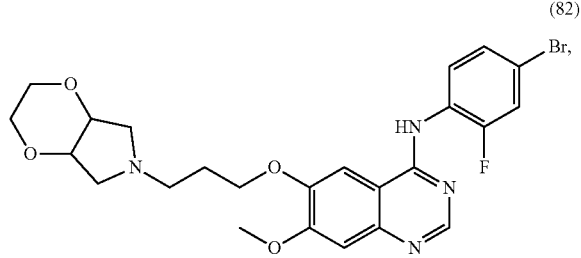
(83)
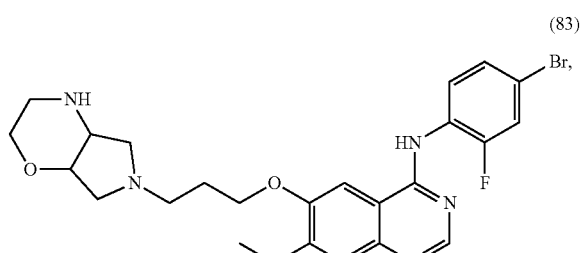
(84)
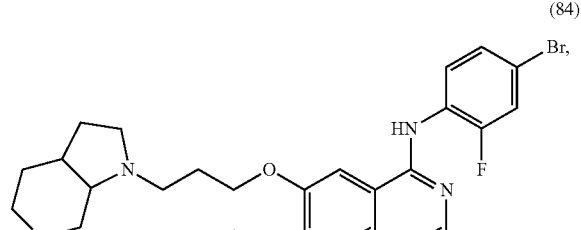
(85)
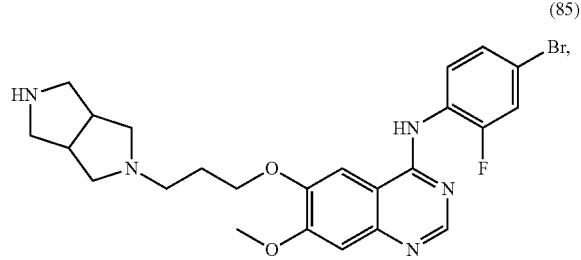
(86)
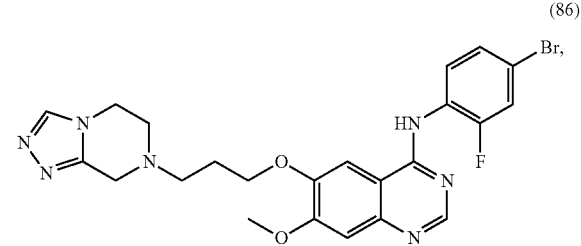
(87)
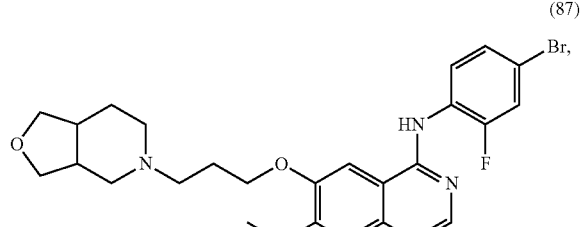

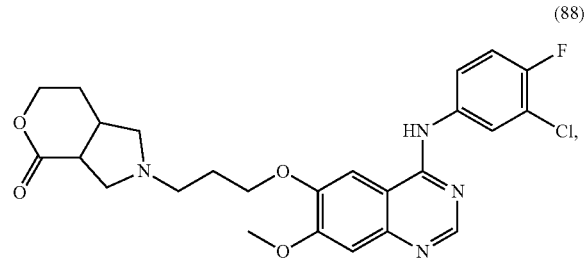

(88)

(89)

(90)

(91)

(92)

(93)

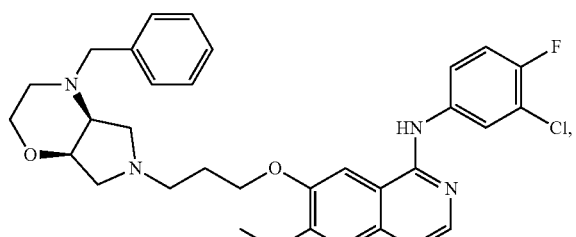

(94)

(95)

(96)

or a stereoisomer, a geometric isomer, a tautomer, an N-oxide, a hydrate, a solvate or a pharmaceutically acceptable salt thereof.

Provided herein includes the use of a compound disclosed herein, or a pharmaceutically acceptable salt thereof, in the manufacture of a medicament for the treatment either acutely or chronically of an angiogenesis mediated disease state, including those described herein. The compounds disclosed herein are useful in the manufacture of an anti-cancer medicament. The compounds disclosed herein are also useful in the manufacture of a medicament to attenuate, prevent, manage or treat disorders through inhibition of EGFR. Also provided herein is a pharmaceutical composition comprising a therapeutically effective amount of a compound of Formula (I) in association with at least one pharmaceutically acceptable carrier, adjuvant or diluent.

Also provided herein is a method of treating angiogenesis related disorders in a subject having or susceptible to such disorder, the method comprising treating the subject with a therapeutically effective amount of a compound of Formula (I).

Unless otherwise stated, all stereoisomers, geometric isomers, tautomers, N-oxides, hydrates, solvates, metabolites, salts, and pharmaceutically acceptable prodrugs of the compounds disclosed herein are within the scope of the invention.

In certain embodiments, the salt is a pharmaceutically acceptable salt. The phrase "pharmaceutically acceptable" refers to that the substance or composition must be compatible chemically and/or toxicologically, with the other ingredients comprising a formulation, and/or the mammal being treated therewith.

The compounds disclosed herein also include salts of the compounds which are not necessarily pharmaceutically acceptable salts, and which may be useful as intermediates for preparing and/or purifying compounds of Formula (I) and/or for separating enantiomers of compounds of Formula (I).

If the compound disclosed herein is a base, the desired salt may be prepared by any suitable method available in the art, for example, treatment of the free base with an inorganic acid, such as hydrochloric acid, hydrobromic acid, sulfuric acid, nitric acid, phosphoric acid, and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, and the like.

If the compound disclosed herein is an acid, the desired salt may be prepared by any suitable method, for example, treatment of the free acid with an inorganic or organic base, such as an amine (primary, secondary or tertiary), an alkali metal hydroxide or alkaline earth metal hydroxide, and the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum, lithium, and the like.

Composition, Formulations and Administration of Compounds of the Invention

According to another aspect, the invention features pharmaceutical compositions that include a compound of Formula (I), a compound listed herein, or a compound named in Examples 1-53, and a pharmaceutically acceptable carrier, adjuvant, or vehicle. The amount of the compound in the compositions disclosed herein is such that is effective to detectably inhibit a protein kinase in a biological sample or in a patient.

It will also be appreciated that certain of the compounds disclosed herein can exist in free form for treatment, or where appropriate, as a pharmaceutically acceptable derivative thereof. Some non-limiting examples of the pharmaceutically acceptable derivative include pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof.

As described above, the pharmaceutically acceptable compositions disclosed herein additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. In Remington: *The Science and Practice of Pharmacy,* 21st edition, 2005, ed. D. B. Troy, Lippincott Williams & Wilkins, Philadelphia, and *Encyclopedia of Pharmaceutical Technology*, eds. J. Swarbrick and J. C. Boylan, 1988-1999, Marcel Dekker, New York, the contents of each of which is incorporated by reference herein, are disclosed various carriers used in formulating pharmaceutically acceptable compositions and known techniques for the preparation thereof. Except insofar as any conventional carrier medium is incompatible with the compounds disclosed herein, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants.

The compositions disclosed herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intraocular, intrahepatic, intralesional and intracranial injection or infusion techniques. In some embodiments, the compositions are administered orally, intraperitoneally or intravenously. Sterile injectable forms of the compositions disclosed herein include aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that include water, Ringer's solution and isotonic sodium chloride solution. In addition, sterile, fixed oils are conventionally employed as a solvent or suspending medium.

For this purpose, any bland fixed oil includes synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions disclosed herein include orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions disclosed herein include administered in the form of suppositories for rectal administration. These can be prepared by mixing the agent with a suitable non-irrigating excipient that is solid at room temperature but liquid at rectal temperature and therefore will melt in the rectum to release the drug. Such materials include cocoa butter, beeswax and polyethylene glycols. The pharmaceutically acceptable compositions disclosed herein also include administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used. For topical applications, the pharmaceutically acceptable compositions may be formulated in a suitable ointment containing the active component suspended or dissolved in one or more carriers. Carriers for topical administration of the compounds disclosed herein include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, Span 60 (sorbitan monostearate), Tween 60 (polysorbate 60), cetyl esters wax, cetearyl alcohol, 2-octyldodecanol, benzyl alcohol and water.

For ophthalmic use, the pharmaceutically acceptable compositions may be formulated, e.g., as micronized suspensions in isotonic, pH adjusted sterile saline or other aqueous solution, or in other embodiments, as solutions in isotonic, pH adjusted sterile saline or other aqueous solution, either with or without a preservative such as benzalkonium chloride. Alternatively, for ophthalmic uses, the pharmaceutically acceptable compositions may be formulated in an ointment such as petrolatum. The pharmaceutically acceptable compositions disclosed herein may also be administered by nasal aerosol or inhalation. Such compositions are prepared according to techniques well known in the art of pharmaceutical formulation and may be prepared as solutions in saline, employing benzyl alcohol or other suitable preservatives, absorption promoters, fluorocarbons, and/or other conventional solubilizing or dispersing agents to enhance bioavailability.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, 2-tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injections or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. In order to prolong the effect of a compound disclosed herein, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, dissolving or suspending the compound in an oil vehicle accomplishes delayed absorption of a parenterally administered compound form.

Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Some non-limiting examples of other biodegradable polymers include poly (orthoesters) and poly (anhydrides). Depot injectable formulations are also prepared by entrapping the compound in liposomes or microemulsions that are compatible with body tissues.

Compositions for rectal or vaginal administration are preferably suppositories which can be prepared by mixing the compounds disclosed herein with suitable non-irrigating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or calcium phosphate and/or a) fillers or extenders such as starches, lactose, sucrose, glucose, mannitol, and silicic acid; b) binders such as, for example, carboxymethylcellulose, alginates, gelatin, polyvinyl pyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as, for example, cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms, the active compound may be admixed with at least one inert diluent such as sucrose, lactose or starch. Such dosage forms may also comprise, as is normal practice, additional substances other than inert diluents, e.g., tableting lubricants and other tableting aids such as magnesium stearate and microcrystalline cellulose. In the case of capsules, tablets and pills, the dosage forms may also comprise buffering agents. They may optionally contain pacifying agents and can also be of a composition that they release the active ingredient(s) only, or in other embodiments, in a certain part of the intestinal tract, optionally, in a delayed manner. Some non-limiting examples of embedding compositions that can be used include polymeric substances and waxes.

Dosage forms for topical or transdermal administration of a compound disclosed herein include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eyedrops are also contemplated as being within the scope of this invention. Additionally, contemplated herein is the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compounds disclosed herein are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions disclosed herein will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

The amount of the compounds disclosed herein that may be combined with the carrier materials to produce a composition in a single dosage form will vary depending upon the host treated, the particular mode of administration. In other embodiments, the compositions should be formulated so that a dosage of between 0.01-200 mg/kg body weight/day of the inhibitor can be administered to a patient receiving these compositions.

Compounds disclosed herein can be administered as the sole pharmaceutical agent or in combination with one or more other additional therapeutic (pharmaceutical) agents where the combination causes no unacceptable adverse effects. This may be of particular relevance for the treatment of hyperproliferative diseases such as cancer. In this instance, the compounds disclosed herein can be combined with known cytotoxic agents, signal transduction inhibitors, or with other anti-cancer agents, as well as with admixtures and combinations thereof. As used herein, additional therapeutic agents that are normally administered to treat a particular disease, or condition, are known as "appropriate for the disease, or condition, being treated". As used herein, "additional therapeutic agents" refers to include chemotherapeutic agents and other anti-proliferative agents. For example, chemotherapeutic agents or other antiproliferative agents may be combined with the compounds disclosed herein to treat proliferative disease or cancer.

Examples of chemotherapeutic agents or other antiproliferative agents include HDAC inhibitors including, but are not limited to, SAHA, MS-275, MGO 103, and those described in WO 2006/010264, WO 03/024448, WO 2004/069823, US 2006/0058298, US 2005/0288282, WO 00/71703, WO 01/38322, WO 01/70675, WO 03/006652, WO 2004/035525, WO 2005/030705, WO 2005/092899, and demethylating agents including, but not limited to, 5-aza-dC, Vidaza and Decitabine and those described in U.S. Pat. No. 6,268,137, U.S. Pat. No. 5,578,716, U.S. Pat. No. 5,919,772, U.S. Pat. No. 6,054,439, U.S. Pat. No. 6,184,211, U.S. Pat. No. 6,020,318, U.S. Pat. No. 6,066,625, U.S. Pat. No. 6,506,735, U.S. Pat. No. 6,221,849, U.S. Pat. No. 6,953,783, U.S. Ser. No. 11/393,380.

In another embodiment disclosed herein, for example, chemotherapeutic agents or other anti-proliferative agents may be combined with the compounds disclosed herein to treat proliferative diseases and cancer. Examples of known chemotherapeutic agents include, but are not limited to, for example, other therapies or anticancer agents that may be used in combination with the inventive anticancer agents disclosed herein and include surgery, radiotherapy (in but a few examples, gamma-radiation, neutron beam radiotherapy, electron beam radiotherapy, proton therapy, brachytherapy, and systemic radioactive isotopes, to name a few), endocrine therapy, taxanes (taxol, taxotere etc), platinum derivatives, biologic response modifiers (interferons, interleukins, and tumor necrosis factor (TNF), TRAIL receptor targeting, agents, to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate, Pemetrexed etc), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), Cell cycle inhibitors (KSP mitotic kinesin inhibitors, CENP-E and CDK inhibitors), enzymes (Asparaginase), and hormones (Tamoxifen, Leuprolide, Flutamide, and Megestrol), Gleevec, adriamycin, dexamethasone, and cyclophosphamide. Antiangiogenic agents (Avastin and others). Kinase inhibitors (Imatinib, Sutent, Nexavar, Erbitux, Herceptin, Tarceva, Iressa and others). Agents inhibiting or activating cancer pathways such as the mTOR, HIF (hypoxia induced factor) pathways and others. For a more comprehensive discussion of updated cancer therapies see, http://www.nci.nih.gov/, a list of the FDA approved oncology drugs at http://www.fda.gov/cder/cancer/druglist-rame.htm, and The Merck Manual, Eighteenth Ed. 2006, the entire contents of which are hereby incorporated by reference.

In another embodiment, the compounds disclosed herein can be combined with cytotoxic anti-cancer agents. Examples of such agents can be found in the 13th Edition of the Merck Index (2001). These agents include, by no way of limitation, asparaginase, bleomycin, carboplatin, carmustine, chlorambucil, cisplatin, colaspase, cyclophosphamide, cytarabine, dacarbazine, dactinomycin, daunorubicin, doxorubicin (adriamycin), epirubicin, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, or vindesine.

Other cytotoxic drugs suitable for use with the compounds disclosed herein include, but are not limited to, those compounds acknowledged to be used in the treatment of neoplastic diseases, such as those for example in Goodman and Gilman's The Pharmacological Basis of Therapeutics (Ninth Edition, 1996, McGraw-Hill). These agents include, by no way of limitation, aminoglutethimide, L-asparaginase, azathioprine, 5-azacytidine, cladribine, busulfan, diethylstilbestrol, 2',2'-difluorodeoxycytidine, docetaxel, erythro hydroxy nonyl adenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentostatin, N-phosphonoacetyl-Laspartate (PALA), plicamycin, semustine, teniposide, testosterone propionate, thiotepa, trimethylmelamine, uridine or vinorelbine.

Other cytotoxic anti-cancer agents suitable for use in combination with the compounds disclosed herein also include newly discovered cytotoxic principles, some examples of cytotoxic principles include, but are not limited to, oxaliplatin, gemcitabine, capecitabine, macrolide and its natural or synthetic derivatives, temozolomide (Quinn et al., *J Clin. Oncology*, 2003, 21(4), 646-651), tositumomab (BEXXAR®), trabectedin (Vidal et al., *Proceedings of the American Society for Clinical Oncology*, 2004, 23, abstract, 3181), and the inhibitors of the kinesin spindle protein Eg5 (Wood et al., *Curr. Opin. Pharmacol.* 2001, 1, 370-377).

In another embodiment, the compounds disclosed herein can be combined with other signal transduction inhibitors. Of particular interest are signal transduction inhibitors which target the EGFR family, such as EGFR, HER-2, and HER-4 (Raymond et al., *Drugs*, 2000, 60 (Suppl. 1), 15-23; Harari et al., *Oncogene*, 2000, 19 (53), 6102-6114), and their respective ligands. Examples of such agents include, by no way of limitation, antibody therapies such as HERCEPTIN® (trastuzumab), erbitux, and pertuzumab. Examples of such therapies also include, by no way of limitation, small-molecule kinase inhibitors such as IRESSA® (Gefitinib), TARCEVA® (Erlotinib), TYKERB® (Lapatinib), Canertinib (CI1033), AEE788 (Traxler et al., Cancer Research, 2004, 64, 4931-4941).

In another embodiment, the compounds disclosed herein can be combined with other signal transduction inhibitors targeting receptor kinases of the split-kinase domain families (VEGFR, FGFR, PDGFR, flt-3, c-kit, c-fms, and the like), and their respective ligands. These agents include, by no way of limitation, antibodies such as AVASTIN® (bevacizumab). These agents also include, by no way of limitation, small-molecule inhibitors such as GLEEVEC® (Imanitib), SPRYCEL® (Dasatinib), TASIGNA® (Nilotinib), NEXAVAR® (Vandetanib), Vatalanib (PTK787/ZK222584) (Wood et al., *Cancer Res.* 2000, 60(8), 2178-2189), Telatinib/BAY-57-9352, BMS-690514, BMS-540215, Axitinib/AG-013736, Motesanib/AMG706, Sutent/Sunitinib/SU-11248, ZD-6474 (Hennequin et al., *92nd AACR Meeting*, New Orleans, Mar. 24-28, 2001, abstract 3152), KRN-951 (Taguchi et al., *95th AACR Meeting*, Orlando, Fla., 2004, abstract 2575), CP-547,632 (Beebe et al., *Cancer Res.* 2003, 63, 7301-7309), CP-673,451 (Roberts et al., *Proceedings of the American Association of Cancer Research*, 2004, 45, abstract 3989), CHIR-258 (Lee et al., *Proceedings of the American Association of Cancer Research,* 2004, 45, abstract 2130), MLN-518 (Shen et al., *Blood*, 2003, 102, 11, abstract 476).

In another embodiment, the compounds disclosed herein can be combined with inhibitors of histone deacetylase. Examples of such agents include, by no way of limitation, suberoylanilide hydroxamic acid (SAHA), LAQ-824 (Ottmann et al., *Proceedings of the American Society for Clinical Oncology,* 2004, 23, abstract, 3024), LBH-589 (Beck et al., *Proceedings of the American Society for Clinical Oncology,* 2004, 23, abstract, 3025), MS-275 (Ryan et al., *Proceedings of the American Association of Cancer Research,* 2004, 45, abstract, 2452), FR-901228 (Piekarz et al., *Proceedings of the American Society for Clinical Oncology,* 2004, 23, abstract, 3028) and MGCDOI 03 (U.S. Pat. No. 6,897,220).

In another embodiment, the compounds disclosed herein can be combined with other anti-cancer agents such as proteasome inhibitors, and m-TOR inhibitors. These include, by no way of limitation, bortezomib (Mackay et al., *Proceedings of the American Society for Clinical Oncology,* 2004, 23, Abstract, 3109), and CCI-779 (Wu et al., *Proceedings of the American Association of Cancer Research,* 2004, 45, abstract, 3849). The compounds disclosed herein can be combined with other anti-cancer agents such as topoisomerase inhibitors, including but not limited to camptothecin.

Those additional agents may be administered separately from the compound-containing composition, as part of a multiple dosage regimen. Alternatively, those agents may be part of a single dosage form, mixed together with the compound disclosed herein in a single composition. If administered as part of a multiple dosage regimen, the two active agents may be submitted simultaneously, sequentially or within a period of time from one another which would result in the desired activity of the agents.

The amount of both the compound and the additional therapeutic agent (in those compositions which comprise an additional therapeutic agent as described above) that may be combined with the carrier materials to produce a single dosage form will vary depending upon the host treated and the particular mode of administration. Normally, the amount of additional therapeutic agent present in the compositions disclosed herein will be no more than the amount that would normally be administered in a composition comprising that therapeutic agent as the only active agent. In other embodiments, the amount of additional therapeutic agent in the presently disclosed compositions will range from about 50% to 100% of the amount normally present in a composition comprising that agent as the only therapeutically active agent. In those compositions which comprise an additional therapeutic agent, that additional therapeutic agent and the compound disclosed herein may act synergistically.

Uses of the Compounds and Compositions of the Invention

The invention features pharmaceutical compositions that include a compound of Formula (I) or a compound listed herein, and a pharmaceutically acceptable carrier, adjuvant, or vehicle. The amount of compound in the compositions disclosed herein is such that is effective to detectably inhibit a protein kinase, such as EGFR inhibitory activity. The compounds disclosed herein are useful in therapy as antineoplasia agents or to minimize deleterious effects of EGFR.

Compounds disclosed herein would be useful for, but not limited to, the prevention or treatment of proliferative diseases, conditions, or disorders in a patient by administering to the patient a compound or a composition disclosed herein in an effective amount. Such diseases, conditions, or disorders include cancer, particularly metastatic cancer, non-small cell lung cancer and epidermoid carcinoma.

Compounds disclosed herein would be useful for the treatment of neoplasia including cancer and metastasis, including, but not limited to: carcinoma such as cancer of the epidermis, bladder, breast, colon, kidney, liver, lung (including small cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocitic leukemia, acute lymphoblastic leukemia, B-cell lymphoma, T-cell lymphoma, Hodgkin's lymphoma, non-Hodgkin's lymphoma, hairy cell leukemia and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g. soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma).

The compounds also would be useful for treatment of ophthalmological conditions such as corneal graft rejection, ocular neovascularization, retinal neovascularization including neovascularization following injury or infection, diabetic retinopathy, retrolental fibroplasia and neovascular glaucoma; retinal ischemia; vitreous hemorrhage; ulcerative diseases such as gastric ulcer; pathological, but non-malignant, conditions such as hemangiomas, including infantile hemaginomas, angiofibroma of the nasopharynx and avascular necrosis of bone; and disorders of the female reproductive system such as endometriosis. The compounds are also useful for the treatment of edema, and conditions of vascular hyperpermeability.

The compounds disclosed herein are also useful in the treatment of diabetic conditions such as diabetic retinopathy and microangiopathy. The compounds disclosed herein are also useful in the reduction of blood flow in a tumor in a subject. The compounds disclosed herein are also useful in the reduction of metastasis of a tumor in a subject.

Besides being useful for human treatment, these compounds are also useful for veterinary treatment of companion animals, exotic animals and farm animals, including mammals, rodents, and the like. In other embodiments, animals include horses, dogs, and cats. As used herein, the compounds disclosed herein include the pharmaceutically acceptable derivatives thereof.

Where the plural form is used for compounds, salts, and the like, this is taken to refer to also a single compound, salt, and the like.

The treatment method that includes administering a compound or composition disclosed herein can further include administering to the patient an additional therapeutic agent (combination therapy) selected from: a chemotherapeutic or anti-proliferative agent, or an anti-inflammatory agent, wherein the additional therapeutic agent is appropriate for the disease being treated and the additional therapeutic agent is administered together with a compound or composition disclosed herein as a single dosage form or separately from the compound or composition as part of a multiple dosage form. The additional therapeutic agent may be administered at the same time as a compound disclosed herein or at a different time.

The invention also features a method of inhibiting the growth of a cell that expresses EGFR, which includes contacting the cell with a compound or composition disclosed herein, thereby causing inhibition of growth of the cell. Examples of a cell whose growth can be inhibited include: a epidermoid carcinoma cell, a breast cancer cell, a colorectal cancer cell, a lung cancer cell, a papillary carcinoma cell, a prostate cancer cell, a lymphoma cell, a colon cancer cell, a pancreatic cancer cell, an ovarian cancer cell, a cervical cancer cell, a central nervous system cancer cell, an osteogenic sarcoma cell, a renal carcinoma cell, a hepatocellular carcinoma cell, a bladder cancer cell, a gastric carcinoma cell, a head and neck squamous carcinoma cell, a melanoma cell, or a leukemia cell.

Provided herein is a method of inhibiting EGFR kinase activity in a biological sample that includes contacting the biological sample with a compound or composition disclosed herein. The term "biological sample" as used herein, means a sample outside a living organism and includes, without limitation, cell cultures or extracts thereof; biopsied materials obtained from a mammal or extracts thereof; and blood, saliva, urine, feces, semen, tears, or other body fluids or extracts thereof. Inhibition of kinase activity, particularly EGFR kinase activity, in a biological sample is useful for a variety of purposes known to one of skill in the art. Examples of such purposes include, but are not limited to, blood transfusion, organ-transplantation, biological specimen storage, and biological assays.

In certain embodiments disclosed herein, an "effective amount" or "effective dose" of the compound or pharmaceutically acceptable composition is that amount effective for treating or lessening the severity of one or more of the aforementioned disorders. The compounds and compositions, according to the method disclosed herein, may be administered using any amount and any route of administration effective for treating or lessening the severity of the disorder or disease. The exact amount required will vary from subject to subject, depending on the species, age, and general condition of the subject, the severity of the infection, the particular agent, its mode of administration, and the like. A compound or composition can also be administered with one or more other therapeutic agents, as discussed above.

The compounds disclosed herein or pharmaceutical compositions thereof may also be used for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a compound disclosed herein.

Suitable coatings and the general preparation of coated implantable devices are described in U.S. Pat. Nos. 6,099,562, 5,886,026, and 5,304,121, the contents of each of which are incorporated by reference herein. The coatings are typically biocompatible polymeric materials such as a hydrogel polymer, polymethyldisiloxane, polycaprolactone, polyethylene glycol, polylactic acid, ethylene-vinyl acetate, and mixtures thereof. The coatings may optionally be further covered by a suitable topcoat of fluorodimethicone, polysaccharide enzymes, polyethylene glycol, phospholipids or combinations thereof to impart controlled release characteristics into the composition. Implantable devices coated with a compound disclosed herein are another embodiment disclosed herein. The compounds may also be coated on implantable medical devices, such as beads, or co-formulated with a polymer or other molecule, to provide a "drug depot" thus permitting the drug to be released over a longer time period than administration of an aqueous solution of the drug.

General Synthetic Procedures

Generally, the compounds disclosed herein may be prepared by methods described herein, wherein the substituents are as defined for formulas (I) above, except where further noted. The following non-limiting schemes and examples are presented to further exemplify the invention.

Persons skilled in the art will recognize that the chemical reactions described may be readily adapted to prepare a number of other compounds disclosed herein, and alternative methods for preparing the compounds disclosed herein are deemed to be within the scope disclosed herein. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds disclosed herein.

In the examples described below, unless otherwise indicated all temperatures are set forth in degrees Celsius. Reagents were purchased from commercial suppliers such as Aldrich Chemical Company, Arco Chemical Company and Alfa Chemical Company, and were used without further purification unless otherwise indicated. Common solvents were purchased from commercial suppliers such as Shantou XiLong Chemical Factory, Guangdong Guanghua Reagent Chemical Factory Co. Ltd., Guangzhou Reagent Chemical Factory, Tianjin YuYu Fine Chemical Ltd., Qingdao Tenglong Reagent Chemical Ltd., and Qingdao Ocean Chemical Factory.

Anhydrous THF, dioxane, toluene, and ether were obtained by refluxing the solvent with sodium. Anhydrous $CH_2Cl_2$ and $CHCl_3$ were obtained by refluxing the solvent with $CaH_2$. EtOAc, PE, hexane, DMAC and DMF were treated with anhydrous $Na_2SO_4$ prior to use.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was conducted using a silica gel column. Silica gel (300-400 mesh) was purchased from Qingdao Ocean Chemical Factory. $^1H$ NMR spectra were recorded with a Bruker 400 MHz spectrometer at ambient temperature. $^1H$ NMR spectra were obtained as $CDCl_3$, $d_6$-DMSO, $CD_3OD$ or $d_6$-acetone solutions (reported in ppm), using TMS (0 ppm) or chloroform (7.25 ppm) as the reference standard. When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Low-resolution mass spectral (MS) data were determined by Agilent 6320 Series LC-MS equipped with a G1312A binary pump and a G1316A TCC (column was operated at 30° C.). G1329A autosampler and G1315B DAD were applied in analysis, and an ESI source was used in LC-MS spectrometer.

Low-resolution mass spectral (MS) data were determined by Agilent 6120 Series LC-MS equipped with a G1311A quaternary pump and a G1316A TCC (column was operated at 30° C.). G1329A autosampler and G1315D DAD were applied in analysis, and an ESI source was used in LC-MS spectrometer.

Both spectrometers described above were equipped with Agilent Zorbax SB-C18 (2.1×30 mm, 5 micron). Injection volume was determined by sample concentration; Flow rate was 0.6 mL/min; and data was recorded by high performance liquid chromatography (HPLC) with UV-Vis detection at 210/254 nm. 0.1% formic acid in $CH_3CN$ (A) and 0.1% formic acid in $H_2O$ (B) were used as mobile phase, and gradient elution conditions were shown in Table 1:

TABLE 1

| Time (min) | A ($CH_3CN$, 0.1% HCOOH) | B ($H_2O$, 0.1% HCOOH) |
|---|---|---|
| 0-3 | 5-100 | 95-0 |
| 3-6 | 100 | 0 |
| 6-6.1 | 100-5 | 0-95 |
| 6.1-8 | 5 | 95 |

Purities of compounds were assessed by Agilent 1100 Series high performance liquid chromatography (HPLC) with UV detection at 210 nm and 254 nm (Zorbax SB-C18, 2.1×30 mm, 4 micron, 10 min, 0.6 mL/min flow rate, 5 to 95% (0.1% formic acid in $CH_3CN$) in (0.1% formic acid in $H_2O$). Column was operated at 40° C.

The following abbreviations are used throughout the specification:
$HCOONH_4$ ammonium formate
$CH(OMe)_3$ trimethoxymethane
MeOH, $CH_3OH$ methanol
$CH_3SO_3H$ methanesulfonic acid
$Ac_2O$ acetic anhydride
$SOCl_2$ thionyl chloride
i-PrOH isopropanol NaOH sodium hydroxide
$K_2CO_3$ potassium carbonate
KI potassium iodide
DMF N,N-dimethylformamide
$H_2NNH_2$—$H_2O$ hydrazine hydrate
PPA polyphosphoric acid
$H_2$ hydrogen
Pd/C palladium on carbon
EtOH ethanol
PhCHO benzaldehyde
DCM, $CH_2Cl_2$ methylene chloride
$NaBH_4$ sodium borohydride
KOH potassium hydroxide
c-$C_5H_{11}$MgCl cyclopentylmagnesium chloride
ClTi(O$^i$Pr)$_3$ chlorotitanium triisopropoxide
Pd(OH)$_2$ palladium hydroxide
$OsO_4$ osmium tetroxide
NMO N-Methylmorpholine-N-oxide
ClCH$_2$CH$_2$Cl 1,2-dichloroethane
TBAB Tetrabutyl ammonium bromide
HCO$_2$H methanoic acid
TFA trifluoroacetic acid
(CF$_3$CO)$_2$O trifluoroacetic anhydride
LiAlH$_4$ lithium aluminum hydride
THF tetrahydrofuran
(Boc)$_2$O di-tert-butyl dicarbonate
Et$_3$N,TEA,NEt$_3$ triethylamine
NBS N-bromosuccinimide
TsCl tosyl chloride
DMAP 4-dimethylaminopyridine
HCHO formaldehyde
NaB(OCOCH$_3$)$_3$H sodium triacetoxyborohyride
HCl hydrochloric acid
i-PrMgBr isopropylmagnesium bromide
Me$_3$Al trimethylaluminum
NHMe$_2$ dimethylamine
Ag$_2$CO$_3$ silver carbonate
CH$_3$CN,MeCN acetonitrile
PtO$_2$ platinum dioxide
AcOH,CH$_3$COOH acetic acid
MsCl methylsulfonyl chloride
PCC pyridinium chlorochromate
DBU 1,8-diazabicyclo[5.4.0]undec-7-ene
Ac acetyl
Boc tert-butoxycarbonyl
Ts tosyl
Bn benzyl
Et ethyl
TMS trimethylsilyl
Ms methylsulfonyl
toluene methylbenzene
LiBH$_4$ lithium borohydride
Na$_2$CO$_3$ sodium carbonate
Dess-Martin Dess-Martin oxidant
LDA lithium diisopropylamide
NH$_2$OH.HCl hydroxylamine hydrochloride
Glycol monomethyl ether ethylene glycol monomethyl ether
r.t, RT room temperature
BnBr benzyl bromide
MnO$_2$ manganese dioxide
CHCl$_3$ chloroform, trichloromethane
LiBr lithium bromide
HBr hydrogen bromide
Na$_2$SO$_4$ sodium sulfate
H$_2$O water
N$_2$ nitrogen
CDCl$_3$ deuterochloroform PE petroleum ether
DMSO dimethylsulfoxide
mL, ml milliliter
g gram
mg milligram
h hour
eq electrochemical equivalent
mmol millimole
NH$_3$H$_2$O ammonium hydroxide
EA, EtOAc ethyl acetate
HPLC high performance liquid chromatography
Mpa Megapascal
ATP Adenosine Triphosphate
NADPH Coenzyme II reduced
PBS phosphate buffer solution

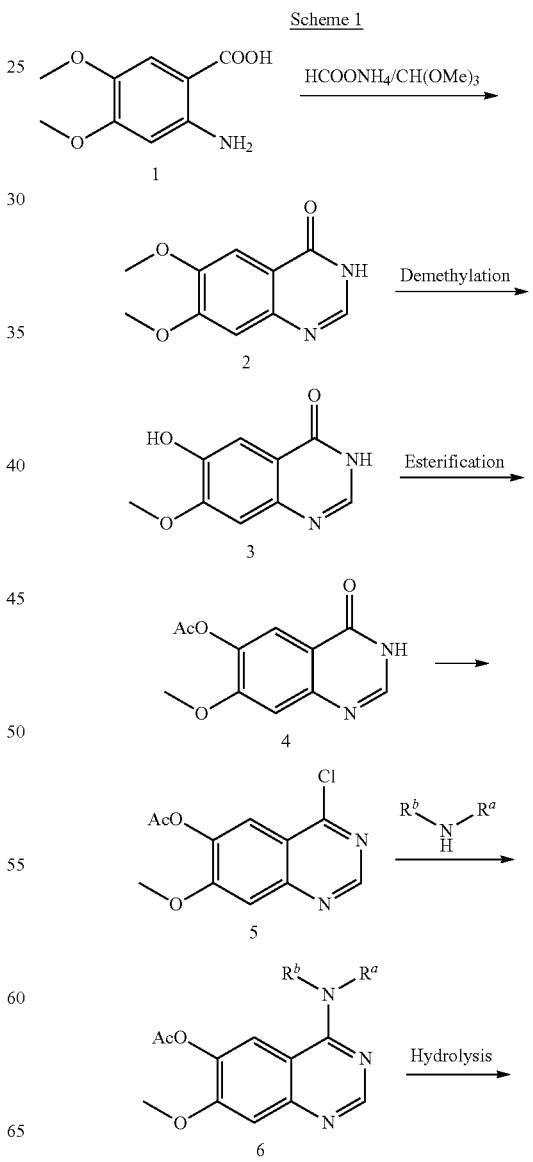

Scheme 1

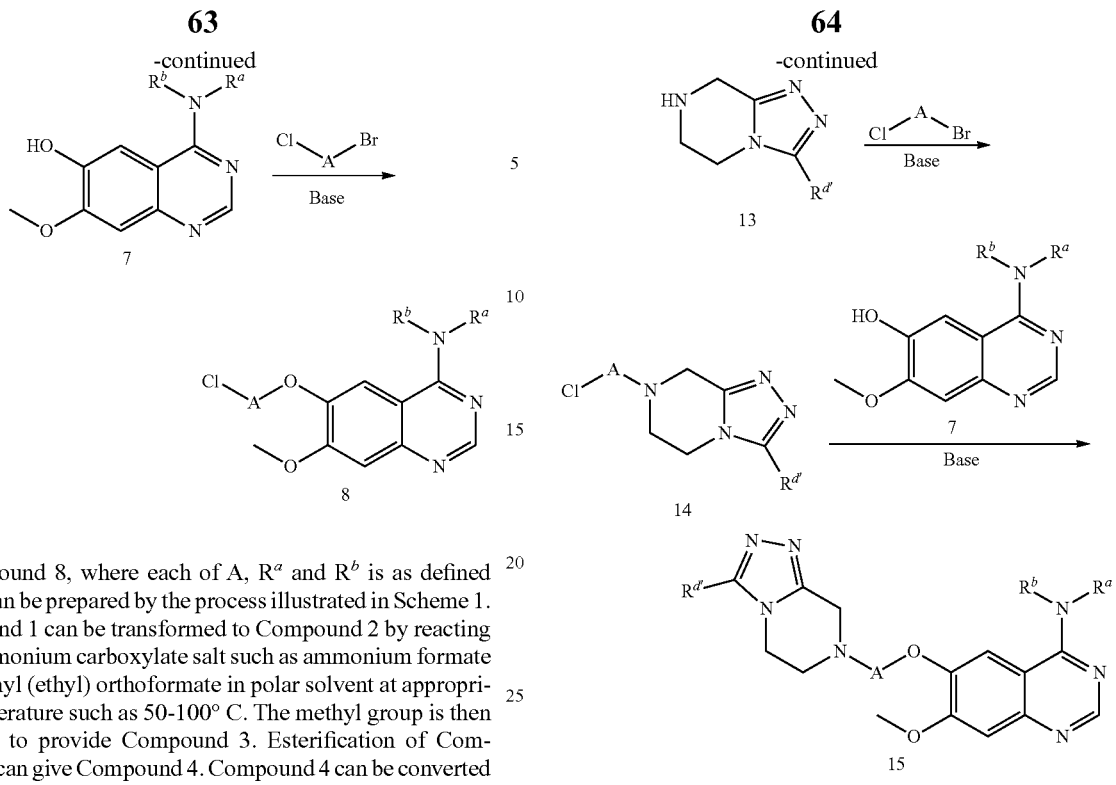

Compound 8, where each of A, $R^a$ and $R^b$ is as defined above, can be prepared by the process illustrated in Scheme 1. Compound 1 can be transformed to Compound 2 by reacting with ammonium carboxylate salt such as ammonium formate and methyl (ethyl) orthoformate in polar solvent at appropriate temperature such as 50-100° C. The methyl group is then removed to provide Compound 3. Esterification of Compound 3 can give Compound 4. Compound 4 can be converted to Compound 5 in the presence of chlorinating agents such as $SOCl_2$ under heating condition. Compound 5 can be reacted with suitable amine derivatives to yield Compound 6. Compound 6 can be hydrolysed to afford Compound 7. Compound 7 can be reacted with halogenated alkanes to afford Compound 8 by base catalysis at appropriate temperature, such as 30-60° C.

Compound 15, where each of A, $R^{d'}$, $R^a$ and $R^b$ is as defined above, can be prepared by the process illustrated in Scheme 2. Compound 9 can be transformed to Compound 10 by reacting with hydrazine hydrate under heating condition. Acylation of Compound 10 can give Compound 11, then cyclic condensation of Compound 11 can yield Compound 12 under condensation agents. Reduction of pyrazine ring in Compound 12 with a reducing agent, such as Pd/C through the process of catalytic hydrogenation can afford piperazine 13. Reaction of Compound 13 with halogenated alkanes under basic condition can give Compound 14. Reaction of Compound 14 with Compound 7 can give Compound 15 by base catalysis.

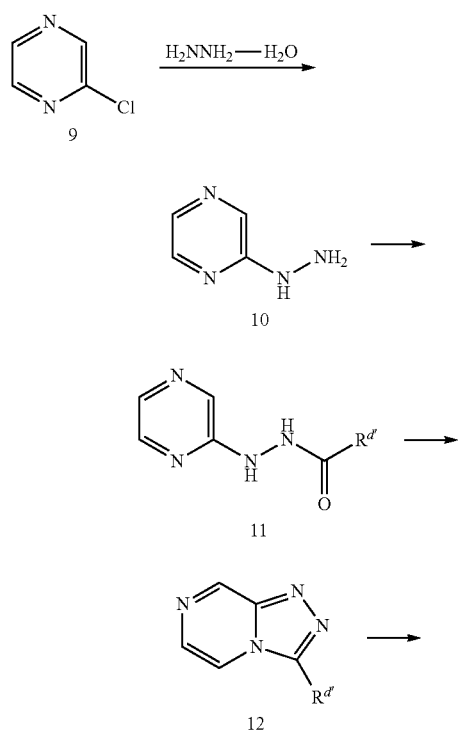

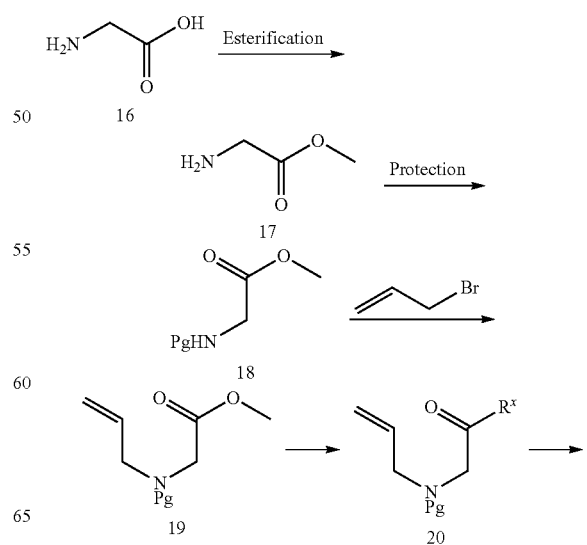

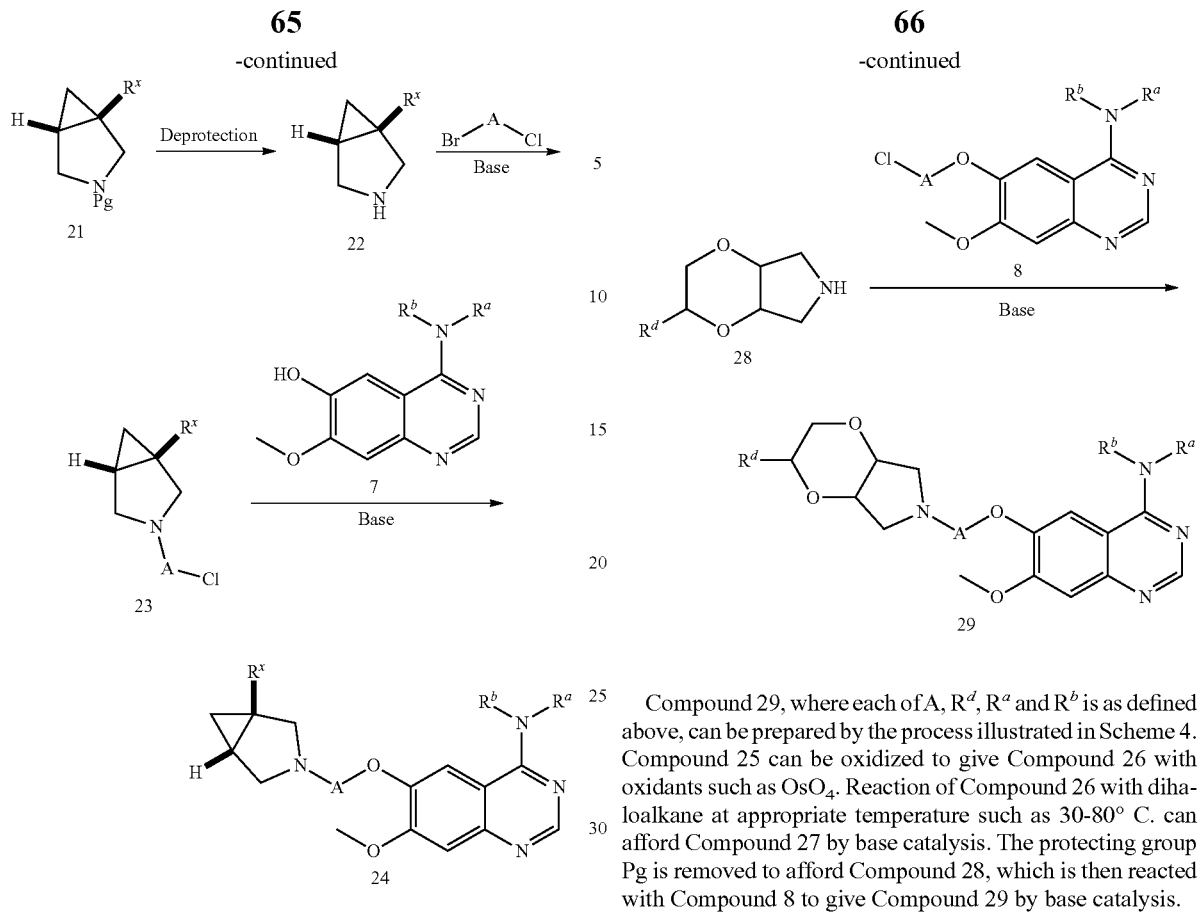

Compound 24, where each of A, $R^x$, $R^a$ and $R^b$ is as defined above, can be prepared by the process illustrated in Scheme 3. Esterification of Compound 16 can yield Compound 17 Amino protection of Compound 17 can give Compound 18, followed by base catalysis with allyl bromide to give Compound 19. When $R^x$ is not a hydroxy group, reaction of Compound 19 can afford Compound 20 which is then cyclized to Compound 21 in the presence of catalyst ClTi(O$^i$Pr)$_3$ and Grignard reagent such as i-PrMgBr. When $R^x$ is a hydroxy group, cyclization reaction of Compound 19 can be converted directly to Compound 21 in the presence of catalyst ClTi(O$^i$Pr)$_3$ and Grignard reagent such as i-PrMgBr. Compound 22 can be reacted with halogenated alkanes under basic condition to afford Compound 23 after removal of the protecting group Pg. Reaction of Compound 23 with Compound 7 can give Compound 24 by base catalysis.

Compound 29, where each of A, $R^d$, $R^a$ and $R^b$ is as defined above, can be prepared by the process illustrated in Scheme 4. Compound 25 can be oxidized to give Compound 26 with oxidants such as OsO$_4$. Reaction of Compound 26 with dihaloalkane at appropriate temperature such as 30-80° C. can afford Compound 27 by base catalysis. The protecting group Pg is removed to afford Compound 28, which is then reacted with Compound 8 to give Compound 29 by base catalysis.

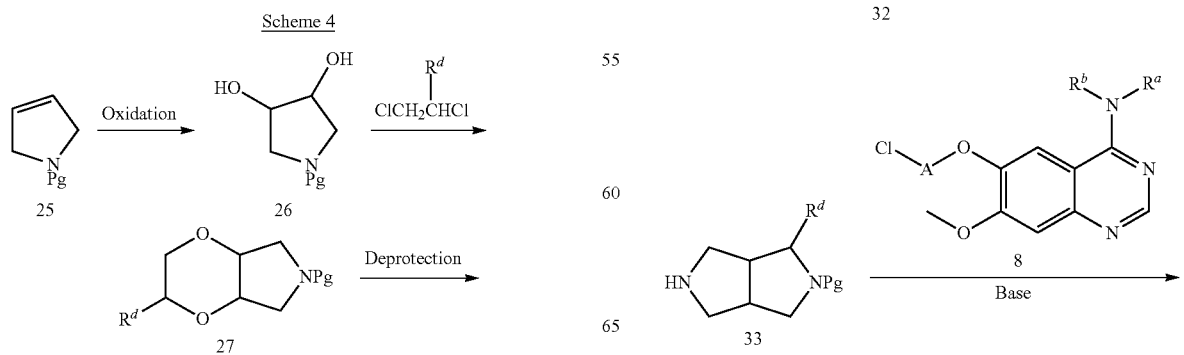

Scheme 5

-continued

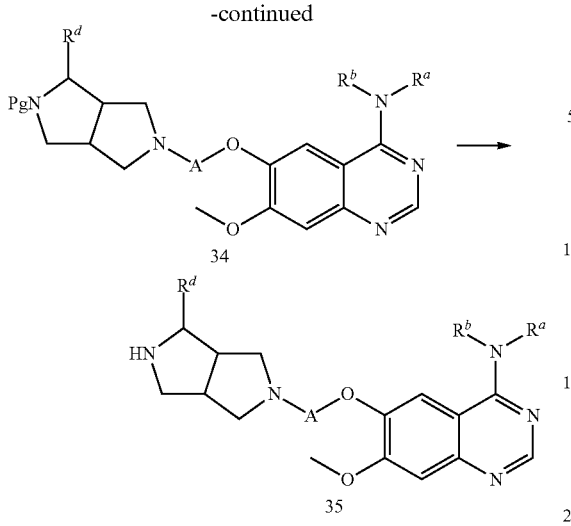

Compound 35, where each of A, $R^d$, $R^a$ and $R^b$ is as defined above, can be prepared by the process illustrated in Scheme 5. Compound 30 can be converted to Compound 32 by reacting with Compound 31 in the presence of an acid such as TFA. Compound 32 can be then reduced to give Compound 33 with reductant in polar solvent and at appropriate temperature such as 50-100° C. Reaction of Compound 33 with Compound 8 can yield Compound 34 by base catalysis. Then the protecting group Pg in Compound 34 can be removed to afford Compound 35.

Scheme 6

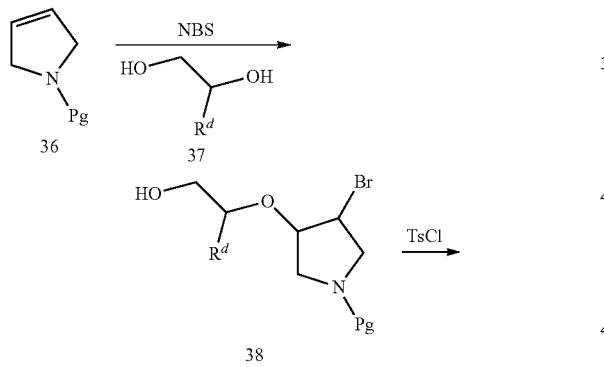

-continued

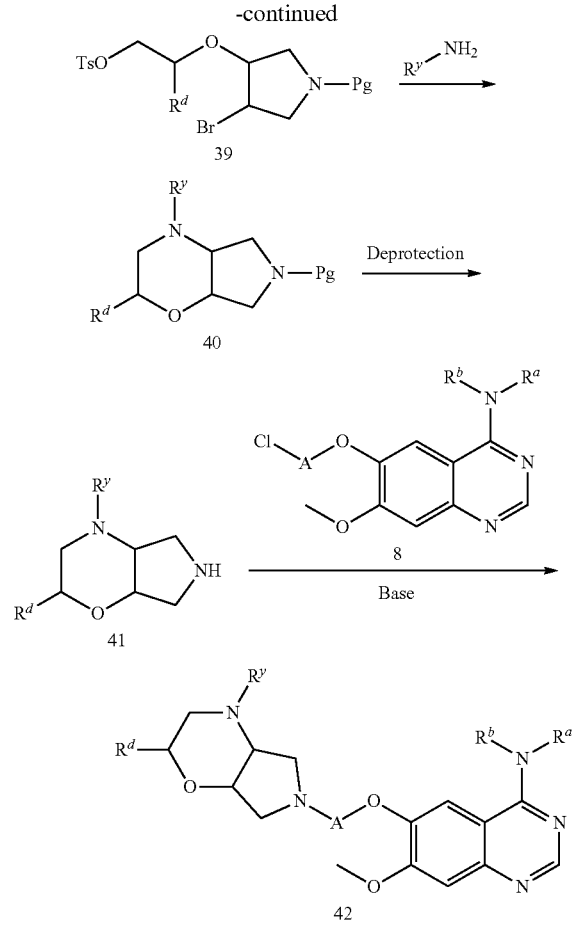

Compound 42, where each of A, $R^d$, $R^y$, $R^a$ and $R^b$ is as defined above, can be prepared by the process illustrated in Scheme 6. Compound 36 can be converted to Compound 38 through free radical reaction. Reaction of Compound 38 with tosyl chloride can afford Compound 39. Compound 39 can be then converted to Compound 40 by reacting with primary amine. Then the protecting group Pg in Compound 40 can be removed to give Compound 41. Reaction of Compound 41 with Compound 8 by base catalysis can yield Compound 42.

Scheme 7

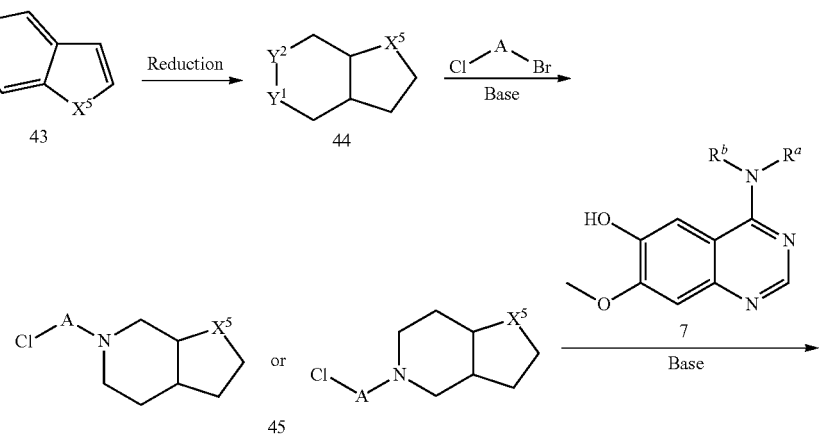

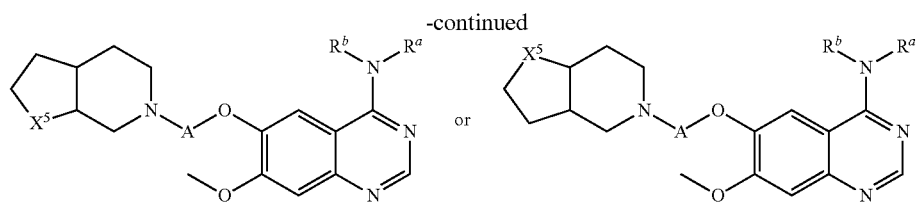

46

Compound 46 can be synthesized through the procedure depicted in Scheme 7. Where each of A, $X^5$, $R^a$ and $R^b$ is as defined above, and each of $Y^1$ and $Y^2$ is independently N or CH, with the proviso that $Y^1$ and $Y^2$ are different. Compound 43 can be reduced to give Compound 44 with reductants such as $PtO_2$ through the process of catalytic hydrogenation. Compound 44 can be reacted with halogenated alkanes to give Compound 45 in polar aprotic solvents at appropriate temperature such as 40-100° C. by base catalysis. Reaction of Compound 45 with Compound 7 by base catalysis can yield Compound 46.

Scheme 8

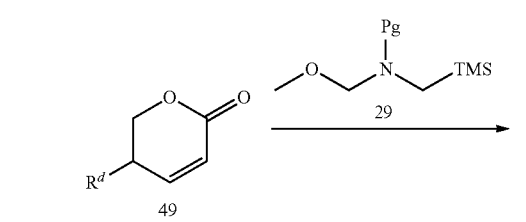

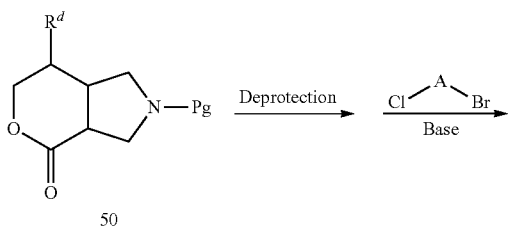

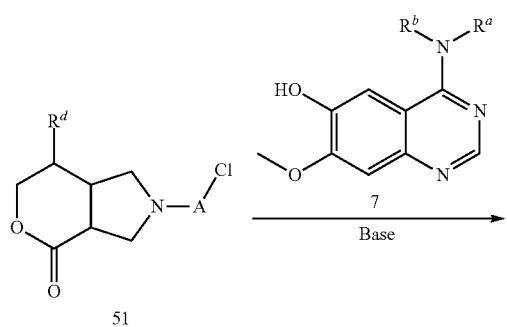

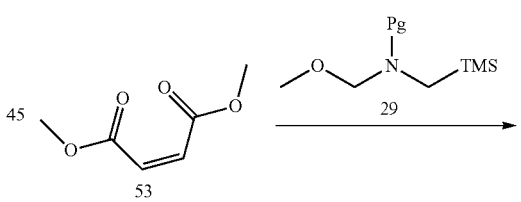

52

Compound 52 can be synthesized through the procedure depicted in Scheme 8. Where each of A, $R^d$, $R^a$ and $R^b$ is as defined above. Elimination of Compound 47 in the presence of basic catalyst such as DBU can provide Compound 48, which is then oxidized to give Compound 49 with an oxidant. Compound 49 can be converted to Compound 50 by reacting with Compound 29 in the presence of an acid such as TFA. Compound 50 can be reacted with halogenated alkanes in basic and polar solvent at appropriate temperature such as 50-100° C. to yield Compound 51 after removal of protecting group Pg. Reaction of Compound 51 with Compound 7 by base catalysis can afford Compound 52.

Scheme 9

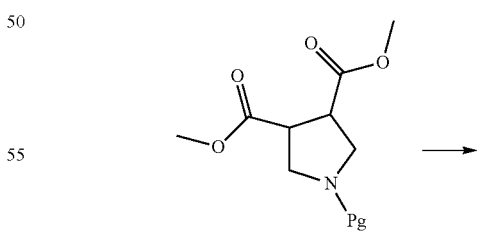

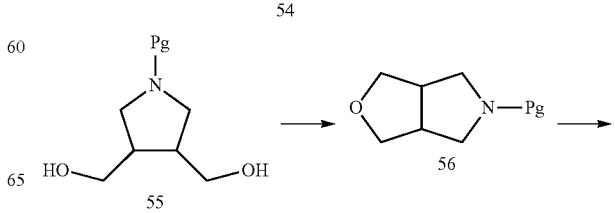

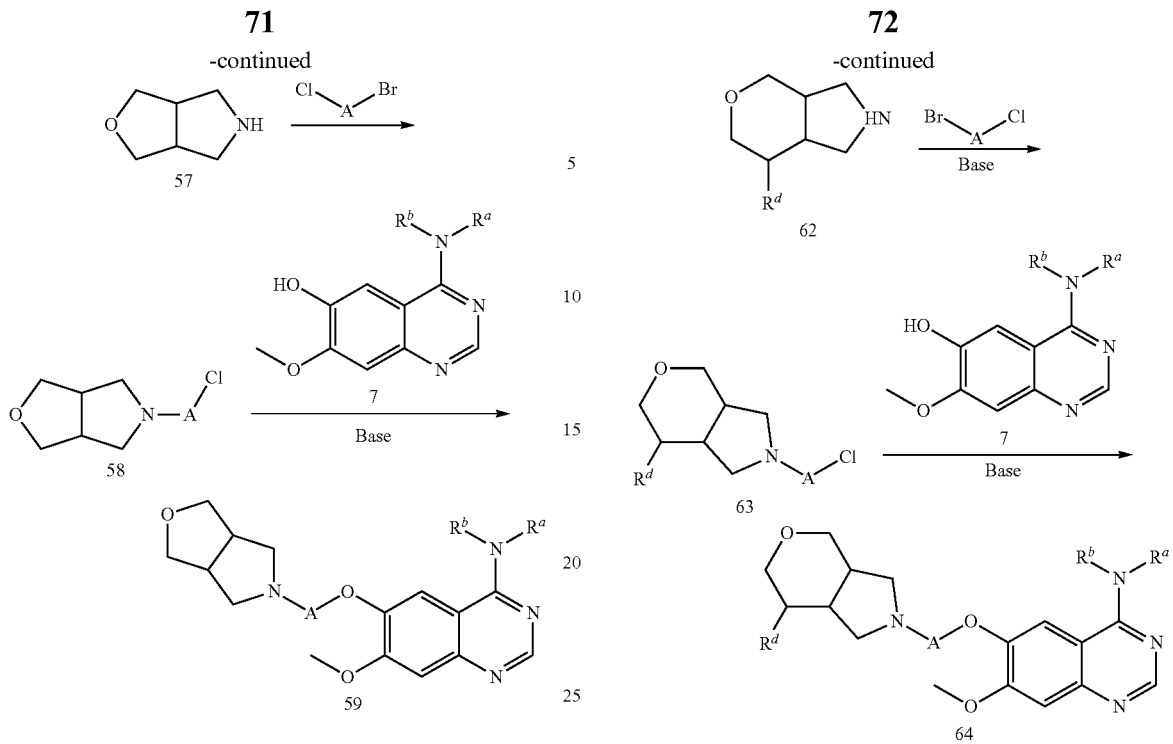

Compound 59 can be synthesized through the procedure depicted in Scheme 9. Where each of A, $R^a$ and $R^b$ is as defined above. Compound 53 can be converted to Compound 54 by reacting with Compound 29 in the presence of an acid such as TFA and polar solvent such as $CH_2Cl_2$ at appropriate temperature. Compound 54 can be then reduced to give Compound 55 with reductants in polar aprotic solvent. Cyclization of Compound 55 can afford Compound 56. The protecting group Pg of Compound 56 can be removed to give Compound 57, which followed by reaction with haloalkanes in basic solvent can yield Compound 58. Reaction of Compound 58 with Compound 7 can afford Compound 59 by base catalysis.

Compound 64 can be synthesized through the procedure depicted in Scheme 10. Where each of A, $R^d$, $R^a$ and $R^b$ is as defined above. Reduction of Compound 50 with a reducing agent can give Compound 60. Cyclization of Compound 60 at appropriate temperature can afford Compound 61. Then the protecting group Pg in Compound 61 can be removed to give Compound 62. Reaction of Compound 62 with haloalkanes in the presence of base can give Compound 63, which is followed reacted with Compound 7 by base catalysis to give Compound 64.

Scheme 10

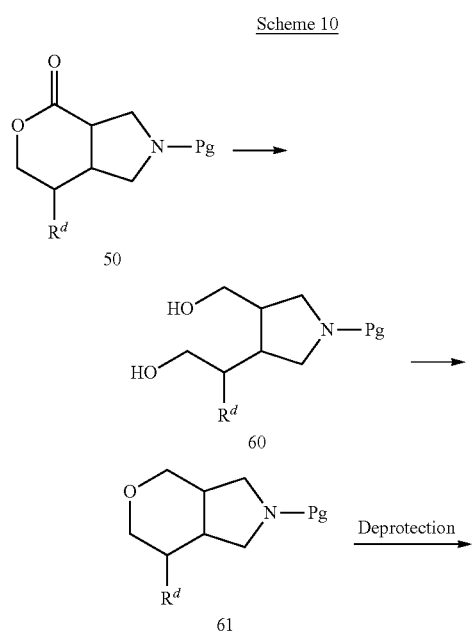

Scheme 11

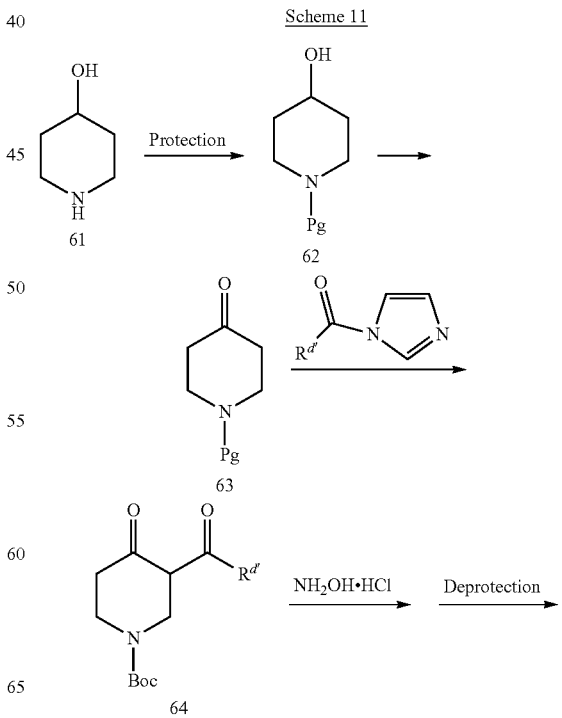

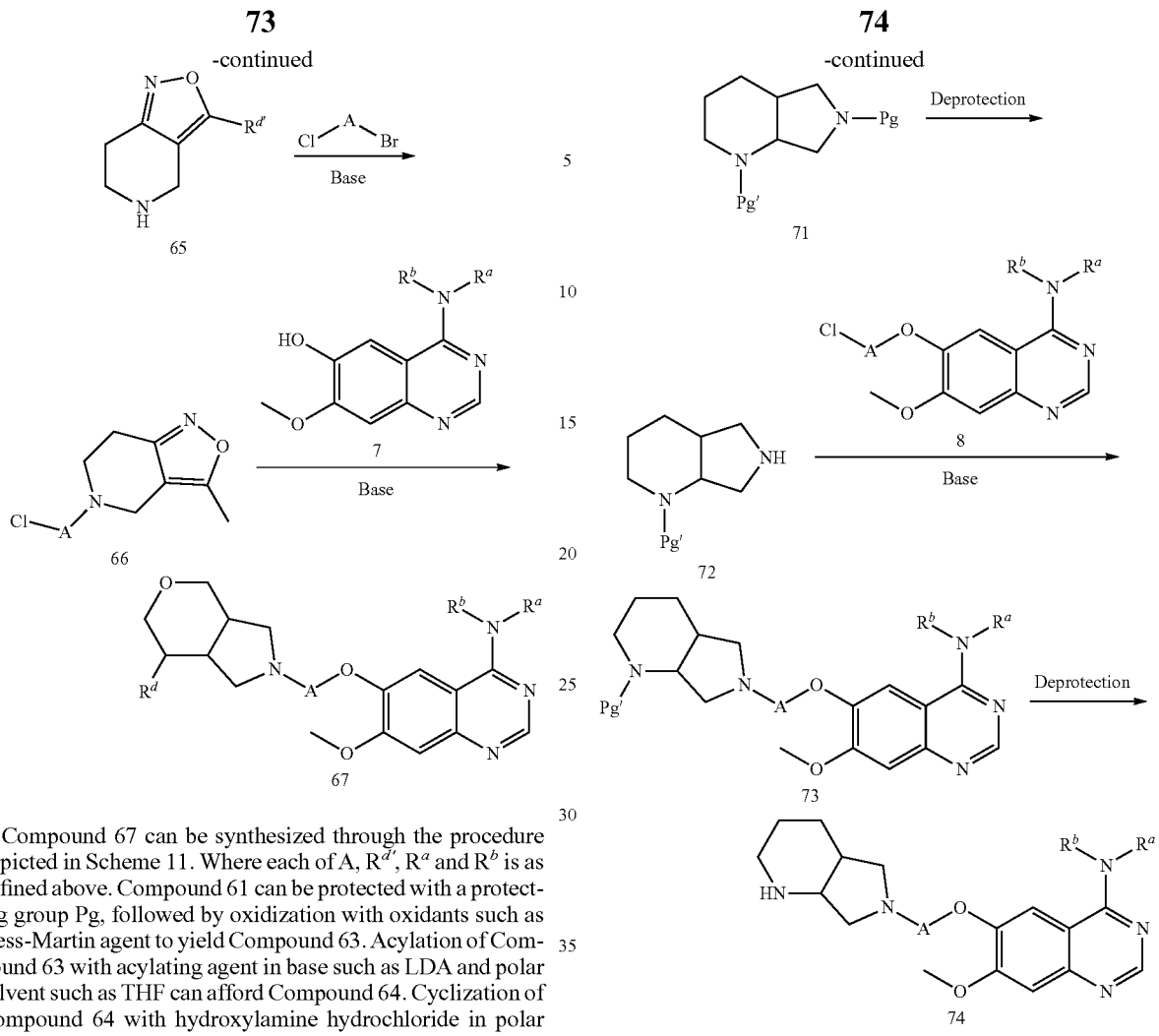

Compound 67 can be synthesized through the procedure depicted in Scheme 11. Where each of A, $R^{d'}$, $R^a$ and $R^b$ is as defined above. Compound 61 can be protected with a protecting group Pg, followed by oxidization with oxidants such as Dess-Martin agent to yield Compound 63. Acylation of Compound 63 with acylating agent in base such as LDA and polar solvent such as THF can afford Compound 64. Cyclization of Compound 64 with hydroxylamine hydrochloride in polar solvent such as ethanol at appropriate temperature such as 50-100° C., and followed by the removal of protecting group Pg can give Compound 65. Reaction of Compound 65 with haloalkanes under basic condition can afford Compound 66. Compound 66 can be reacted with Compound 7 to provide Compound 67 by base catalysis.

Compound 74 can be synthesized through the procedure depicted in Scheme 12. Where each of A, $R^a$ and $R^b$ is as defined above. Compound 68 can be reduced with reductants such as Pd/C to give Compound 69 through the process of catalytic hydrogenation in solvent such as ethyleneglycol monomethylether at appropriate temperature such as 60-110° C. Compound 69 can be reduced with reductants such as LiAlH$_4$ to give Compound 70 in polar solvent such as THF at appropriate temperature such as 40-80° C. Compound 70 can be protected with protecting group Pg', and followed by deprotected of the protecting group Pg to provide Compound 72. Compound 72 can be reacted with Compound 8 to give Compound 73 by base catalysis. Then the protecting group Pg' in Compound 73 can be removed to afford Compound 74.

Scheme 12

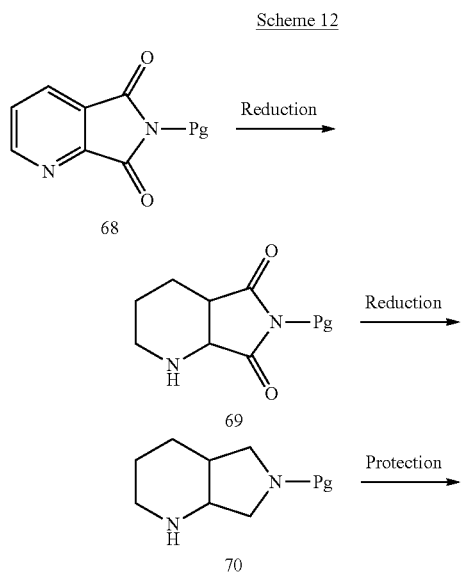

Scheme 13

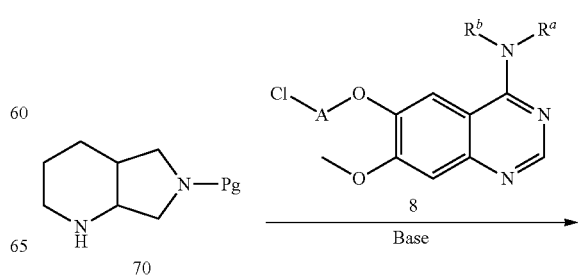

75

-continued

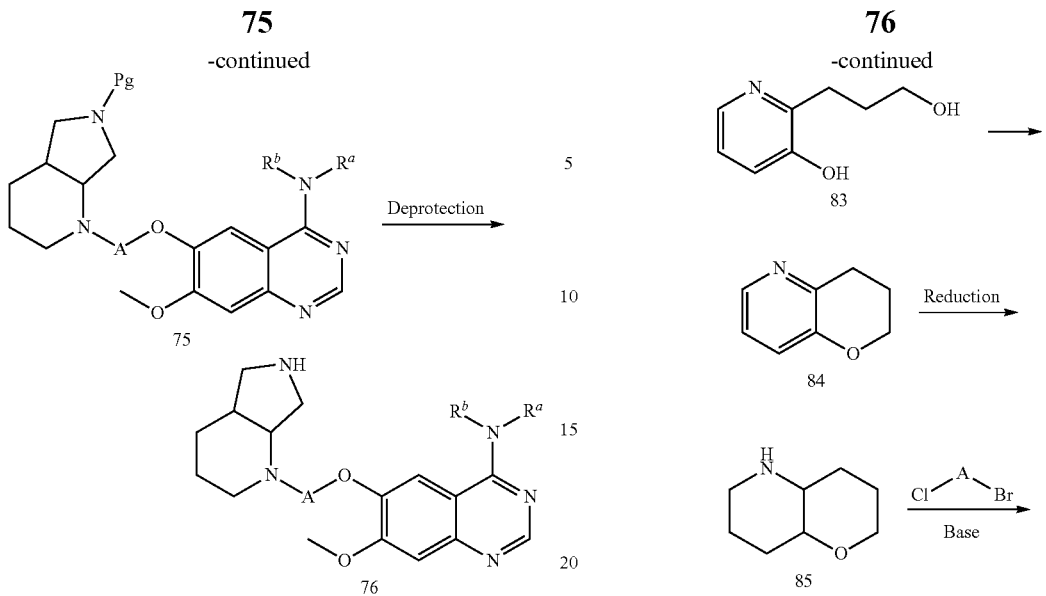

Compound 76 can be synthesized through the procedure depicted in Scheme 13. Where each of A, $R^a$ and $R^b$ is as defined above. Compound 70 can be reacted with Compound 8 to give Compound 75 by base catalysis. The protecting group Pg can be removed to give Compound 76.

Scheme 14

76

-continued

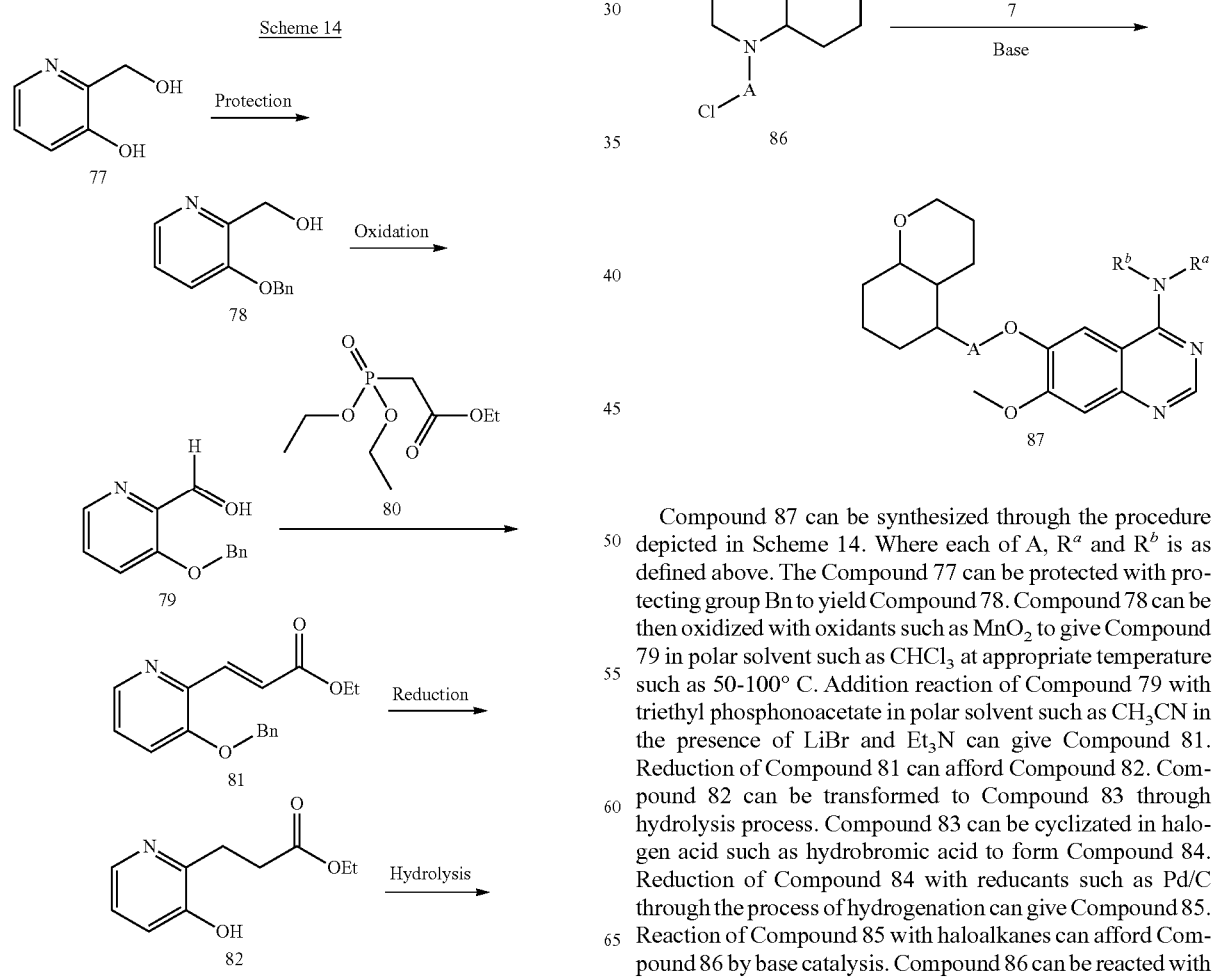

Compound 87 can be synthesized through the procedure depicted in Scheme 14. Where each of A, $R^a$ and $R^b$ is as defined above. The Compound 77 can be protected with protecting group Bn to yield Compound 78. Compound 78 can be then oxidized with oxidants such as $MnO_2$ to give Compound 79 in polar solvent such as $CHCl_3$ at appropriate temperature such as 50-100° C. Addition reaction of Compound 79 with triethyl phosphonoacetate in polar solvent such as $CH_3CN$ in the presence of LiBr and $Et_3N$ can give Compound 81. Reduction of Compound 81 can afford Compound 82. Compound 82 can be transformed to Compound 83 through hydrolysis process. Compound 83 can be cyclizated in halogen acid such as hydrobromic acid to form Compound 84. Reduction of Compound 84 with reducants such as Pd/C through the process of hydrogenation can give Compound 85. Reaction of Compound 85 with haloalkanes can afford Compound 86 by base catalysis. Compound 86 can be reacted with Compound 7 to give Compound 87 by base catalysis.

EXAMPLES

Example 1

N-(3-chloro-4-fluorophenyl)-7-methoxy-6-(3-(3-(trifluoromethyl)-5,6-dihydro-[1,2,4]triazolo[4,3-a]pyrazin-7(8H)-yl)propoxy)quinazolin-4-amine

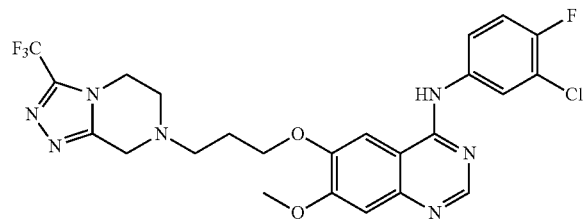 [SMILES: COc1cc2ncnc(Nc3ccc(F)c(Cl)c3)c2cc1OCCCN1CCn2c(nnc2C(F)(F)F)C1]

Step 1) 6,7-dimethoxyquinazolin-4(3H)-one

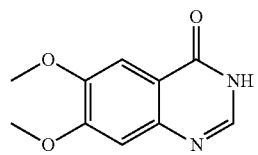

A suspension of 2-amino-4,5-dimethoxybenzoic acid (23.40 g), trimethoxymethane (52 mL), ammonium formate (30.00 g) and methanol (400 mL) was heated to 70° C. and refluxed for 4 h. After the reaction mixture was cooled to room temperature, 160 mL of water was added to the reaction. The mixture was filtered to afford the title compound as a yellow solid (22.70 g, 93.00%). The compound was characterized by the following spectroscopic data: $^1$H NMR (400 MHz, d$^6$-DMSO) δ: 3.87 (s, 3H), 3.91 (s, 3H), 7.13 (s, 1H), 7.45 (s, 1H), 7.98 (s, 1H).

Step 2) 6-hydroxy-7-methoxyquinazolin-4(3H)-one

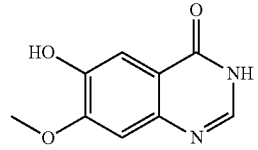

A suspension of 6,7-dimethoxyquinazolin-4(3H)-one (6.18 g), methionine (4.70 g) and methanesulfonic acid (40 mL) was stirred at 130° C. for 3 h, then poured into ice-water. The reaction mixture was adjusted to pH 7 with 40% sodium hydroxide. The mixture was filtered to give the title compound (7.10 g).

Step 3) 7-methoxy-4-oxo-3,4-dihydroquinazolin-6-yl acetate

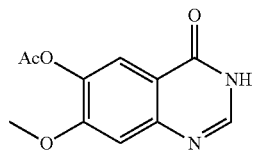

To a suspension of 6-hydroxy-7-methoxyquinazolin-4 (3H)-one (0.57 g) and pyridine (4 mL) was added acetic anhydride (10 mL) at room temperature. The reaction mixture was stirred at 100° C. for 3 hours, and then poured into ice-water. The resulting mixture was filtered to give the title compound (0.40 g, 53.00%). The compound was characterized by the following spectroscopic data: $^1$H NMR (400 MHz, d$^6$-DMSO) δ: 2.30 (s, 3H), 3.92 (s, 3H), 7.28 (s, 1H), 7.75 (s, 1H), 8.08 (s, 1H).

Step 4) 4-chloro-7-methoxyquinazolin-6-yl acetate

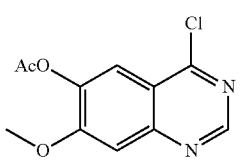 [SMILES: COc1cc2ncnc(Cl)c2cc1OC(C)=O]

A suspension of 7-methoxy-4-oxo-3,4-dihydroquinazolin-6-yl acetate (2.00 g), DMF (0.20 mL) and thionyl chloride (30 mL) was stirred at 70° C. for 3 h. The mixture was concentrated in vacuo, and the residue was used for the next step without further purification.

Step 5) 4-((3-chloro-4-fluorophenyl)amino)-7-methoxyquinazolin-6-yl acetate

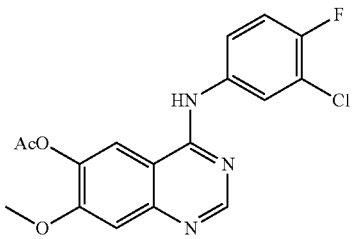 [SMILES: COc1cc2ncnc(Nc3ccc(F)c(Cl)c3)c2cc1OC(C)=O]

A suspension of 4-chloro-7-methoxyquinazolin-6-yl acetate (2.52 g), 3-chloro-4-fluoroaniline (1.49 g) and isopropanol (60 mL) was stirred at 88° C. for 5 h. The reaction mixture was cooled to room temperature, filtered to afford the desired compound as a solid (2.51 g, 81.00%).

Step 6) 4-((3-chloro-4-fluorophenyl)amino)-7-methoxyquinazolin-6-ol

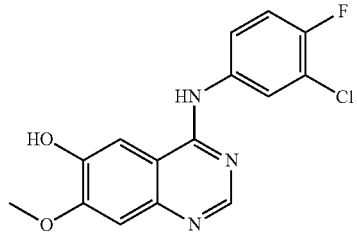 [SMILES: COc1cc2ncnc(Nc3ccc(F)c(Cl)c3)c2cc1O]

To a suspension of 4-((3-chloro-4-fluorophenyl)amino)-7-methoxyquinazolin-6-yl acetate (2.51 g) and methanol (50 mL) was added 5 mol/L NaOH (5.00 mL) at room temperature. The reaction mixture was stirred at room temperature for 6 h, and was adjusted to pH 5 with 0.1 N HCl (aq). The mixture was filtered to give the title compound as a solid (1.99 g, 90.00%).

Step 7) N-(3-chloro-4-fluorophenyl)-6-(3-chloropropoxy)-7-methoxyquinazolin-4-amine

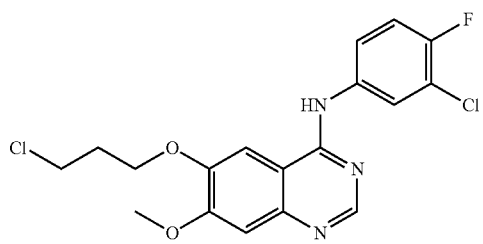 [SMILES: COc1cc2ncnc(Nc3ccc(F)c(Cl)c3)c2cc1OCCCCl]

A suspension of 4-((3-chloro-4-fluorophenyl)amino)-7-methoxyquinazolin-6-ol (20.00 g), $K_2CO_3$ (10.37 g), KI (1.04 g), 1-bromo-3-chloropropane (7.50 mL) and DMF (150 mL) was stirred at 40° C. for 6 h. The reaction mixture was poured into water and filtered. The filter residue was purified by a silica gel column chromatography (eluting agent: EA) to give the title compound as pale yellow liquid (22.05 g, 89.00%). The compound was characterized by the following spectroscopic data: MS (ESI, pos. ion) m/z: 396.1 (M+1); $^1$H NMR (400 MHz, $CDCl_3$) δ: 2.01 (m, 2H), 3.68 (t, J=4.2 Hz, 2H), 4.00 (s, 3H), 4.10 (t, J=4.2 Hz, 2H), 6.80 (s, 1H), 7.16 (s, 1H), 7.26 (s, 1H), 7.30 (s, 1H), 7.47 (s, 1H), 8.64 (s, 1H) ppm.

Step 8) 2-hydrazinopyrazine

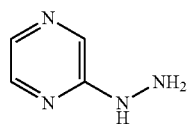

A mixture of 2-chloropyrazine (4.00 g) and hydrazine hydrate was heated at 110° C. for 1 h, and then cooled to room temperature. The mixture was filtered to give the title compound as a solid (2.30 g, 60.00%). The compound was characterized by the following spectroscopic data: MS (ESI, pos. ion) m/z: 111.0 (M+1).

Step 9) 3-(trifluoromethyl)-[1,2,4]triazolo[4,3-a]pyrazine

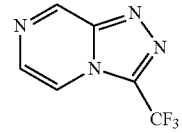 [SMILES: FC(F)(F)c1nnc2cnccn12]

A solution of 2-hydrazinopyrazine (1.10 g) in trifluoroacetic anhydride (10 mL) was stirred at room temperature for 4 h. To the mixture was added PPA (12 mL). The reaction mixture was heated at 80° C. for another 15 h. The reaction mixture was cooled to room temperature and filtered to afford the title compound as a white solid (0.94 g, 50.00%). The compound was characterized by the following spectroscopic data: MS (ESI, pos. ion) m/z: 189.0 (M+1); $^1$H NMR (400 MHz, $CDCl_3$) δ: 8.64 (s, 3H).

Step 10) 3-(trifluoromethyl)-5,6,7,8-tetrahydro-[1,2,4]triazolo[4,3-a]pyrazine

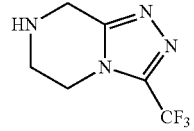

To a solution of 3-(trifluoromethyl)[1,2,4]triazolo[4,3-a]pyrazine (1.60 g) in methanol (20 mL) was added a catalytic amount of Pd/C. The suspension was stirred under $H_2$ for 5 h, and then filtered. The filtrate was concentrated in vacuo to give a residue, which was used for next step without further purification.

Step 11) 7-(3-chloropropyl)-3-(trifluoromethyl)-5,6,7,8-tetrahydro-[1,2,4]triazolo[4,3-a]pyrazine

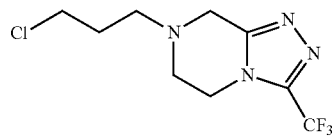 [SMILES: FC(F)(F)c1nnc2n1CCN(CCCCl)C2]

To a solution of 3-(trifluoromethyl)-5,6,7,8-tetrahydro-[1,2,4]triazolo[4,3-a]pyrazine (1.90 g) in DMF (10 mL) was added $K_2CO_3$ (2.35 g) and 1-bromo-3-chloropropane (1.70 mL) at rt. The reaction mixture was heated at 80° C. for 3 h, diluted with water and extracted with ethyl acetate. The combined organic phases were dried over anhydrous $Na_2SO_4$ for 1 h, and filtered. The filtrate was concentrated in vacuo and the residue was chromatographed with a silica gel column (eluting agent: 30:1 (v/v) DCM/MeOH) to give the title compound as transparent liquid (0.68 g, 30.00%).

Step 12) N-(3-chloro-4-fluorophenyl)-7-methoxy-6-(3-(3-(trifluoromethyl)-5,6-dihydro-[1,2,4]triazolo[4,3-a]pyrazin-7(8H)-yl)propoxy)quinazolin-4-amine

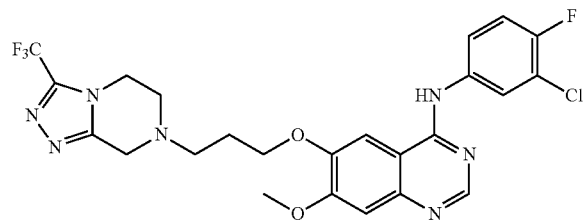 [SMILES: COc1cc2ncnc(Nc3ccc(F)c(Cl)c3)c2cc1OCCCN1CCn2c(nnc2C(F)(F)F)C1]

To a mixture of 4-((3-chloro-4-fluorophenyl)amino)-7-methoxyquinazolin-6-yl acetate (0.62 g) and K₂CO₃ (0.35 g) in 10 mL of DMF was added 7-(3-chloropropyl)-3-(trifluoromethyl)-5,6,7,8-tetrahydro-[1,2,4]triazolo[4,3-a]pyrazine (0.68 g) at rt. The reaction mixture was heated at 80° C. for 6 h, diluted with water and extracted with CH₂Cl₂. The combined organic phases were dried over anhydrous Na₂SO₄ for 1 h, and filtered. The filtrate was concentrated in vacuo and the residue was chromatographed with a silica gel column (eluting agent: 30:1 (v/v) DCM/MeOH) to give the title compound as a white solid (0.43 g, 40.00%), HPLC: 95.00%. The compound was characterized by the following spectroscopic data: MS (ESI, pos. ion) m/z: 552.2 (M+1); ¹H NMR (400 MHz, CDCl₃) δ: 1.80 (m, 2H), 2.46 (t, J=4.2 Hz, 2H), 2.78 (t, J=3.6 Hz, 2H), 3.58 (s, 2H), 4.03 (s, 3H), 4.10 (t, J=4.2 Hz, 2H), 4.15 (t, J=3.6 Hz, 2H), 7.16 (s, 1H), 7.26 (s, 1H), 7.45 (s, 1H), 7.57 (m, 1H), 7.91 (m, 1H), 8.64 (s, 1H) ppm.

Example 2

N-(3-chloro-4-fluorophenyl)-6-(3-(3-ethyl-5,6-dihydro-[1,2,4]triazolo[4,3-a]pyrazin-7(8H)-yl)propoxy)-7-methoxyquinazolin-4-amine

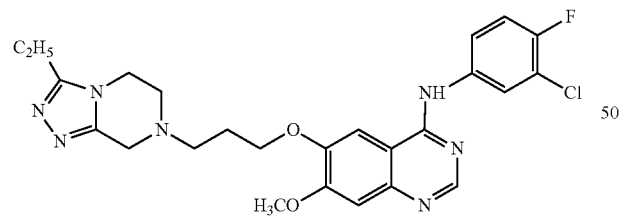

Step 1) 3-ethyl-5,6,7,8-tetrahydro-[1,2,4]triazolo[4,3-a]pyrazine

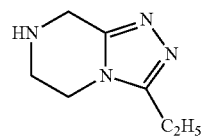

To a solution of 8-chloro-3-ethyl[1,2,4]triazolo[4,3-a]piperazine (2.24 g) in MeOH (150 mL) was added PtO₂ (1.36 g) and 10% Pd/C (0.63 g) at rt. The reaction mixture was stirred under H₂ for 16 h at room temperature and filtered, and the filtrate was concentrated in vacuo and the residue was chromatographed with a silica gel column to give the title compound (0.71 g, 31.17%). The compound was characterized by the following spectroscopic data: MS (ESI, pos. ion) m/z: 153.2 (M+1).

Step 2) N-(3-chloro-4-fluorophenyl)-6-(3-(3-ethyl-5,6-dihydro-[1,2,4]triazolo[4,3-a]pyrazin-7(8H)-yl)propoxy)-7-methoxyquinazolin-4-amine

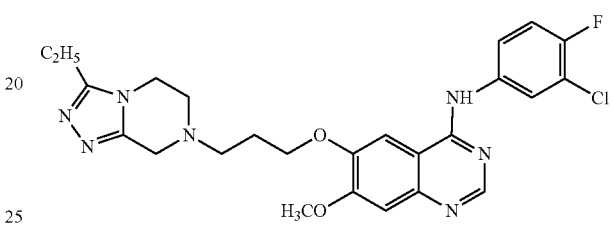

To a solution of 3-ethyl-5,6,7,8-tetrahydro-[1,2,4]triazolo[4,3-a]pyrazine (0.12 g) in DMF (5 mL) was added Ag₂CO₃ (0.73 g, 5 eq). The mixture was then added into a solution of N-(3-chloro-4-fluorophenyl)-6-(3-chloropropoxy)-7-methoxyquinazolin-4-amine (0.21 g) in DMF (2 mL) with stirring. The reaction mixture was heated at 80° C. for 40 h under N₂, and cooled to room temperature. To the reaction mixture was added CH₂Cl₂ (100 mL), and the reaction mixture was washed with brine (100 mL×3). The organic phase was dried over anhydrous Na₂SO₄ and filtered. The filtrate was concentrated in vacuo and the residue was chromatographed with a silica gel column (eluting agent: 20:1 (v/v) CH₂Cl₂/CH₃OH) to give the title compound (63.00 mg, 15.56%), HPLC: 90.54%. The compound was characterized by the following spectroscopic data: MS (ESI, pos. ion) m/z: 512.1 (M+1); ¹H NMR (400 MHz, CDCl₃) δ: 1.29 (t, J=12.80 Hz, 3H), 2.61-2.69 (m, 2H), 2.70 (t, J=13.60 Hz, 2H), 2.86 (t, J=11.20 Hz, 3H), 3.49 (s, 2H), 3.65 (s, 2H), 3.81 (t, J=13.60 Hz, 2H), 3.91 (s, 1H), 4.08 (t, J=12.40 Hz, 2H), 7.09 (m, 1H), 7.23-7.27 (m, 1H), 7.55-7.59 (m, 2H), 7.76-7.78 (m, 1H), 8.64 (s, 1H), 8.76 (s, 1H) ppm.

Example 3

N-(3-chloro-4-fluorophenyl)-6-(3-(5,6-dihydro-[1,2,4]triazolo[4,3-a]pyrazin-7(8H)-yl)propoxy)-7-methoxyquinazolin-4-amine

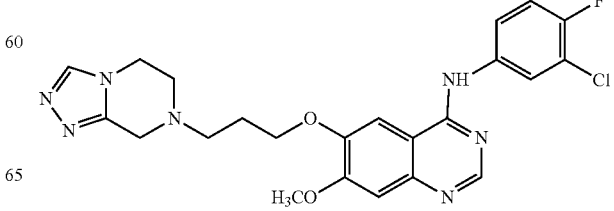

Step 1)
5,6,7,8-tetrahydro-[1,2,4]triazolo[4,3-a]pyrazine

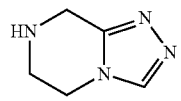

To a solution of [1,2,4]triazolo[4,3-a]pyrazine (1.50 g) in MeOH (150 mL) was added PtO$_2$ (1.10 g) and 10% Pd/C (0.46 g) at rt. The suspension was stirred under H$_2$ at room temperature for 16 h and filtered. The filtrate was concentrated in vacuo and the residue was chromatographed with a silica gel column to give the title compound (0.18 g, 11.54%). The compound was characterized by the following spectroscopic data: MS (ESI, pos. ion) m/z: 125.1 (M+1).

Step 2) N-(3-chloro-4-fluorophenyl)-6-(3-(5,6-dihydro-[1,2,4]triazolo[4,3-a]pyrazin-7(8H)-yl)propoxy)-7-methoxyquinazolin-4-amine

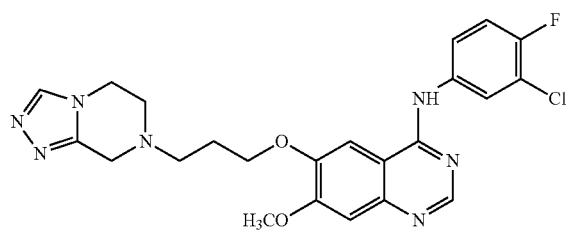 [SMILES: COc1cc2ncnc(Nc3ccc(F)c(Cl)c3)c2cc1OCCCN1CCn2cnnc2C1]

To a solution of 5,6,7,8-tetrahydro-[1,2,4]triazolo[4,3-a]pyrazine (0.18 g) in DMF (8 mL) was added Ag$_2$CO$_3$ (1.12 g, 5 eq). The mixture was then added into a solution of N-(3-chloro-4-fluorophenyl)-6-(3-chloropropoxy)-7-methoxyquinazolin-4-amine (0.21 g) in DMF (2 mL) at rt under stirring. The reaction mixture was heated at 80° C. for 36 h under N$_2$, and cooled to room temperature. To the reaction mixture was added CH$_2$Cl$_2$ (100 mL), and the reaction mixture was washed with brine (100 mL×3). The organic layer was dried over anhydrous Na$_2$SO$_4$ and filtered. The filtrate was concentrated in vacuo and the residue was chromatographed with a silica gel column (eluting agent: 20:1 (v/v) CH$_2$Cl$_2$/CH$_3$OH) to give the title compound (80.00 mg, 17.62%), HPLC: 88.57%. The title compound was characterized by the following spectroscopic data: MS (ESI, pos. ion) m/z: 484.2 (M+1); and $^1$H NMR (400 MHz, CDCl$_3$) δ: 22.02-2.08 (m, 2H), 2.75 (t, J=13.20 Hz, 2H), 2.89 (t, J=10.80 Hz, 2H), 3.73 (s, 2H), 3.94 (s, 3H), 4.01 (t, J=10.80 Hz, 2H), 4.12 (t, J=12.40 Hz, 2H), 7.10 (m, 1H), 7.24 (s, 1H), 7.27 (t, J=6.00 Hz, 1H), 7.43 (s, 1H), 7.54-7.58 (m, 1H), 7.82-7.84 (m, 1H), 8.05 (s, 1H), 8.44 (s, 1H), 8.64 (s, 1H) ppm.

Example 4

(1R,5S)-3-(3-((4-((3-chloro-4-fluorophenyl)amino)-7-methoxyquinazolin-6-yl)oxy)propyl)-3-azabicyclo[3.1.0]hexan-1-ol

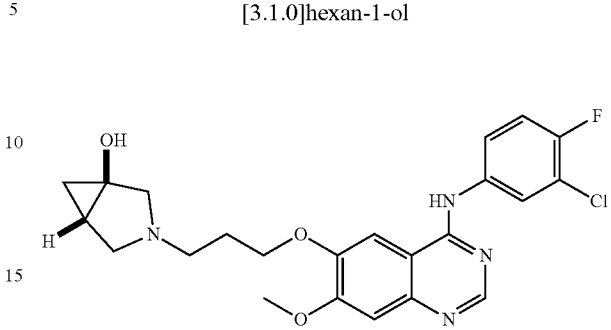

Step 1) methyl 2-aminoacetate

To a solution of glycine (15.00 g, 1.0 eq) in anhydrous MeOH (200 mL) was added SOCl$_2$ (17.4 mL, 1.2 eq) dropwise at 0° C. The mixture was stirred at 0° C. for 15 min, then heated at 65° C. for 4 h and concentrated in vacuo to give the title compound as a white solid (17.80 g, 100%).

Step 2) methyl 2-(benzylamino)acetate

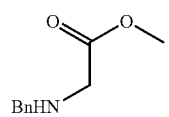

To a solution of methyl 2-aminoacetate hydrochloride (15.00 g, 116.00 mmol, 1.0 eq) in CH$_2$Cl$_2$ (150 mL) was added Et$_3$N (20 mL, 143.3 mmol, 1.2 eq) and PhCHO (14.6 mL, 143.3 mmol, 1.2 eq) in turn. The reaction mixture was stirred at room temperature overnight, and concentrated in vacuo. The residue was diluted with EtOAc and filtered. The filtrate was concentrated in vacuo to afford the crude product methyl 2-(benzylideneamino)acetate, which was used for the next step without further purification. To a solution of methyl 2-(benzylideneamino)acetate in MeOH (200 mL) at −5° C. was added NaBH$_4$ (2.80 g, 72.8 mmol, 0.55 eq) slowly. The reaction mixture was stirred at −5° C. for 2 h. The reaction mixture was then quenched with water and extracted with EtOAc (100 mL×3). The combined organic phases were washed with water followed by brine, dried over anhydrous Na$_2$SO$_4$ and concentrated in vacuo. The residue was purified by a silica gel column chromatography (20:1 (v/v) PE/EtOAc) to afford the title compound as colorless oil (21.30 g, 99%).

Step 3) methyl 2-(allyl(benzyl)amino)acetate

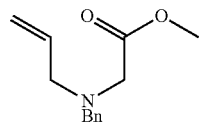 [SMILES: C=CCN(CC(=O)OC)Cc1ccccc1]

To a solution of methyl 2-(benzylamino)acetate (21.30 g, 119.2 mmol, 1.0 eq) in DMF (150 mL) was added anhydrous K$_2$CO$_3$ (8.02 g, 143.02 mmol, 1.2 eq) followed by allyl bromide (12.37 mL, 143.02 mmol, 1.2 eq) at room temperature. The mixture was stirred for 4 h, quenched with water and extracted with EtOAc (100 mL×3). The combined organic phases were washed with water and brine, dried over anhydrous Na$_2$SO$_4$ and concentrated in vacuo. The residue was purified by a silica gel column chromatography (20:1 (v/v) PE/EtOAc) to afford the title compound as colorless oil (18.30 g, 70%). The compound was characterized by the following spectroscopic data: $^1$H NMR (400 MHz, CDCl$_3$) δ: 3.27 (2H, d, J=6.4 Hz), 3.32 (2H, s), 3.68 (3H, s), 3.78 (2H, s), 5.19 (2H, m), 5.88 (1H, m), 7.23-7.35 (5H, m) ppm.

Step 4) (1R,5S)-3-benzyl-3-azabicyclo[3.1.0]hexan-1-ol

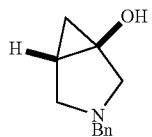 [SMILES: O[C@]12C[C@H]1CN(Cc1ccccc1)C2]

To a solution of methyl 2-(allyl(benzyl)amino)acetate (0.76 g, 3.5 mmol, 1.0 eq) in anhydrous THF (50 mL) at 20° C. under N$_2$ was added ClTi(O$^i$Pr)$_3$ (3.50 mL, 3.50 mmol, 1.0 eq) followed by cyclopentylmagnesium chloride (7.80 mL, 15.6 mmol, 4.5 eq) dropwise via a syringe pump over 4 h. The reaction mixture was quenched with a little of water and extracted with EtOAc (20 mL×3). The combined organic phases were washed with water followed by brine, dried over anhydrous Na$_2$SO$_4$ and concentrated in vacuo. The residue was purified by a silica gel column chromatography (1:1 (v/v) PE/EtOAc) to afford the title compound as colorless oil (0.48 g, 73%). The compound was characterized by the following spectroscopic data: MS (ESI, pos. ion) m/z: 190.2 (M+1); $^1$H NMR (400 MHz, CDCl$_3$) δ: 0.83 (2H, m), 1.09 (1H, t, J=4.8 Hz), 1.36 (1H, m), 2.57 (2H, m), 2.72 (1H, d, J=8.8 Hz), 3.05 (1H, d, J=8.4 Hz), 3.60 (2H, s), 7.25 (5H, m) ppm.

Step 5) (1R,5S)-3-(3-chloropropyl)-3-azabicyclo[3.1.0]hexan-1-ol

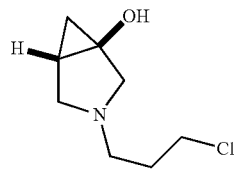 [SMILES: O[C@]12C[C@H]1CN(CCCCl)C2]

To a solution of (1R,5S)-3-benzyl-3-azabicyclo[3.1.0]hexan-1-ol (0.48 g, 2.54 mmol) in MeOH (50 mL) was added 20% Pd(OH)$_2$ (50 mg) at room temperature. The mixture was stirred at rt under H$_2$ overnight and filtered. The filtrate was concentrated in vacuo to give the crude product (1R,5S)-3-azabicyclo[3.1.0]hexan-1-ol, which was used for the next step without further purification. To a solution of the residue in acetone (5 mL) was added anhydrous K$_2$CO$_3$ (0.70 g, 5.08 mmol, 2.0 eq) and 1-bromo-3-chloropropane (0.37 mL, 3.8 mmol, 1.5 eq) in turn. The reaction mixture was heated at 65° C. for 4 h, then cooled to room temperature. To the mixture was added H$_2$O (10 mL) and the mixture was extracted with EtOAc (10 mL×3). The combined organic phases were washed with water and brine, dried over anhydrous Na$_2$SO$_4$ and concentrated in vacuo. The residue was purified by a silica gel column chromatography (30:1 (v/v) CH$_2$Cl$_2$/CH$_3$OH) to give the title compound as colorless oil (116 mg, 25%). The compound was characterized by the following spectroscopic data: MS (ESI, pos. ion) m/z: 175.9 (M+1);

Step 6) (1R,5S)-3-(3-((4-((3-chloro-4-fluorophenyl)amino)-7-methoxyquinazolin-6-yl)oxy)propyl)-3-azabicyclo[3.1.0]hexan-1-ol

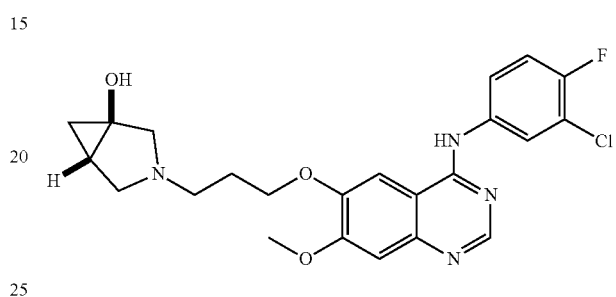

To a mixture of 4-((3-chloro-4-fluorophenyl)amino)-7-methoxyquinazolin-6-ol (136 mg, 0.42 mmol, 1.0 eq) and anhydrous K$_2$CO$_3$ (290 mg, 2.10 mmol, 5.0 eq) in DMF (3 mL) was added a solution of (1R,5S)-3-(3-chloropropyl)-3-azabicyclo[3.1.0]hexan-1-ol (92 mg, 0.52 mmol, 1.2 eq) in DMF (2 mL) at rt. The mixture was heated at 80° C. for 7 h, then cooled to room temperature and quenched with H$_2$O (10 mL). The mixture was diluted with EtOAc (20 mL). The water layer was then extracted with EtOAc (5 mL×3). The combined organic phases were dried over anhydrous Na$_2$SO$_4$ and concentrated in vacuo. The residue was chromatographed with a silica gel column (10:1 (v/v) CH$_2$Cl$_2$/CH$_3$OH) to give the crude product, which was recrystallized from CH$_2$Cl$_2$/PE to afford the title compound as a pale yellow solid (90 mg, 46.70%), HPLC:91.67%. The compound was characterized by the following spectroscopic data: MS (ESI, pos. ion) m/z: 459.2 (M+1); $^1$H NMR (400 MHz, CDCl$_3$) δ: 0.83 (2H, m), 1.09 (1H, t, J=4.8 Hz), 1.36 (1H, m), 2.57 (2H, m), 2.72 (1H, d, J=8.8 Hz), 3.05 (1H, d, J=8.4 Hz), 3.56 (2H, m), 3.80 (2H, m), 3.99 (3H, s), 4.12 (2H, t, J=6.8 Hz), 7.14 (1H, t, J=8.8 Hz), 7.23 (1H, s), 7.29 (1H, d, J=15.8 Hz), 7.60 (1H, m), 7.89 (1H, dd, J=2.5, 6.5 Hz), 8.63 (1H, s) ppm.

Example 5

N-3-chloro-4-fluorophenyl)-6-(3-((1R,5S)-1-(dimethylamino)-3-azabicyclo[3.1.0]hexan-3-yl)propoxy)-7-methoxyquinazolin-4-amine

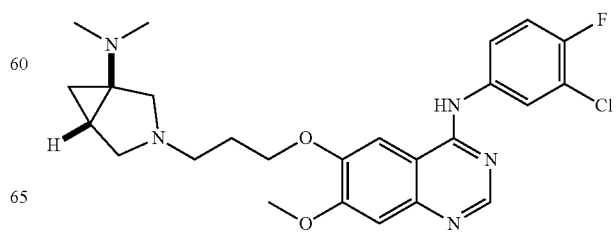

Step 1) 2-(allyl(benzyl)amino)-N,N-dimethylacetamide

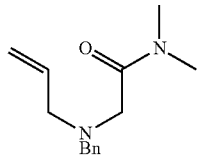 [SMILES: C=CCN(CC(=O)N(C)C)Cc1ccccc1]

To a solution of dimethylamine hydrochloride (2.08 g, 25.5 mmol, 8.0 eq) in anhydrous toluene (10 mL) at 5° C. under N₂ was added trimethyl aluminum (1.0M in toluene, 25.5 mL, 25.5 mmol, 8.0 eq) dropwise over 1 h. The reaction mixture was heated to 20° C. and stirred for another 2 h. To a mixture of methyl 2-(allyl(benzyl)amino)acetate (0.70 g, 3.19 mmol, 1.0 eq) in anhydrous toluene (50 mL) and THF (15 mL) at 5° C. was added the above reaction mixture and the reaction mixture was heated at 70° C. for 48 h. Then the mixture was cooled to 0° C. and quenched with a small amount of water. The organic phase was separated from the mixture, and the water phase was extracted with EtOAc (10 mL×3). The combined organic phases were washed with brine, dried over anhydrous Na₂SO₄ and filtrated. The filtrate was concentrated in vacuo and the residue was chromatographed with a silica gel column (50:1 (v/v) CH₂Cl₂/CH₃OH) to afford the title compound as colorless oil (0.62 g, 77%). The compound was characterized by the following spectroscopic data: MS (ESI, pos. ion) m/z: 233.3 (M+1); ¹H NMR (400 MHz, CDCl₃) δ: 2.86 (3H, s), 2.94 (3H, s), 3.16 (2H, d, J=6.8 Hz), 3.24 (2H, s), 5.16 (2H, m), 5.86 (1H, m), 7.18-7.27 (5H, m) ppm.

Step 2) (1R,5S)-3-benzyl-N,N-dimethyl-3-azabicyclo[3.1.0]hexan-1-amine

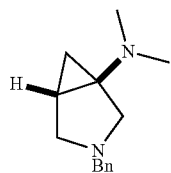 [SMILES: CN(C)[C@]12C[C@H]1CN(Cc1ccccc1)C2]

To a solution of 2-(allyl(benzyl)amino)-N,N-dimethylacetamide (0.57 g, 2.45 mmol, 1.0 eq) in anhydrous THF (25 mL) at room temperature under N₂ was added ClTi(O$^i$Pr)₃ (2.45 mL, 2.45 mmol, 1.0 eq) followed by i-PrMgBr (1.0M in ether, 11.0 mL, 11.0 mmol, 4.5 eq) via a syringe pump over 1 h. The reaction mixture was stirred for another 2 h, and then quenched with a small amount of water. The mixture was extracted with EtOAc (20 mL×3), the combined organic phases were washed with water and brine, dried over anhydrous Na₂SO₄ and filtered. The filtrate was concentrated in vacuo and the residue was purified by a silica gel column chromatography (30:1 (v/v) CH₂Cl₂/CH₃OH) to give the title compound as colorless oil (0.33 g, 63%). The compound was characterized by the following spectroscopic data: MS (ESI, pos. ion) m/z: 217.35 (M+1).

Step 3) (1R,5S)-3-(3-chloropropyl)-N,N-dimethyl-3-azabicyclo[3.1.0]hexan-1-amine

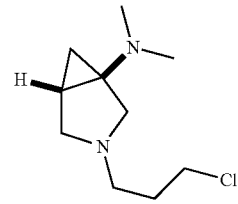

To a solution of (1R,5S)-3-benzyl-N,N-dimethyl-3-azabicyclo[3.1.0]hexan-1-amine (0.28 g, 1.29 mmol) in MeOH (20 mL) was added 20% Pd(OH)₂ (30 mg). The mixture was stirred at rt under H₂ overnight and filtered. The filtrate was concentrated in vacuo to give the crude product (1R,5S)—N,N-dimethyl-3-azabicyclo[3.1.0]hexan-1-amine (0.16 g), which was used for the next step without further purification. To a solution of (1R,5S)—N,N-dimethyl-3-azabicyclo[3.1.0]hexan-1-amine in acetone (5 mL) was added anhydrous K₂CO₃ (0.35 g, 2.54 mmol, 2.0 eq) and 1-bromo-3-chloropropane (0.20 mL, 1.91 mmol, 1.5 eq) in turn. The reaction mixture was heated at 65° C. for 4 h, and then cooled to rt. To the reaction mixture was added water (5 mL) and the mixture was extracted with EtOAc (10 mL×3). The combined organic phases were washed with water and brine, dried over anhydrous Na₂SO₄ and filtered. The filtrate was concentrated in vacuo and the residue was purified by a silica gel column chromatography (30:1 (v/v) CHCl₃/CH₃OH) to give the title compound as colorless oil (103 mg, 40%). The compound was characterized by the following spectroscopic data: MS (ESI, pos. ion) m/z: 203.2 (M+1).

Step 4) N-(3-chloro-4-fluorophenyl)-6-(3-((1R,5S)-1-(dimethylamino)-3-azabicyclo[3.1.0]hexan-3-yl)propoxy)-7-methoxyquinazolin-4-amine

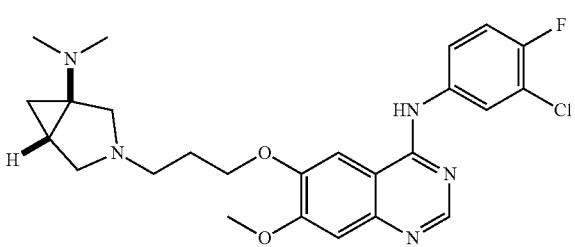 [SMILES: COc1cc2ncnc(Nc3ccc(F)c(Cl)c3)c2cc1OCCCN1C[C@@H]2C[C@]2(N(C)C)C1]

To a mixture of 4-((3-chloro-4-fluorophenyl)amino)-7-methoxyquinazolin-6-ol (136 mg, 0.42 mmol, 1.0 eq) and anhydrous K₂CO₃ (290 mg, 2.10 mmol, 5.0 eq) in DMF (3 mL) was added a solution of (1R,5S)-3-(3-chloropropyl)-N,N-dimethyl-3-azabicyclo[3.1.0]hexan-1-amine (103 mg, 0.52 mmol, 1.2 eq) in DMF (2 mL) at room temperature. The reaction mixture was heated at 80° C. for 11 h and cooled to room temperature. Then the reaction mixture was quenched with water (5 mL) and diluted with EtOAc (10 mL). The organic phase was separated from the mixture, and the water phase was extracted with EtOAc (5 mL×3). The combined organic phases were, dried over anhydrous Na₂SO₄ and filtered. The filtrate was concentrated in vacuo, and the residue was purified by a silica gel column chromatography (10:1 (v/v)CH₂Cl₂/CH₃OH) to give the crude product, which was then recrystallized from CH₂Cl₂/PE to afford title compound as a yellow solid (138 mg, 67.7%), HPLC: 96.5%. The compound was characterized by the following spectroscopic data: MS (ESI, pos. ion) m/z: 486.2 (M+1); ¹H NMR (400 MHz, CDCl₃) δ: 0.81 (1H, m), 1.11 (1H, m), 1.26 (1H, br s), 1.52 (1H, m), 2.38 (6H, s), 2.65-2.81 (3H, m), 3.11 (2H, m), 3.42 (1H, br s), 3.98 (3H, s), 4.18 (2H, t, J=6.8 Hz), 7.14 (1H, t, J=8.8 Hz), 7.25 (1H, d, J=14.4 Hz), 7.41 (1H, s), 7.66 (1H, m), 7.98 (1H, dd, J=5.2, 6.8 Hz), 8.64 (1H, s) ppm.

Example 6

N-(3-chloro-4-fluorophenyl)-7-methoxy-6-(3-(tetrahydro-2H-[1,4]dioxino[2,3-c]pyrrol-6(3H)-yl) propoxy)quinazolin-4-amine

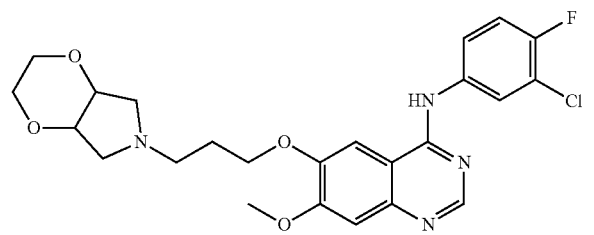 [SMILES: COc1cc2ncnc(Nc3ccc(F)c(Cl)c3)c2cc1OCCCN1CC2OCCOC2C1]

Step 1) benzyl 3,4-dihydroxypyrrolidine-1-carboxylate

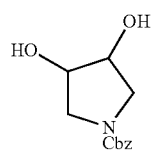

To a solution of N-carbobenzoxy-3-pyrroline (1.00 g, 4.92 mmol, 1.0 eq) in acetone (20 mL) was added NMO (1.0 g, 7.38 mmol, 1.5 eq) followed by OsO₄ (cat. 10 mg in 1 mL ⁱPrOH). The mixture was stirred for 3 h. To this, saturated NaHSO₃ aqueous solution (5 mL) was added, and the mixture was stirred for another 0.5 h. The organic phase was separated from the mixture, and the water phase was extracted with EtOAc (20 mL×3). The combined organic phases were dried over anhydrous Na₂SO₄ and filtered. The filtrate was concentrated in vacuo and the residue was purified by a silica gel column chromatography (EtOAc) to give the compound as colorless oil (1.16 g, 100%).

Step 2) benzyl tetrahydro-2H-[1,4]dioxino[2,3-c]pyrrole-6(3H)— carboxylate

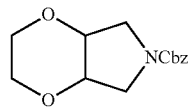 [SMILES: O=C(OCc1ccccc1)N1CC2OCCOC2C1]

A mixture of NaOH aqueous solution (35 w/w %, 21 mL, aq.), ClCH₂CH₂Cl (21 mL), benzyl 3,4-dihydroxypyrrolidine-1-carboxylate (1.16 g, 4.9 mmol, 1.0 eq) and TBAB (0.31 g, 0.98 mmol, 0.2 eq) was heated at 55° C. for 48 h in a round-bottom flask. The reaction mixture was cooled to room temperature and poured into water (50 mL), extracted with EtOAc (50 mL). The organic phase was separated from the mixture, and the water phase was extracted with EtOAc (20 mL×3). The combined organic phases were dried over anhydrous Na₂SO₄ and filtered. The filtrate was concentrated in vacuo and the residue was purified with a silica gel column chromatography (1:1 (v/v) PE/EtOAc) to give the product as colorless oil (0.50 g, 39%).

Step 3) hexahydro-2H-[1,4]dioxino[2,3-c]pyrrole

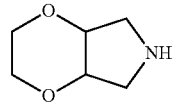

To a solution of benzyl tetrahydro-2H-[1,4]dioxino[2,3-c]pyrrole-6(3H)-carboxylate (0.46 g, 1.94 mmol) in MeOH (20 mL) was added two drops of HCO₂H followed by 20% Pd(OH)₂ (50 mg). The reaction mixture was stirred under H₂ for 4 h at rt and was filtered. The filtrate was concentrated in vacuo to give the crude product, which was used for the next step without further purification.

Step 4) N-(3-chloro-4-fluorophenyl)-7-methoxy-6-(3-(tetrahydro-2H-[1,4]dioxino[2,3-c]pyrrol-6(3H)-yl)propoxy)quinazolin-4-amine A mixture of hexahydro-2H-[1,4]dioxino[2,3-c]pyrrole (1.0 eq), N-(3-chloro-4-fluorophenyl)-6-(3-chloropropoxy)-7-methoxyquinazolin-4-amine (710 mg, 1.8 mmol, 0.95 eq), K₂CO₃ (524 mg, 3.8 mmol, 2.0 eq) and KI (16 mg, 0.095 mmol, 0.05 eq) in DMF (12 mL) was heated at 60° C. for 3 h and cooled to room temperature. The reaction mixture was quenched with water (10 mL) and diluted with EtOAc (20 mL). The organic phase was separated from the mixture, and the water phase was extracted with EtOAc (20 mL×3). The combined organic phases were dried over anhydrous Na$_2$SO$_4$ and concentrated in vacuo. The residue was purified by a silica gel column chromatography (20:1 (v/v) CH$_2$Cl$_2$/CH$_3$OH) to give the crude product, which was recrystallized from CH$_2$Cl$_2$/PE to afford the title compound as a grayish-white solid (230 mg, 25.00%), HPLC: 99.11%. The compound was characterized by the following spectroscopic data: MS (ESI, pos. ion) m/z: 489.9 (M+1); $^1$H NMR (400 MHz, CDCl$_3$) δ: 2.09 (2H, m), 2.74 (4H, m), 2.99 (2H, dd, J=3.3, 10.4 Hz), 3.56 (2H, m), 3.80 (2H, m), 3.99 (3H, s), 4.12 (2H, t, J=3.5 Hz), 4.22 (2H, t, J=6.8 Hz), 7.14 (1H, t, J=8.8 Hz), 7.23 (1H, s), 7.29 (1H, d, J=15.8 Hz), 7.60 (1H, m), 7.89 (1H, dd, J=2.5, 6.5 Hz), 8.63 (1H, s) ppm.

Example 7

N-(4-fluorophenyl)-7-methoxy-6-(3-(tetrahydro-2H-[1,4]dioxino[2,3-c]pyrrol-6(3H)-yl)propoxy)quinazolin-4-amine

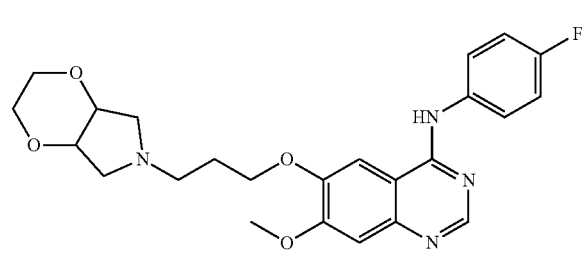 [SMILES: COc1cc2ncnc(Nc3ccc(F)cc3)c2cc1OCCCN1CC2OCCOC2C1]

Step 1) 4-((4-fluorophenyl)amino)-7-methoxyquinazolin-6-yl acetate

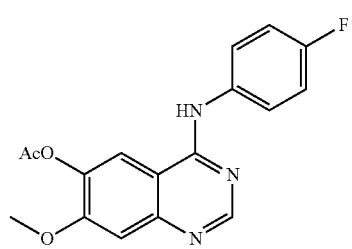 [SMILES: COc1cc2ncnc(Nc3ccc(F)cc3)c2cc1OC(C)=O]

A suspension of 4-chloro-7-methoxyquinazolin-6-yl acetate (2.17 g), 4-fluoroaniline (1.00 mL) and isopropanol (40 mL) was stirred at 83° C. overnight. The reaction mixture was cooled to room temperature and filtered, the residue was washed with 100 mL of isopropanol and dried to afford the desired compound as a solid (2.42 g, 85.90%)

Step 2) 4-((4-fluorophenyl)amino)-7-methoxyquinazolin-6-ol

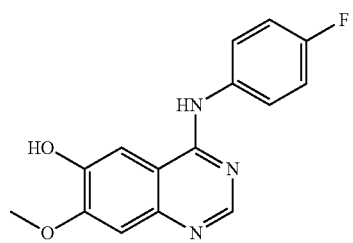 [SMILES: COc1cc2ncnc(Nc3ccc(F)cc3)c2cc1O]

To a suspension of 4-((4-fluorophenyl)amino)-7-methoxyquinazolin-6-yl acetate (2.42 g) and methanol (30 mL) was added 5 mol/L NaOH (5.00 mL) at room temperature. The reaction mixture was stirred at room temperature for 4 h, and was adjusted to pH 7 with 0.1 N HCl (aq). The mixture was filtered to give the title compound as a white solid (1.83 g, 86.90%).

Step 3) N-(4-fluorophenyl)-6-(3-chloropropoxy)-7-methoxyquinazolin-4-amine

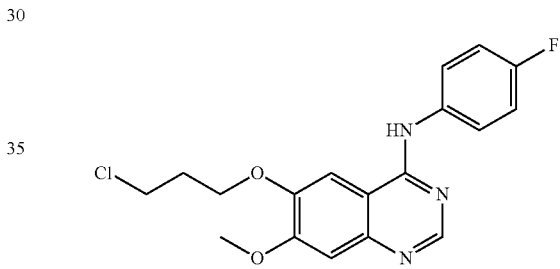

To a suspension of 4-((4-fluorophenyl)amino)-7-methoxyquinazolin-6-ol (1.83 g), K$_2$CO$_3$ (2.21 g), in DMF (20 mL) was added 1-bromo-3-chloropropane (1.90 mL) at rt, the mixture was stirred at 40° C. overnight. The reaction mixture was poured into water and filtered. The filter residue was purified by a silica gel column chromatography (eluting agent: 3:1 (v/v) PE/EA) to give the title compound as a white solid (2.11 g, 91.02%).

Step 4) N-(4-fluorophenyl)-7-methoxy-6-(3-(tetrahydro-2H-[1,4]dioxino[2,3-c]pyrrol-6(3H)-yl) propoxy) quinazolin-4-amine

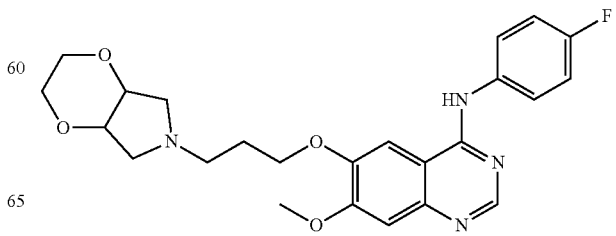

A mixture of hexahydro-2H-[1,4]dioxino[2,3-c]pyrrole (0.39 g, 3.0 mmol, 1.0 eq), N-(4-fluorophenyl)-6-(3-chloropropoxy)-7-methoxyquinazolin-4-amine (868 mg, 2.40 mmol, 0.80 eq), anhydrous K₂CO₃ (2.07 g, 15.0 mmol, 5.0 eq) and tetrabutylammonium iodide (55 mg, 0.15 mmol, 0.05 eq) in DMF (10 mL) was heated at 70° C. for 11 h. The reaction mixture was cooled to room temperature and quenched with water (10 mL). The resulted mixture was diluted with EtOAc (20 mL) and the organic phase was separated from the mixture. The water phase was extracted with EtOAc (20 mL×3). The combined organic phases were dried over anhydrous Na₂SO₄ and concentrated in vacuo. The residue was purified by a silica gel column chromatography (20:1 (v/v) CH₂Cl₂/CH₃OH) to give the crude product, which was recrystallized from CH₂Cl₂/PE to afford the title compound as a pale yellow solid (196 mg, 22.00%), HPLC:96.21%. The compound was characterized by the following spectroscopic data: MS (ESI, pos. ion) m/z: 455.2 (M+1); $^1$H NMR (400 MHz, CDCl₃) δ: 2.00 (2H, m), 2.63 (2H, m), 2.72 (2H, m), 2.90 (2H, dd, J=2.8, 6.1 Hz), 3.28 (1H, br s), 3.52 (2H, m), 3.76 (2H, m), 3.91 (3H, s), 4.05 (4H, d, J=4.4 Hz), 7.03 (1H, t, J=8.4 Hz), 7.18 (1H, s), 7.29 (1H, s), 7.63 (1H, dd, J=4.8, 8.4 Hz), 8.42 (1H, br s), 8.60 (1H, s) ppm.

Example 8

N-(3-ethynylphenyl)-7-methoxy-6-(3-(tetrahydro-2H-[1,4]dioxino[2,3-c]pyrrol-6(3H)-yl)propoxy)quinazolin-4-amine

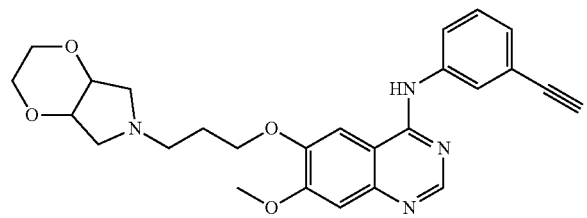 [SMILES: C#Cc1cccc(Nc2ncnc3cc(OC)c(OCCCN4CC5OCCOC5C4)cc23)c1]

Step 1) 4-((3-ethynylphenyl)amino)-7-methoxyquinazolin-6-yl acetate

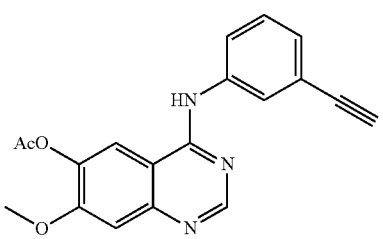 [SMILES: C#Cc1cccc(Nc2ncnc3cc(OC)c(O)cc23)c1]

A suspension of 4-chloro-7-methoxyquinazolin-6-yl acetate (4.31 g), 3-ethynylaniline (3.00 g) and isopropanol (65 mL) was stirred at 83° C. overnight. The reaction mixture was cooled to room temperature and filtered, the residue was washed with 100 mL of isopropanol and dried to afford the desired compound as a solid (4.89 g, 85.90%)

Step 2) 4-((3-ethynylphenyl)amino)-7-methoxyquinazolin-6-ol

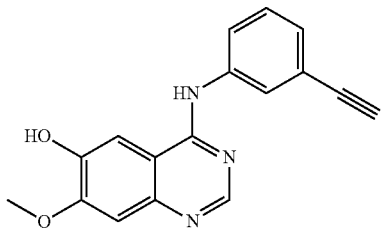

To a suspension of 4-((3-ethynylphenyl)amino)-7-methoxyquinazolin-6-yl acetate (4.54 g) and methanol (30 mL) was added 5 mol/L NaOH (10.00 mL) at room temperature. The reaction mixture was stirred at room temperature for 5 h, and was adjusted to pH 7 with 0.1 N HCl (aq). The mixture was filtered to give the title compound as a white solid (3.30 g, 86.00%).

Step 3) N-(3-ethynylphenyl)-6-(3-chloropropoxy)-7-methoxyquinazolin-4-amine

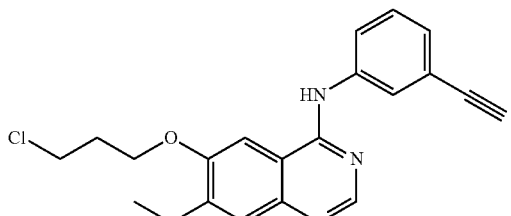

To a suspension of 4-((3-ethynylphenyl)amino)-7-methoxyquinazolin-6-ol (5.59 g), K₂CO₃ (7.06 g) in DMF (60 mL) was added 1-bromo-3-chloropropane (6.06 mL) at rt, the mixture was stirred at 40° C. for 6 h. The reaction mixture was poured into water and filtered. The filter residue was purified by a silica gel column chromatography (eluting agent: 3:1 (v/v) PE/EA) to give the title compound as a white solid (5.80 g, 77.00%).

Step 4) N-(3-ethynylphenyl)-7-methoxy-6-(3-(tetrahydro-2H-[1,4]dioxino[2,3-c]pyrrol-6(3H)-yl)propoxy)quinazolin-4-amine

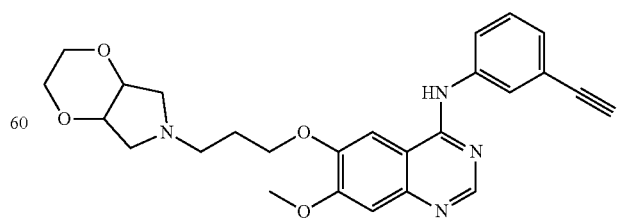

A mixture of hexahydro-2H-[1,4]dioxino[2,3-c]pyrrole (0.31 g, 2.40 mmol, 1.20 eq), N-(3-ethynylphenyl)-6-(3-chloropropoxy)-7-methoxyquinazolin-4-amine (0.74 g, 2.00 mmol, 1.00 eq), anhydrous K$_2$CO$_3$ (1.00 g, 7.20 mmol, 3.60 eq) and tetrabutylammonium iodide (37 mg, 0.10 mmol, 0.05 eq) in DMF (8 mL) was heated at 70° C. for 11 h. The reaction mixture was cooled to room temperature and quenched with water (10 mL). The resulted mixture was diluted with EtOAc (20 mL) and the organic phase was separated from the mixture. The water phase was extracted with EtOAc (20 mL×3). The combined organic phases were dried over anhydrous Na$_2$SO$_4$ and concentrated in vacuo. The residue was purified by a silica gel column chromatography (20:1 (v/v) CH$_2$Cl$_2$/CH$_3$OH) to give the crude product, which was recrystallized from CH$_2$Cl$_2$/PE to afford the title compound as a pale yellow solid (0.46 g, 50.00%), HPLC: 96.10%. The compound was characterized by the following spectroscopic data: MS (ESI, pos. ion) m/z: 461.2 (M+1); $^1$H NMR (400 MHz, CDCl$_3$) δ: 1.98 (3H, s), 2.09 (2H, m), 2.73 (2H, m), 2.78 (2H, m), 2.97 (2H, dd, J=4.4, 10.4 Hz), 3.09 (1H, s), 3.55 (2H, m), 3.79 (2H, m), 3.99 (3H, s), 4.11 (2H, m), 4.22 (2H, t, J=6.8 Hz), 7.24 (2H, m), 7.25-7.28 (1H, m), 7.35 (1H, t, J=8.0 Hz), 7.67 (1H, br s), 7.80 (1H, m), 786 (1H, m) ppm.

Example 9

N-(3-ethynyl-4-fluorophenyl)-7-methoxy-6-(3-(tetrahydro-2H-[1,4]dioxino[2,3-c]pyrrol-6(3H)-yl) propoxy)quinazolin-4-amine

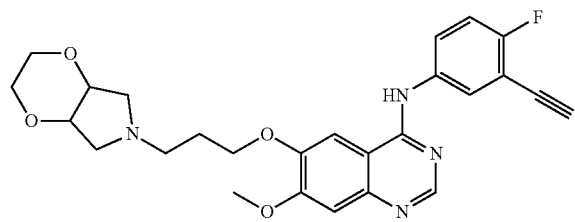 [SMILES: C#Cc1cc(Nc2ncnc3cc(OC)c(OCCCN4CC5OCCOC5C4)cc23)ccc1F]

Step 1) 4-((3-ethynyl-4-fluorophenyl)amino)-7-methoxyquinazolin-6-yl acetate

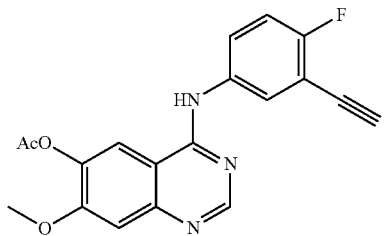

A suspension of 4-chloro-7-methoxyquinazolin-6-yl acetate (4.31 g), 3-ethynyl-4-fluoroaniline (2.77 g) and isopropanol (65 mL) was stirred at 83° C. overnight. The reaction mixture was cooled to room temperature and filtered, the residue was washed with 100 mL of isopropanol and dried to afford the desired compound as a solid (5.29 g, 88.30%).

Step 2) 4-((3-ethynyl-4-fluorophenyl)amino)-7-methoxyquinazolin-6-ol

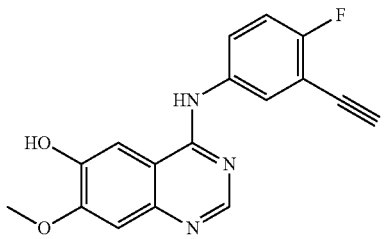 [SMILES: C#Cc1cc(Nc2ncnc3cc(OC)c(OC(C)=O)cc23)ccc1F]

To a suspension of 4-((3-ethynyl-4-fluorophenyl)amino)-7-methoxyquinazolin-6-yl acetate (5.29 g) and methanol (30 mL) was added 5 mol/L NaOH (10.00 mL) at room temperature. The reaction mixture was stirred at room temperature for 4 h, and was adjusted to pH 7 with 0.1 N HCl (aq). The mixture was filtered to give the title compound as a white solid (3.90 g, 83.69%).

Step 3) N-(3-ethynyl-4-fluorophenyl)-6-(3-chloropropoxy)-7-methoxyquinazolin-4-amine

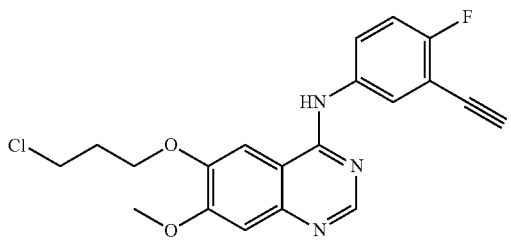 [SMILES: C#Cc1cc(Nc2ncnc3cc(OC)c(OCCCCl)cc23)ccc1F]

To a suspension of 4-((3-ethynyl-4-fluorophenyl)amino)-7-methoxyquinazolin-6-ol (3.90 g), K$_2$CO$_3$ (4.36 g) in DMF (30 mL) was added 1-bromo-3-chloropropane (3.80 mL) at rt, the mixture was stirred at 40° C. overnight. The reaction mixture was poured into water and filtered. The filter residue was purified by a silica gel column chromatography (eluting agent: 3:1 (v/v) PE/EA) to give the title compound as a white solid (3.30 g, 68.00%).

Step 4) N-(3-ethynyl-4-fluorophenyl)-7-methoxy-6-(3-(tetrahydro-2H-[1,4]dioxino[2,3-c]pyrrol-6(3H)-yl) propoxy)quinazolin-4-amine

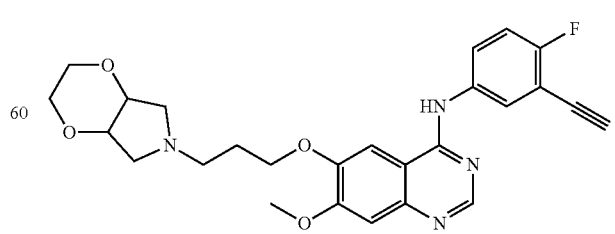

A mixture of hexahydro-2H-[1,4]dioxino[2,3-c]pyrrole (0.40 g, 3.01 mmol, 1.0 eq), N-(3-ethynyl-4-fluorophenyl)-

6-(3-chloropropoxy)-7-methoxyquinazolin-4-amine (0.87 g, 2.25 mmol, 0.75 eq), anhydrous K$_2$CO$_3$ (1.24 g, 9.0 mmol, 3.0 eq) and tetrabutylammonium iodide (55 mg, 0.15 mmol, 0.05 eq) in DMF (10 mL) was heated at 70° C. for 11 h. The reaction mixture was cooled to room temperature and quenched with water (10 mL). The resulted mixture was diluted with EtOAc (20 mL) and the organic phase was separated from the mixture. The water phase was extracted with EtOAc (20 mL×3). The combined organic phases were dried over anhydrous Na$_2$SO$_4$ and filtered. The filtrate was concentrated in vacuo and the residue was purified by a silica gel column chromatography (20:1 (v/v) CH$_2$Cl$_2$/CH$_3$OH) to give the crude product, which was recrystallized from CH$_2$Cl$_2$/PE to afford the title compound as a pale yellow solid (0.47 g, 44.00%), HPLC: 96.10%. The compound was characterized by the following spectroscopic data: MS (ESI, pos. ion) m/z: 480.1 (M+1); $^1$H NMR (400 MHz, CDCl$_3$) δ: 2.05 (2H, m), 2.68 (2H, m), 2.72 (2H, m), 2.95 (2H, dd, J=3.6, 10.0 Hz), 3.06 (1H, br s), 3.56 (2H, m), 3.76 (2H, m), 3.95 (3H, s), 4.08 (2H, m), 4.15 (2H, t, J=8.4 Hz), 7.20 (1H, t, J=8.8 Hz), 8.07-8.15 (2H, m), 8.43 (1H, s), 8.64 (1H, s) ppm.

Example 10

N-(4-bromo-2-fluorophenyl)-7-methoxy-6-(3-(tetrahydro-2H-[1,4]dioxino[2,3-c]pyrrol-6(3H)-yl) propoxy)quinazolin-4-amine

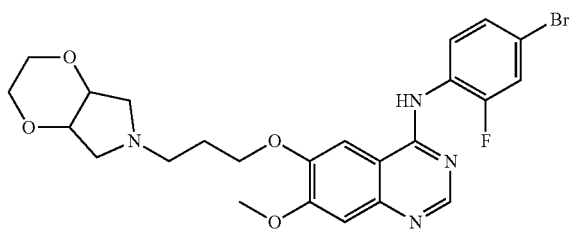 [SMILES: COc1cc2ncnc(Nc3ccc(Br)cc3F)c2cc1OCCCN1CC2OCCOC2C1]

Step 1) 4-((4-bromo-2-fluorophenyl)amino)-7-methoxyquinazolin-6-yl acetate

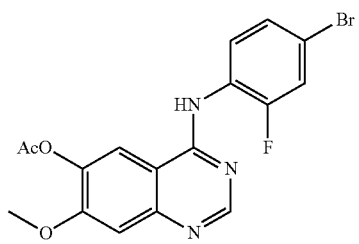 [SMILES: COc1cc2ncnc(Nc3ccc(Br)cc3F)c2cc1OC(C)=O]

A suspension of 4-chloro-7-methoxyquinazolin-6-yl acetate (2.05 g), 4-bromo-2-fluoroaniline (2.11 g, 1.30 eq) and isopropanol (40 mL) was stirred at 83° C. overnight. The reaction mixture was cooled to room temperature and filtered, the residue was washed with 100 mL of isopropanol and dried to afford the desired compound as a solid (2.78 g, 84.50%).

Step 2) 4-((4-bromo-2-fluorophenyl)amino)-7-methoxyquinazolin-6-ol

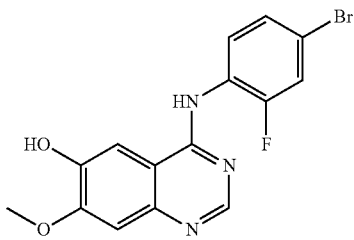 [SMILES: COc1cc2ncnc(Nc3ccc(Br)cc3F)c2cc1O]

To a suspension of 4-((4-bromo-2-fluorophenyl)amino)-7-methoxyquinazolin-6-yl acetate (2.78 g) and methanol (30 mL) was added 5 mol/L NaOH (5.00 mL) at room temperature. The reaction mixture was stirred at room temperature for 4 h, and was adjusted to pH 7 with 0.1 N HCl (aq). The mixture was filtered to give the title compound as a white solid (2.17 g, 87.15%).

Step 3) N-(4-bromo-2-fluorophenyl)-6-(3-chloropropoxy)-7-methoxyquinazolin-4-amine

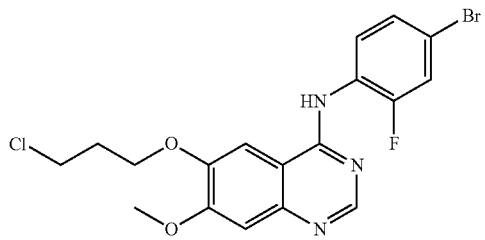 [SMILES: COc1cc2ncnc(Nc3ccc(Br)cc3F)c2cc1OCCCCl]

To a suspension of 4-((4-bromo-2-fluorophenyl)amino)-7-methoxyquinazolin-6-ol (2.17 g), K$_2$CO$_3$ (0.99 g) in DMF (20 mL) was added 1-bromo-3-chloropropane (0.71 mL) at rt, the mixture was stirred at 40° C. overnight. The reaction mixture was poured into water and filtered. The filter residue was purified by a silica gel column chromatography (eluting agent: 3:1 (v/v) PE/EA) to give the title compound as a white solid (2.18 g, 82.89%).

Step 4) N-(4-bromo-2-fluorophenyl)-7-methoxy-6-(3-(tetrahydro-2H-[1,4]dioxino[2,3-c]pyrrol-6(3H)-yl)propoxy)quinazolin-4-amine

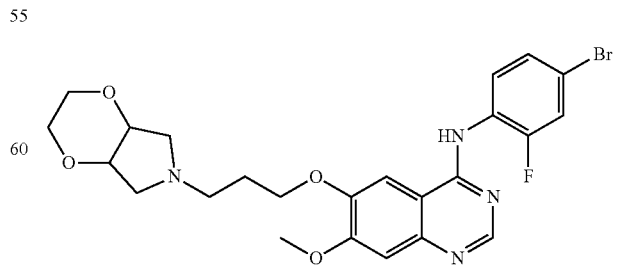

A mixture of 6-(3-chloropropyl)hexahydro-2H-[1,4]dioxino[2,3-c]pyrrole (0.58 g, 2.82 mmol, 1.2 eq), 4-((2-fluoro- 4-bromophenyl)amino)-7-methoxyquinazolin-6-ol (0.49 g, 1.35 mmol, 1.0 eq), anhydrous K₂CO₃ (0.56 g, 4.05 mmol, 3.0 eq) and tetrabutylammonium iodide (25 mg, 0.06 mmol, 0.05 eq) in DMF (8 mL) was heated at 80° C. for 11 h. The reaction mixture was cooled to room temperature and quenched with water (10 mL). The resulted mixture was diluted with EtOAc (20 mL) and the organic phase was separated from the mixture. The water phase was extracted with EtOAc (20 mL×3). The combined organic phases were dried over anhydrous Na₂SO₄ and filtered. The filtrate was concentrated in vacuo and the residue was purified by a silica gel column chromatography (20:1 (v/v) CH₂Cl₂/CH₃OH) to give the crude product, which was recrystallized from CH₂Cl₂/PE to afford the title compound as a pale yellow solid (0.39 g, 54.00%), HPLC: 96.20%. The compound was characterized by the following spectroscopic data: MS (ESI, pos. ion) m/z: 535.1 (M+1); ¹H NMR (400 MHz, CDCl₃) δ: 2.13 (2H, m), 2.77 (2H, t, J=7.2 Hz), 2.84 (2H, dd, J=6.4, 10.4 Hz), 2.95 (2H, dd, J=4.0, 10.4 Hz), 3.56 (2H, m), 3.80 (2H, m), 4.02 (3H, s), 4.10 (2H, m), 4.25 (2H, t, J=6.4 Hz), 7.13 (1H, s), 7.26-7.37 (3H, m), 8.38 (1H, t, J=8.4 Hz), 8.67 (1H, s) ppm.

Example 11

N-(3-chloro-4-fluorophenyl)-6-(3-(hexahydropyrrolo[3,4-c]pyrrol-2(1H)-yl)propoxy)-7-methoxyquinazolin-4-amine

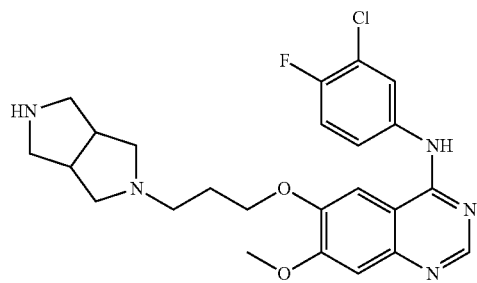 [SMILES: COc1cc2ncnc(Nc3ccc(F)c(Cl)c3)c2cc1OCCCN1CC2CNCC2C1]

Step 1) 5-benzyltetrahydropyrrolo[3,4-c]pyrrole-1,3(2H,3aH)-dione

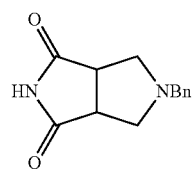 [SMILES: O=C1NC(=O)C2CN(Cc3ccccc3)CC12]

To a suspension of TFA (1.02 g) and 1H-Pyrrole-2,5-dione (10.22 g) in CH₂Cl₂ (250 mL) at −5° C. was added a solution of N-(methoxymethyl)-N-(trimethylsilylmethyl)benzylamine (29.99 g) in CH₂Cl₂ (20 mL) dropwise over 1 h. The reaction mixture was stirred at room temperature for another 5 h and evaporated in vacuo. The residue was stirred in the mixed solvent (EA: PE=3:7) at −10° C. for 1 h, and the mixture was filtered to afford the title compound as a white solid (10.18 g, 42.00%).

Step 2) 2-benzyloctahydropyrrolo[3,4-c]pyrrole

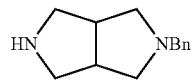

To a suspension of 5-benzyltetrahydropyrrolo[3,4-c]pyrrole-1,3(2H,3aH)-dione (3.88 g) in THF (80 mL) at −5° C. was added LiAlH₄ (1.92 g) slowly. The reaction mixture was heated to reflux for 4 h, and then quenched with water, the mixture was extracted with EtOAc. The organic phase was dried over anhydrous Na₂SO₄ for 1 h and filtered. The filtrate was concentrated in vacuo and the residue was chromatographed with a silica gel column (eluting agent: 200:30:1 (v/v) DCM/MeOH/NH₃H₂O) to give the title compound as oil (2.07 g, 61.00%).

Step 3) tert-butyl 5-benzylhexahydropyrrolo[3,4-c]pyrrole-2(1H)— carboxylate

To a solution of 3-benzyl-3,7-diazabicyclo[3.3.0]octane (3.41 g) in CH₂Cl₂ (50 mL) at 0° C. was added (Boc)₂O (5.15 g) dropwise. The reaction mixture was stirred overnight at rt and washed with water. The water layer was extracted with CH₂Cl₂. The combined organic phases were dried over anhydrous Na₂SO₄ for 1 h and filtered. The filtrate was concentrated in vacuo and the residue was chromatographed with a silica gel column (eluting agent: 50:1 (v/v) EA/MeOH) to give the compound as oil (2.50 g, 49.00%).

Step 4) tert-butyl hexahydropyrrolo[3,4-c]pyrrole-2(1H)-carboxylate

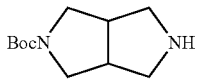

To a solution of tert-butyl 5-benzylhexahydropyrrolo[3,4-c]pyrrole-2(1H)-carboxylate (2.50 g) in MeOH (100 mL) was added a catalytic amount of Pd(OH)₂. The suspension was stirred under H₂ overnight and filtered. The filtrate was concentrated in vacuo and the residue was chromatographed with a silica gel column (eluting agent: 7:1 (v/v) DCM/MeOH) to give the compound as oil (1.60 g, 90.00%).

Step 5) tert-butyl 5-(3-((4-((3-chloro-4-fluorophenyl)amino)-7-methoxyquinazolin-6-yl)oxy)propyl)hexahydropyrrolo[3,4-c]pyrrole-2 (1H)-carboxylate

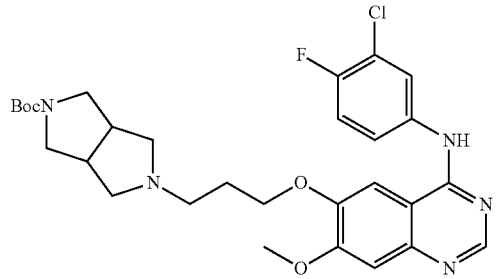 [SMILES: COc1cc2ncnc(Nc3ccc(F)c(Cl)c3)c2cc1OCCCN1CC2CN(C(=O)OC(C)(C)C)CC2C1]

To a mixture of N-(3-chloro-4-fluorophenyl)-6-(3-chloropropoxy)-7-methoxyquinazolin-4-amine (2.1 g), K₂CO₃ (1.46 g) and a catalytic amount of KI in DMF (20 mL) was added tert-butyl hexahydropyrrolo[3,4-c]pyrrole-2(1H)-carboxylate (1.58 g). The reaction mixture was continued to stir at 80° C. for 8 h, diluted with water and extracted with CH₂Cl₂. The organic phase was dried over anhydrous Na₂SO₄ for 1 h and filtered. The filtrate was concentrated in vacuo and the residue was chromatographed with a silica gel column (developing agent: 10:1 (v/v) DCM/MeOH, eluting agent: 30:1 (v/v) DCM/MeOH) to afford the title compound as a white solid (1.70 g, 56.00%).

Step 6) N-(3-chloro-4-fluorophenyl)-6-(3-(hexahydropyrrolo[3,4-c]pyrrol-2(1H)-yl)propoxy)-7-methoxyquinazolin-4-amine

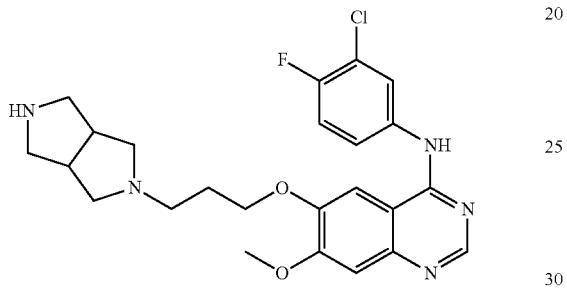

To a solution of tert-butyl 5-(3-((4-((3-chloro-4-fluorophenyl)amino)-7-methoxyquinazolin-6-yl)oxy)propyl)hexahydropyrrolo[3,4-c]pyrrole-2(1H)-carboxylate (1.70 g) in DCM (30 mL) was added a solution of HCl in EtOAc. The reaction mixture was stirred at room temperature for 6 h and filtered to obtain the crude product. The crude product was recrystallized from MeOH/EA to give the title compound as a white solid (1.30 g, 80.00%), HPLC: 85.68%. The compound was characterized by the following spectroscopic data: MS (ESI, pos. ion) m/z: 472.2 (M+1); ¹H NMR (400 MHz, CDCl₃) δ: 1.81-1.88 (m, 4H), 2.35-2.43 (m, 6H), 2.68-2.74 (m, 4H), 3.99 (s, 3H), 4.13 (t, J=7.2 Hz, 2H), 7.16 (s, 1H), 7.26 (s, 1H), 7.45 (s, 1H), 7.57-7.62 (m, 1H), 7.91-7.93 (m, 1H), 8.64 (s, 1H) ppm.

Example 12

N-(3-chloro-4-fluorophenyl)-7-methoxy-6-(3-(5-methylhexahydropyrrolo[3,4-c]pyrrol-2(1H)-yl)propoxy)quinazolin-4-amine

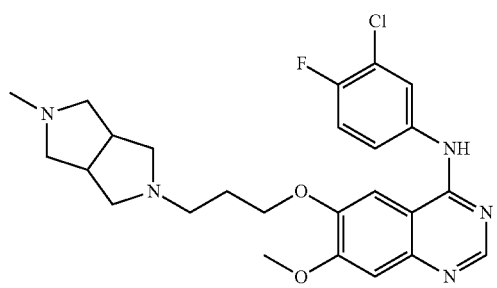 [SMILES: COc1cc2ncnc(Nc3ccc(F)c(Cl)c3)c2cc1OCCCN1CC2CN(C)CC2C1]

To a solution of N-(3-chloro-4-fluorophenyl)-6-(3-(hexahydropyrrolo[3,4-c]pyrrol-2(1H)-yl) propoxy)-7-methoxyquinazolin-4-amine (0.20 g) in a mixture of CH₂Cl₂ and MeOH was added 37% HCHO (0.10 mL), AcOH (0.15 mL) and NaB(O₂CCH₃)₃H (0.26 g) in turn. The mixture was stirred for 1.5 h, then diluted with water and extracted with CH₂Cl₂. The organic layer was dried over anhydrous Na₂SO₄ for 1 h and filtered. The filtrate was concentrated and redissolved in EA, to this, a solution of HCl in EtOAc (10 mL) was added under stifling. The mixture was filtered to give the title compound as a solid (0.13 g, 68.00%), HPLC: 98.69%. The compound was characterized by the following spectroscopic data: MS (ESI, pos. ion) m/z: 486.2 (M+1); ¹H NMR (400 MHz, CDCl₃) δ: 1.81-1.92 (m, 4H), 2.10-2.15 (m, 4H), 2.30 (s, 3H), 2.35-2.41 (m, 4H), 2.44 (t, J=8.2 Hz, 2H), 4.03 (s, 3H), 4.10 (t, J=7.8 Hz, 2H), 7.16 (s, 1H), 7.26 (s, 1H), 7.45 (s, 1H), 7.57-7.62 (m, 1H), 7.91-7.93 (m, 1H), 8.64 (s, 1H) ppm.

Example 13

N-(3-chloro-4-fluorophenyl)-6-(3-(hexahydropyrrolo[3,4-b]pyrrol-1(2H)-yl)propoxy)-7-methoxyquinazolin-4-amine

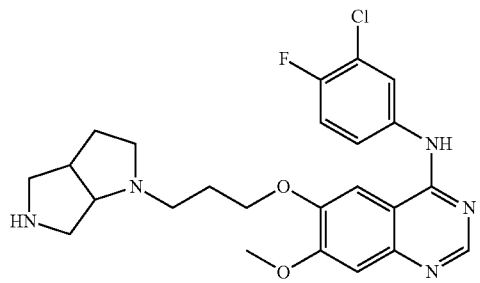

Step 1) tert-butyl 1-(3-((4-((3-chloro-4-fluorophenyl)amino)-7-methoxyquinazolin-6-yl)oxy)propyl)hexahydropyrrolo[3,4-b]pyrrole-5(1H)-carboxylate

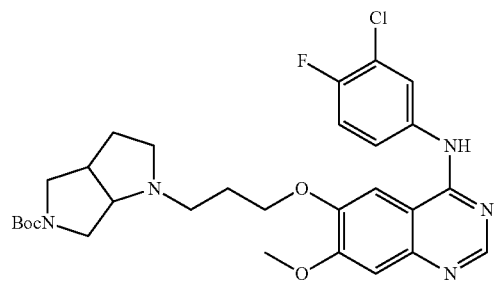 [SMILES: COc1cc2ncnc(Nc3ccc(F)c(Cl)c3)c2cc1OCCCN1CCC2CN(C(=O)OC(C)(C)C)CC21]

To a mixture of N-(3-chloro-4-fluorophenyl)-6-(3-chloropropoxy)-7-methoxyquinazolin-4-amine (1.00 g) and K₂CO₃ (0.49 g) in DMF (15 mL) was added 7-benzyloxycarbonyl-2,7-diazabicyclo[3.3.0]octane (0.64 g). The reaction mixture was heated at 80° C. for 6 h, washed with water and extracted with CH₂Cl₂. The organic layer was dried over anhydrous Na₂SO₄ for 1 h and filtered. The filtrate was concentrated in vacuo and the residue was chromatographed with a silica gel column (developing agent: 10:1 (v/v) DCM/

MeOH, eluting agent: 30:1 (v/v) DCM/MeOH) to give the title compound as a white solid (0.58 g, 40.00%).

Step 2) N-(3-chloro-4-fluorophenyl)-6-(3-(hexahydropyrrolo[3,4-b]pyrrol-1(2H)-yl)propoxy)-7-methoxyquinazolin-4-amine

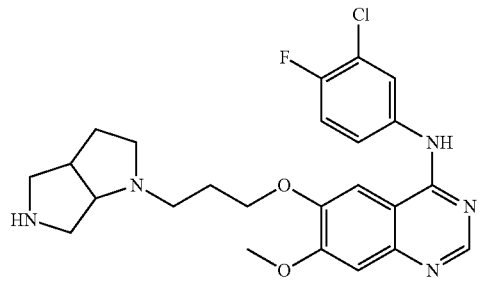 [SMILES: COc1cc2ncnc(Nc3ccc(F)c(Cl)c3)c2cc1OCCCN1CCC2CNCC21]

To a solution of tert-butyl 1-(3-((4-((3-chloro-4-fluorophenyl)amino)-7-methoxyquinazolin-6-yl)oxy)propyl)hexahydropyrrolo[3,4-b]pyrrole-5(1H)-carboxylate (0.50 g) was added a solution of HCl in EtOAc (10 mL). The reaction mixture was continued to stir at room temperature for 2 h and filtered to afford the title compound as a solid (0.28 g, 64.00%), HPLC: 98.79%. The compound was characterized by the following spectroscopic data: MS (ESI, pos. ion) m/z: 472.2 (M+1); $^1$H NMR (400 MHz, CDCl$_3$) δ: 1.55-1.58 (m, 2H), 1.83-1.88 (m, 3H), 2.25 (t, J=5.7 Hz, 2H), 2.40-2.45 (m, 3H), 2.70-2.73 (m, 4H), 3.93 (s, 3H), 4.08 (t, J=5.4 Hz, 2H), 7.16 (s, 1H), 7.26 (s, 1H), 7.45 (s, 1H), 7.57-7.60 (m, 1H), 7.91-7.95 (m, 1H), 8.64 (s, 1H) ppm.

Example 14

1-(1-(3-((4-((3-chloro-4-fluorophenyl)amino)-7-methoxyquinazolin-6-yl)oxy)propyl)hexahydropyrrolo[3,4-b]pyrrol-5(1H)-yl)ethanone

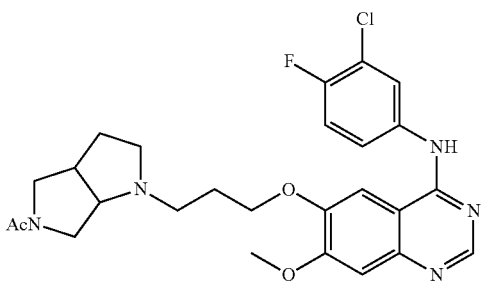

To a mixture of N-(3-chloro-4-fluorophenyl)-6-(3-(hexahydropyrrolo[3,4-b]pyrrol-1(2H)-yl)propoxy)-7-methoxyquinazolin-4-amine (0.10 g) and Et$_3$N (0.072 g) at 0° C. was added acetyl chloride (0.019 g) dropwise and the reaction was continued to stir for 2 h at same temperature. Then the mixture was diluted with water and extracted with EtOAc. The organic layer was dried over anhydrous Na$_2$SO$_4$ and filtered. The solvent of the filtrate was removed by reduce vacuum pressure, and the residue was recrystallized from DCM/PE to give the title compound (0.04 g, 40.00%), HPLC: 96.24%. The compound was characterized by the following spectroscopic data: MS (ESI, pos. ion) m/z: 514.2 (M+1); $^1$H NMR (400 MHz, CDCl$_3$) δ: 1.50-1.53 (m, 2H), 1.83-1.87 (m, 2H), 2.25-2.29 (m, 3H), 2.30 (s, 3H), 2.44 (t, J=4.2 Hz, 2H), 2.90-2.93 (m, 1H), 3.50-3.61 (m, 4H), 4.03 (s, 3H), 4.08 (t, J=4.8 Hz, 2H), 7.16 (s, 1H), 7.26 (s, 1H), 7.45 (s, 1H), 7.57-7.60 (m, 1H), 7.91-7.95 (m, 1H), 8.64 (s, 1H) ppm.

Example 15

N-(3-chloro-4-fluorophenyl)-7-methoxy-6-(3-(4-methylhexahydropyrrolo[3,4-b][1,4]oxazin-6(2H)-yl) propoxy)quinazolin-4-amine

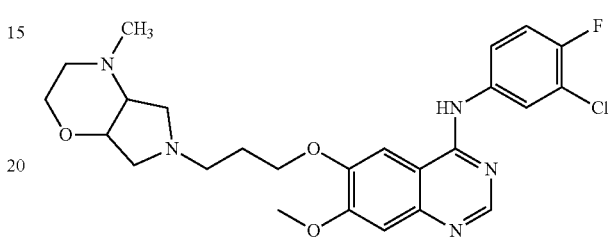

Step 1) tert-butyl 3-bromo-4-(2-hydroxyethoxy)pyrrolidine-1-carboxylate

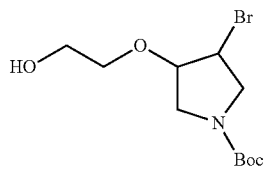 [SMILES: CC(C)(C)OC(=O)N1CC(Br)C(OCCO)C1]

To a solution of N-benzyloxycarbonyl-3-pyrroline (10.00 g) in ethylene glycol (40.00 g) was added NBS (10.90 g, 1.04 eq) in five portions. The reaction mixture was stirred at room temperature for 12 h under N$_2$, then poured into 100 mL of water and extracted with EtOAc (100 mL×2). The combined organic phases were washed with saturated NaHSO$_3$ aqueous solution and brine, dried over anhydrous Na$_2$SO$_4$ and concentrated in vacuo, the residue was chromatographed with a silica gel column (eluting agent: 2:1 (v/v) PE/EtOAc) to give the title compound (15.33 g, 83.63%). The compound was characterized by the following spectroscopic data: MS (ESI, pos. ion) m/z: 334.2 (M+23); $^1$H NMR (400 MHz, CDCl$_3$) δ: 1.45 (s, 9H), 2.11 (s, 1H), 3.41 (s, 1H), 3.44-3.47 (m, 2H), 3.72 (t, J=9.32 Hz, 2H), 3.77-3.80 (m, 1H), 3.82-3.85 (m, 1H), 4.10-4.14 (m, 1H), 4.28 (s, 1H) ppm.

Step 2) tert-butyl 3-bromo-4-(2-(tosyloxy)ethoxy)pyrrolidine-1-carboxylate

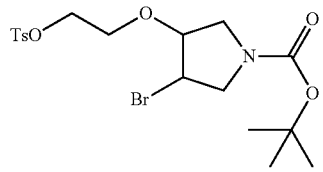 [SMILES: Cc1ccc(S(=O)(=O)OCCOC2CN(C(=O)OC(C)(C)C)CC2Br)cc1]

To a solution of tert-butyl 3-bromo-4-(2-hydroxyethoxy) pyrrolidine-1-carboxylate (10.00 g, 1 eq) in toluene (150 mL)

was added Et₃N (1.3 eq), 4-dimethylamino pyrimidine (0.035 eq) and a solution of TsCl (1.3 eq) in toluene (50 mL) dropwise. The reaction mixture was stirred at room temperature for 24 h, washed with water (100 mL×2) and brine (100 mL). The organic layer was dried over anhydrous Na₂SO₄ and filtered. The filtrate was concentrated in vacuo and the residue was chromatographed with a silica gel column (eluting agent: 4:1 (v/v) PE/EtOAc) to give the title compound as colorless oil (11.34 g, 75.70%). The compound was characterized by the following spectroscopic data: MS (ESI, pos. ion) m/z: 487.4 (M+23); ¹H NMR (400 MHz, CDCl₃) δ: 1.47 (s, 9H), 2.46 (s, 3H), 3.36 (m, 1H), 3.68-3.71 (m, 3H), 3.85 (m, 1H), 4.06-4.15 (m, 3H), 7.35-7.37 (d, J=8.08 Hz, 2H), 7.78-7.80 (d, J=8.32 Hz, 2H) ppm.

Step 3) tert-butyl 4-benzylhexahydropyrrolo[3,4-b][1,4]oxazine-6(2H)-carboxylate

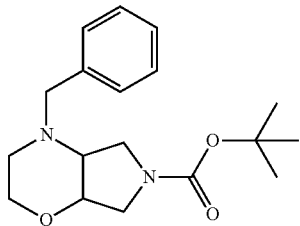 [SMILES: CC(C)(C)OC(=O)N1CC2OCCN(Cc3ccccc3)C2C1]

To a solution of tert-butyl 3-bromo-4-(2-(tosyloxy)ethoxy)pyrrolidine-1-carboxylate (7.00 g) in dimethylbenzene (180 mL) was added benzylamine (3 eq). The reaction mixture was heated to reflux for 12 h, then poured into water (100 mL) and extracted with EtOAc (100 mL×3). The combined organic phases were washed with brine and dried over anhydrous Na₂SO₄. The mixture was filtered and the filtrate was concentrated in vacuo, the residue was chromatographed with silica gel (eluting agent: 4:1 (v/v) PE/EtOAc) to give the title compound (3.14 g, 76.21%). The compound was characterized by the following spectroscopic data: MS (ESI, pos. ion) m/z: 319.4 (M+1), 341.4 (M+23).

Step 4) tert-butyl4-methylhexahydropyrrolo[3,4-b][1,4]oxazine-6(2H)-carboxylate

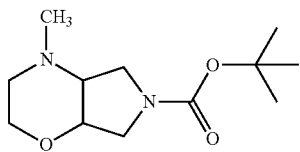 [SMILES: CN1CCOC2CN(C(=O)OC(C)(C)C)CC21]

To a solution of tert-butyl 4-benzylhexahydropyrrolo[3,4-b][1,4]oxazine-6(2H)-carboxylate (1.00 g) in EtOH (20 mL) was added 20% Pd(OH)₂/C (0.30 g). The reaction mixture was heated to reflux for 8 h and filtered. The filtrate was evaporated in vacuo. To a solution of the residue in CH₃CN (30 mL) was added formaldehyde aqueous solution (15 eq) and NaB(OCOCH₃)₃H (2.5 eq). The mixture was stirred at room temperature for 6 h under N₂. The solvent of the mixture was removed under reduce vacuum pressure, and the residue was chromatographed with a silica gel column to give the title compound (0.33 g, 43.42%). The compound was characterized by the following spectroscopic data: MS (ESI, pos. ion) m/z: 243.3 (M+1).

Step 5) N-(3-chloro-4-fluorophenyl)-7-methoxy-6-(3-(4-methylhexahydropyrrolo[3,4-b][1,4]oxazin-6(2H)-yl)propoxy)quinazolin-4-amine

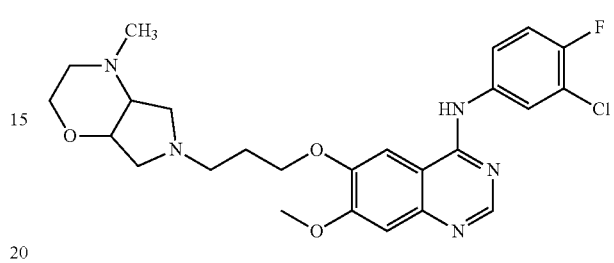

tert-Butyl 4-methylhexahydropyrrolo[3,4-b][1,4]oxazine-6 (2H)-carboxylate (0.70 g) was dissolved in a solution of HCl in MeOH (10 mL), the mixture was stirred at room temperature for 1 h. The solvent was removed under reduced pressure. To a solution of the residue in DMF (10 mL) was added K₂CO₃ (2.00 g), N-(3-chloro-4-fluorophenyl)-6-(3-chloropropoxy)-7-methoxyquinazolin-4-amine (0.95 g) and tetrabutylammonium iodide (30 mg). The reaction mixture was heated at 90° C. for 20 h. To the resulted mixture was added CH₂Cl₂ (50 mL). The mixture was washed with water (50 mL×3) and brine. The organic layer was dried over anhydrous Na₂SO₄ and filtered. The filtrate was concentrated in vacuo and the residue was chromatographed with a silica gel column (eluting agent: 20:1 (v/v) CH₂Cl₂/CH₃OH) to afford the title compound (367 mg, 30.19%), HPLC: 93.68%. The compound was characterized by the following spectroscopic data: MS (ESI, pos. ion) m/z: 503.0 (M+1); ¹H NMR (400 MHz, CDCl₃) δ: 2.11-2.14 (m, 2H), 2.17-2.20 (m, 3H), 2.20 (s, 1H), 2.35-2.39 (m, 1H), 2.75-2.77 (m, 1H), 2.80-2.86 (m, 3H), 3.00-3.07 (m, 1H), 3.19-3.21 (m, 2H), 3.61-3.85 (m, 2H), 3.80-3.89 (s, 1H), 4.00 (s, 1H), 4.06 (s, 1H), 4.26-4.28 (m, 2H) 7.16 (t, J=8.76 Hz, 1H), 7.25 (d, J=9.12 Hz, 1H), 7.38 (s, 1H), 7.63 (t, J=4.08 Hz, 1H), 7.87 (s, 1H), 7.95 (m, 3H), 8.64 (s, 1H) ppm.

Example 16

6-(3-(4-benzylhexahydropyrrolo[3,4-b][1,4]oxazin-6(2H)-yl)propoxy)-N-(3-chloro-4-fluorophenyl)-7-methoxyquinazolin-4-amine

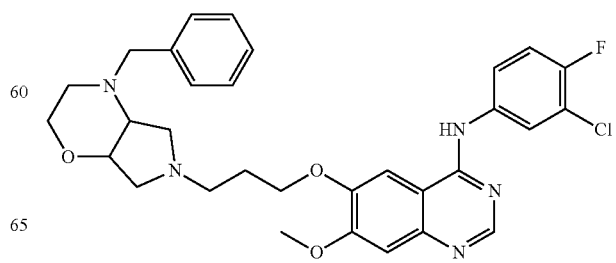

Step 1) 4-benzyl-6-(3-chloropropyl)octahydropyrrolo[3,4-b][1,4]oxazine

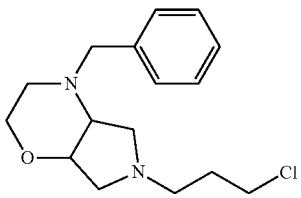 [SMILES: ClCCCN1CC2OCCN(Cc3ccccc3)C2C1]

tert-butyl 4-benzylhexahydropyrrolo[3,4-b][1,4]oxazine-6(2H)-carboxylate (6.05 g) was dissolved in a saturated solution of HCl in MeOH (60 mL), the mixture was stirred at room temperature for 1.5 h. The mixture was evaporated in vacuo, and to a solution of the residue in acetone (150 mL) was added $K_2CO_3$ (26.22 g) and 1-bromo-3-chloropropane (5.93 g). The reaction mixture was refluxed for 20 h, and filtered. The filtrate was evaporated in vacuo and the residue was dissolved in EtOAc (100 mL), washed with water (100 mL×2) and brine (100 mL), and dried over anhydrous $Na_2SO_4$. The mixture was filtered and the filtrate was concentrated in vacuo, the residue was chromatographed with a silica gel column (eluting agent: 20:1 (v/v) $EA/CH_3OH$) to give the title compound (1.82 g, 32.56%). The compound was characterized by the following spectroscopic data: MS (ESI, pos. ion) m/z: 295.8 (M+1); $^1$H NMR (400 MHz, CDCl$_3$) δ: 1.93 (m, 2H), 2.36-2.39 (m, 1H), 2.62 (m, 1H), 2.63-2.64 (m, 3H), 2.93-2.97 (m, 1H), 3.00-3.04 (m, 1H), 3.24 (s, 1H), 3.58 (m, 3H), 3.61-3.64 (m, 1H), 3.79 (s, 1H), 3.97 (t, J=8.20 Hz, 1H), 7.23 (s, 1H), 7.29 (t, J=6.28 Hz, 5H) ppm.

Step 2) 6-(3-(4-benzylhexahydropyrrolo[3,4-b][1,4]oxazin-6(2H)-yl) propoxy)-N-(3-chloro-4-fluorophenyl)-7-methoxyquinazolin-4-amine

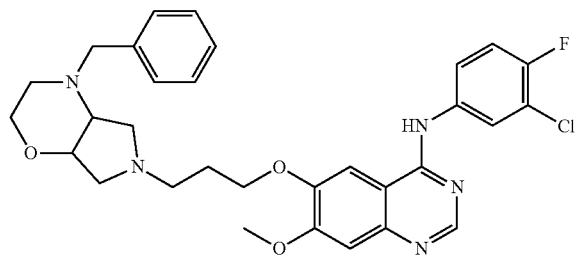 [SMILES: COc1cc2ncnc(Nc3ccc(F)c(Cl)c3)c2cc1OCCCN1CC2OCCN(Cc3ccccc3)C2C1]

To a solution of 4-benzyl-6-(3-chloropropyl)octahydropyrrolo[3,4-b][1,4]oxazine (0.30 g) in DMF (5 mL) was added $K_2CO_3$ (0.59 g), 4-((3-chloro-4-fluorophenyl)amino)-7-methoxyquinazolin-6-ol (0.27 g) and tetrabutylammonium iodide (20 mg). The reaction mixture was heated at 90° C. for 18 h, cooled to room temperature. The mixture was diluted with $CH_2Cl_2$ (100 mL), washed with water (100 mL×3) and brine (100 mL), and dried over anhydrous $Na_2SO_4$. The mixture was filtered and the filtrate was concentrated in vacuo. The residue was chromatographed with a silica gel column (eluting agent: 20:1 (v/v) $CH_2Cl_2/CH_3OH$) to afford the title compound (390 mg, 79.59%). The compound was characterized by the following spectroscopic data: MS (ESI, pos. ion) m/z: 579.1 (M+1); $^1$H NMR (400 MHz, CDCl$_3$) δ: 2.07-2.09 (t, J=13.36 Hz, 2H), 2.09-2.10 (m, 1H), 2.40-2.43 (m, 1H), 2.66-2.68 (m, 2H), 2.70-2.78 (m, 2H), 3.00-3.02 (m, 1H), 3.08-3.13 (m, 1H), 3.65 (s, 3H), 3.77 (s, 1H), 3.99 (s, 3H), 4.02-4.04 (m, 1H), 4.20-4.22 (m, 2H), 5.30 (s, 1H), 7.13 (m, 1H), 7.26 (d, J=2.04 Hz, 1H), 7.30-7.31 (m, 1H), 7.56 (d, J=1.20 Hz, 5H), 7.81 (s, 1H), 7.90 (s, 1H), 7.92 (d, J=2.60 Hz, 1H), 8.64 (s, 1H) ppm.

Example 17

N-(3-chloro-4-fluorophenyl)-6-(3-(hexahydro-1H-pyrrolo[2,3-c]pyridin-6(2H)-yl)propoxy)-7-methoxyquinazolin-4-amine

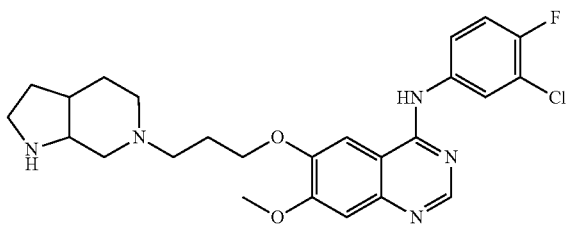 [SMILES: COc1cc2ncnc(Nc3ccc(F)c(Cl)c3)c2cc1OCCCN1CCC2CCNC2C1]

Step 1) tert-butyl 1H-pyrrolo[2,3-c]pyridine-1-carboxylate

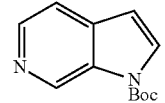

To a solution of 6-azaindole (6.02 g) and $Et_3N$ (14 mL) at 0° C. was added $(Boc)_2O$ (16.50 mL) dropwise. The reaction mixture was stirred at room temperature for 3 h, washed with water and extracted with EtOAc. The organic layer was dried over anhydrous $Na_2SO_4$ for 1 h and concentrated in vacuo. The residue was chromatographed with a silica gel column (eluting agent: 3:1 (v/v) PE/EA) to afford the title compound as transparent liquid (11.10 g, 100.00%). The compound was characterized by the following spectroscopic data: $^1$H NMR (400 MHz, CDCl$_3$) δ: 1.70 (s, 9H), 6.59 (d, J=3.6 Hz, 1H), 7.49 (d, J=5.3 Hz, 1H), 7.75 (d, J=3.5 Hz, 1H), 8.40 (d, J=5.3 Hz, 1H), 9.39 (s, 1H) ppm.

Step 2) tert-butyl octahydro-1H-pyrrolo[2,3-c]pyridine-1-carboxylate

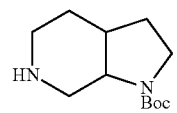

A mixture of tert-butyl 1H-pyrrolo[2,3-c]pyridine-1-carboxylate (1.85 g) and a catalytic amount of $PtO_2$ in the mixture solvent of EtOH (10 mL) and AcOH (10 mL) was heated overnight under $H_2$ (2.0 MPa). The reaction mixture was filtered, and the filtrate was concentrated in vacuo. The residue was chromatographed with a silica gel column (eluting agent: 10:1 (v/v) $CH_2Cl_2/MeOH$) to afford the product as viscous liquid (2.18 g, 100.00%).

Step 3) tert-butyl 6-(3-chloropropyl)octahydro-1H-pyrrolo[2,3-c]pyridine-1-carboxylate

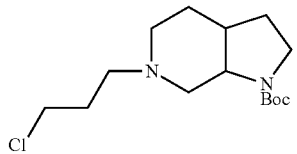 [SMILES: CC(C)(C)OC(=O)N1CCC2CCN(CCCCl)CC21]

To a solution of tert-butyl octahydro-1H-pyrrolo[2,3-c]pyridine-1-carboxylate (1.21 g) in acetone (15 mL) was added K₂CO₃ (3.00 g) and 1-bromo-3-chloropropane (1.6 mL). The reaction mixture was heated to reflux for 7 h, diluted with water and extracted with EtOAc. The organic layer was dried over anhydrous Na₂SO₄ for 1 h and filtered. The filtrate was concentrated in vacuo and the residue was chromatographed with a silica gel column (eluting agent: 30:1 (v/v) CH₂Cl₂/MeOH) to afford the title compound as pale yellow liquid (1.20 g, 75.00%).

Step 4) tert-butyl 6-(3-((4-((3-chloro-4-fluorophenyl)amino)-7-methoxyquinazo-lin-6-yl)oxy)propyl)octahydro-1H-pyrrolo[2,3-c]pyridine-1-carboxylate

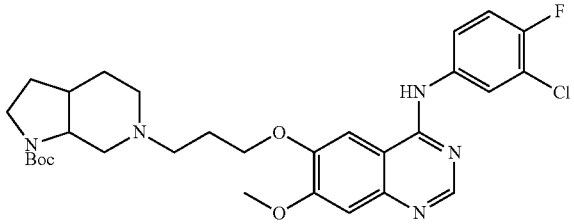

To a mixture of 4-((3-chloro-4-fluorophenyl)amino)-7-methoxyquinazolin-6-ol (0.94 g) and K₂CO₃ (0.81 g) in DMF (10 mL) was added tert-butyl 6-(3-chloropropyl)octahydro-1H-pyrrolo[2,3-c]pyridine-1-carboxylate (1.16 g). The reaction mixture was heated at 80° C. for 6 h, diluted with water and extracted with CH₂Cl₂. The organic layer was dried over anhydrous Na₂SO₄ and filtered. The filtrate was concentrated in vacuo and the residue was chromatographed with a silica gel column (eluting agent: 10:1 (v/v) CH₂Cl₂/MeOH) to afford the title compound as a white solid (1.16 g, 67.00%).

Step 5) N-(3-chloro-4-fluorophenyl)-6-(3-(hexahydro-1H-pyrrolo[2,3-c]pyridin-6(2H)-yl)propoxy)-7-methoxyquinazolin-4-amine

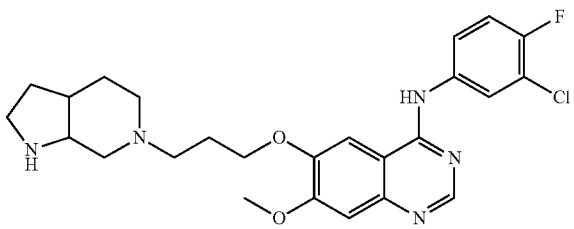 [SMILES: COc1cc2ncnc(Nc3ccc(F)c(Cl)c3)c2cc1OCCCN1CCC2CCNC2C1]

To a solution of tert-butyl 6-(3-((4-((3-chloro-4-fluorophenyl)amino)-7-methoxyquinazolin-6-yl)oxy) propyl)octahydro-1H-pyrrolo[2,3-c]pyridine-1-carboxylate (1.16 g) in the mixture solvent of CH₂Cl₂ and MeOH was added a solution of HCl in EtOAc (30 mL). The reaction mixture was stirred at room temperature for 4 h, and filtered to give the title compound as a solid (1.20 g, 100%), HPLC: 99.69%. The compound was characterized by the following spectroscopic data: MS (ESI, pos. ion) m/z: 486.2 (M+1); ¹H NMR (400 MHz, CDCl₃) δ: 1.45 (m, 2H), 1.78 (m, 3H), 1.80 (m, 2H), 2.10 (m, 1H), 2.42 (m, 5H), 2.82 (m, 3H), 4.03 (s, 3H), 4.10 (m, 2H), 6.76 (s, 1H), 7.16 (d, J=8.2 Hz, 1H), 7.24 (s, 1H), 7.28 (d, J=8.2 Hz, 1H), 7.41 (s, 1H), 8.54 (s, 1H) ppm.

Example 18

N-(3-chloro-4-fluorophenyl)-7-methoxy-6-(3-(1-methylhexahydro-1H-pyrrolo[2,3-c]pyridin-6(2H)-yl) propoxy)quinazolin-4-amine

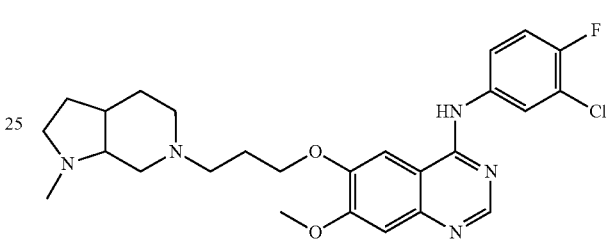

To a solution of tert-butyl 6-(3-((4-((3-chloro-4-fluorophenyl)amino)-7-methoxyquinazolin-6-yl)oxy) propyl)octahydro-1H-pyrrolo[2,3-c]pyridine-1-carboxylate (0.20 g) in the mixture solvent of CH₂Cl₂ and MeOH was added 37% HCHO (0.10 mL), AcOH (0.15 mL) and NaB(O₂CCH₃)₃H (0.26 g) in turn at room temperature. The mixture was stirred for 1.5 h, diluted with water and extracted with CH₂Cl₂. The organic layer was dried over anhydrous Na₂SO₄ for 1 h and filtered. The filtrate was concentrated and redissolved in EA, to this, a solution of HCl in EtOAc (10 mL) was added under stirring. The mixture was filtered to give the title compound as a solid (0.13 g, 68.00%), HPLC: 98.22%. The compound was characterized by the following spectroscopic data: MS (ESI, pos. ion) m/z: 500.2 (M+1); ¹H NMR (400 MHz, CDCl₃) δ: 1.45 (m, 2H), 1.68 (m, 3H), 1.80 (m, 2H), 2.10 (m, 1H), 2.22 (m, 5H), 2.25 (s, 3H), 2.42 (m, 3H), 4.03 (s, 3H), 4.10 (m, 2H), 6.76 (s, 1H), 7.16 (d, J=8.2 Hz, 1H), 7.24 (s, 1H), 7.28 (d, J=8.0 Hz, 1H), 7.41 (s, 1H), 8.54 (s, 1H) ppm.

Example 19

N-(3-chloro-4-fluorophenyl)-6-(3-(hexahydro-1H-pyrrolo[3,2-c]pyridin-5(6H)-yl)propoxy)-7-methoxyquinazolin-4-amine

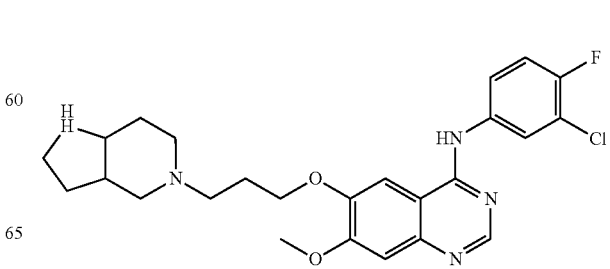

Step 1) tert-butyl 1H-pyrrolo[3,2-c]pyridine-1-carboxylate

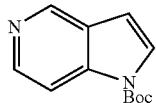

To a solution of 5-azaindole (5.00 g) and Et₃N (12 mL) was added (Boc)₂O (14 mL) dropwise at 0° C. The mixture was stirred for 6 h, then diluted with water and extracted with EtOAc. The organic layer was dried over Na₂SO₄ for 1 h and filtered. The filtrate was concentrated in vacuo and the residue was chromatographed with a silica gel column (eluting agent: 3:1 (v/v) PE/EA) to give the title compound as transparent liquid (9.00 g, 97.00%). The compound was characterized by the following spectroscopic data: ¹H NMR (400 MHz, CDCl₃) δ: 1.65 (s, 9H), 6.62 (d, J=3.6 Hz, 1H), 7.25 (d, J=5.3 Hz, 1H), 7.50 (d, J=3.5 Hz, 1H), 8.42 (d, J=5.3 Hz, 1H), 9.43 (s, 1H) ppm.

Step 2) tert-butyl octahydro-1H-pyrrolo[3,2-c]pyridine-1-carboxylate

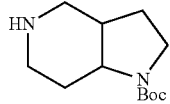

To a solution of tert-butyl 1H-pyrrolo[3,2-c]pyridine-1-carboxylate (2.55 g) in the mixture solvent of glycol monomethyl ether (40 mL) and AcOH (1 mL) was added a catalytic amount of Pd(OH)₂/C. The suspension was heated at 70° C. for 24 h under H₂ (2.0 MPa) and filtered. The filtrate was concentrated in vacuo and the residue was chromatographed with a silica gel column (eluting agent: 10:1 (v/v) CH₂Cl₂/MeOH) to give the product as viscous liquid (2.64 g, 100.00%).

Step 3) tert-butyl 5-(3-chloropropyl)octahydro-1H-pyrrolo[3,2-c]pyridine-1-carboxylate

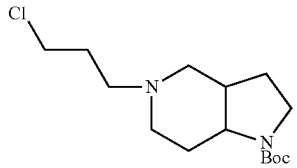 [SMILES: CC(C)(C)OC(=O)N1CCC2CN(CCCCl)CCC21]

To a solution of tert-butyl octahydro-1H-pyrrolo[3,2-c]pyridine-1-carboxylate (0.63 g) in acetone (15 mL) was added K₂CO₃ (1.54 g) and 1-bromo-3-chloropropane (1.45 mL). The reaction mixture was heated to reflux overnight, diluted with water and extracted with EtOAc. The organic layer was dried over anhydrous Na₂SO₄ for 1 h and filtered. The filtrate was concentrated in vacuo and the residue was chromatographed with a silica gel column (eluting agent: 10:1 (v/v) CH₂Cl₂/MeOH) to give the title compound as pale yellow liquid (0.65 g, 77.00%).

Step 4) tert-butyl5-(3-((4-((3-chloro-4-fluorophenyl)amino)-7-methoxyquinazolin-6-yl)oxy)propyl)octahydro-1H-pyrrolo[3,2-c]pyridine-1-carboxylate

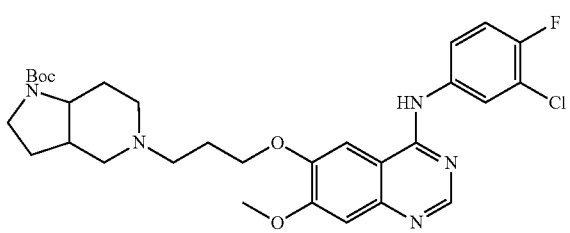 [SMILES: COc1cc2ncnc(Nc3ccc(F)c(Cl)c3)c2cc1OCCCN1CCC2C(CCN2C(=O)OC(C)(C)C)C1]

To a mixture of 4-((3-chloro-4-fluorophenyl)amino)-7-methoxyquinazolin-6-ol (0.52 g), K₂CO₃ (0.52 g) and a catalytic amount of KI in DMF (15 mL) was added tert-butyl 5-(3-chloropropyl) octahydro-1H-pyrrolo[3,2-c]pyridine-1-carboxylate (0.65 g) at room temperature. The reaction mixture was heated at 80° C. for 6 h, and then washed with water, extracted with CH₂Cl₂. The organic layer was dried over anhydrous Na₂SO₄ for 1 h, and concentrated in vacuo. The residue was chromatographed with a silica gel column (eluting agent: 10:1 (v/v) CH₂Cl₂/MeOH) to give the title compound as a white solid (0.64 g, 67.00%).

Step 5) N-(3-chloro-4-fluorophenyl)-6-(3-(hexahydro-1H-pyrrolo[3,2-c]pyridin-5(6H)-yl)propoxy)-7-methoxyquinazolin-4-amine

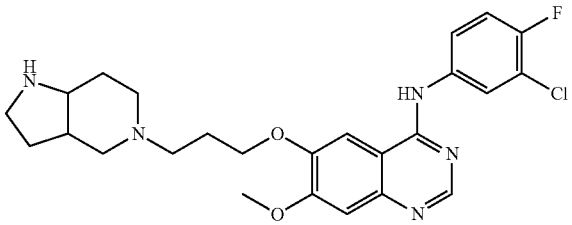

To a mixture of tert-butyl 5-(3-((4-((3-chloro-4-fluorophenyl)amino)-7-methoxyquinazolin-6-yl)oxy) propyl)octahydro-1H-pyrrolo[3,2-c]pyridine-1-carboxylate (0.64 g) in the mixture solvent of CH₂Cl₂ and MeOH was added a solution of HCl in EtOAC (30 mL). The reaction mixture was stirred at room temperature for another 4 h and filtered to give the title compound as a solid (0.33 g, 62.00%), HPLC: 98.69%. The compound was characterized by the following spectroscopic data: MS (ESI, pos. ion) m/z: 486.2 (M+1); ¹H NMR (400 MHz, CDCl₃) δ: 1.45 (m, 2H), 1.78 (m, 3H), 1.80 (m, 2H), 2.10 (m, 1H), 2.42 (m, 5H), 2.72 (m, 3H), 4.03 (s, 3H), 4.10 (m, 2H), 6.76 (s, 1H), 7.16 (d, J=8.0 Hz, 1H), 7.24 (s, 1H), 7.28 (d, J=8.0 Hz, 1H), 7.41 (s, 1H), 8.54 (s, 1H) ppm.

Example 20

2-(3-((4-((3-chloro-4-fluorophenyl)amino)-7-methoxyquinazolin-6-yl)oxy)propyl)hexahydropyrano[3,4-c]pyrrol-4(2H)-one

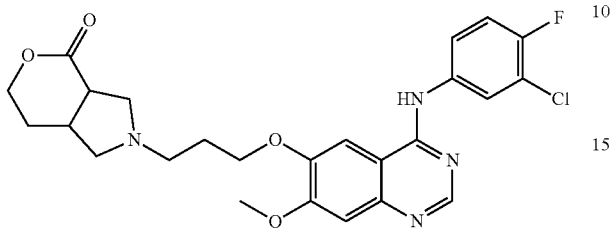

Step 1) 3,6-dihydro-2H-pyran

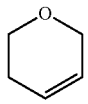

To a solution of tetrahydro-4-pyranol (30.00 g) in CH$_2$Cl$_2$ (250 mL) was added Et$_3$N (35.68 g) at rt, and methylsulfonyl chloride (36.84 g) dropwise at 0° C. under N$_2$. The reaction mixture was stirred at 0° C. for 1 h, then heated to room temperature and stirred for 12 h. The reaction mixture was quenched with water, washed with water and brine, and dried over anhydrous Na$_2$SO$_4$. The mixture was filtered and evaporated in vacuo to give the crude product. A mixture of the residue and DBU (50 mL) was heated at 100° C. for 3 h. The resulted mixture was distilled under normal pressure, the fraction of 150-160° C. was collected to afford the title compound (17.40 g, 70.44%). The compound was characterized by the following spectroscopic data: MS (ESI, pos. ion) m/z: 85.1 (M+1).

Step 2) 5,6-dihydro-2H-pyran-2-one

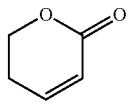

To a solution of 3,6-dihydro-2H-pyran (4.00 g, 1 eq) in CH$_2$Cl$_2$ (150 mL) was added PCC (1.2 eq). The mixture was heated to reflux for 4 h, to the mixture was added PCC (0.6 eq) additional. The reaction mixture was refluxed for another 4 h and filtered. The filtrate was concentrated in vacuo and the residue was chromatographed with a silica gel column (eluting agent: 2:1 (v/v) PE/EA) to give the title compound as colorless oil (0.77 g, 16.52%). The compound was characterized by the following spectroscopic data: MS (ESI, pos. ion) m/z: 99 (M+1); $^1$H NMR (400 MHz, CDCl$_3$) δ: 2.44-2.49 (m, 2H), 4.42-4.45 (m, 2H), 6.02-6.05 (m, 1H), 6.93-6.97 (m, 1H) ppm.

Step 3) 2-benzylhexahydropyrano[3,4-c]pyrrol-4(2H)-one

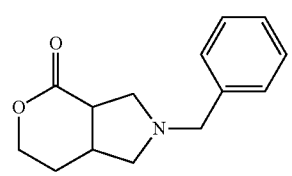 [SMILES: O=C1OCCC2CN(Cc3ccccc3)CC12]

To a solution of 5,6-dihydro-2H-pyran-2-one (1.00 g, 1 eq) in CH$_2$Cl$_2$ (150 mL) was added N-(methoxymethyl)-N-(trimethylsilylmethyl)benzylamine (1.2 eq). After the mixture was cooled to 0° C., a solution of TFA in CH$_2$Cl$_2$ (0.1 eq, 1M) was added slowly. The reaction mixture was slowly heated to room temperature and stirred for 6 h. The reaction mixture was washed with water and brine, dried over anhydrous Na$_2$SO$_4$ and concentrated in vacuo. The residue was chromatographed with a silica gel column (eluting agent: 2:1 (v/v) PE/EA) to give the title compound as colorless oil (1.95 g, 82.87%). The compound was characterized by the following spectroscopic data: MS (ESI, pos. ion) m/z: 232.3 (M+1).

Step 4) 2-(3-chloropropyl)hexahydropyrano[3,4-c]pyrrol-4(2H)-one

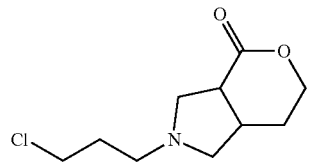 [SMILES: O=C1OCCC2CN(CCCCl)CC12]

To a solution of 2-benzylhexahydropyrano[3,4-c]pyrrol-4(2H)-one (0.50 g) in EtOH (20 mL) was added 20% Pd(OH)$_2$/C (0.30 g). The reaction mixture was heated to reflux under H$_2$ for 8 h, and filtered. The filtrate was concentrated in vacuo to give product (0.32 g). To a solution of the residue (0.32 g) in acetone (30 mL) was added K$_2$CO$_3$ (0.94 g) and 1-bromo-3-chloropropane (0.71 g). The mixture was heated to reflux for 12 h and filtered. The filtrate was concentrated in vacuo and the residue was chromatographed with a silica gel column (eluting agent: 1:1 (v/v) PE/EtOAc) to give the title compound as colorless oil (0.19 g, 40.00%). The compound was characterized by the following spectroscopic data: MS (ESI, pos. ion) m/z: 218.7 (M+1); $^1$H NMR (400 MHz, CDCl$_3$) δ: 1.24-1.28 (m, 1H), 1.93-1.96 (m, 1H), 2.03-2.06 (m, 2H), 2.17-2.18 (m, 1H), 2.33-2.37 (m, 1H), 2.55-2.58 (m, 2H), 2.81-2.84 (m, 1H), 2.91-2.95 (m, 2H), 3.07-3.09 (m, 1H), 3.59 (t, J=13.00 Hz, 2H), 4.20-4.26 (m, 1H), 4.38-4.40 (t, J=5.36 Hz, 1H) ppm.

Step 5) 2-(3-((4-((3-chloro-4-fluorophenyl)amino)-7-methoxyquinazolin-6-yl)oxy)propyl) hexahydropyrano[3,4-c]pyrrol-4(2H)-one

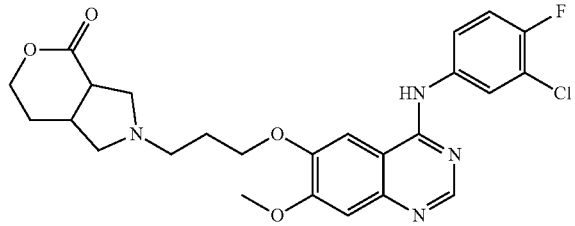 [SMILES: COc1cc2ncnc(Nc3ccc(F)c(Cl)c3)c2cc1OCCCN1CC2CCOC(=O)C2C1]

To a solution of 2-(3-chloropropyl)hexahydropyrano[3,4-c]pyrrol-4(2H)-one (0.19 g) in DMF (8 mL) was added K$_2$CO$_3$ (3.0 eq), 4-((3-chloro-4-fluorophenyl)amino)-7-methoxyquinazolin-6-ol (0.25 g) and tetrabutylammonium iodide (0.1 eq). The reaction mixture was heated at 90° C. for 20 h, and then treated with CH$_2$Cl$_2$ (100 mL). The mixture was washed with water (100 mL×3) and brine (100 mL), and dried over anhydrous Na$_2$SO$_4$. The mixture was filtered and the filtrate was concentrated in vacuo. The residue was chromatographed with a silica gel column (eluting agent: 20:1 (v/v) CH$_2$Cl$_2$/CH$_3$OH) to give the title compound (113 mg, 19.62%), HPLC: 95.64%. The compound was characterized by the following spectroscopic data: MS (ESI, pos. ion) m/z: 502.0 (M+1); $^1$H NMR (400 MHz, CDCl$_3$) δ: 2.06-2.12 (m, 4H), 2.35 (d, J=2.92 Hz, 1H), 2.51-2.58 (m, 3H), 2.76-2.79 (m, 2H), 2.97-3.02 (m, 1H), 3.49-3.50 (m, 1H), 3.52 (s, 1H), 4.00 (s, 3H), 4.18 (d, J=1.80 Hz, 1H), 4.21-4.24 (m, 1H), 4.35-4.40 (m, 1H), 7.13 (t, J=8.80 Hz, 1H), 7.24 (d, J=9.48 Hz, 1H), 7.41 (s, 1H), 7.68 (m, 1H), 7.95-7.98 (m, 1H), 8.28 (s, 1H), 8.63 (s, 1H) ppm.

Example 21

N-(3-chloro-4-fluorophenyl)-6-(3-(hexahydrocyclopenta[c]pyrrol-2(1H)-yl)propoxy)-7-methoxyquinazolin-4-amine

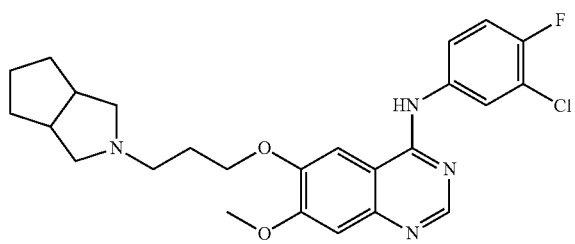 [SMILES: COc1cc2ncnc(Nc3ccc(F)c(Cl)c3)c2cc1OCCCN1CC2CCCC2C1]

Step 1) 2-(3-chloropropyl)octahydrocyclopenta[c]pyrrole

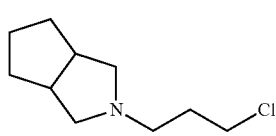 [SMILES: ClCCCN1CC2CCCC2C1]

To a suspension of octahydrocyclopenta[c]pyrrole hydrochloride (5.00 g, 33.86 mmol) in acetone (150 mL) was added K$_2$CO$_3$ (35.68 g, 101.59 mmol) and 1-chloro-3-bromopropane (10.56 g, 67.72 mmol) in turn. The reaction mixture was heated to reflux for 12 h under N$_2$. The solvent was removed, and the residue was treated with 200 mL of EtOAc. The mixture was washed with water followed by brine. The mixture was dried over anhydrous Na$_2$SO$_4$ and concentrated in vacuo. The residue was chromatographed with a silica gel column (eluting agent: 1:1 (v/v) PE/EtOAc) to afford the title compound (3.06 g, 56.63%). The compound was characterized by the following spectroscopic data: MS (ESI, pos. ion) m/z: 188.7 (M+1); $^1$H NMR (400 MHz, CDCl$_3$) δ: 1.24-1.28 (m, 1H), 1.38-1.40 (m, 2H), 2.06 (m, 1H), 2.46-2.50 (m, 2H), 2.56-2.57 (m, 3H), 2.63-2.68 (m, 2H), 2.70 (d, J=2.24 Hz, 2H), 2.71-2.73 (m, 2H), 3.60 (m, 2H) ppm.

Step 2) N-(3-chloro-4-fluorophenyl)-6-(3-(hexahydrocyclopenta[c]pyrrol-2(1H)-yl)propoxy)-7-methoxyquinazolin-4-amine

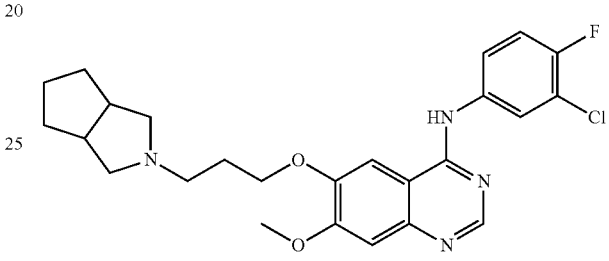

To a solution of 2-(3-chloropropyl)octahydrocyclopenta[c]pyrrole (2.00 g, 1.2 eq) in DMF (15 mL) was added K$_2$CO$_3$ (2.46 g, 2.0 eq), 4-((3-chloro-4-fluorophenyl)amino)-7-methoxyquinazolin-6-ol (2.84 g, 1.0 eq) and tetrabutylammonium iodide (0.1 eq). The reaction mixture was stirred at 90° C. for 12 h under N$_2$, and 100 mL of CH$_2$Cl$_2$ was added. The mixture was washed with water followed by brine. The mixture was dried over anhydrous Na$_2$SO$_4$ and concentrated in vacuo. The residue was chromatographed with a silica gel column (eluting agent: 20:1 (v/v) CH$_2$Cl$_2$/CH$_3$OH) to afford the title compound (2.23 g, 75.59%), HPLC: 94.23%. The compound was characterized by the following spectroscopic data: MS (ESI, pos. ion) m/z: 472.0 (M+1); $^1$H NMR (400 MHz, CDCl$_3$) δ: 1.40-1.43 (m, 2H), 1.58-1.65 (m, 4H), 2.01 (t, J=8.92 Hz, 2H), 2.10 (t, J=13.48 Hz, 2H), 2.57-2.60 (m, 4H), 2.90 (t, J=16.32 Hz, 2H), 3.49 (s, 2H), 4.00 (s, 3H), 4.21 (t, J=12.00 Hz, 2H), 7.13-7.20 (m, 2H), 7.57 (d, J=1.28 Hz, 2H), 7.59-7.60 (m, 1H), 7.91 (m, 1H), 7.93 (m, 1H), 8.65 (s, 1H) ppm.

Example 22

N-(3-chloro-4-fluorophenyl)-7-methoxy-6-(3-(tetrahydro-1H-furo[3,4-c]pyrrol-5(3H)-yl)propoxy)quinazolin-4-amine

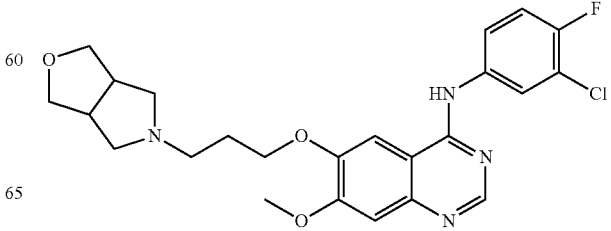

Step 1) dimethyl 1-benzylpyrrolidine-3,4-dicarboxylate

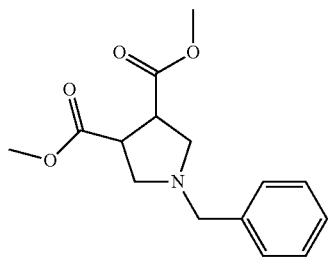 [SMILES: COC(=O)C1CN(Cc2ccccc2)CC1C(=O)OC]

To a solution of dimethyl maleate (4.00 g) in CH$_2$Cl$_2$ (100 mL) was added N-(methoxymethyl)-N-(trimethylsilylmethyl)benzylamine (1.2 eq) followed by a solution of TFA in CH$_2$Cl$_2$ (0.1 eq, 1 M) dropwise at 0° C. under N$_2$. The reaction mixture was heated to room temperature and stirred for 6 h, washed with water followed by brine. The mixture was dried over anhydrous Na$_2$SO$_4$ and concentrated in vacuo. The residue was chromatographed with a silica gel column (eluting agent: 3:1 (v/v) PE/EA) to yield the title compound (6.62 g, 86.02%). The compound was characterized by the following spectroscopic data: MS (ESI, pos. ion) m/z: 278 (M+1); $^1$H NMR (400 MHz, CDCl$_3$) δ: 2.70-2.75 (m, 2H), 3.12-3.17 (m, 1H), 3.30-3.33 (m, 2H), 3.66 (s, 6H), 7.24-7.31 (m, 5H).

Step 2) (1-benzylpyrrolidine-3,4-diyl)dimethanol

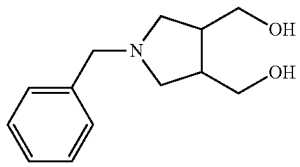 [SMILES: OCC1CN(Cc2ccccc2)CC1CO]

To a solution of dimethyl 1-benzylpyrrolidine-3,4-dicarboxylate (0.50 g) in THF (20 mL) was added LiAlH$_4$ (3.0 eq) at 0° C. under N$_2$. The reaction mixture was heated to the room temperature and stirred for 24 h. The reaction was quenched with water, 10% NaOH and water in turn. The mixture was filtered and the filtrate was concentrated in vacuo. The residue was chromatographed with a silica gel column (eluting agent: 10:1 (v/v) CH$_2$Cl$_2$/CH$_3$OH) to give the title compound (0.31 g, 63.79%). The compound was characterized by the following spectroscopic data: MS (ESI, pos. ion) m/z: 222.3 (M+1).

Step 3) 5-benzylhexahydro-1H-furo[3,4-c]pyrrole

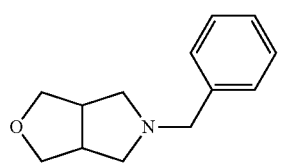 [SMILES: c1ccc(CN2CC3COCC3C2)cc1]

To a solution of (1-benzylpyrrolidine-3,4-diyl)dimethanol (1.44 g) in toluene (60 mL) was added Et$_3$N (1.72 mL), TsCl (1.75 g) and DMAP (40 mg). The reaction mixture was stirred at room temperature for 12 h under N$_2$, washed with water once, dried over anhydrous Na$_2$SO$_4$ and filtered. The filtrate was concentrated in vacuo and the residue was used for next step. To a solution of the above product in toluene (20 mL) was added Et$_3$N (0.85 mL). The reaction mixture was heated to reflux for 4 h and cooled to room temperature. The reaction mixture was washed with water followed by brine, dried over anhydrous Na$_2$SO$_4$ and filtrated. The filtrate was concentrated in vacuo and the residue was chromatographed with a silica gel column (eluting agent: 20:1 (v/v) CH$_2$Cl$_2$/CH$_3$OH) to afford the title compound (0.51 g, 62.30%). The compound was characterized by the following spectroscopic data: MS (ESI, pos. ion) m/z: 204.3 (M+1); $^1$H NMR (400 MHz, CDCl$_3$) δ: 2.31-2.35 (m, 2H), 2.71 (m, 2H), 2.79-2.81 (m, 2H), 3.57-3.60 (m, 4H), 3.76-3.80 (m, 2H), 7.24-7.34 (m, 5H) ppm.

Step 4) hexahydro-1H-furo[3,4-c]pyrrole

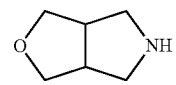

To a solution of 5-benzylhexahydro-1H-furo[3,4-c]pyrrole (0.45 g) in EtOH (30 mL) was added 20% Pd(OH)$_2$ (0.30 g). The reaction mixture was stirred at room temperature for 12 h under H$_2$, and then filtered. The filtrate was evaporated in vacuo to give the title compound (0.15 g). The compound was characterized by the following spectroscopic data: MS (ESI, pos. ion) m/z: 114.2 (M+1).

Step 5) 5-(3-chloropropyl)hexahydro-1H-furo[3,4-c]pyrrole

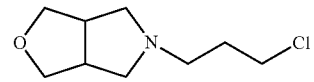 [SMILES: ClCCCN1CC2COCC2C1]

To a solution of hexahydro-1H-furo[3,4-c]pyrrole (0.15 g) in acetone (50 mL) was added K$_2$CO$_3$ (0.46 g) and 1-chloro-3-bromopropane (0.42 g, 2.0 eq) in turn. The reaction mixture was heated to reflux for 12 h and filtered. The filtrate was concentrated in vacuo and the residue was dissolved in EtOAc (100 mL). The solution was washed with water twice followed by brine once. The solution was dried over anhydrous Na$_2$SO$_4$ and concentrated in vacuo. The residue was chromatographed with a silica gel column (eluting agent: 20:1 (v/v) EA/CH$_3$OH) to give the title compound (0.13 g, 50.04%). The compound was characterized by the following spectroscopic data: MS (ESI, pos. ion) m/z: 190.7 (M+1).

Step 6) N-(3-chloro-4-fluorophenyl)-7-methoxy-6-(3-(tetrahydro-1H-furo[3,4-c]pyrrol-5(3H)-yl) propoxy)quinazolin-4-amine

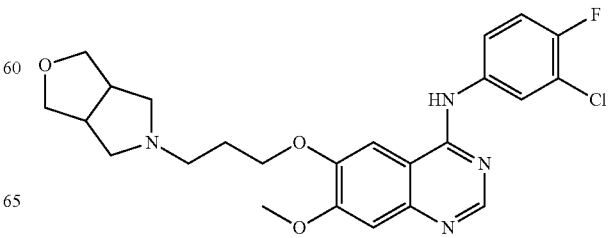

To a solution of 4-((3-chloro-4-fluorophenyl)amino)-7-methoxyquinazolin-6-ol (0.19 g) in DMF (6 mL) was added K$_2$CO$_3$ (0.42 g) and tetrabutylammonium iodide (20 mg). The mixture was stirred at room temperature for 10 min, to this, a solution of 5-(3-chloropropyl)hexahydro-1H-furo[3,4-c]pyrrole (0.13 g) in DMF (2 mL) was added. The reaction mixture was heated at 80° C. for 14 h under N$_2$ and treated with CH$_2$Cl$_2$ (100 mL), then washed with water and brine. The mixture was dried over anhydrous Na$_2$SO$_4$ and filtered. The filtrate was concentrated in vacuo and the residue was chromatographed with a silica gel column (eluting agent: 20:1 (v/v) CH$_2$Cl$_2$/CH$_3$OH) to give the title compound (180 mg, 60.04%), HPLC: 95.78%. The compound was characterized by the following spectroscopic data: MS (ESI, pos. ion) m/z: 474.0 (M+1); $^1$H NMR (400 MHz, CDCl$_3$) δ: 2.12 (t, J=13.28 Hz, 2H), 2.54 (s, 2H), 2.72 (t, J=13.32 Hz, 2H), 2.83 (d, J=9.00 Hz, 2H), 2.90 (s, 2H), 3.73 (t, J=5.36 Hz, 3H), 3.99 (s, 3H), 4.28 (t, J=13.24 Hz, 2H), 7.15 (t, J=17.60 Hz, 1H), 7.25 (d, J=7.32 Hz, 1H), 7.44 (s, 1H), 7.60-7.64 (m, 1H), 7.93-7.96 (m, 1H), 7.99 (s, 1H), 8.64 (s, 1H) ppm.

Example 23

N-(3-chloro-4-fluorophenyl)-6-(3-(hexahydropyrano[3,4-c]pyrrol-2(3H)-yl)propoxy)-7-methoxyquinazolin-4-amine

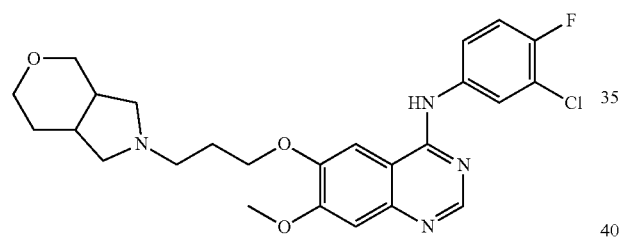

Step 1) 2-(1-benzyl-4-(hydroxymethyl)pyrrolidin-3-yl)ethanol

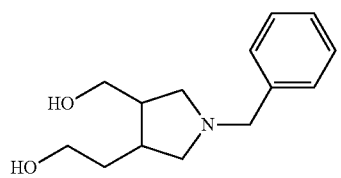 [SMILES: OCCC1CN(Cc2ccccc2)CC1CO]

To a solution of 2-benzylhexahydropyrano[3,4-c]pyrrol-4(2H)-one (2.82 g) in THF (70 mL) was added LiBH$_4$ (0.40 g) at 0° C. under N$_2$. The reaction mixture was stirred for 7 h at room temperature and concentrated in vacuo. The residue was dissolved in MeOH (50 mL) and heated to reflux for 16 h. The mixture was concentrated in vacuo and redissolved in EtOAc (100 mL), then washed with water followed by brine, dried over anhydrous Na$_2$SO$_4$ and filtered. The filtrate was concentrated in vacuo to give the title compound (2.31 g, 80.62%). The compound was characterized by the following spectroscopic data: MS (ESI, pos. ion) m/z: 236.3 (M+1).

Step 2) 2-benzyloctahydropyrano[3,4-c]pyrrole

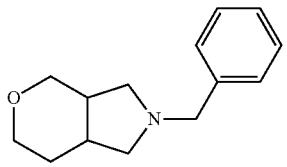 [SMILES: c1ccc(CN2CC3CCOCC3C2)cc1]

To a solution of 2-(1-benzyl-4-(hydroxymethyl)pyrrolidin-3-yl)ethanol (0.50 g) in toluene (30 mL) was added Et$_3$N (0.8 mL), TsCl (0.75 g) and DMAP (10 mg). The mixture was stirred for 12 h at room temperature under N$_2$, washed with water, dried over anhydrous Na$_2$SO$_4$ and filtered. The filtrate was concentrated in vacuo and the residue was used for the next step. To a solution of the above product in toluene (20 mL) was added Et$_3$N (0.85 mL). The reaction mixture was heated to reflux for 4 h and cooled to room temperature. The reaction mixture was washed with water followed by brine. The mixture was dried over anhydrous Na$_2$SO$_4$ and concentrated in vacuo. The residue was chromatographed with a silica gel column (eluting agent: 10:1 (v/v) CH$_2$Cl$_2$/CH$_3$OH) to give the title compound (0.18 g, 13.61%). The compound was characterized by the following spectroscopic data: MS (ESI, pos. ion) m/z: 218.3 (M+1).

Step 3) octahydropyrano[3,4-c]pyrrole

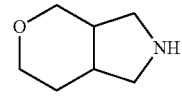

To a solution of 2-benzyloctahydropyrano[3,4-c]pyrrole (0.45 g) in EtOH (30 mL) was added 20% Pd(OH)$_2$ (0.30 g). The suspension was stirred under H$_2$ for 12 h and filtered. The filtrate was concentrated in vacuo to give the title compound (0.14 g). The compound was characterized by the following spectroscopic data: MS (ESI, pos. ion) m/z: 128.3 (M+1).

Step 4) 2-(3-chloropropyl)octahydropyrano[3,4-c]pyrrole

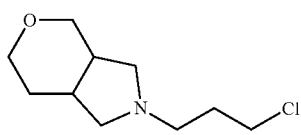

To a solution of octahydropyrano[3,4-c]pyrrole (0.14 g) in acetone (30 mL) was added K$_2$CO$_3$ (0.76 g) followed by 1-chloro-3-bromopropane (0.57 g, 2.0 eq). The reaction mixture was heated to reflux for 12 h and filtered. The filtrate was concentrated in vacuo, and the residue was dissolved in EtOAc (100 mL). The solution was washed with water (100 mL×2) followed by brine (100 mL), dried over anhydrous Na$_2$SO$_4$ and concentrated in vacuo. The residue was chromatographed with a silica gel column (eluting agent: 20:1 (v/v) EA/CH$_3$OH) to give the title compound (38 mg, 16.96%). The compound was characterized by the following spectroscopic data: MS (ESI, pos. ion) m/z: 204.7 (M+1).

Step 5) N-(3-chloro-4-fluorophenyl)-6-(3-(hexahydropyrano[3,4-c]pyrrol-2(3H)-yl)propoxy)-7-methoxyquinazolin-4-amine

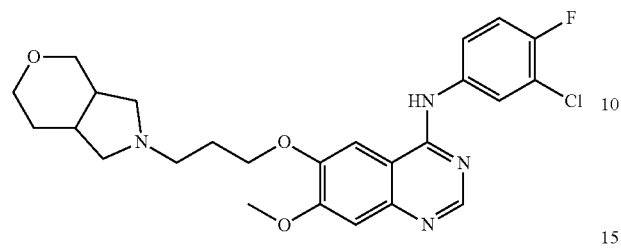

To a solution of 4-((3-chloro-4-fluorophenyl)amino)-7-methoxyquinazolin-6-ol (60 mg) in DMF (6 mL) was added K₂CO₃ (66 mg) and tetrabutylammonium iodide (5 mg). The mixture was stirred for 10 min at room temperature, to this, a solution of 2-(3-chloropropyl)octahydropyrano[3,4-c]-pyrrole (38 mg) in DMF (1 mL) was added. The reaction mixture was heated at 90° C. for 12 h under N₂ and CH₂Cl₂ (100 mL) was added. Then the mixture was washed with water followed by brine, dried over anhydrous Na₂SO₄ and concentrated in vacuo. The residue was chromatographed with a silica gel column (eluting agent: 20:1 (v/v) CH₂Cl₂/CH₃OH) to give the title compound (40 mg, 43.95%), HPLC: 98.50%. The compound was characterized by the following spectroscopic data: MS (ESI, pos. ion) m/z: 488.0 (M+1); ¹H NMR (400 MHz, CDCl₃) δ: 1.26-1.29 (m, 2H), 1.37 (s, 3H), 2.33-2.37 (m, 3H), 2.59 (s, 1H), 3.03 (s, 1H), 3.44-3.47 (m, 1H), 3.50 (s, 1H), 3.72 (d, J=3.28 Hz, 1H), 3.78 (d, J=1.76 Hz, 1H), 3.81 (s, 1H), 3.87-3.89 (m, 1H), 3.99 (s, 3H), 4.50-4.55 (m, 2H), 7.11 (t, J=17.68 Hz, 1H), 7.25 (d, J=15.28 Hz, 1H), 7.35 (m, 1H), 7.82-7.86 (m, 1H), 8.13 (s, 1H), 8.22-8.25 (m, 1H), 8.63 (s, 1H), 8.92 (s, 1H) ppm.

Example 24

N-(3-chloro-4-fluorophenyl)-7-methoxy-6-(3-(3-methyl-6,7-dihydroisoxazolo[4,3-c]pyridin-5(4H)-yl) propoxy)quinazolin-4-amine

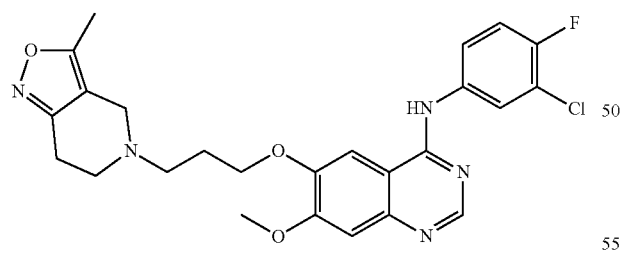

Step 1) tert-butyl 4-hydroxypiperidine-1-carboxylate

To a solution of 4-hydroxypiperidine (30.00 g) in THF (300 mL) was added a solution of Na₂CO₃ (60.60 g) in water (300 mL), and then (Boc)₂O (85 mL) dropwise at 0° C. The reaction mixture was stirred at room temperature overnight, and extracted with CH₂Cl₂ (200 mL×3). The combined organic phases were dried over anhydrous Na₂SO₄ and filtered. The filtrate was concentrated in vacuo and the residue was chromatographed with a silica gel column (eluting agent: 2:1 (v/v) PE/EA) to give the title compound as a white solid (53.10 g, 90.00%), HPLC: 95.00%. The compound was characterized by the following spectroscopic data: MS (ESI, pos. ion) m/z: 202.2 (M+1); ¹H NMR (400 MHz, CDCl₃): 1.38 (s, 9H), 1.52-1.77 (m, J=7.8 Hz, 4H), 3.23 (m, J=7.8 Hz, 1H), 3.29 (t, J=7.8 Hz, 4H), 3.53 (s, 1H) ppm.

Step 2) tert-butyl 4-oxopiperidine-1-carboxylate

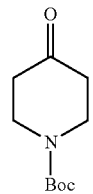 [SMILES: CC(C)(C)OC(=O)N1CCC(=O)CC1]

To a solution of tert-butyl 4-hydroxypiperidine-1-carboxylate (58.50 g) in CH₂Cl₂ was added Dess-Martin agent (174.10 g) in portions at 0° C. The reaction mixture was stirred for 2 h at room temperature, and quenched with water. The resulted mixture was extracted with CH₂Cl₂ (200 mL×3). The combined organic phases were dried over anhydrous Na₂SO₄ and filtered. The filtrate was concentrated in vacuo and the residue was chromatographed with a silica gel column (eluting agent: 3:1 (v/v) PE/EA) to give the title compound as a white solid (52.00 g, 90.00%), HPLC: 97.50%. The compound was characterized by the following spectroscopic data: MS (ESI, pos. ion) m/z: 200.5 (M+1); ¹H NMR (400 MHz, CDCl₃) δ: 2.42 (s, 9H), 2.78 (m, J=6.4 Hz, 2H), 3.56 (t, J=6.4 Hz, 2H), 4.28 (t, J=6.4 Hz, 2H), 4.50 (s, 2H) ppm.

Step 3) tert-butyl 3-acetyl-4-oxopiperidine-1-carboxylate

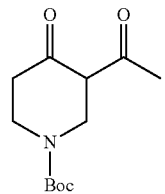 [SMILES: CC(=O)C1CN(C(=O)OC(C)(C)C)CCC1=O]

To a solution of tert-butyl 4-oxopiperidine-1-carboxylate (6.00 g) in THF was added LDA (16 mL, 1 M) dropwise at −78° C. The mixture was stirred at −78° C. for 2 h. To this, a solution of N-acetylimidazole (3.50 g) in THF was added, and the reaction mixture was stirred at −78° C. for another 7 h, then quenched with 10 mL of ice-water and extracted with CH₂Cl₂ (50 mL×3). The combined organic phases were dried over anhydrous Na₂SO₄ and filtered. The filtrate was concentrated in vacuo and the residue was chromatographed with a silica gel column (eluting agent: 3:1 (v/v) PE/EA) to give the title compound as yellow oil (2.98 g, 41.00%), HPLC: 89.00%. The compound was characterized by the following spectroscopic data: MS (ESI, pos. ion) m/z: 242.4 (M+1); ¹H NMR (400 MHz, CDCl₃) δ: 1.47 (s, 9H), 2.13 (s, 3H), 2.28 (s, 1H), 2.44 (t, J=4.0 Hz, 2H), 3.58 (t, J=8.0 Hz, 2H), 3.97 (s, 2H) ppm.

Step 4) 3-methyl-4,5,6,7-tetrahydroisoxazolo[4,3-c]pyridine

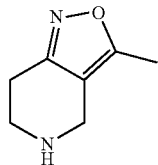

A mixture of tert-butyl 3-acetyl-4-oxopiperidine-1-carboxylate (1.50 g) and NH$_2$OH.HCl (0.50 g) in anhydrous EtOH was heated to reflux for 0.5 h. The reaction mixture was cooled to rt, and then poured into 20 mL of water. The resulted mixture was extracted with CH$_2$Cl$_2$ (20 mL×3). The combined organic phases were dried over Na$_2$SO$_4$ and concentrated in vacuo, the residue was chromatographed with a silica gel column (eluting agent: 10:1 (v/v) DCM/MeOH) to give the title compound as yellow oil (0.45 g, 52.00%), HPLC: 90.00%. The compound was characterized by the following spectroscopic data: MS (ESI, pos. ion) m/z: 139.3 (M+1); $^1$H NMR (400 MHz, CDCl$_3$) δ: 2.31 (s, 3H), 2.86 (t, J=8.0 Hz, 2H), 3.15 (t, J=8.0 Hz, 2H), 3.92 (s, 2H) ppm.

Step 5) 5-(3-chloropropyl)-3-methyl-4,5,6,7-tetrahydroisoxazolo[4,3-c]pyridine

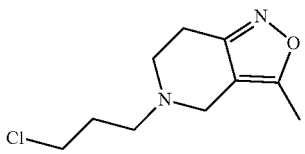

A mixture of 3-methyl-4,5,6,7-tetrahydroisoxazolo[4,3-c]pyridine (1.60 g), 1-bromo-3-chloropropane (3.50 mL) and cesium carbonate in acetone was heated to reflux for 24 h. The reaction mixture was cooled to room temperature and filtered. The filtrate was concentrated in vacuo and the residue was chromatographed with a silica gel column (eluting agent: 20:1 (v/v) DCM/MeOH) to give the title compound as yellow oil (0.97 g, 39.00%), HPLC: 85.00%. The compound was characterized by the following spectroscopic data: MS (ESI, pos. ion) m/z: 215.2 (M+1).

Step 6) N-(3-chloro-4-fluorophenyl)-7-methoxy-6-(3-(3-methyl-6,7-dihydroisoxazolo[4,3-c]pyridin-5(4H)-yl)propoxy)quinazolin-4-amine

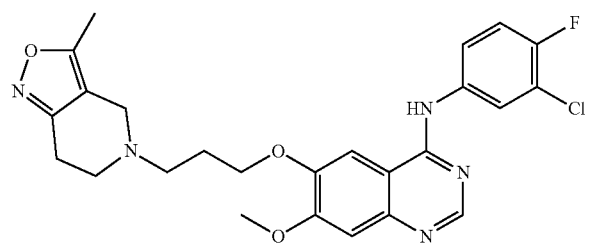 [SMILES: COc1cc2ncnc(Nc3ccc(F)c(Cl)c3)c2cc1OCCCN1CCc2noc(C)c2C1]

A mixture of 4-((3-chloro-4-fluorophenyl)amino)-7-methoxyquinazolin-6-ol (1.20 g), K$_2$CO$_3$ (2.60 g) and 5-(3-chloropropyl)-3-methyl-4,5,6,7-tetrahydroisoxazolo[4,3-c]pyridine (0.97 g) in 10 mL of DMF was stirred at 80° C. for 7 h, and treated with 250 mL of ice-water. Then the mixture was extracted with CH$_2$Cl$_2$ (50 mL×2). The combined organic phases were dried over Na$_2$SO$_4$ and filtered. The filtrate was concentrated in vacuo and the residue was chromatographed with a silica gel column (eluting agent: 20:1 (v/v) DCM/MeOH) to give the title compound as a pale yellow solid (0.80 g, 45.00%), HPLC: 95.00%. The compound was characterized by the following spectroscopic data: MS (ESI, pos. ion) m/z: 498.1 (M+1); $^1$H NMR (400 MHz, d$^6$-DMSO) δ: 2.08 (m, J=4.0 Hz 2H), 2.51 (s, 3H), 2.70 (m, J=4.0 Hz, 6H), 2.37 (m, J=4.0 Hz, 2H), 3.94 (s, 3H), 4.20 (m, J=8.0 Hz, 2H), 7.21 (s, 1H), 7.42 (t, J=8.0 Hz, 1H), 7.44 (s, 2H), 8.11 (t, J=4.0 Hz, 1H), 8.50 (s, 1H) ppm.

Example 25

N-(3-chloro-4-fluorophenyl)-6-(3-(hexahydro-1H-pyrrolo[3,4-b]pyridin-6(2H)-yl)propoxy)-7-methoxyquinazolin-4-amine

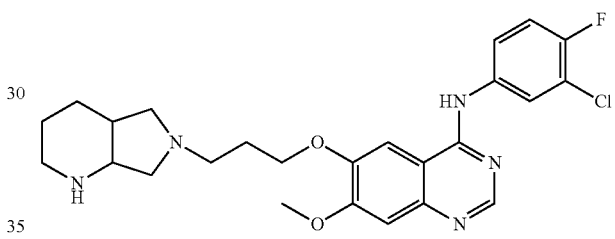

Step 1) 6-benzyltetrahydro-1H-pyrrolo[3,4-b]pyridine-5,7(6H,7aH)-dione

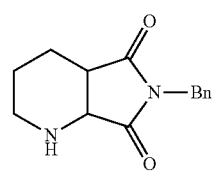 [SMILES: O=C1C2CCCNC2C(=O)N1Cc1ccccc1]

To a solution of 6-benzyl-5H-pyrrolo[3,4-b]pyridine-5,7(6H)-dione (5.00 g) in glycol monomethyl ether was added a catalytic amount of 10% Pd/C. The reaction mixture was heated to 90° C. and stirred for 6 h under H$_2$, then cooled to rt. The resulted mixture was poured into 100 mL of water and extracted with CH$_2$Cl$_2$ (50 mL×3). The combined organic phases were dried over anhydrous Na$_2$SO$_4$ and filtered. The filtrate was concentrated in vacuo and the residue was chromatographed with a silica gel column (eluting agent: 1:2 (v/v) PE/EA) to give the title compound as colorless oil (3.00 g, 60.00%), HPLC: 95.00%. The compound was characterized by the following spectroscopic data: MS (ESI, pos. ion) m/z: 245.1 (M+1); $^1$H NMR (400 MHz, CDCl$_3$) δ: 1.47-1.53 (m, 4H), 2.12 (s, 1H), 2.63-2.69 (m, 1H), 2.76-2.88 (m, 2H), 3.83 (d, J=8.2, 2H), 4.64 (s, 1H), 7.25-7.36 (m, 5H) ppm.

Step 2) 6-benzyloctahydro-1H-pyrrolo[3,4-b]pyridine

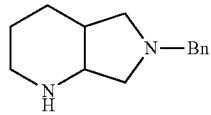

To a solution of LiAlH₄ (1.20 g) in THF was added slowly 6-benzyltetrahydro-1H-pyrrolo[3,4-b]pyridine-5,7(6H,7aH)-dione (3.00 g) at 0° C. The reaction mixture was refluxed for 6 h under N₂, and then cooled to rt. The reaction mixture was quenched with water at 0° C. and filtered. The filtrate was concentrated in vacuo and the residue was chromatographed with a silica gel column (eluting agent: 10:1 (v/v) EA/MeOH) to give the title compound as yellow oil (1.50 g, 47.00%), HPLC: 90.00%. The compound was characterized by the following spectroscopic data: MS (ESI, pos. ion) m/z: 217.1 (M+1); ¹H NMR (400 MHz, CDCl₃) δ: 1.49-1.50 (m, 2H), 1.63-1.66 (m, 2H), 2.76-2.88 (m, 2H), 1.90 (s, 1H), 2.17-2.19 (m, 1H), 2.52-2.63 (m, 4H), 2.74 (t, J=10.4 Hz, 1H), 2.81-2.84 (m, 1H), 2.95-2.98 (m, 1H), 3.21-3.22 (m, J=4.0 Hz), 3.66 (q, J=12.6 Hz, 1H), 7.22-7.34 (m, 5H) ppm.

Step 3) tert-butyl 6-benzyloctahydro-1H-pyrrolo[3,4-b]pyridine-1-carboxylate

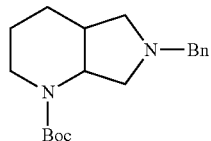 [SMILES: CC(C)(C)OC(=O)N1CCCC2CN(Cc3ccccc3)CC21]

To a solution of 6-benzyloctahydro-1H-pyrrolo[3,4-b]pyridine (1.66 g) in THF (25 mL) was added a solution of Na₂CO₃ (2.30 g) in water (25 mL) followed by (Boc)₂O (3.00 mL) dropwise at 0° C. The reaction mixture was stirred at room temperature overnight, and extracted with CH₂Cl₂ (20 mL×3). The combined organic phases were dried over anhydrous Na₂SO₄ and filtered. The filtrate was concentrated in vacuo and the residue was chromatographed with a silica gel column (eluting agent: 10:1 (v/v) PE/EA) to give the title compound as a white solid (1.70 g, 74.00%), HPLC: 95.00%. The compound was characterized by the following spectroscopic data: MS (ESI, pos. ion) m/z: 317.3 (M+1); ¹H NMR (400 MHz, CDCl₃) δ: 1.49 (s, 9H), 1.66 (m, 4H), 2.76-2.88 (m, 2H), 1.90 (s, 1H), 2.19 (m, 5H), 2.76 (t, J=8.0 Hz, 1H), 2.84 (m, J=4.0 Hz, 1H), 2.95-2.98 (m, J=4.0 Hz, 1H), 3.21-3.22 (m, 2H), 3.56 (q, J=12.0 Hz, 1H), 7.22-7.34 (m, 5H) ppm.

Step 4) tert-butyl octahydro-1H-pyrrolo[3,4-b]pyridine-1-carboxylate

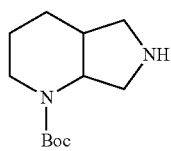 [SMILES: CC(C)(C)OC(=O)N1CCCC2CNCC21]

To a solution of tert-butyl 6-benzyloctahydro-1H-pyrrolo[3,4-b]pyridine-1-carboxylate (2.00 g) in MeOH was added a catalytic amount of 20% Pd(OH)₂/C. The suspension was stirred for 2 h at room temperature under H₂ and filtered. The filtrate was concentrated in vacuo and the residue was used for the next step without further purification. The compound was characterized by the following spectroscopic data: MS (ESI, pos. ion) m/z: 227.6 (M+1).

Step 5) tert-butyl 6-(3-((4-((3-chloro-4-fluorophenyl)amino)-7-methoxyquinazolin-6-yl)oxy)propyl)octahydro-1H-pyrrolo[3,4-b]pyridine-1-carboxylate

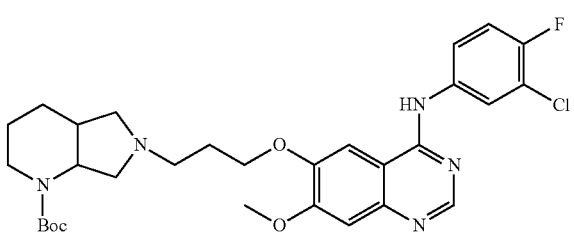 [SMILES: COc1cc2ncnc(Nc3ccc(F)c(Cl)c3)c2cc1OCCCN1CC2CCCN(C(=O)OC(C)(C)C)C2C1]

A mixture of N-(3-chloro-4-fluorophenyl)-6-(3-chloropropoxy)-7-methoxyquinazolin-4-amine (2.00 g), K₂CO₃ (5.00 g) and tert-butyl octahydro-1H-pyrrolo[3,4-b]pyridine-1-carboxylate (1.20 g) in 20 mL of DMF was stirred at 80° C. for 7 h, then poured into 50 mL of ice-water and extracted with CH₂Cl₂ (50 mL×2). The combined organic phases were dried over anhydrous Na₂SO₄ and filtered. The filtrate was concentrated in vacuo and the residue was chromatographed with a silica gel column (eluting agent: 20:1 (v/v) DCM/MeOH) to give the title compound as a pale yellow solid (1.10 g, 45.00%), HPLC: 92.00%. The compound was characterized by the following spectroscopic data: MS (ESI, pos. ion) m/z: 586.2 (M+1); ¹H NMR (400 MHz, CDCl₃) δ: 1.38 (s, 9H), 1.34-1.82 (m, 6H), 2.09-2.43 (m, 7H), 3.29 (m, 2H), 3.68 (m, 1H), 3.83 (s, 3H), 4.06 (m, 2H), 6.93 (s, 1H), 7.06 (s, 1H), 7.30 (s, 1H), 7.44 (d, J=4.0 Hz, 1H), 7.87 (d, J=4.0 Hz, 1H), 8.54 (s, 1H) ppm.

Step 6) N-(3-chloro-4-fluorophenyl)-6-(3-(hexahydro-1H-pyrrolo[3,4-b]pyridin-6(2H)-yl)propoxy)-7-methoxyquinazolin-4-amine

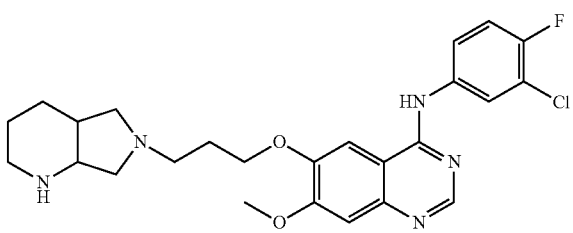 [SMILES: COc1cc2ncnc(Nc3ccc(F)c(Cl)c3)c2cc1OCCCN1CC2CCCNC2C1]

To a solution of tert-butyl 6-(3-((4-((3-chloro-4-fluorophenyl)amino)-7-methoxyquinazolin-6-yl)oxy)propyl)octahydro-1H-pyrrolo[3,4-b]pyridine-1-carboxylate (0.60 g) in CH₂Cl₂ was added a saturated solution of HCl in MeOH. Solid was precipitated out after 2 h reaction. The reaction mixture was filtered, and the residue was dried to give the title compound as a pale yellow solid (0.70 g, 80.00%), HPLC: 96.00%. The compound was characterized by the following spectroscopic data: MS (ESI, pos. ion) m/z: 486.3 (M+1); ¹H NMR (400 MHz, CDCl₃) δ: 1.13-1.96 (m, 6H), 2.09-2.43 (m, 2H), 3.29 (m, 2H), 3.68-3.70 (m, 6H), 3.83 (s, 3H), 4.06 (m, 2H), 6.93 (t, J=8.2 Hz, 1H), 7.06 (s, 1H), 7.27 (m, 1H), 7.44 (d, J=8.0 Hz, 1H), 7.87 (d, J=4.2 Hz, 1H), 8.45 (s, 1H) ppm.

Example 26

N-(3-chloro-4-fluorophenyl)-7-methoxy-6-(3-(octahydro-1H-pyrrolo[3,4-b]pyridin-1-yl)propoxy)quinazolin-4-amine

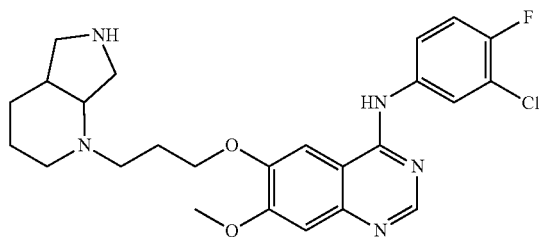 [SMILES: COc1cc2ncnc(Nc3ccc(F)c(Cl)c3)c2cc1OCCCN1CCCC2CNCC21]

Step 1) tert-butyl 5H-pyrrolo[3,4-b]pyridine-6(7H)-carboxylate

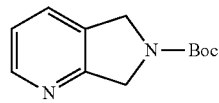

To a solution of 6,7-dihydro-5H-pyrrolo[3,4-b]pyridine (2.00 g) and Et₃N (8.00 mL) in CH₂Cl₂ was added (Boc)₂O (7.00 mL) dropwise at 0° C. The reaction mixture was stirred at room temperature overnight, then poured into water and extracted with CH₂Cl₂ (50 mL×3). The combined organic phases were dried over anhydrous Na₂SO₄ and filtered. The filtrate was concentrated in vacuo and the residue was chromatographed with a silica gel column (eluting agent: 2:1 (v/v) PE/EA) to give the title compound as pale yellow oil (1.65 g, 45.00%), HPLC: 92.00%. The compound was characterized by the following spectroscopic data: MS (ESI, pos. ion) m/z: 221.2 (M+1); ¹H NMR (400 MHz, CDCl₃) δ: 1.52 (s, 9H), 4.67-4.71 (m, 4H), 7.18 (t, J=8.4 Hz, 1H), 7.58 (q, J=8.2 Hz, 1H), 8.46 (d, J=4.2 Hz, 1H) ppm.

Step 2) tert-butyl hexahydro-1H-pyrrolo[3,4-b]pyridine-6(2H)-carboxylate

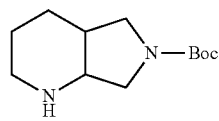 [SMILES: CC(C)(C)OC(=O)N1CC2CCCNC2C1]

To a solution of tert-butyl 5H-pyrrolo[3,4-b]pyridine-6(7H)-carboxylate (1.50 g) in glycol monomethyl ether was added a catalytic amount of 10% Pd/C. The suspension was heated to 70° C. and stirred for 6 h under H₂. The resulted mixture was cooled to rt, poured into 100 mL of water and extracted with CH₂Cl₂ (50 mL×3). The combined organic phases were dried over anhydrous Na₂SO₄ and filtered. The filtrate was concentrated in vacuo to give the title compound as pale yellow oil (0.95 g, 65.00%). The crude product was used for the next step without further purification. The compound was characterized by the following spectroscopic data: MS (ESI, pos. ion) m/z: 227.2 (M+1).

Step 3) tert-butyl 1-(3-chloropropyl)hexahydro-1H-pyrrolo[3,4-b]pyridine-6(2H)-carboxylate

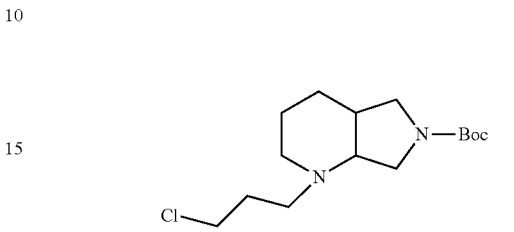

A mixture of tert-butyl hexahydro-1H-pyrrolo[3,4-b]pyridine-6(2H)-carboxylate (1.60 g), 1-bromo-3-chloropropane (1.50 mL) and K₂CO₃ (3.00 g) in acetone was heated to reflux for 9 h. The reaction mixture was cooled to rt and filtered. The filtrate was concentrated in vacuo and the residue was chromatographed with a silica gel column (eluting agent: 1:1 (v/v) PE/EA) to give the title compound as yellow oil (0.53 g, 65.00%), HPLC: 89.00%. The compound was characterized by the following spectroscopic data: MS (ESI, pos. ion) m/z: 303.2 (M+1).

Step 4) tert-butyl 1-(3-((4-((3-chloro-4-fluorophenyl)amino)-7-methoxyquinazolin-6-yl)oxy)propyl)hexahydro-1H-pyrrolo[3,4-b]pyridine-6(2H)-carboxylate

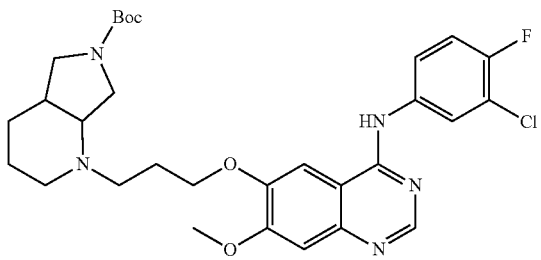 [SMILES: COc1cc2ncnc(Nc3ccc(F)c(Cl)c3)c2cc1OCCCN1CCCC2CN(C(=O)OC(C)(C)C)CC21]

A mixture of 4-((3-chloro-4-fluorophenyl)amino)-7-methoxyquinazolin-6-ol (0.90 g), K₂CO₃ (2.90 g) and tert-butyl 1-(3-chloropropyl)hexahydro-1H-pyrrolo[3,4-b]pyridine-6(2H)-carboxylate (1.00 g) in 20 mL of DMF was stirred at 80° C. for 7 h, then poured into 100 mL of ice-water and extracted with CH₂Cl₂ (50 mL×3). The combined organic phases were dried over anhydrous Na₂SO₄ and filtered. The filtrate was concentrated in vacuo and the residue was chromatographed with a silica gel column (eluting agent: 20:1 (v/v) DCM/MeOH) to give the title compound as a pale yellow solid (0.60 g, 45.00%), HPLC: 95.00%. The compound was characterized by the following spectroscopic data: MS (ESI, pos. ion) m/z: 586.2 (M+1); ¹H NMR (400 MHz, d⁶-DMSO) δ: 1.72 (s, 9H), 1.29 (m, 2H), 1.56 (m, 2H), 1.94-1.98 (m, 2H), 2.19 (d, J=4.4 Hz, 1H), 2.49-2.54 (m, 2H), 2.85-2.87 (m, 2H), 2.91-2.95 (m, 1H), 3.37 (s, 3H), 4.05-4.10 (m, 3H), 4.13-4.14 (m, 1H), 4.15-4.16 (m, 2H), 7.18 (d, J=4.8 Hz, 1H), 7.43 (t, J=8.6 Hz, 1H), 7.76-7.81 (m, 2H), 8.12-8.13 (m, 1H), 8.49 (s, 1H) ppm.

Step 5) N-(3-chloro-4-fluorophenyl)-7-methoxy-6-(3-(octahydro-1H-pyrrolo[3,4-b]pyridin-1-yl) propoxy)quinazolin-4-amine

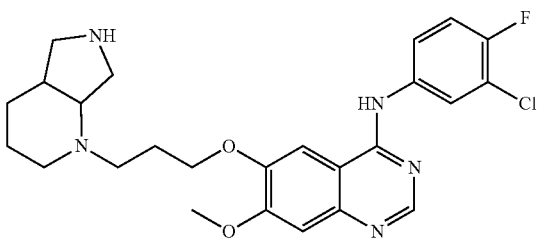 [SMILES: COc1cc2ncnc(Nc3ccc(F)c(Cl)c3)c2cc1OCCCN1CCCC2CNCC21]

To a solution of tert-butyl 1-(3-((4-((3-chloro-4-fluorophenyl)amino)-7-methoxyquinazolin-6-yl)oxy)propyl)hexahydro-1H-pyrrolo[3,4-b]pyridine-6(2H)-carboxylate (0.60 g) in CH$_2$Cl$_2$ was added a solution of 3M HCl in EtOAC. Solid was precipitated out after 2 h reaction. The reaction mixture was filtered, and the residue was dried to give the title compound as a yellow solid (0.50 g, 80.00%), HPLC: 96.00%. The compound was characterized by the following spectroscopic data: MS (ESI, pos. ion) m/z: 486.3 (M+1); $^1$H NMR (400 MHz, d$^6$-DMSO) δ: 1.99 (m, 3H), 1.56 (m, 2H), 1.94-1.98 (m, 2H), 2.19 (d, J=4.8 Hz, 1H), 2.50-2.53 (m, 2H), 2.85-2.87 (m, 2H), 2.91-2.95 (m, 1H), 3.37 (s, 3H), 4.05-4.07 (m, 3H), 4.13-4.14 (m, 1H), 4.15-4.17 (m, 2H), 7.44 (s, 1H), 7.50 (t, J=4.4 Hz, 1H), 7.83-7.88 (m, 1H), 8.07-8.09 (m, 1H), 8.99-9.02 (m, 1H), 9.15 (s, 1H) ppm.

Example 27

N-(3-chloro-4-fluorophenyl)-7-methoxy-6-(3-(6-methyloctahydro-1H-pyrrolo[3,4-b]pyridin-1-yl) propoxy)quinazolin-4-amine

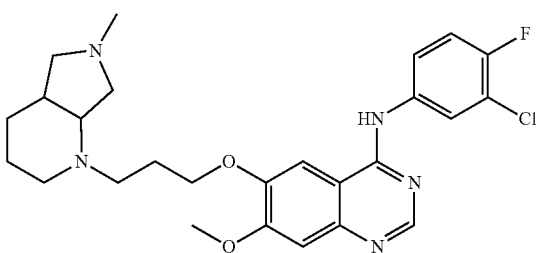 [SMILES: COc1cc2ncnc(Nc3ccc(F)c(Cl)c3)c2cc1OCCCN1CCCC2CN(C)CC21]

To a solution of N-(3-chloro-4-fluorophenyl)-7-methoxy-6-(3-(octahydro-1H-pyrrolo[3,4-b]pyridin-1-yl) propoxy)quinazolin-4-amine (0.45 g) in the mixture solvent of MeOH and CH$_2$Cl$_2$ (1:1) was added 37% HCHO (1.00 mL) and acetic acid (0.50 mL) dropwise. The reaction mixture was stirred for 30 min at room temperature, NaB(OCOCH$_3$)$_3$H (1.50 g) was added in portions. The reaction mixture was stirred for another 2 h at room temperature, poured into water and extracted with CH$_2$Cl$_2$ (50 mL×3). The combined organic phases were dried over anhydrous Na$_2$SO$_4$ and filtered. The filtrate was concentrated in vacuo and the residue was chromatographed with a silica gel column (eluting agent: 20:1 (v/v) DCM/MeOH) to give the title compound as a pale yellow solid (0.60 g, 70.00%), HPLC: 98.00%. The compound was characterized by the following spectroscopic data: MS (ESI, pos. ion) m/z: 500.1 (M+1); $^1$H NMR (400 MHz, d$^6$-DMSO) δ: 1.82 (m, 1H), 2.33 (m, 4H), 1.94 (m, 1H), 2.19-2.20 (m, 2H), 2.50-2.52 (m, 1H), 2.67-2.70 (m, 2H), 3.58 (s, 3H), 4.01-4.02 (m, 2H), 4.03-4.04 (m, 5H), 4.05-4.07 (m, 1H), 4.40 (s, 2H), 7.44 (s, 1H), 7.50 (t, J=4.8 Hz, 1H), 7.83-7.88 (m, 1H), 8.07-8.08 (m, 1H), 8.89-8.91 (m, 1H), 9.05 (s, 1H) ppm.

Example 28

N-(3-chloro-4-fluorophenyl)-7-methoxy-6-(3-(1-methylhexahydro-1H-pyrrolo[3,4-b]pyridin-6(2H)-yl) propoxy)quinazolin-4-amine

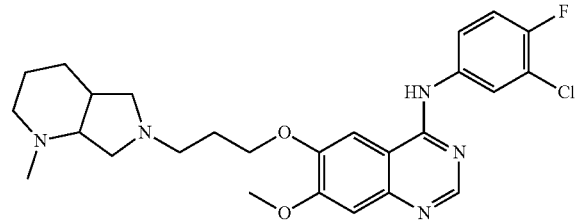 [SMILES: COc1cc2ncnc(Nc3ccc(F)c(Cl)c3)c2cc1OCCCN1CC2CCCN(C)C2C1]

Step 1) 6-benzyl-1-methyloctahydro-1H-pyrrolo[3,4-b]pyridine

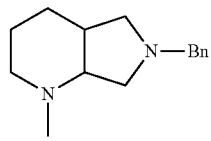 [SMILES: CN1CCCC2CN(Cc3ccccc3)CC21]

A solution of 6-benzyloctahydro-1H-pyrrolo[3,4-b]pyridine (2.00 g) and 37% HCHO (6.0 mL) in HCO$_2$H was heated to 90° C. and stirred for 4 h. The reaction mixture was cooled to rt and poured into ice-water. The mixture was adjusted to pH 10 with 2M NaOH aqueous solution and extracted with CH$_2$Cl$_2$ (70 mL×3). The combined organic phases were dried over anhydrous Na$_2$SO$_4$ and filtered. The filtrate was concentrated in vacuo and the residue was chromatographed with a silica gel column (eluting agent: 20:1 (v/v) DCM/MeOH) to give the title compound as pale yellow oil (0.95 g, 45.00%), HPLC: 85.00%. The compound was characterized by the following spectroscopic data: MS (ESI, pos. ion) m/z: 231.2 (M+1).

Step 2) 1-methyloctahydro-1H-pyrrolo[3,4-b]pyridine

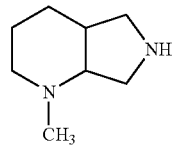

To a solution of 6-benzyl-1-methyloctahydro-1H-pyrrolo[3,4-b]pyridine (2.00 g) in the mixture solvent of MeOH and EtOAc was added a catalytic amount of 20% Pd(OH)$_2$/C. The reaction mixture was stirred for 2 h at room temperature under H₂. The resulted mixture was filtered and the filtrate was concentrated to in vacuo to give the crude product, which was used for the next step without further purification. The compound was characterized by the following spectroscopic data: MS (ESI, pos. ion) m/z: 141.2 (M+1).

Step 3) N-(3-chloro-4-fluorophenyl)-7-methoxy-6-(3-(1-methylhexahydro-1H-pyrrolo[3,4-b]pyridine-6(2H)-yl)propoxy) quinazolin-4-amine

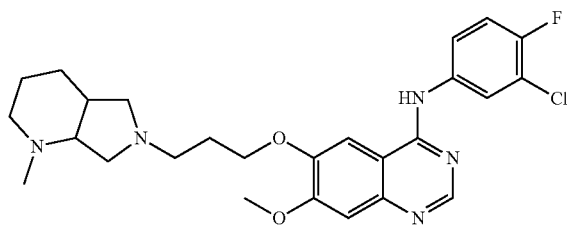 [SMILES: COc1cc2ncnc(Nc3ccc(F)c(Cl)c3)c2cc1OCCCN1CC2CCCN(C)C2C1]

A mixture of N-(3-chloro-4-fluorophenyl)-6-(3-chloropropoxy)-7-methoxyquinazolin-4-amine (1.50 g), K₂CO₃ (5.00 g) and 1-methyloctahydro-1H-pyrrolo[3,4-b]pyridine (0.90 g) in 25 mL of DMF was stirred at 80° C. for 7 h, poured into 50 mL of ice-water and extracted with CH₂Cl₂ (50 mL×3). The combined organic phases were dried over anhydrous Na₂SO₄ and filtered. The filtrate was concentrated in vacuo and chromatographed with a silica gel column (eluting agent: 20:1 (v/v) DCM/MeOH) to give the title compound as a pale yellow solid (0.60 g, 35.00%), HPLC: 95.00%. The compound was characterized by the following spectroscopic data: MS (ESI, pos. ion) m/z: 501.1 (M+1); ¹H NMR (400 MHz, d⁶-DMSO) δ: 1.52-1.62 (m, 4H), 1.97-2.00 (m, 3H), 2.07-2.09 (m, 2H), 2.08-2.11 (m, 4H), 2.51-2.56 (m, 1H), 2.57-2.61 (m, 2H), 2.88-2.92 (m, 2H), 3.94 (s, 3H), 4.18 (t, J=8.6 Hz, 2H), 7.19 (s, 1H), 7.44 (t, J=10.4 Hz, 1H), 7.82 (s, 2H), 8.13 (t, J=6.8 Hz, 1H), 8.50 (s, 1H) ppm.

Example 29

N-(3-chloro-4-fluorophenyl)-6-(3-(6-ethyloctahydro-1H-pyrrolo[3,4-b]pyridin-1-yl)propoxy)-7-methoxyquinazolin-4-amine

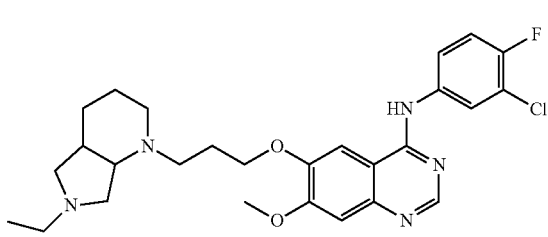 [SMILES: CCN1CC2CCCN(CCCOc3cc4c(Nc5ccc(F)c(Cl)c5)ncnc4cc3OC)C2C1]

Step 1)
6-ethyl-6,7-dihydro-5H-pyrrolo[3,4-b]pyridine

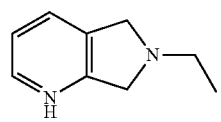

To a solution of 6,7-dihydro-5H-pyrrolo[3,4-b]pyridine (5.00 g) in THF was added 80% NaH (3.00 g) at rt. The reaction mixture was stirred for 30 min at room temperature, and 5.3 mL of iodoethane was added dropwise. The reaction mixture was stirred for another 5 h, then quenched with ice water, and extracted with CH₂Cl₂ (70 mL×5). The combined organic phases were dried over anhydrous Na₂SO₄ and filtered. The filtrate was concentrated in vacuo and the residue was chromatographed with a silica gel column (eluting agent: 30:1 (v/v) DCM/MeOH) to give the title compound as a pale yellow solid (2.80 g, 45.00%), HPLC: 90.00%. The compound was characterized by the following spectroscopic data: MS (ESI, pos. ion) m/z: 149.3 (M+1); ¹H NMR (400 MHz, d⁶-DMSO) δ: 1.02 (t, J=4.8 Hz, 3H), 2.64 (m, 2H), 3.62 (s, 2H), 3.95 (s, 2H), 7.11-7.83 (m, 3H) ppm.

Step 2) 6-ethyloctahydro-1H-pyrrolo[3,4-b]pyridine

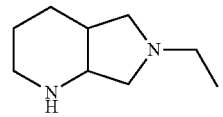

To a solution of 6-ethyl-6,7-dihydro-5H-pyrrolo[3,4-b]pyridine (2.00 g) in glycol monomethyl ether was added a catalytic amount of 10% Pd/C. The suspension was heated to 70° C. and stirred for 6 h under H₂ (2 MPa), then cooled to rt, and poured into 100 mL of water. The mixture was extracted with CH₂Cl₂ (50 mL×3). The combined organic phases were dried over anhydrous Na₂SO₄ and filtered. The filtrate was concentrated in vacuo to give the title compound as yellow oil (1.50 g, 70.00%). The crude product was used for the next step without further purification. The compound was characterized by the following spectroscopic data: MS (ESI, pos. ion) m/z: 155.0 (M+1).

Step 3) N-(3-chloro-4-fluorophenyl)-6-(3-(6-ethyloctahydro-1H-pyrrolo[3,4-b]pyridin-1-yl)propoxy)-7-methoxyquinazolin-4-amine

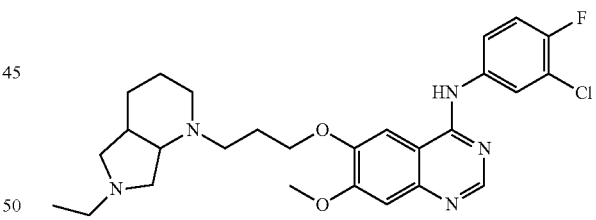

A mixture of N-(3-chloro-4-fluorophenyl)-6-(3-chloropropoxy)-7-methoxyquinazolin-4-amine (0.80 g), K₂CO₃ (3.00 g) and 6-ethyloctahydro-1H-pyrrolo[3,4-b]pyridine (0.40 g) in 25 mL of DMF was stirred at 80° C. for 7 h, then cooled to rt, poured into 50 mL of ice-water and extracted with CH₂Cl₂ (50 mL×3). The combined organic phases were dried over anhydrous Na₂SO₄ and filtered. The filtrate was concentrated in vacuo and the residue was chromatographed with a silica gel column (eluting agent: 20:1 (v/v) DCM/MeOH) to give the title compound as a pale yellow solid (0.36 g, 35.00%), HPLC: 95.00%. The compound was characterized by the following spectroscopic data: MS (ESI, pos. ion) m/z: 515.4 (M+1); ¹H NMR (400 MHz, d⁶-DMSO) δ: 1.93 (t, J=4.6 Hz, 3H), 2.21-2.33 (m, 4H), 2.43-2.50 (m, 5H), 2.54-2.60 (m, 2H), 2.98-3.02 (m, 2H), 3.17-3.20 (m, 3H), 3.35-3.41 (m, 1H), 3.48-3.52 (m, 1H), 4.29 (s, 3H), 4.34 (t, J=8.6

Hz, 2H), 7.20 (s, 1H), 7.41 (t, J=8.0 Hz, 1H), 7.43 (s, 2H), 7.91 (t, J=4.2 Hz, 1H), 8.47 (s, 1H) ppm.

Example 30

N-(3-chloro-4-fluorophenyl)-6-(3-(hexahydro-1H-pyrrolo[3,4-c]pyridin-2(3H)-yl)propoxy)-7-methoxyquinazolin-4-amine

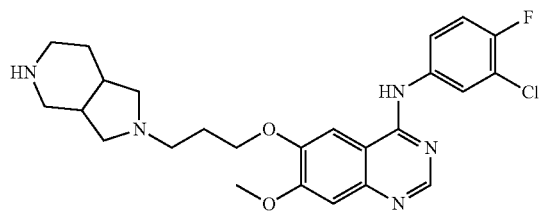 [SMILES: COc1cc2ncnc(Nc3ccc(F)c(Cl)c3)c2cc1OCCCN1CC2CCNCC2C1]

Step 1) 2-benzyl-1H-pyrrolo[3,4-c]pyridine-1,3(2H)-dione

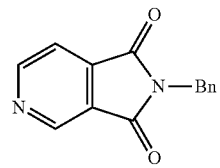 [SMILES: O=C1c2ccncc2C(=O)N1Cc1ccccc1]

To a solution of 1H-pyrrolo[3,4-c]pyridine-1,3(2H)-dione (5.00 g) and N,N-diisopropylethylamine (20.00 mL) in acetone was added benzyl bromide (5.0 mL). The reaction mixture was heated to reflux for 5 h, then cooled to rt and filtered. The filtrate was poured into water and extracted with CH$_2$Cl$_2$ (50 mL×3). The combined organic phases were dried over anhydrous Na$_2$SO$_4$ and filtered. The filtrate was concentrated in vacuo and the residue was chromatographed with a silica gel column (eluting agent: 2:1 (v/v) PE/EA) to give the title compound as a brown solid (4.00 g, 50.00%), HPLC: 92.00%. The compound was characterized by the following spectroscopic data: MS (ESI, pos. ion) m/z: 239.2 (M+1); $^1$H NMR (400 MHz, d$^6$-DMSO) δ: 4.92 (s, 2H), 7.26-7.34 (m, 3H), 7.45 (m, 2H), 7.60 (m, 1H), 8.14 (d, J=8.4 Hz, 1H), 8.96 (d, J=10.4 Hz, 1H) ppm.

Step 2) 2-benzylhexahydro-1H-pyrrolo[3,4-c]pyridine-1,3(2H)-dione

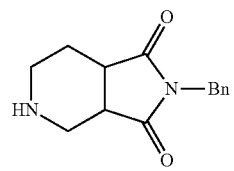 [SMILES: O=C1C2CCNCC2C(=O)N1Cc1ccccc1]

To a solution of 2-benzyl-1H-pyrrolo[3,4-c]pyridine-1,3(2H)-dione (3.50 g) in glycol monomethyl ether was added a catalytic amount of 10% Pd/C. The suspension was heated to 35° C. and stirred for 6 h under H$_2$, then cooled to rt, poured into 100 mL of water and extracted with CH$_2$Cl$_2$ (70 mL×3). The combined organic phases were dried over anhydrous Na$_2$SO$_4$ and filtered. The filtrate was concentrated in vacuo to give the title compound as yellow oil (2.20 g, 60%). The crude product was used for the next step without further purification. The compound was characterized by the following spectroscopic data: MS (ESI, pos. ion) m/z: 245.2 (M+1).

Step 3) 2-benzyloctahydro-1H-pyrrolo[3,4-c]pyridine

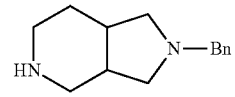 [SMILES: c1ccc(CN2CC3CCNCC3C2)cc1]

To a solution of LiAlH$_4$ (1.00 g) in THF was added slowly 2-benzylhexahydro-1H-pyrrolo[3,4-c]pyridine-1,3(2H)-dione (2.00 g) at 0° C. The reaction mixture was refluxed for 6 h under N$_2$, and cooled to rt, quenched with ice-water and filtered. The filtrate was concentrated in vacuo to give the title compound as yellow oil (0.45 g, 25%). The crude product was used for the next step without further purification. The compound was characterized by the following spectroscopic data: MS (ESI, pos. ion) m/z: 217.2 (M+1).

Step 4) tert-butyl 2-benzylhexahydro-1H-pyrrolo[3,4-c]pyridine-5(6H)-carboxylate

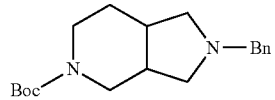

To a solution of 2-benzyloctahydro-1H-pyrrolo[3,4-c]pyridine (0.85 g) in THF was added a solution of Na$_2$CO$_3$ (0.85 g) in water, and (Boc)$_2$O (1.30 mL) dropwise at 0° C. The reaction mixture was stirred overnight at room temperature, and extracted with CH$_2$Cl$_2$ (20 mL×3). The combined organic phases were dried over anhydrous Na$_2$SO$_4$ and filtered. The filtrate was concentrated in vacuo and the residue was chromatographed with a silica gel column (eluting agent: 2:1 (v/v) PE/EA) to give the title compound as colorless oil (1.00 g, 80.00%), HPLC: 95.00%. The compound was characterized by the following spectroscopic data: MS (ESI, pos. ion) m/z: 317.7 (M+1); $^1$H NMR (400 MHz, CDCl$_3$) δ: 1.45 (s, 9H), 2.27-2.34 (m, 2H), 2.71-2.79 (m, 4H), 3.14-3.18 (m, 2H), 3.15-3.22 (m, 2H), 3.59 (m, 2H), 3.62 (s, 2H), 7.21-7.23 (m, 5H) ppm.

Step 5) tert-butyl hexahydro-1H-pyrrolo[3,4-c]pyridine-5(6H)-carboxylate

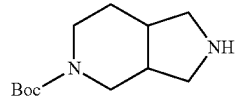

To a solution of tert-butyl 2-benzylhexahydro-1H-pyrrolo[3,4-c]pyridine-5(6H)-carboxylate (1.60 g) in EtOAc was added a catalytic amount of 20% Pd(OH)$_2$/C. The suspension was stirred for 3 h at room temperature under $H_2$ and filtered. The filtrate was concentrated in vacuo to give the title compound as colorless oil (0.68 g, 60%). The crude product was used for the next step without further purification. The compound was characterized by the following spectroscopic data: MS (ESI, pos. ion) m/z: 227.4 (M+1).

Step 6) tert-butyl 2-(3-chloropropyl)hexahydro-1H-pyrrolo[3,4-c]pyridine-5(6H)-carboxylate

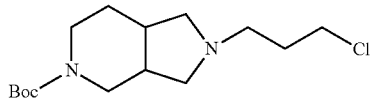 [SMILES: CC(C)(C)OC(=O)N1CCC2CN(CCCCl)CC2C1]

A mixture of tert-butyl hexahydro-1H-pyrrolo[3,4-c]pyridine-5(6H)-carboxylate (1.70 g), 1-bromo-3-chloropropane (1.70 mL) and $K_2CO_3$ (3.30 g) in acetone was heated to reflux for 10 h, then cooled to rt and filtered. The filtrate was concentrated in vacuo and the residue was chromatographed with a silica gel column (eluting agent: 20:1 (v/v) DCM/MeOH) to give the title compound as yellow oil (0.79 g, 35.00%), HPLC: 80.00%. The compound was characterized by the following spectroscopic data: MS (ESI, pos. ion) m/z: 303.2 (M+1).

Step 7) tert-butyl 2-(3-((4-((3-chloro-4-fluorophenyl)amino)-7-methoxyquinazolin-6-yl)oxy) propyl)hexahydro-1H-pyrrolo[3,4-c]pyridine-5(6H)-carboxylate

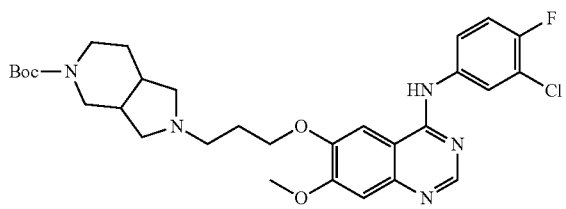 [SMILES: COc1cc2ncnc(Nc3ccc(F)c(Cl)c3)c2cc1OCCCN1CC2CCN(C(=O)OC(C)(C)C)CC2C1]

A mixture of 4-((3-chloro-4-fluorophenyl)amino)-7-methoxyquinazolin-6-ol (0.70 g), $K_2CO_3$ (0.61 g) and tert-butyl 2-(3-chloropropyl)hexahydro-1H-pyrrolo[3,4-c]pyridine-5 (6H)-carboxylate (0.80 g) in 30 mL of DMF was stirred at 80° C. for 7 h, then poured into 50 mL of ice-water and extracted with $CH_2Cl_2$ (50 mL×3). The combined organic phases were dried over anhydrous $Na_2SO_4$ and filtered. The filtrate was concentrated in vacuo and the residue was chromatographed with a silica gel column (eluting agent: 30:1 (v/v) DCM/MeOH) to give the title compound as colorless oil (0.48 g, 35.00%), HPLC: 95.00%. The compound was characterized by the following spectroscopic data: MS (ESI, pos. ion) m/z: 587.2 (M+1); $^1$H NMR (400 MHz, d$^6$-DMSO) δ: 1.45 (s, 9H), 1.99-2.06 (m, 4H), 2.32-2.38 (m, 2H), 2.46-2.50 (m, 4H), 2.67-2.71 (m, 2H), 3.40-3.45 (m, 2H), 4.17-4.19 (m, 2H), 4.19 (s, 3H), 4.20-2.26 (m, 2H), 7.21 (s, 1H), 7.42 (t, J=8.0 Hz, 1H), 7.44 (s, 2H), 7.78 (t, J=4.4 Hz, 1H), 8.50 (s, 1H) ppm.

Step 8) N-(3-chloro-4-fluorophenyl)-6-(3-(hexahydro-1H-pyrrolo[3,4-c]pyridin-2(3H)-yl)propoxy)-7-methoxyquinazolin-4-amine

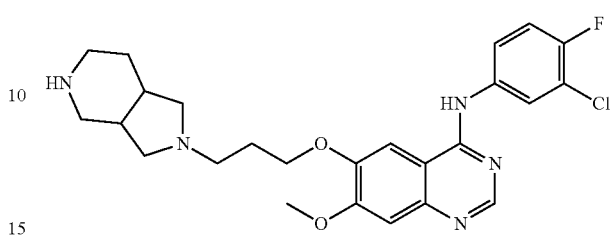

To a solution of tert-butyl 2-(3-((4-((3-chloro-4-fluorophenyl)amino)-7-methoxyquinazolin-6-yl)oxy) propyl)hexahydro-1H-pyrrolo[3,4-c]pyridine-5(6H)-carboxylate (0.40 g) in $CH_2Cl_2$ was added a solution of HCl in EtOAc (3 M, 10 mL). White solid was precipitated out after 2 h reaction. The resulted mixture was filtered and the residue was dried to give the title compound as a pale yellow solid (0.30 g, 80.00%), HPLC: 99.00%. The compound was characterized by the following spectroscopic data: MS (ESI, pos. ion) m/z: 486.2 (M+1); $^1$H NMR (400 MHz, $D_2O$) δ: 1.97-2.03 (m, 4H), 2.68-2.71 (m, 2H), 2.80-2.86 (m, 4H), 2.87-2.91 (m, 2H), 3.40-3.45 (m, 2H), 4.07-4.11 (m, 2H), 4.19 (s, 3H), 4.39-4.43 (m, 2H), 7.441 (s, 1H), 7.50 (t, J=8.6 Hz, 1H), 7.84 (s, 2H), 8.68 (t, J=4.6 Hz, 1H), 8.89 (s, 1H) ppm.

Example 31

N-(3-chloro-4-fluorophenyl)-6-(3-(hexahydro-2H-pyrano[3,2-b]pyridin-5(3H)-yl)propoxy)-7-methoxyquinazolin-4-amine

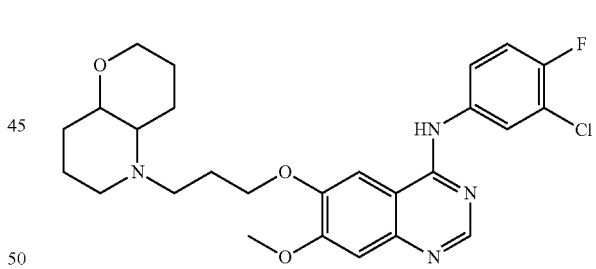

Step 1) (3-(benzyloxy)pyridin-2-yl)methanol

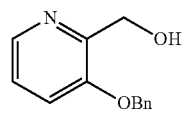 [SMILES: OCc1ncccc1OCc1ccccc1]

To a solution of 3-hydroxy-2-(hydroxymethyl)pyridine (10.00 g) and KOH (7.00 g) in anhydrous EtOH was added benzyl bromide (7.30 mL) at room temperature under stirring. The reaction mixture was heated to reflux for 24 h, then cooled to rt and filtered. The filtrate was concentrated in vacuo and the residue was chromatographed with a silica gel column (eluting agent: 20:1 (v/v) DCM/MeOH) to give the title compound as a pale yellow solid (7.50 g, 65.00%), HPLC: 95.00%. The compound was characterized by the following spectroscopic data: MS (ESI, pos. ion) m/z: 216.4 (M+1); $^1$H NMR (400 MHz, CDCl$_3$) δ: 4.39 (br s, 1H), 4.82 (s, 2H), 5.11 (s, 2H), 7.16-7.17 (m, 2H), 7.34-7.40 (m, 5H), 8.15-8.17 (m, 1H) ppm.

Step 2) 3-(benzyloxy)picolinaldehyde

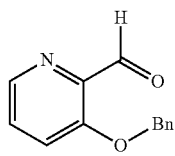 [SMILES: O=Cc1ncccc1OCc1ccccc1]

A mixture of (3-(benzyloxy)pyridin-2-yl)methanol (7.50 g) and MnO$_2$ (30.00 g) in CHCl$_3$ was heated to reflux for 90 min, and then cooled to rt. The reaction mixture was filtered. The filtrate was concentrated in vacuo and the residue was chromatographed with a silica gel column (eluting agent: 2:1 (v/v) PE/EA) to give the title compound as a pale yellow solid (5.40 g, 73.00%), HPLC: 93.00%. The compound was characterized by the following spectroscopic data: MS (ESI, pos. ion) m/z: 214.6 (M+1); $^1$H NMR (400 MHz, CDCl$_3$) δ: 5.26 (s, 2H), 7.34-7.47 (m, 7H), 8.41 (t, J=2.5 Hz, 1H), 10.40 (s, 1H) ppm.

Step 3) (E)-ethyl 3-(3-(benzyloxy)pyridin-2-yl)acrylate

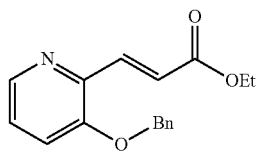 [SMILES: CCOC(=O)/C=C/c1ncccc1OCc1ccccc1]

To a solution of LiBr (2.08 g) in dried CH$_3$CN was added Et$_3$N (3.00 mL), phosphate ester (2.48 g) and 3-(benzyloxy) picolinaldehyde (4.26 g). The reaction mixture was stirred for 72 h at room temperature, quenched with water and extracted with CH$_2$Cl$_2$ (50 mL×3). The combined organic phases were dried over anhydrous Na$_2$SO$_4$ and filtered. The filtrate was concentrated in vacuo and the residue was chromatographed with a silica gel column (eluting agent: 4:1 (v/v) PE/EA) to give the title compound as pale yellow oil (3.69 g, 65.00%), HPLC: 92.00%. The compound was characterized by the following spectroscopic data: MS (ESI, pos. ion) m/z: 197.1 (M+1); $^1$H NMR (400 MHz, CDCl$_3$) δ: 1.32 (t, J=7.4 Hz, 3H), 4.26 (q, J=7.6 Hz, 2H), 5.15 (s, 2H), 7.04 (d, J=15.8 Hz, 1H), 7.15-7.45 (m, 7H), 8.16 (dd, J=15.8, 4.4 Hz, 1H), 8.22 (d, J=4.4 Hz, 1H) ppm.

Step 4) ethyl 3-(3-hydroxypyridin-2-yl)propanoate

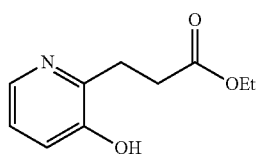 [SMILES: CCOC(=O)CCc1ncccc1O]

To a solution of (E)-ethyl 3-(3-(benzyloxy)pyridin-2-yl) acrylate (3.00 g) in MeOH was added a catalytic amount of 10% Pd/C. The reaction mixture was stirred for 2 h at room temperature under H$_2$ and filtered. The filtrate was concentrated in vacuo to give the title compound as a yellow solid (1.34 g, 65.00%), and the crude product was used for the next step without further purification. The compound was characterized by the following spectroscopic data: MS (ESI, pos. ion) m/z: 196.1 (M+1); $^1$H NMR (400 MHz, CDCl$_3$) δ: 9.41 (bs, 1H), 8.15-8.21 (m, 1H), 7.3-7.0 (m, 2H), 4.15-4.05 (m, 2H), 3.15 (t, J=4.2 Hz, 2H), 2.85 (t, J=8.0 Hz, 2H), 1.2 (t, J=4.2 Hz, 2H) ppm.

Step 5) 2-(3-hydroxypropyl)pyridin-3-ol

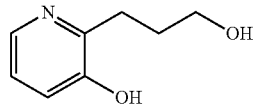 [SMILES: OCCCc1ncccc1O]

To a solution of LiAlH$_4$ (0.94 g) in THF was added ethyl 3-(3-hydroxypyridin-2-yl)propanoate (2.40 g) slowly at 0° C. The reaction mixture was stirred for 5 h at room temperature under N$_2$, then cooled to rt and quenched with water at 0° C. The mixture was filtered. The filtrate was concentrated in vacuo to give the compound as yellow oil (0.95 g, 50%), and the crude product was used for the next step without further purification. The compound was characterized by the following spectroscopic data: MS (ESI, pos. ion) m/z: 154.7 (M+1).

Step 6) 3,4-dihydro-2H-pyrano[3,2-b]pyridine

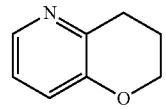

A solution of 2-(3-hydroxypropyl)pyridin-3-ol (0.90 g) in 48% hydrobromic acid (20 mL) in a sealed tube was heated at 150° C. for 5 h. The reaction mixture was cooled to rt, concentrated in vacuo and poured into a solution of NaOH in MeOH (1 M). The mixture was concentrated in vacuo and the residue was chromatographed with a silica gel column (eluting agent: 2:1 (v/v) PE/EA) to afford the title compound as pale yellow oil (0.24 g, 30.00%), HPLC: 92.00%. The compound was characterized by the following spectroscopic data: MS (ESI, pos. ion) m/z: 136.3 (M+1); $^1$H NMR (400 MHz, CDCl$_3$) δ: 7.99-7.98 (m, 1H), 7.19-7.11 (m, 2H), 4.19 (t, J=7.8 Hz, 2H), 2.91 (t, J=7.8 Hz, 2H), 2.12-2.07 (m, 2H) ppm.

Step 7) octahydro-2H-pyrano[3,2-b]pyridine

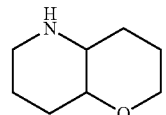

To a solution of 3,4-dihydro-2H-pyrano[3,2-b]pyridine (0.60 g) in glycol monomethyl ether was added a catalytic amount of 10% Pd/C. The reaction mixture was stirred at 70° C. for 3 hours under H$_2$ (2 MPa) and filtered. The filtrate was concentrated in vacuo to give the title compound as colorless oil (0.56 g, 90.00%), which was used for the next step without further purification. The compound was characterized by the following spectroscopic data: MS (ESI, pos. ion) m/z: 142.2 (M+1).

Step 8) 5-(3-chloropropyl)octahydro-2H-pyrano[3,2-b]pyridine

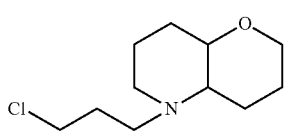 [SMILES: ClCCCN1CCCC2OCCCC21]

A mixture of octahydro-2H-pyrano[3,2-b]pyridine (0.50 g), 1-bromo-3-chloropropane (0.90 mL) and K$_2$CO$_3$ (0.70 g) in acetone was heated to reflux for 10 h, then cooled to rt and filtered. The filtrate was concentrated in vacuo and the residue was chromatographed with a silica gel column (eluting agent: 25:1 (v/v) DCM/MeOH) to give the title compound as yellow oil (0.23 g, 30.00%), HPLC: 80.00%. The compound was characterized by the following spectroscopic data: MS (ESI, pos. ion) m/z: 218.5 (M+1).

Step 9) N-(3-chloro-4-fluorophenyl)-6-(3-(hexahydro-2H-pyrano[3,2-b]pyridin-5(3H)-yl)propoxy)-7-methoxyquinazolin-4-amine

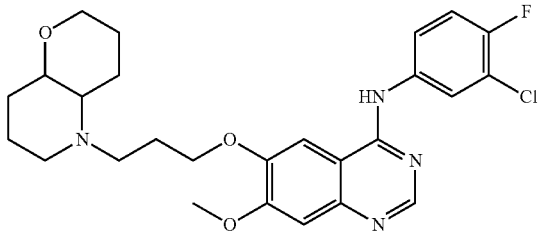 [SMILES: COc1cc2ncnc(Nc3ccc(F)c(Cl)c3)c2cc1OCCCN1CCCC2OCCCC21]

A mixture of 5-(3-chloropropyl)octahydro-2H-pyrano[3, 2-b]pyridine (0.23 g), K$_2$CO$_3$ (0.26 g) and 4-((3-chloro-4-fluorophenyl)amino)-7-methoxyquinazolin-6-ol (0.30 g) in 20 mL of DMF was stirred at 80° C. for 7 h and cooled to rt. To this, 50 mL of ice-water was added and the mixture was extracted with CH$_2$Cl$_2$ (50 mL×3). The combined organic phases were dried over anhydrous Na$_2$SO$_4$ and filtered. The filtrate was concentrated in vacuo and the residue was chromatographed with a silica gel column eluting agent: 20:1 (v/v) DCM/MeOH) to afford the title compound as a pale yellow solid (0.11 g, 25.00%), HPLC: 96.00%. The compound was characterized by the following spectroscopic data: MS (ESI, pos. ion) m/z: 501.3 (M+1); $^1$H NMR (400 MHz, d$^6$-DMSO) δ: 9.54 (s, 1H), 7.78 (d, J=4.0 Hz, 1H), 7.70 (t, J=8.0 Hz, 1H), 7.64 (s, 2H), 7.24 (d, J=4.2 Hz, 1H), 7.09 (t, J=8.0 Hz, 1H), 4.19 (m, 2H), 3.93 (s, 3H), 3.33-3.30 (m, 2H), 2.51-2.49 (m, 4H), 2.14-1.93 (m, 6H), 1.74-1.71 (m, 3H), 1.36-1.23 (m, 3H) ppm.

Example 32

N-(3-chloro-4-fluorophenyl)-6-(3-(6-(dimethylamino)-3-azabicyclo[3.1.0]hexan-3-yl)propoxy)-7-methoxyquinazolin-4-amine

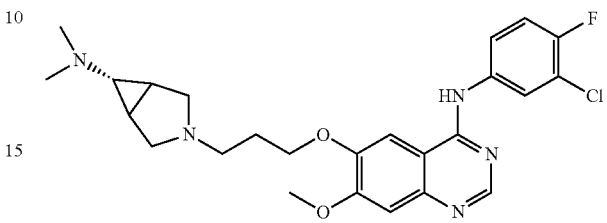

Step 1) 3-benzyl-6-nitro-3-azabicyclo[3.1.0]hexane-2,4-dione

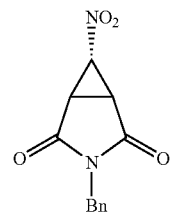

To a mixture of N-benzylmaleimide (7.40 g) and K$_2$CO$_3$ (5.50 g) in 500 mL of CH$_3$CN was added bromonitromethane (5.60 g) dropwise. The reaction mixture was stirred for 24 h at room temperature and filtered. The filtrate was concentrated in vacuo and the residue was chromatographed with a silica gel column (eluting agent: 4:1 (v/v) PE/EA) to give the title compound as a pale yellow solid (3.90 g, 40.00%), HPLC: 93.00%. The compound was characterized by the following spectroscopic data: MS (ESI, pos. ion) m/z: 247.1 (M+1); $^1$H NMR (400 MHz, CDCl$_3$) δ: 3.34 (d, J=1.8 Hz, 2H), 4.51 (t, J=1.6 Hz, 1H), 4.53 (s, 2H), 7.22-7.42 (m, 5H) ppm.

Step 2) 3-benzyl-6-nitro-3-azabicyclo[3.1.0]hexane

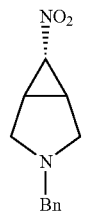

To a solution of 3-benzyl-6-nitro-3-azabicyclo[3.1.0]hexane-2,4-dione (6.00 g) in THF was added a solution of borane in THF (1 M, 100 mL) dropwise. The reaction mixture was refluxed for 1 h, then cooled to rt and quenched with MeOH. The mixture was concentrated in vacuo and the residue was chromatographed by a silica gel column (eluting agent: 2:1 (v/v) PE/EA) to afford the title compound as pale yellow oil (4.30 g, 80.00%), HPLC: 94.00%. The compound was characterized by the following spectroscopic data: MS (ESI, pos. ion) m/z: 219.2 (M+1); $^1$H NMR (400 MHz, CDCl$_3$) δ: 2.51 (m, 2H), 3.14 (d, J=1.8 Hz, 2H), 3.60 (s, 2H), 4.63 (s, 1H), 7.3 (m, 5H) ppm.

Step 3) 3-benzyl-3-azabicyclo[3.1.0]hexan-6-amine

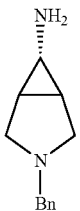

To a mixture of 3-benzyl-6-nitro-3-azabicyclo[3.1.0]hexane (4.00 g) and a catalytic amount of Raney nickel in MeOH was added slowly a solution of 98% H$_2$NNH$_2$—H$_2$O (70 mL) at rt. The mixture was stirred for 5 h at room temperature and filtered. The filtrate was concentrated in vacuo to give the title compound as brown oil (3.60 g) and the crude product was used for the next step without further purification. The compound was characterized by the following spectroscopic data: MS (ESI, pos. ion) m/z: 204.3 (M+1).

Step 4) 3-benzyl-N,N-dimethyl-3-azabicyclo[3.1.0]hexan-6-amine

To a solution of 3-benzyl-3-azabicyclo[3.1.0]hexan-6-amine (3.60 g) in MeOH was added 37% HCHO (7 mL) and acetic acid (17 mL). The reaction mixture was stirred for 30 min at room temperature, and sodium triacetoxyborohydride (20.00 g) was added in portions. The reaction mixture was stirred for another 7 h at room temperature, then quenched with water at 0° C. and filtered. The filtrate was concentrated in vacuo, poured in to water and extracted with CH$_2$Cl$_2$ (50 mL×4). The combined organic phases were dried over anhydrous Na$_2$SO$_4$ and filtered. The filtrate was concentrated in vacuo and the residue was chromatographed with a silica gel column (eluting agent: 40:1 (v/v) DCM/MeOH) to afford the title compound as yellow oil (1.8 g, 45.00%), HPLC: 91.00%. The compound was characterized by the following spectroscopic data: MS (ESI, pos. ion) m/z: 218.5 (M+1); $^1$H NMR (400 MHz, CDCl$_3$) δ: 2.26 (s, 6H), 2.41-2.38 (m, 2H), 3.04 (d, J=1.8 Hz, 2H), 3.61 (s, 2H), 4.53 (s, 1H), 7.3-7.25 (m, 5H) ppm.

Step 5) N,N-dimethyl-3-azabicyclo[3.1.0]hexan-6-amine

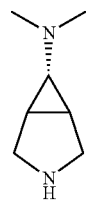

To a solution of 3-benzyl-N,N-dimethyl-3-azabicyclo[3.1.0]hexan-6-amine (1.80 g) in MeOH was added a catalytic amount of 20% Pd(OH)$_2$/C. The reaction mixture was stirred for 3 h at room temperature under H$_2$ and filtered. The filtrate was concentrated in vacuo and the residue was chromatographed with a silica gel column (eluting agent: 20:1 (v/v) DCM/MeOH) to afford the title compound as brown oil (0.74 g, 70.00%), HPLC: 99.00%. The compound was characterized by the following spectroscopic data: MS (ESI, pos. ion) m/z: 127.5 (M+1); $^1$H NMR (400 MHz, CDCl$_3$) δ: 1.25-1.28 (m, 3H), 1.72-1.76 (m, 2H), 2.31 (s, 6H), 3.19-3.29 (m, 2H) ppm.

Step 6) 3-(3-chloropropyl)-N,N-dimethyl-3-azabicyclo[3.1.0]hexan-6-amine

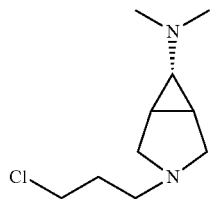

A mixture of N,N-dimethyl-3-azabicyclo[3.1.0]hexan-6-amine (1.45 g), 1-bromo-3-chloropropane (4.05 mL) and cesium carbonate (11.20 g) in acetone was heated to reflux for 7 h, cooled to rt and filtered. The filtrate was concentrated in vacuo and the residue was chromatographed with a silica gel column (eluting agent: 35:1 (v/v) DCM/MeOH) to afford the title compound as yellow oil (0.93 g, 40.00%), HPLC: 80.00%. The compound was characterized by the following spectroscopic data: MS (ESI, pos. ion) m/z: 203.7 (M+1).

Step 7) N-(3-chloro-4-fluorophenyl)-6-(3-(6-(dimethylamino)-3-azabicyclo[3.1.0]hexan-3-yl) propoxy)-7-methoxyquinazolin-4-amine

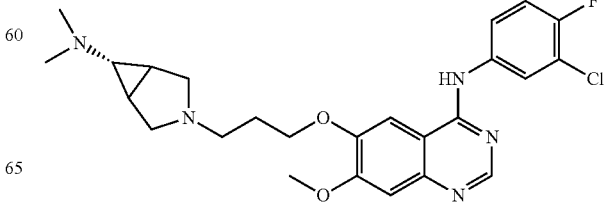

A mixture of 3-(3-chloropropyl)-N,N-dimethyl-3-azabicyclo[3.1.0]hexan-6-amine (0.70 g), $K_2CO_3$ (0.78 g) and 4-((3-chloro-4-fluorophenyl)amino)-7-methoxyquinazolin-6-ol (0.70 g) in 30 mL of DMF was stirred at 80° C. for 7 h, and cooled to rt. To this, 50 mL of ice-water was added, and the resulted mixture was extracted with $CH_2Cl_2$ (50 mL×3). The combined organic phases were dried over anhydrous $Na_2SO_4$ and filtered. The filtrate was concentrated in vacuo and the residue was chromatographed with a silica gel column (diluting agent: 20:1 (v/v) DCM/MeOH) to give the title compound as a pale yellow solid (0.47 g, 35.00%), HPLC: 96.00%. The compound was characterized by the following spectroscopic data: MS (ESI, pos. ion) m/z: 486.1 (M+1); $^1$H NMR (400 MHz, d$^6$-DMSO) δ: 9.45 (s, 1H), 7.80 (d, J=4.0 Hz, 1H), 7.70 (t, J=8.0 Hz, 1H), 7.54 (s, 2H), 7.12 (d, J=4.2 Hz, 1H), 7.01 (t, J=8.0 Hz, 1H), 4.19-4.12 (m, 2H), 3.93 (s, 3H), 2.45-3.30 (m, 6H), 2.51 (s, 6H), 2.14-1.93 (m, 6H), 1.33 (m, 1H) ppm.

Example 33

N-(3-chloro-4-fluorophenyl)-7-methoxy-6-(3-(octahydro-2,7-naphthyridin-2(1H)-yl)propoxy)quinazolin-4-amine

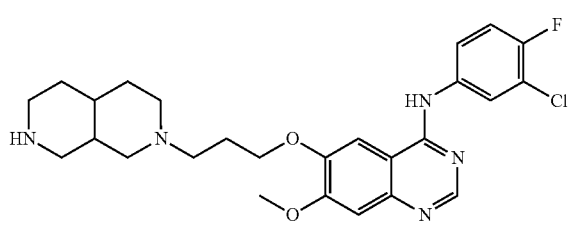 [SMILES: COc1cc2ncnc(Nc3ccc(F)c(Cl)c3)c2cc1OCCCN1CCC2CCNCC2C1]

Step 1)
2,7-naphthyridine-1,3,6,8(2H,4H,5H,7H)-tetraone

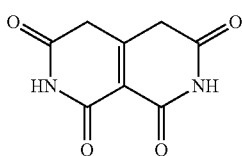

To a solution of diethyl 1,3-acetonedicarboxylate (272 mg, 1.35 mmol, 1 eq), propanedinitrile (100 mg, 1.52 mmol, 1.1 eq) in anhydrous EtOH (5 mL) was added a drop of ethylamine. The reaction mixture was stirred for 48 h at room temperature and concentrated in vacuo. The residue was treated with 70% sulfuric acid (0.2 mL) and heated at 100° C. for 10 min, then cooled to room temperature, poured into ice-water and filtered to give the title compound as a yellow solid (236 mg, 90%).

Step 2) 1,3,6,8-tetrachloro-2,7-naphthyridine

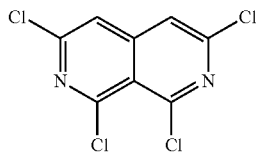 [SMILES: Clc1cc2cc(Cl)nc(Cl)c2c(Cl)n1]

A mixture of 2,7-naphthyridine-1,3,6,8(2H,4H,5H,7H)-tetraone (3.00 g, 1.50 mmol) and phosphorus oxychloride (25 mL) in a 125 mL sealed tube was heated to 180° C. and stirred for 24 h. The resulted mixture was poured into 500 mL of ice-water, adjusted to pH 10 with saturated $K_2CO_3$ aqueous solution and extracted with EtOAc (50 mL×3). The organic layer was dried over anhydrous $Na_2SO_4$ and filtered. The filtrate was concentrated in vacuo to afford the product as a yellow solid (1.80 g, 44%).

Step 3) 1,2,3,4-tetrahydro-2,7-naphthyridine

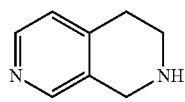

A mixture of 1,3,6,8-tetrachloro-2,7-naphthyridine (1.00 g, 2.67 mmol, 1 eq), Pd/C (200 mg, 0.2 eq) and potassium acetate (6.00 g, 61 mmol, 16 eq) in 300 mL of MeOH was stirred for 24 h at room temperature under $H_2$, and then filtered through a Celite pad. The filtrate was concentrated in vacuo and treated with 100 mL of saturated $Na_2CO_3$ aqueous solution. The mixture was extracted with $CH_2Cl_2$ (50 mL×3). The organic layer was dried over $Na_2SO_4$ and concentrated in vacuo to afford the title compound as pale yellow oil (450 mg, 90%). The compound was characterized by the following spectroscopic data: MS (ESI, pos. ion) m/z: 135.2 (M+1); $^1$H NMR (400 MHz, CDCl$_3$) δ: 2.95 (2H, m), 3.38 (2H, m), 3.83 (2H, s), 7.08 (1H, m), 8.14 (1H, m), 8.28 (1H, m) ppm.

Step 4) tert-butyl 3,4-dihydro-2,7-naphthyridine-2(1H)-carboxylate

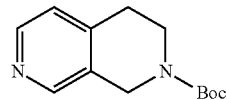

To a solution of 1,2,3,4-tetrahydro-2,7-naphthyridine (1.10 g, 8.20 mmol, 1 eq) and DMAP (200 mg, 1.60 mmol, 10%) in CH$_3$CN (30 mL) was added (Boc)$_2$O (2.68 g, 12.30 mmol, 1.5 eq) dropwise at 0° C. The reaction mixture was stirred at rt overnight and concentrated in vacuo. To this, 50 mL of water was added. The mixture was extracted with CH$_2$Cl$_2$ (20 mL×3). The organic layer was dried over anhydrous Na$_2$SO$_4$ and concentrated in vacuo to afford the title compound as yellow oil (550 mg, 46%). The compound was characterized by the following spectroscopic data: MS (ESI, pos. ion) m/z: 235.2 (M+1).

Step 5) tert-butyl octahydro-2,7-naphthyridine-2(1H)-carboxylate

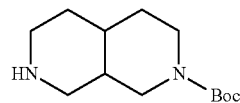

A suspension of tert-butyl 3,4-dihydro-2,7-naphthyridine-2(1H)-carboxylate (1.00 g, 4.27 mmol, 1 eq) and Pd(OH)$_2$ (400 mg, 0.1 eq) in 150 mL of acetic acid was heated at 80° C. overnight under H$_z$, then cooled to room temperature, filtered and concentrated in vacuo. To this, 100 mL of water was added. The mixture was adjusted to pH 7-8 with NH$_3$—H$_2$O, extracted with CH$_2$Cl$_2$ (50 mL×3). The organic layer was dried over anhydrous Na$_2$SO$_4$ and concentrated in vacuo, and the residue was purified by a silica gel column chromatography (10:1 (v/v) EtOAc/MeOH) to give the title compound as pale yellow oil (700 mg, 69%). The compound was characterized by the following spectroscopic data: MS (ESI, pos. ion) m/z: 241.1 (M+1).

Step 6) tert-butyl 7-(3-chloropropyl)octahydro-2,7-naphthyridine-2(1H)-carboxylate

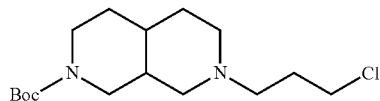 [SMILES: CC(C)(C)OC(=O)N1CCC2CCN(CCCCl)CC2C1]

A mixture of tert-butyl octahydro-2,7-naphthyridine-2(1H)-carboxylate (320 mg, 1.33 mmol, 1 eq), chloro bromopropane (530 mg, 3.33 mmol, 2.5 eq) and K$_2$CO$_3$ (736 mg, 5.33 mmol, 4 eq) in acetone (25 mL) was heated to reflux overnight, then cooled to room temperature and filtered. The filtrate was concentrated in vacuo and the residue was purified by a silica gel column chromatography (20:1 (v/v) CH$_2$Cl$_2$/MeOH) to afford the title compound as pale yellow oil (190 mg, 47%). The compound was characterized by the following spectroscopic data: MS (ESI, pos. ion) m/z: 317.2 (M+1).

Step 7) tert-butyl 7-(3-((4-((3-chloro-4-fluorophenyl)amino)-7-methoxy-quinazolin-6-yl)oxy)propyl) octahydro-2,7-naphthyridine-2(1H)-carboxylate

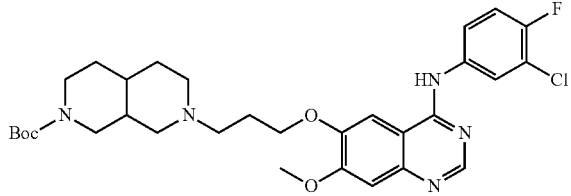 [SMILES: COc1cc2ncnc(Nc3ccc(F)c(Cl)c3)c2cc1OCCCN1CCC2CCN(C(=O)OC(C)(C)C)CC2C1]

A mixture of tert-butyl 7-(3-chloropropyl)octahydro-2,7-naphthyridine-2(1H)-carboxylate (200 mg, 0.63 mmol, 1 eq), 4-((3-chloro-4-fluorophenyl)amino)-7-methoxyquinazolin-6-ol (200 mg, 0.63 mmol, 1 eq) and K$_2$CO$_3$ (175 mg, 1.27 mmol, 2 eq) in DMF (10 mL) was heated at 80° C. overnight, cooled to room temperature. To this, 50 mL of CH$_2$Cl$_2$ was added. The mixture was washed with brine (20 mL×3) and water (20 mL×2). The organic layer was dried over anhydrous Na$_2$SO$_4$ and concentrated in vacuo. The residue was purified by a silica gel column chromatography (20:1 (v/v) CH$_2$Cl$_2$/MeOH) to give the title compound as a yellow solid (120 mg, 32%). The compound was characterized by the following spectroscopic data: MS (ESI, pos. ion) m/z: 600.2 (M+1).

Step 8) N-(3-chloro-4-fluorophenyl)-7-methoxy-6-(3-(octahydro-2,7-naphthyridin-2(1H)-yl) propoxy) quinazolin-4-amine

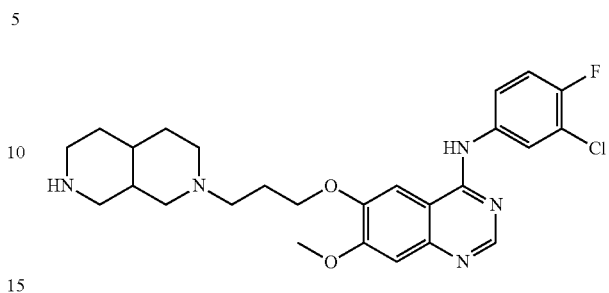

A mixture of tert-butyl 7-(3-((4-((3-chloro-4-fluorophenyl)amino)-7-methoxy-quinazolin-6-yl)oxy)propyl) octahydro-2,7-naphthyridine-2(1H)-carboxylate (300 mg, 0.50 mmol) in a solution of HCl in EtOAc (3 M, 10 mL) was stirred for 1 h at room temperature and concentrated in vacuo to give the title compound as a yellow solid (153 mg, 58%), HPLC: 92.00%. The compound was characterized by the following spectroscopic data: MS (ESI, pos. ion) m/z: 500.0 (M+1); $^1$H NMR (CDCl$_3$, 400 MHz) δ: 1.69-2.00 (4H, m), 2.03-2.08 (3H, m), 2.53 (1H, m), 2.90-3.08 (2H, m), 3.22-3.26 (4H, m), 3.30-3.22 (1H, m), 3.40-3.22 (2H, m), 3.52-3.53 (1H, m), 3.97 (3H, s), 4.24 (2H, m), 7.05-7.09 (2H, m), 7.35-7.37 (1H, m), 7.53-7.58 (2H, m), 8.50 (1H, s) ppm.

Example 34

N-(3-chloro-4-fluorophenyl)-6-(3-(1-ethylhexahydro-1H-pyrrolo[3,4-b]pyridin-6(2H)-yl)propoxy)-7-methoxyquinazolin-4-amine

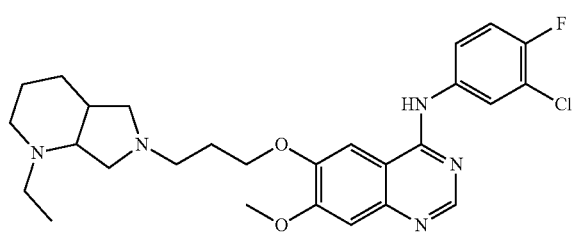

Step 1) 6-benzyl-1-ethyloctahydro-1H-pyrrolo[3,4-b]pyridine

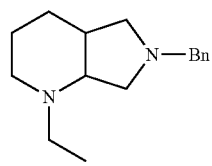 [SMILES: CCN1CCCC2CN(Cc3ccccc3)CC21]

To a solution of 6-benzyloctahydro-1H-pyrrolo[3,4-b]pyridine (5.00 g) in THF was added 80% NaH (3.00 g) at room temperature. The reaction mixture was stirred for 30 min, and 5.3 mL of iodoethane was added dropwise. The reaction mixture was stirred for another 5 h, and then quenched with ice-water. The resulted mixture was extracted with $CH_2Cl_2$ (70 mL×5). The combined organic phases were dried over anhydrous $Na_2SO_4$ and concentrated in vacuo. The residue was chromatographed with a silica gel column (eluting agent: 30:1 (v/v) DCM/MeOH) to give the title compound as a pale yellow solid (2.58 g, 45.60%). The compound was characterized by the following spectroscopic data: MS (ESI, pos. ion) m/z: 245.2 (M+1).

Step 2) 1-ethyloctahydro-1H-pyrrolo[3,4-b]pyridine

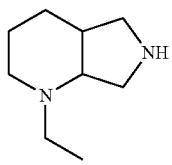

To a solution of 6-benzyl-1-ethyloctahydro-1H-pyrrolo[3,4-b]pyridine (2.58 g) in the mixture solvent of MeOH and EtOAc was added a catalytic amount of 20% $Pd(OH)_2$/C. The mixture was stirred for 2 h at room temperature under $H_2$ and filtered. The filtrate was concentrated in vacuo and the residue was used for the next step without further purification. The compound was characterized by the following spectroscopic data: MS (ESI, pos. ion) m/z: 155.2 (M+1).

Step 3) N-(3-chloro-4-fluorophenyl)-6-(3-(1-ethylhexahydro-1H-pyrrolo[3,4-b]pyridin-6(2H)-yl)propoxy)-7-methoxyquinazolin-4-amine

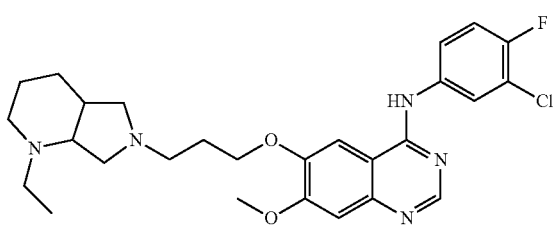 [SMILES: CCN1CCCC2CN(CCCOc3cc4c(Nc5ccc(F)c(Cl)c5)ncnc4cc3OC)CC21]

A mixture of N-(3-chloro-4-fluorophenyl)-6-(3-chloropropoxy)-7-methoxyquinazolin-4-amine (1.50 g), $K_2CO_3$ (5.00 g) and 1-ethyloctahydro-1H-pyrrolo[3,4-b]pyridine (0.90 g) in 25 mL of DMF was stirred for 7 h at 80° C., and then cooled down. The resulted mixture was poured into 50 mL of ice-water and extracted with $CH_2Cl_2$ (50 mL×3). The combined organic phases were dried over anhydrous $Na_2SO_4$ and filtered. The filtrate was concentrated in vacuo and the residue was chromatographed with a silica gel column (eluting agent: 20:1 (v/v) DCM/MeOH) to give the title compound as a pale yellow solid (0.75 g, 38.60%), HPLC: 98.30%. The compound was characterized by the following spectroscopic data: MS (ESI, pos. ion) m/z: 514.1 (M+1); $^1$H NMR (400 MHz, $d^6$-DMSO) δ: 1.03 (t, J=4.6 Hz, 3H), 1.52-1.62 (m, 2H), 1.97-2.00 (m, 3H), 2.07-2.09 (m, 2H), 2.08-2.11 (m, 4H), 2.40 (q, J=4.6 Hz, 2H), 2.51-2.56 (m, 1H), 2.57-2.61 (m, 2H), 2.88-2.92 (m, 2H), 3.94 (s, 3H), 4.18 (t, J=8.6 Hz, 2H), 7.19 (s, 1H), 7.44 (t, J=10.4 Hz, 1H), 7.82 (s, 2H), 8.13 (t, J=6.8 Hz, 1H), 8.50 (s, 1H) ppm.

Example 35

N-(3-chloro-4-fluorophenyl)-7-methoxy-6-(3-(octahydroisoquinolin-2(1H)-yl)propoxy)quinazolin-4-amine

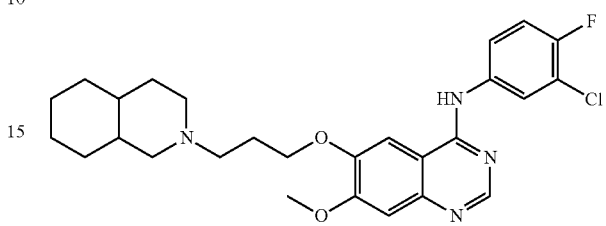

A mixture of decahydroisoquinoline (200 mg, 1.44 mmol, 1 eq), N-(3-chloro-4-fluorophenyl)-6-(3-chloropropoxy)-7-methoxyquinazolin-4-amine (570 mg, 1.44 mmol, 1 eq) and $K_2CO_3$ (238 mg, 1.70 mmol, 1.2 eq) in DMF (15 mL) was heated at 80° C. overnight and cooled to room temperature. To this, 100 mL of $CH_2Cl_2$ was added, the mixture was washed with brine (20 mL×3) and water (20 mL×2). The organic layer was dried over anhydrous $Na_2SO_4$ and concentrated in vacuo and the residue was chromatographed with a silica gel column (20:1 (v/v) $CH_2Cl_2$/MeOH) to afford the title compound as a yellow solid (350 mg, 49.00%), HPLC: 90.00%. The compound was characterized by the following spectroscopic data: MS (ESI, pos. ion) m/z: 499.2 (M+1); $^1$H NMR (CDCl$_3$, 400 MHz) δ: 1.27-1.59 (12H, m), 1.80-1.82 (2H, m), 2.07-2.33 (2H, m), 2.40-2.51 (2H, m), 3.22-3.26 (2H, m), 4.22-4.24 (2H, m), 7.14-7.16 (1H, m), 7.23 (1H, s), 7.47 (1H, s), 7.65-7.69 (1H, m), 8.00-8.02 (1H, m), 8.64 (1H, s) ppm.

Example 36

N-(3-chloro-4-fluorophenyl)-6-(3-(hexahydro-[1,4]dioxino[2,3-c]pyridin-6(7H)-yl)propoxy)-7-methoxyquinazolin-4-amine

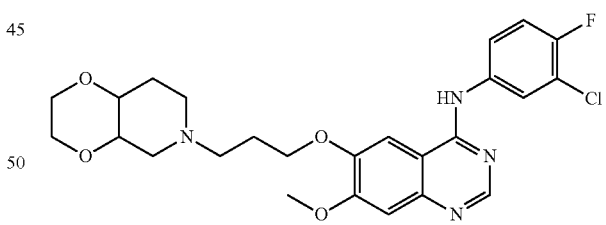

Step 1) tert-butyl 4-(tosyloxy)piperidine-1-carboxylate

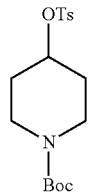

A mixture of tert-butyl 4-hydroxypiperidine-1-carboxylate (5.00 g, 24.80 mmol, 1 eq), TsCl (5.70 g, 29.80 mmol, 1.2 eq) and Et₃N (10.7 mL, 74.40 mmol, 3 eq) in 100 mL of anhydrous CH₂Cl₂ was stirred for 8 h at room temperature. The resulted mixture was washed with brine (30 mL) and water (30 mL). The organic phase was dried over anhydrous Na₂SO₄ and concentrated in vacuo. The residue was purified by a silica gel column chromatography (5:1 (v/v) PE/EtOAc) to afford the title compound as a white solid (5.50 g, 68.00%). The compound was characterized by the following spectroscopic data: MS (ESI, pos. ion) m/z: 356.2 (M+1).

Step 2) tert-butyl 5,6-dihydropyridine-1(2H)-carboxylate

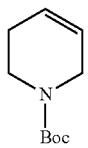 [SMILES: CC(C)(C)OC(=O)N1CC=CCC1]

A mixture of tert-butyl 4-(tosyloxy)piperidine-1-carboxylate (5.50 g, 15.40 mmol, 1 eq) and DBU (5.70 g, 31.00 mmol, 2 eq) in DMF (100 mL) was heated at 150° C. overnight and cooled to room temperature. To this, 100 mL of CH₂Cl₂ was added, and the mixture was washed with brine (20 mL×3) and water (30 mL×2). The organic phase was dried over anhydrous Na₂SO₄ and concentrated in vacuo. The residue was purified by a silica gel column chromatography (10:1 (v/v) PE/EtOAc) to give the title compound as pale yellow oil (2.40 g, 85.00%). The compound was characterized by the following spectroscopic data: MS (ESI, pos. ion) m/z: 184.1 (M+1).

Step 3) tert-butyl 3,4-dihydroxypiperidine-1-carboxylate

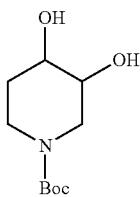 [SMILES: CC(C)(C)OC(=O)N1CCC(O)C(O)C1]

To a mixture of tert-butyl 5,6-dihydropyridine-1(2H)-carboxylate (2.40 g, 13.10 mmol, 1 eq) and NMO (2.65 g, 19.60 mmol, 1.5 eq) in acetone (60 mL) was added a solution of OsO₄ (20 mg) in isopropanol (5 mL). The mixture was stirred overnight at room temperature. To this, 10 mL of saturated NaHSO₃ aqueous solution was added dropwise, the reaction mixture was stirred for 0.5 h at room temperature and concentrated in vacuo. The pH was adjusted to 5-6 by adding dilute hydrochloric acid. The organic phase was extracted with CH₂Cl₂ (50 mL×2), dried over anhydrous Na₂SO₄ and concentrated in vacuo to give the title compound as colorless oil (2.60 g, 92.00%). The compound was characterized by the following spectroscopic data: MS (ESI, pos. ion) m/z: 218.2 (M+1).

Step 4) tert-butyl hexahydro-[1,4]dioxino[2,3-c]pyridine-6(7H)-carboxylate

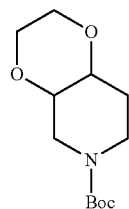 [SMILES: CC(C)(C)OC(=O)N1CCC2OCCOC2C1]

A mixture of tert-butyl 3,4-dihydroxypiperidine-1-carboxylate (300 mg, 1.38 mmol, 1 eq), 1,2-dichloroethane (6 mL) and TBAB (90 mg, 0.28 mmol, 0.2 eq) in 35% NaOH (10 mL) aqueous solution was heated at 55° C. for 72 h, then cooled to room temperature and extracted with CH₂Cl₂ (100 mL). The organic phase was washed with water (30 mL), dried over anhydrous Na₂SO₄ and concentrated in vacuo. The residue was purified by a silica gel column chromatography (20:1 (v/v) CH₂Cl₂/MeOH) to afford the title compound as pale yellow oil (250 mg, 75.00%). The compound was characterized by the following spectroscopic data: MS (ESI, pos. ion) m/z: 244.2 (M+1).

Step 5) 6-(3-chloropropyl)octahydro-[1,4]dioxino[2,3-c]pyridine

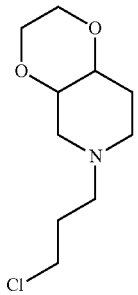

A mixture of tert-butyl hexahydro-[1,4]dioxino[2,3-c]pyridine-6(7H)-carboxylate (800 mg, 4.47 mmol, 1 eq) in a solution of HCl in MeOH (15 mL) was stirred for 1 h at room temperature and concentrated in vacuo to give octahydro-[1,4]dioxino[2,3-c]pyridine. A mixture of the above residue, 1-bromo-3-chloropropane (2.84 g, 8.17 mmol, 4 eq) and K₂CO₃ (2.46 mg, 17.80 mmol, 4 eq) in acetone (60 mL) was heated to reflux overnight, cooled to room temperature and filtered. The filtrate was concentrated in vacuo and the residue was purified by a silica gel column chromatography (20:1 (v/v) CH₂Cl₂/MeOH) to give the title compound as pale yellow oil (500 mg, 45.00%). The compound was characterized by the following spectroscopic data: MS (ESI, pos. ion) m/z: 220.1 (M+1).

Step 6) N-(3-chloro-4-fluorophenyl)-6-(3-(hexahydro-[1,4]dioxino[2,3-c]pyridin-6(7H)-yl)propoxy)-7-methoxyquinazolin-4-amine

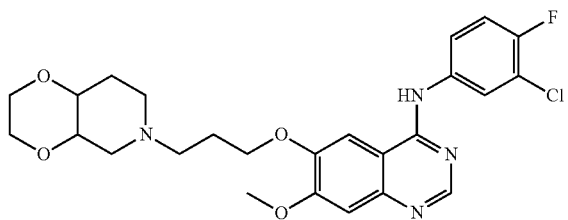 [SMILES: COc1cc2ncnc(Nc3ccc(F)c(Cl)c3)c2cc1OCCCN1CCC2OCCOC2C1]

A mixture of 6-(3-chloropropyl)octahydro-[1,4]dioxino[2,3-c]pyridine (100 mg, 0.46 mmol, 1 eq), 4-((3-chloro-4-fluorophenyl)amino)-7-methoxyquinazolin-6-ol (145 mg, 0.46 mmol, 1 eq) and K$_2$CO$_3$ (128 mg, 0.92 mmol, 2 eq) in DMF (10 mL) was heated at 80° C. overnight under N$_2$, and cooled to room temperature. To this, 100 mL of CH$_2$Cl$_2$ was added. The mixture was washed with brine (20 mL×3) and water (20 mL×2). The organic layer was dried over anhydrous Na$_2$SO$_4$ and concentrated in vacuo. The residue was chromatographed with a silica gel column (20:1 (v/v) CH$_2$Cl$_2$/MeOH) to afford the title compound as a yellow solid (60 mg, 28.00%), HPLC: 95.00%. The compound was characterized by the following spectroscopic data: MS (ESI, pos. ion) m/z: 503.1 (M+1); $^1$H NMR (400 MHz, CDCl$_3$) δ: 2.04-2.10 (2H, m), 2.21-2.48 (3H, m), 2.60-2.63 (2H, m), 2.92-3.08 (2H, m), 3.56-3.62 (2H, m), 3.67-3.72 (1H, m), 3.76-3.82 (2H, m), 3.52-3.53 (1H, m), 3.97 (2H, s), 4.08-4.15 (2H, m), 7.10-7.15 (1H, m), 7.21 (1H, s), 7.31 (1H, s), 7.62-7.65 (1H, m), 7.93-7.94 (1H, m), 8.62 (1H, s) ppm.

Example 37

N-(3-chloro-4-fluorophenyl)-6-(3-(hexahydrofuro[3,4-c]pyridin-5(3H)-yl)propoxy)-7-methoxy quinazolin-4-amine

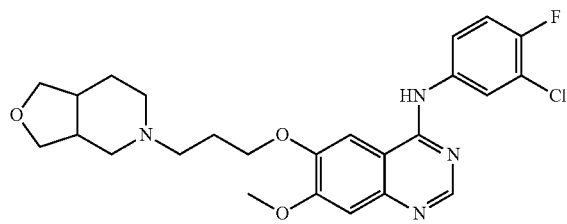 [SMILES: COc1cc2ncnc(Nc3ccc(F)c(Cl)c3)c2cc1OCCCN1CCC2COCC2C1]

Step 1) dimethyl pyridine-3,4-dicarboxylate

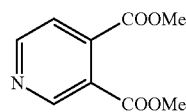

To a mixture of pyridine-3,4-dicarboxylic acid (10.00 g, 60.00 mmol, 1 eq) and a catalytic amount of DMAP (50 mg) in 300 mL of anhydrous MeOH was added dropwise SOCl$_2$ (21.4 mL, 300.00 mmol, 5 eq) at 0° C. The reaction mixture was heated to reflux for 48 h, cooled to room temperature and concentrated in vacuo. The crude product was dissolved in CH$_2$Cl$_2$ (200 mL), and the solution was washed with saturated K$_2$CO$_3$ aqueous solution and water (50 mL), dried over anhydrous Na$_2$SO$_4$ and concentrated in vacuo to afford the title compound as pale yellow oil (8.00 g, 68.00%). The compound was characterized by the following spectroscopic data: MS (ESI, pos. ion) m/z: 196.05 (M+1).

Step 2) dimethyl piperidine-3,4-dicarboxylate

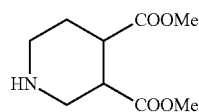

A mixture of dimethyl pyridine-3,4-dicarboxylate (1.00 g, 5.10 mmol, 1 eq) and Pd(OH)$_2$ (20 mg, 0.2 eq) in 20 mL of acetic acid was heated at 80° C. overnight under H$_2$, and then cooled to room temperature. The resulted mixture was filtered and concentrated in vacuo. To the mixture was added 100 mL of water. The pH was adjusted to 7-8 by adding NH$_3$H$_2$O. The mixture was extracted with CH$_2$Cl$_2$ (50 mL×3). The organic layer was dried over anhydrous Na$_2$SO$_4$ and concentrated in vacuo to give the title compound as pale yellow oil (600 mg, 57.00%). The compound was characterized by the following spectroscopic data: MS (ESI, pos. ion) m/z: 201.15 (M+1).

Step 3) 1-tert-butyl 3,4-dimethyl piperidine-1,3,4-tricarboxylate

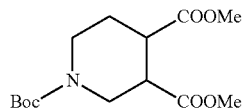

To a mixture of dimethyl piperidine-3,4-dicarboxylate (5.00 g, 24.80 mmol, 1 eq) and a catalytic amount of DMAP (50 mg) in CH$_3$CN (100 mL) was added (Boc)$_2$O (6.50 g, 29.80 mmol, 1.2 eq) dropwise at 0° C. The reaction mixture was stirred at rt overnight and concentrated in vacuo. To this, 50 mL of water was added. The mixture was extracted with CH$_2$Cl$_2$ (20 mL×3). The organic layer was dried over anhydrous Na$_2$SO$_4$ and concentrated in vacuo to give the title compound as yellow oil (6.20 g, 82.00%).

Step 4) tert-butyl 3,4-bis(hydroxymethyl)piperidine-1-carboxylate

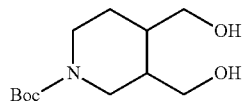

To a mixture of 1-tert-butyl 3,4-dimethyl piperidine-1,3,4-tricarboxylate (4.00 g, 13.30 mmol, 1 eq) in 50 mL of anhydrous EtOH was added NaBH$_4$ (1.26 g, 33.20 mmol, 2.5 eq) in portions at 0° C. The reaction mixture was stirred at rt overnight and concentrated in vacuo. The residue was purified by a silica gel column chromatography (5:1 (v/v) CH$_2$Cl$_2$/MeOH) to afford the title compound as a white solid (3.00 g, 92.00%). The compound was characterized by the following spectroscopic data: MS (ESI, pos. ion) m/z: 246.2 (M+1).

Step 5) octahydrofuro[3,4-c]pyridine

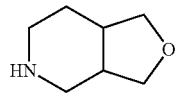

153

Tert-butyl 3,4-bis(hydroxymethyl)piperidine-1-carboxylate (1.00 g, 4 mmol) and concentrated hydrochloric acid (8 mL) were added to a sealed tube (50 mL). The reaction mixture was heated at 95° C. overnight, cooled to room temperature and concentrated in vacuo. The pH was adjusted to 8 by adding aqueous solution of NaOH. The mixture was extracted with $CH_2Cl_2$ (30 mL×2). The organic phase was washed with water (30 mL), dried over anhydrous $Na_2SO_4$ and concentrated in vacuo to afford the crude product as yellow oil (300 mg, 52.00%). The compound was characterized by the following spectroscopic data: MS (ESI, pos. ion) m/z: 128.2 (M+1).

Step 6)
5-(3-chloropropyl)octahydrofuro[3,4-c]pyridine

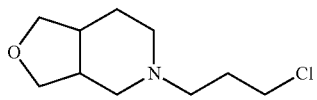 [SMILES: ClCCCN1CCC2COCC2C1]

A mixture of octahydrofuro[3,4-c]pyridine (300 mg, 2.40 mmol, 1 eq), 1-bromo-3-chloropropane (760 mg, 4.80 mmol, 2 eq) and $K_2CO_3$ (736 mg, 9.60 mmol, 4 eq) in acetone (30 mL) was heated to reflux overnight, cooled to rt and filtered. The filtrate was concentrated in vacuo and the residue was purified by a silica gel column chromatography (20:1 (v/v) $CH_2Cl_2$/MeOH) to afford the title compound as pale yellow oil (223 mg, 46.5%). The compound was characterized by the following spectroscopic data: MS (ESI, pos. ion) m/z: 248.05 (M+1).

Step 7) N-(3-chloro-4-fluorophenyl)-6-(3-(hexahydrofuro[3,4-c]pyridin-5(3H)-yl)propoxy)-7-methoxyquinazolin-4-amine

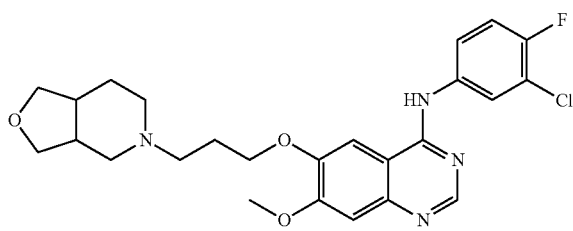 [SMILES: COc1cc2ncnc(Nc3ccc(F)c(Cl)c3)c2cc1OCCCN1CCC2COCC2C1]

A mixture of 4-((3-chloro-4-fluorophenyl)amino)-7-methoxyquinazolin-6-ol (140 mg, 0.44 mmol, 1 eq), 5-(3-bromopropyl)octahydrofuro[3,4-c]pyridine (90 mg, 0.44 mmol, 1 eq) and $K_2CO_3$ (135 mg, 0.98 mmol, 2 eq) in DMF (10 mL) was heated at 80° C. overnight under $N_2$ and cooled to rt. To this, 50 mL of $CH_2Cl_2$ was added. The mixture was washed with brine (20 mL×3) and water (20 mL×2). The organic layer was dried over anhydrous $Na_2SO_4$ and concentrated in vacuo. The residue was purified by a silica gel column chromatography (20:1 (v/v) $CH_2Cl_2$/MeOH) to afford the title compound as a yellow solid (50 mg, 25.00%), HPLC: 96.00%. The compound was characterized by the following spectroscopic data: MS (ESI, pos. ion) m/z: 487.1 (M+1); $^1$H NMR (400 MHz, $CDCl_3$) δ: 1.76-1.77 (1H, m), 2.24-2.48 (3H, m), 2.50-2.64 (2H, m), 2.68-2.71 (2H, m), 2.73-2.75 (2H, m), 2.96-3.03 (3H, m), 3.07-3.12 (1H, m), 3.61-3.90 (2H, m), 4.24-4.27 (2H, m), 7.06-7.10 (1H, m), 7.16 (1H, s), 7.76-7.82 (1H, m), 7.82 (1H, s), 8.09-8.11 (1H, m), 8.59 (1H, s) ppm.

154

Example 38

N-(3-chloro-4-fluorophenyl)-6-(3-(1,3-dimethyl-6,7-dihydro-1H-pyrazolo[4,3-c]pyridin-5(4H)-yl)propoxy)-7-methoxyquinazolin-4-amine

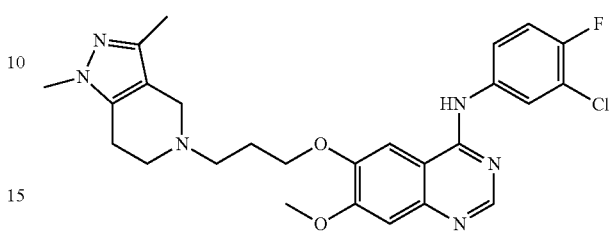

Step 1) tert-butyl 3-methyl-6,7-dihydro-1H-pyrazolo[4,3-c]pyridine-5(4H)-carboxylate

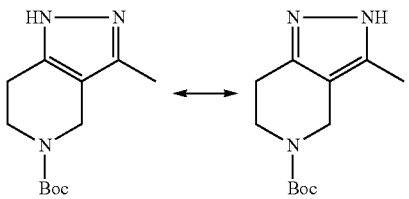 [SMILES: Cc1n[nH]c2c1CN(C(=O)OC(C)(C)C)CC2 ; Cc1[nH]nc2c1CN(C(=O)OC(C)(C)C)CC2]

To a solution of tert-butyl 3-acetyl-4-oxopiperidine-1-carboxylate (10.00 g, 41.44 mmol, 1.0 eq) in EtOH was added 98% $H_2NNH_2$—$H_2O$ (3.11 mL, 62.16 mmol, 1.5 eq). The reaction mixture was heated to 90° C. and refluxed for 2.0 h. The resulted mixture was concentrated in vacuo to give two tautomers as yellow oil (7.5 g, 76.5%), and which were used for the next step without further purification. The compound was characterized by the following spectroscopic data: MS (ESI, pos. ion) m/z: 238.31 (M+1);

Step 2) tert-butyl 1,3-dimethyl-6,7-dihydro-1H-pyrazolo[4,3-c]pyridine-5(4H)-carboxylate and tert-butyl 2,3-dimethyl-6,7-dihydro-2H-pyrazolo[4,3-c]pyridine-5(4H)-carboxylate

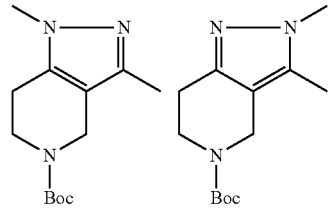

To a solution of tert-butyl 3-methyl-6,7-dihydro-1H-pyrazolo[4,3-c]pyridine-5(4H)-carboxylate (7.50 g, 29.84 mmol, 1.0 eq) in acetone was added $K_2CO_3$ (13.00 g, 3.0 eq) and iodomethane (2.20 mL, 1.2 eq). The reaction mixture was heated to reflux for 1.5 h and concentrated in vacuo. The residue was chromatographed with a silica gel column (eluting agent: 90:1 (v/v) DCM/MeOH) to give the title compounds tert-butyl1,3-dimethyl-6,7-dihydro-1H-pyrazolo[4,3-c]pyridine-5(4H)-carboxylate (3.0 g, 37.97%) and tert-butyl 2,3-dimethyl-6,7-dihydro-2H-pyrazolo[4,3-c]pyridine-5(4H)-carboxylate (3.5 g, 44.30%). The compound was characterized by the following spectroscopic data: MS (ESI, pos. ion) m/z: 252.32 (M+1).

Step 3) 1,3-dimethyl-4,5,6,7-tetrahydro-1H-pyrazolo[4,3-c]pyridine hydrochloride

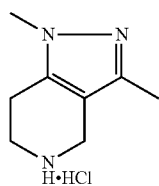

To a solution of tert-butyl 1,3-dimethyl-6,7-dihydro-1H-pyrazolo[4,3-c]pyridine-5(4H)-carboxylate (3.00 g) in MeOH was added a solution of HCl in EtOAc (3.0 M). White solid was precipitated out after 3.0 h reaction. The resulted mixture was filtered and the residue was dried to give the title compound as a white solid (2.00 g, 90.90%). The compound was characterized by the following spectroscopic data: MS (ESI, pos. ion) m/z: 152.21 (M+1).

Step 4) 5-(3-chloropropyl)-1,3-dimethyl-4,5,6,7-tetrahydro-1H-pyrazolo[4,3-c]pyridine

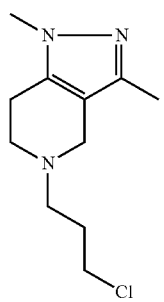

To a mixture of 1,3-dimethyl-4,5,6,7-tetrahydro-1H-pyrazolo[4,3-c]pyridine hydrochloride (2.00 g, 13.22 mmol, 1.0 eq) and $K_2CO_3$ (5.47 g, 39.66 mmol, 3.0 eq) in 40 mL of acetone was added 1-bromo-3-chloropropane (4.16 g, 26.44 mmol, 2.0 eq) at room temperature. The reaction mixture was heated to reflux for 5.0 h and filtered. The filtrate was concentrated in vacuo and the residue was purified by a silica gel column chromatography (eluting agent: 100:1 (v/v) DCM/MeOH) to give the title compound as yellow oil (1.50 g, 51.02%). The compound was characterized by the following spectroscopic data: MS (ESI, pos. ion) m/z: 228.73 (M+1).

Step 5) N-(3-chloro-4-fluorophenyl)-6-(3-(1,3-dimethyl-6,7-dihydro-1H-pyrazolo[4,3-c]pyridine-5(4H)-yl)propoxy)-7-methoxyquinazolin-4-amine

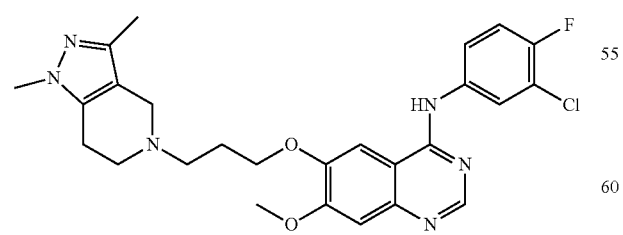

To a mixture of 4-((3-chloro-4-fluorophenyl)amino)-7-methoxyquinazolin-6-ol (0.50 g, 0.16 mmol, 1.0 eq) and $K_2CO_3$ (0.05 g, 0.32 mmol, 2.0 eq) in 20 mL of DMF was added 5-(3-chloropropyl)-1,3-dimethyl-4,5,6,7-tetrahydro-1H-pyrazolo[4,3-c]pyridine (0.05 g, 0.19 mmol, 1.2 eq) at room temperature. The reaction mixture was heated at 80° C. for 8.0 h and concentrated in vacuo. The residue was poured into a mixture of water (100 mL) and $CH_2Cl_2$ (150 mL). The organic phase was dried over anhydrous $Na_2SO_4$ and concentrated in vacuo. The residue was chromatographed with a silica gel column (eluting agent: 30:1 (v/v) DCM/MeOH) to give the title compound as a yellow solid (0.20 g, 24.98%), HPLC: 95.21%. The compound was characterized by the following spectroscopic data: MS (ESI, pos. ion) m/z: 513.02 (M+1); $^1$H NMR (400 MHz, d$^6$-DMSO) δ: 1.91-2.08 (m, J=4.0 Hz 2H), 2.51 (s, 3H), 2.78 (s, 3H), 2.79-2.89 (m, 6H), 2.90-2.96 (m, 2H), 3.95 (s, 3H), 4.19 (m, 2H), 7.25 (s, 1H), 7.47 (t, J=8.12 Hz, 1H), 7.54 (s, 2H), 8.11 (t, J=5.16 Hz, 1H), 8.50 (s, 1H) ppm.

Example 39

N-(3-chloro-4-fluorophenyl)-6-(3-(2,3-dimethyl-6,7-dihydro-2H-pyrazolo[4,3-c]pyridin-5(4H)-yl)propoxy)-7-methoxyquinazolin-4-amine

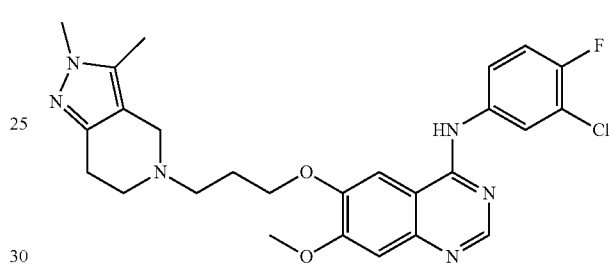

Step 1) 2,3-dimethyl-4,5,6,7-tetrahydro-2H-pyrazolo[4,3-c]pyridine hydrochloride

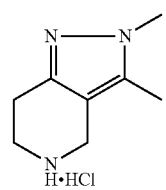

To a solution of tert-butyl 2,3-dimethyl-6,7-dihydro-1H-pyrazolo[4,3-c]pyridine-5(4H)-carboxylate (3.0 g) in MeOH was added a solution of HCl in EtOAc (3.0 M). White solid was precipitated out after 3.0 h reaction. The resulted mixture was filtered and the residue was dried to give the title compound as a white solid (2.10 g, 91.90%). The compound was characterized by the following spectroscopic data: MS (ESI, pos. ion) m/z: 152.21 (M+1).

Step 2) 5-(3-chloropropyl)-2,3-dimethyl-4,5,6,7-tetrahydro-2H-pyrazolo[4,3-c]pyridine

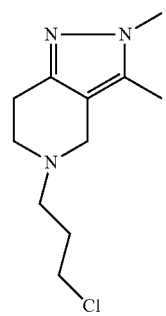

To a mixture of 2,3-dimethyl-4,5,6,7-tetrahydro-2H-pyrazolo[4,3-c]pyridine hydrochloride (2.0 g, 13.22 mmol, 1.0 eq) and K₂CO₃ (5.47, 39.66 mmol, 3.0 eq) in 40 mL of acetone was added 1-bromo-3-chloropropane (4.16 g, 26.44 mmol, 2.0 eq). The reaction mixture was heated to reflux for 5.0 h and filtered. The filtrate was concentrated in vacuo and the residue was purified by a silica gel column chromatography (eluting agent: 100:1 (v/v) DCM/MeOH) to give the title compound as yellow oil (1.3 g, 44.21%). The compound was characterized by the following spectroscopic data: MS (ESI, pos. ion) m/z: 228.73 (M+1).

Step 3) N-(3-chloro-4-fluorophenyl)-6-(3-(2,3-dimethyl-6,7-dihydro-2H-pyrazolo[4,3-c]pyridine-5(4H)-yl)propoxy)-7-methoxyquinazolin-4-amine

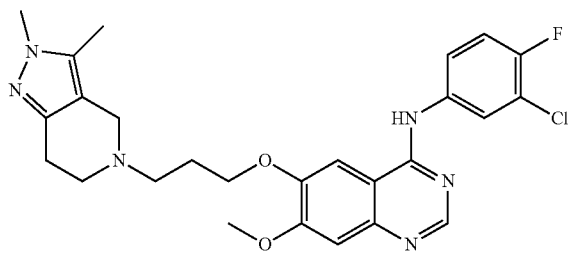 [SMILES: COc1cc2ncnc(Nc3ccc(F)c(Cl)c3)c2cc1OCCCN1CCc2nn(C)c(C)c2C1]

To a mixture of 4-((3-chloro-4-fluorophenyl)amino)-7-methoxyquinazolin-6-ol (0.50 g, 0.16 mmol, 1.0 eq) and K₂CO₃ (0.05 g, 0.32 mmol, 2.0 eq) in 20 mL of DMF was added 5-(3-chloropropyl)-2,3-dimethyl-4,5,6,7-tetrahydro-2H-pyrazolo[4,3-c]pyridine (0.05 g, 0.19 mmol, 1.2 eq). The reaction mixture was heated at 80° C. for 8.0 h and concentrated in vacuo. The residue was poured into a mixture of water (100 mL) and CH₂Cl₂ (150 mL). The organic phase was dried over anhydrous Na₂SO₄ and concentrated in vacuo. The residue was purified by a silica gel column chromatography (eluting agent: 30:1 (v/v) DCM/MeOH) to give the title compound as a yellow solid (0.17 g, 21.23%), HPLC: 96.27%. The compound was characterized by the following spectroscopic data: MS (ESI, pos. ion) m/z: 513.02 (M+1); ¹H NMR (400 MHz, d⁶-DMSO) δ: 1.93-2.18 (m, J=4.0 Hz 2H), 2.41 (s, 3H), 2.88 (s, 3H), 2.90-2.95 (m, 6H), 2.97-3.01 (m, 2H), 3.89 (s, 3H), 4.19-4.25 (m, 2H), 7.35 (s, 1H), 7.49 (t, J=8.42 Hz, 1H), 7.57-7.61 (m, 2H), 8.17 (t, J=5.66 Hz, 1H), 8.61 (s, 1H) ppm.

Example 40

N-(3-chloro-4-fluorophenyl)-7-methoxy-6-(3-((4aS,7aS)-tetrahydro-2H-[1,4]dioxino[2,3-c]pyrrol-6(3H)-yl)propoxy)quinazolin-4-amine

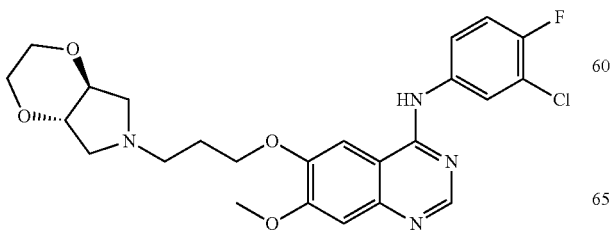

Step 1) (1R,5S)-benzyl 6-oxa-3-azabicyclo[3.1.0]hexane-3-carboxylate

To a solution of benzyl 2,5-dihydro-1H-pyrrole-1-carboxylate (2.00 g, 9.80 mmol) in CH₂Cl₂ (10 mL) was added slowly 3-chloroperbenzoic acid (3.00 g, 14.80 mmol) at 0° C. The reaction mixture was stirred for 13 h at room temperature, then quenched with saturated sodium thiosulfate aqueous solution and extracted with EtOAc. The organic phase was dried over anhydrous Na₂SO₄ and concentrated in vacuo. The residue was chromatographed with a silica gel column (eluting agent: 6:1 (v/v) PE/EtOAc) to give the title compound as colorless oil (1.75 g, 81.02%).

Step 2) (3R,4R)-benzyl 3-(2-bromoethoxy)-4-hydroxypyrrolidine-1-carboxylate

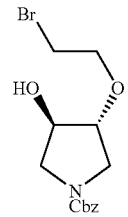

To a mixture of (1R,5S)-benzyl 6-oxa-3-azabicyclo[3.1.0]hexane-3-carboxylate (0.20 mg, 0.91 mmol), ethylene glycol (0.30 mL, 5.45 mmol) in CH₂Cl₂ (10 mL) was added boron trifluoride etherate (11.0 μL, 0.091 mmol) at 0° C. The reaction mixture was stirred for 6 h at rt, then quenched with water and extracted with CH₂Cl₂. The organic phase was dried over anhydrous Na₂SO₄ and concentrated in vacuo. The residue was chromatographed with a silica gel column (eluting agent: 6:1 (v/v) PE/EtOAc) to give the title compound as colorless oil (0.12 g, 38.71%).

Step 3) (4aR,7aR)-benzyl tetrahydro-2H-[1,4]dioxino[2,3-c]pyrrole-6(3H)-carboxylate

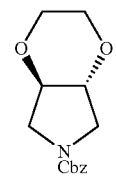

To a solution of (3R,4R)-benzyl 3-(2-bromoethoxy)-4-hydroxypyrrolidine-1-carboxylate (0.20 g, 0.58 mmol) in EtOH (5 mL) was added a solution of KOH (32.0 mg, 0.58 mmol) in EtOH (5 mL). The reaction mixture was stirred for 0.5 h at 85° C., then quenched with water and extracted with CH₂Cl₂. The organic layer was dried over anhydrous Na₂SO₄ and concentrated in vacuo. The residue was chromatographed with a silica gel column (eluting agent: 5:1 (v/v)PE/EtOAc) to give the title compound as colorless oil (0.11 g, 73.33%).

Step 4) (4aR,7aR)-hexahydro-2H-[1,4]dioxino[2,3-c]pyrrole

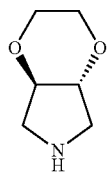

A mixture of (4aR,7aR)-benzyl tetrahydro-2H-[1,4]dioxino[2,3-c]pyrrole-6(3H)-carboxylate (140.0 mg, 0.53 mmol) and 10% Pd/C (0.56 mg, 0.053 mmol) in THF (6 mL) was stirred for 5.0 h at 50° C. The resulted mixture was filtered. The filtrate was concentrated in vacuo and the residue was used for the next step without further purification.

Step 5) N-(3-chloro-4-fluorophenyl)-7-methoxy-6-(3-((4aS,7aS)-tetrahydro-2H-[1,4]dioxino[2,3-c]pyrrol-6(3H)-yl)propoxy)quinazolin-4-amine

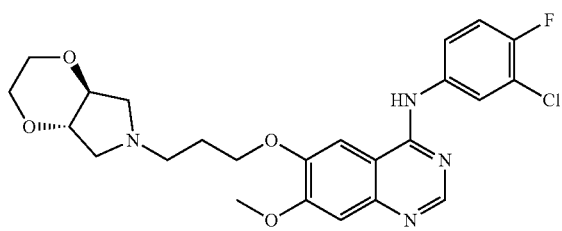 [SMILES: COc1cc2ncnc(Nc3ccc(F)c(Cl)c3)c2cc1OCCCN1C[C@@H]2OCCO[C@H]2C1]

A mixture of (4aR,7aR)-hexahydro-2H-[1,4]dioxino[2,3-c]pyrrole (129.0 mg, 1.0 mmol), K₂CO₃ (217.0 mg, 1.56 mmol), tetrabutylammoniumiodide (44.0 mg, 0.12 mmol) and N-(3-chloro-4-fluorophenyl)-6-(3-chloropropoxy)-7-methoxyquinazolin-4-amine (475.0 mg, 1.20 mmol) in 15 mL of DMF was stirred for 9 h at 60° C., then poured into 10 mL of ice-water and extracted with CH₂Cl₂. The organic phase was dried over anhydrous Na₂SO₄ and concentrated in vacuo. The residue was chromatographed with a silica gel column (eluting agent: 30:1 (v/v) DCM/MeOH) to give the title compound as a pale yellow solid (120 mg, 24.50%), HPLC: 94.43%. The compound was characterized by the following spectroscopic data: MS (ESI, pos. ion) m/z: 489.9 (M+1); ¹H NMR (400 MHz, CDCl₃) δ: 2.04 (m, 2H), 2.6 (br, 1H), 2.72 (m, 2H), 2.82 (m, 2H), 3.04 (m, 2H), 3.64 (t, J=6.08 Hz, 2H), 3.80 (m, 4H), 3.98 (s, 3H), 4.16 (t, J=6.48 Hz, 2H), 7.14 (t, J=8.76 Hz, 1H), 7.23 (d, J=7.8 Hz, 1H), 7.58 (m, 2H), 7.90 (dd, J₁=6.48 Hz, J₂=2.56 Hz, 1H), 8.65 (s, 1H).

Example 41

N-(4-fluorophenyl)-6-(3-(hexahydropyrrolo[3,4-c]pyrrol-2(1H)-yl)propoxy)-7-methoxyquinazolin-4-amine

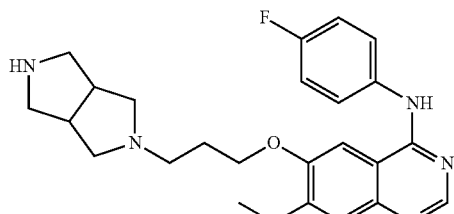

Step 1) tert-butyl 5-(3-((4-((4-fluorophenyl)amino)-7-methoxyquinazolin-6-yl)oxy)propyl) hexahydropyrrolo[3,4-c]pyrrole-2(1H)-carboxylate

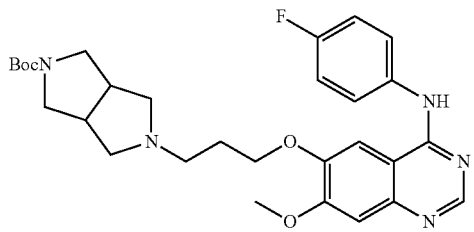 [SMILES: COc1cc2ncnc(Nc3ccc(F)cc3)c2cc1OCCCN1CC2CN(C(=O)OC(C)(C)C)CC2C1]

To a mixture of 6-(3-chloropropoxy)-N-(4-fluorophenyl)-7-methoxyquinazolin-4-amine (1.23 g), K₂CO₃ (1.79 g) and a catalytic amount of KI in DMF (20 mL) was added tert-butyl hexahydropyrrolo[3,4-c]pyrrole-2(1H)-carboxylate (0.94 g) at room temperature. The reaction mixture was heated at 80° C. for 8 h, then diluted with water and extracted with CH₂Cl₂. The organic layer was dried over anhydrous Na₂SO₄ for 1 h and filtered. The filtrate was concentrated in vacuo and chromatographed with a silica gel column (eluting agent: 30:1 (v/v) DCM/MeOH) to give the title compound as a white solid (1.14 g, 62.30%).

Step 2) N-(4-fluorophenyl)-6-(3-(hexahydropyrrolo[3,4-c]pyrrol-2(1H)-yl)propoxy)-7-methoxyquinazolin-4-amine

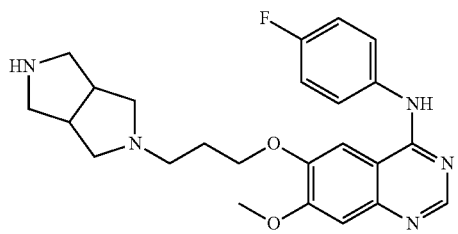 [SMILES: COc1cc2ncnc(Nc3ccc(F)cc3)c2cc1OCCCN1CC2CNCC2C1]

To a solution of tert-butyl 5-(3-((4-((4-fluorophenyl)amino)-7-methoxyquinazolin-6-yl)oxy) propyl)hexahydropyrrolo[3,4-c]pyrrole-2(1H)-carboxylate (1.14 g) in DCM (30 mL) was added a solution of HCl in EtOAc. The reaction mixture was stirred for 6 h at room temperature and filtered to give crude product. The crude product was recrystallized from a mixture of MeOH and EA to give the title compound as a white solid (0.83 g, 89.50%), HPLC: 95.23%. The compound was characterized by the following spectroscopic data: MS (ESI, pos. ion) m/z: 438.2 (M+1); $^1$H NMR (400 MHz, CDCl$_3$) δ: 1.83-1.88 (m, 4H), 2.32-2.45 (m, 6H), 2.66-2.76 (m, 4H), 4.03 (s, 3H), 4.15 (t, J=7.2 Hz, 2H), 7.15 (s, 1H), 7.23 (s, 1H), 7.40 (s, 1H), 7.53-7.60 (m, 2H), 7.90-7.93 (m, 1H), 8.66 (s, 1H) ppm.

Example 42

6-(3-(5,6-dihydro-[1,2,4]triazolo[4,3-a]pyrazin-7(8H)-yl)propoxy)-N-(4-fluorophenyl)-7-methoxyquinazolin-4-amine

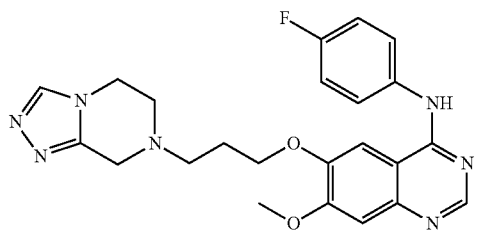 [SMILES: COc1cc2ncnc(Nc3ccc(F)cc3)c2cc1OCCCN1CCn2cnnc2C1]

To a solution of 5,6,7,8-tetrahydro-[1,2,4]triazolo[4,3-a]pyrazine (0.16 g) in DMF (8 mL) was added Ag$_2$CO$_3$ (0.98 g) and a solution of 6-(3-chloropropoxy)-N-(4-fluorophenyl)-7-methoxyquinazolin-4-amine (0.32 g) in DMF (2 mL) at room temperature under stirring. The mixture was heated at 80° C. for 36 h under N$_2$, and cooled to room temperature. To this, CH$_2$Cl$_2$ (100 mL) was added. The mixture was washed with brine (100 mL×3). The organic layer was dried over anhydrous Na$_2$SO$_4$ and filtered. The filtrate was concentrated in vacuo and the residue was chromatographed with a silica gel column (eluting agent: 20:1 (v/v) CH$_2$Cl$_2$/CH$_3$OH) to give the title compound as a white solid (87.70 mg, 20.41%), HPLC: 90.53%. The compound was characterized by the following spectroscopic data: MS (ESI, pos. ion) m/z: 450.2 (M+1); $^1$H NMR (400 MHz, CDCl$_3$) δ: 2.02-2.10 (m, 2H), 2.68 (t, J=13.20 Hz, 2H), 3.03 (t, J=10.80 Hz, 2H), 3.75 (s, 2H), 3.89 (s, 3H), 4.03 (t, J=10.80 Hz, 2H), 4.08 (t, J=12.40 Hz, 2H), 7.12 (m, 1H), 7.26 (s, 1H), 7.29 (t, J=6.00 Hz, 1H), 7.38 (s, 1H), 7.54-7.58 (m, 2H), 7.81-7.84 (m, 1H), 8.07 (s, 1H), 8.46 (s, 1H), 8.70 (s, 1H) ppm.

Example 43

N-(4-fluorophenyl)-6-(3-(hexahydrofuro[3,4-c]pyridin-5(3H)-yl)propoxy)-7-methoxyquinazolin-4-amine

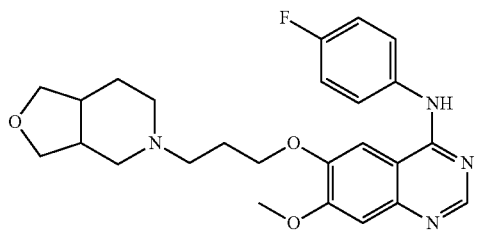 [SMILES: COc1cc2ncnc(Nc3ccc(F)cc3)c2cc1OCCCN1CCC2COCC2C1]

A mixture of 4-((4-fluorophenyl)amino)-7-methoxyquinazolin-6-ol (140 mg, 0.44 mmol, 1 eq), 5-(3-chloropropyl)octahydrofuro[3,4-c]pyridine (90 mg, 0.44 mmol, 1 eq) and K$_2$CO$_3$ (135 mg, 0.98 mmol, 2 eq) in DMF (10 mL) was heated to 80° C. and stirred overnight, then cooled to room temperature. To the resulted mixture was added 50 mL of CH$_2$Cl$_2$. The mixture was washed with brine (20 mL×3) and water (20 mL×2). The organic layer was dried over anhydrous Na$_2$SO$_4$ and filtered. The filtrate was concentrated in vacuo and the residue was chromatographed with a silica gel column (eluting agent: 20:1 (v/v) CH$_2$Cl$_2$/CH$_3$OH) to give the title compound as a yellow solid (50 mg, 25.00%), HPLC: 96.56%. The compound was characterized by the following spectroscopic data: MS (ESI, pos. ion) m/z: 453.2 (M+1); $^1$H NMR (400 MHz, CDCl$_3$) δ: 1.76-1.77 (2H, m), 2.24-2.48 (3H, m), 2.50-2.64 (3H, m), 2.68-2.71 (2H, m), 2.73-2.75 (2H, m), 2.96-3.03 (3H, m), 3.07-3.12 (2H, m), 3.61-3.90 (2H, m), 4.24-4.27 (2H, m), 7.02 (1H, s), 7.06-7.10 (1H, m), 7.16 (1H, s), 7.76-7.82 (1H, m), 7.82 (1H, s), 8.09-8.11 (1H, m), 8.59 (1H, s) ppm.

Example 44

N-(3-ethynyl-4-fluorophenyl)-6-(3-(hexahydropyrrolo[3,4-c]pyrrol-2(1H)-yl)propoxy)-7-methoxyquinazolin-4-amine

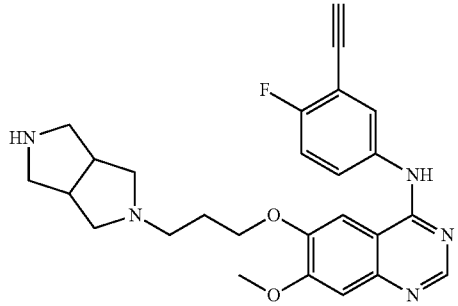 [SMILES: C#Cc1cc(Nc2ncnc3cc(OC)c(OCCCN4CC5CNCC5C4)cc23)ccc1F]

Step 1) tert-butyl 5-(3-((4-((3-ethynyl-4-fluorophenyl)amino)-7-methoxyquinazolin-6-yl)oxy)propyl)hexahydropyrrolo[3,4-c]pyrrole-2(1H)-carboxylate

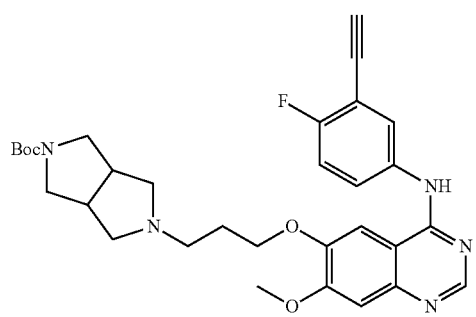 [SMILES: C#Cc1cc(Nc2ncnc3cc(OC)c(OCCCN4CC5CN(C(=O)OC(C)(C)C)CC5C4)cc23)ccc1F]

To a mixture of 6-(3-chloropropoxy)-N-(3-ethynyl-4-fluorophenyl)-7-methoxyquinazolin-4-amine (1.09 g), K$_2$CO$_3$ (0.59 g) and a catalytic amount of KI in DMF (20 mL) was added tert-butyl hexahydropyrrolo[3,4-c]pyrrole-2(1H)-carboxylate (0.78 g) at room temperature. The reaction mixture was heated to 80° C. and stirred for 8 h, then diluted with water and extracted with CH₂Cl₂. The organic layer was dried over anhydrous Na₂SO₄ for 1 h and filtered. The filtrate was concentrated in vacuo and the residue was chromatographed with a silica gel column (eluting agent: 30:1 (v/v) DCM/MeOH) to give the title compound as a white solid (1.03 g, 65.50%)

Step 2) N-(3-ethynyl-4-fluorophenyl)-6-(3-(hexahydropyrrolo[3,4-c]pyrrol-2(1H)-yl)propoxy)-7-methoxyquinazolin-4-amine

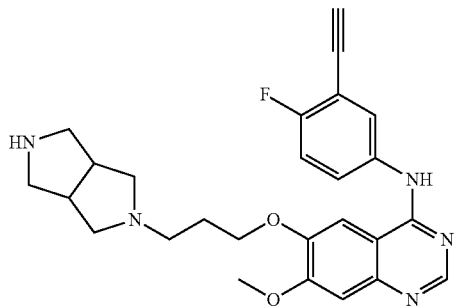 [SMILES: C#Cc1cc(Nc2ncnc3cc(OC)c(OCCCN4CC5CNCC5C4)cc23)ccc1F]

To a solution of tert-butyl 5-(3-((4-((3-ethynyl-4-fluorophenyl)amino)-7-methoxyquinazolin-6-yl)oxy)propyl)hexahydropyrrolo[3,4-c]pyrrole-2(1H)-carboxylate (1.03 g) in DCM (30 mL) was added a solution of HCl in EtOAc at room temperature. The reaction mixture was stirred for 6 h at room temperature and filtered to give crude product. The crude product was recrystallized from a mixture of MeOH and EA to give the title compound as a white solid (0.78 g, 92.60%), HPLC: 95.04%. The compound was characterized by the following spectroscopic data: MS (ESI, pos. ion) m/z: 462.2 (M+1); ¹H NMR (400 MHz, CDCl₃) δ: 1.83-1.88 (m, 4H), 2.32-2.45 (m, 6H), 2.66-2.76 (m, 4H), 4.03 (s, 3H), 4.06 (s, 1H), 4.15 (t, J=7.2 Hz, 2H), 7.15 (s, 1H), 7.23 (s, 1H), 7.40 (s, 1H), 7.53-7.60 (m, 1H), 7.90-7.93 (m, 1H), 8.66 (s, 1H) ppm.

Example 45

6-(3-(5,6-dihydro-[1,2,4]triazolo[4,3-a]pyrazin-7(8H)-yl)propoxy)-N-(3-ethynyl-4-fluorophenyl)-7-methoxyquinazolin-4-amine

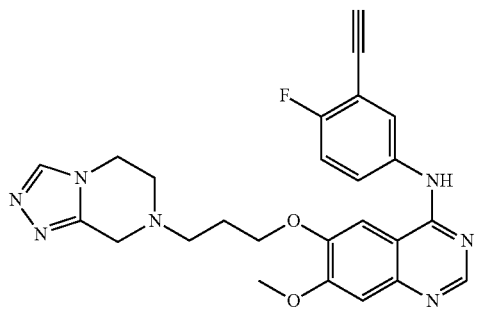 [SMILES: C#Cc1cc(Nc2ncnc3cc(OC)c(OCCCN4CCn5cnnc5C4)cc23)ccc1F]

To a solution of 5,6,7,8-tetrahydro-[1,2,4]triazolo[4,3-a]pyrazine (0.15 g) in DMF (8 mL) was added Ag₂CO₃ (1.02 g) and a solution of 6-(3-chloropropoxy)-N-(4-fluorophenyl)-7-methoxyquinazolin-4-amine (0.36 g) in DMF (2 mL) at room temperature under stirring. The mixture was heated to 80° C. and stirred for 36 h under N₂, and cooled to room temperature. To this, CH₂Cl₂ (100 mL) was added. The mixture was washed with bine (100 mL×3), dried over anhydrous Na₂SO₄ and filtered. The filtrate was concentrated in vacuo and the residue was chromatographed with a silica gel column (eluting agent: 20:1 (v/v) CH₂Cl₂/CH₃OH) to give the title compound as a white solid (92.70 mg, 21.31%), HPLC: 91.45%. The compound was characterized by the following spectroscopic data: MS (ESI, pos. ion) m/z: 474.2 (M+1); ¹H NMR (400 MHz, CDCl₃) δ: 2.03-2.10 (m, 2H), 2.68 (t, J=13.20 Hz, 2H), 3.03 (t, J=10.80 Hz, 2H), 3.75 (s, 2H), 3.89 (s, 3H), 3.99 (s, 1H), 4.03 (t, J=10.80 Hz, 2H), 4.08 (t, J=12.40 Hz, 2H), 7.03 (m, 1H), 7.24 (s, 1H), 7.32 (m, 1H), 7.38 (s, 1H), 7.81-7.84 (m, 1H), 8.46 (s, 1H), 8.70 (s, 1H) ppm.

Example 46

N-(3-ethynyl-4-fluorophenyl)-6-(3-(hexahydrofuro[3,4-c]pyridin-5(3H)-yl)propoxy)-7-methoxyquinazolin-4-amine

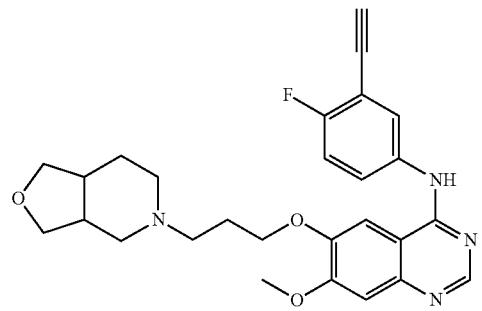 [SMILES: C#Cc1cc(Nc2ncnc3cc(OC)c(OCCCN4CCC5COCC5C4)cc23)ccc1F]

A mixture of 4-((3-ethynyl-4-fluorophenyl)amino)-7-methoxyquinazolin-6-ol (220 mg, 0.71 mmol, 1 eq), 5-(3-chloropropyl)octahydrofuro[3,4-c]pyridine (174 mg, 0.44 mmol, 1.2 eq) and K₂CO₃ (197 mg, 1.42 mmol, 2 eq) in DMF (10 mL) was stirred at 80° C. overnight, and cooled to room temperature. To this, CH₂Cl₂ (50 mL) was added. The mixture was washed with brine (20 mL×3) and water (20 mL×2), then dried over anhydrous Na₂SO₄ and filtered. The filtrate was concentrated in vacuo and the residue was purified by a silica gel column chromatography (eluting agent: 20:1 (v/v) CH₂Cl₂/CH₃OH) to give the title compound as a yellow solid (110 mg, 32.50%), HPLC: 97.45%. The compound was characterized by the following spectroscopic data: MS (ESI, pos. ion) m/z: 477.2 (M+1); ¹H NMR (400 MHz, CDCl₃) δ: 1.76-1.77 (2H, m), 2.24-2.48 (3H, m), 2.50-2.64 (2H, m), 2.68-2.71 (3H, m), 2.73-2.75 (2H, m), 2.96-3.03 (3H, m), 3.07-3.12 (2H, m), 3.61-3.90 (2H, m), 4.07 (1H, s), 4.24-4.27 (2H, m), 7.06-7.10 (1H, m), 7.16 (1H, s), 7.76-7.82 (1H, m), 7.82 (1H, s), 8.09-8.11 (1H, m), 8.59 (1H, s) ppm.

Example 47

N-(3-ethynylphenyl)-6-(3-(hexahydropyrrolo[3,4-c]pyrrol-2(1H)-yl)propoxy)-7-methoxyquinazolin-4-amine

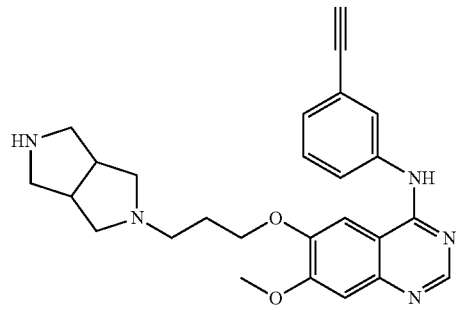 [SMILES: C#Cc1cccc(Nc2ncnc3cc(OC)c(OCCCN4CC5CNCC5C4)cc23)c1]

Step 1) tert-butyl 5-(3-((4-((3-ethynylphenyl)amino)-7-methoxyquinazolin-6-yl)oxy)propyl) hexahydro-pyrrolo[3,4-c]pyrrole-2(1H)-carboxylate

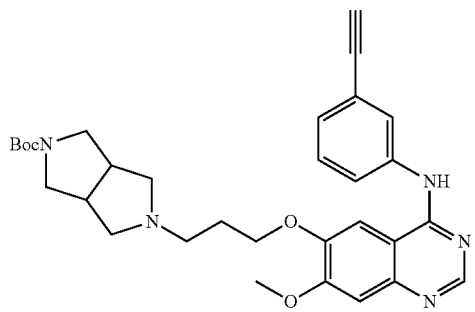 [SMILES: C#Cc1cccc(Nc2ncnc3cc(OC)c(OCCCN4CC5CN(C(=O)OC(C)(C)C)CC5C4)cc23)c1]

To a mixture of 6-(3-chloropropoxy)-N-(3-ethynylphenyl)-7-methoxyquinazolin-4-amine (1.20 g), K$_2$CO$_3$ (0.45 g) and a catalytic amount of KI in DMF (20 mL) was added tert-butyl hexahydropyrrolo[3,4-c]pyrrole-2(1H)-carboxylate (0.85 g) at room temperature. The reaction mixture was heated to 80° C. and stirred for 8 h, then diluted with water and extracted with CH$_2$Cl$_2$. The organic layer was dried over anhydrous Na$_2$SO$_4$ for 1 h and filtered. The filtrate was concentrated in vacuo and the residue was chromatographed with a silica gel column (eluting agent: 30:1 (v/v) DCM/MeOH) to give the title compound as a white solid (1.22 g, 68.70%).

Step 2) N-(3-ethynylphenyl)-6-(3-(hexahydropyrrolo[3,4-c]pyrrol-2(1H)-yl)propoxy)-7-methoxyquinazolin-4-amine

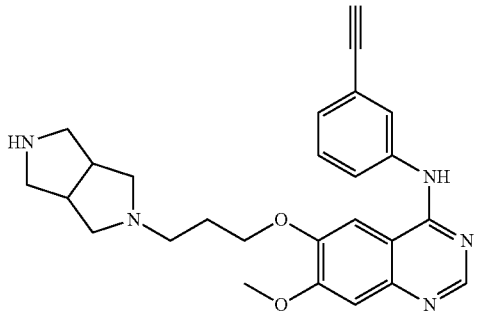 [SMILES: C#Cc1cccc(Nc2ncnc3cc(OC)c(OCCCN4CC5CNCC5C4)cc23)c1]

To a solution of tert-butyl 5-(3-((4-((3-ethynylphenyl)amino)-7-methoxyquinazolin-6-yl)oxy) propyl)hexahydropyrrolo[3,4-c]pyrrole-2(1H)-carboxylate (1.22 g) in DCM (30 mL) was added a solution of HCl in EtOAc at room temperature. The reaction mixture was stirred for 6 h at room temperature and filtered to give crude product. The crude product was recrystallized from a mixture of MeOH and EA to give the title compound as a white solid (0.91 g, 90.50%), HPLC: 94.65%. The compound was characterized by the following spectroscopic data: MS (ESI, pos. ion) m/z: 444.2 (M+1); $^1$H NMR (400 MHz, CDCl$_3$) δ: 1.84-1.89 (m, 4H), 2.38-2.44 (m, 6H), 2.69-2.76 (m, 4H), 3.95 (s, 3H), 4.03 (s, 1H), 4.14 (t, J=7.2 Hz, 2H), 7.13 (s, 1H), 7.25 (s, 1H), 7.43 (s, 1H), 7.55-7.60 (m, 1H), 7.90-7.93 (m, 1H), 8.68 (s, 1H) ppm.

Example 48

6-(3-(5,6-dihydro-[1,2,4]triazolo[4,3-a]pyrazin-7(8H)-yl)propoxy)-N-(3-ethynylphenyl)-7-methoxyquinazolin-4-amine

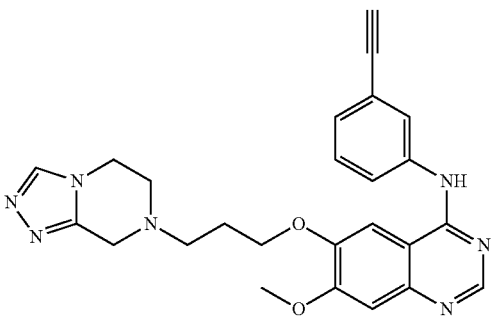 [SMILES: C#Cc1cccc(Nc2ncnc3cc(OC)c(OCCCN4CCn5cnnc5C4)cc23)c1]

To a solution of 5,6,7,8-tetrahydro-[1,2,4]triazolo[4,3-a]pyrazine (0.17 g) in DMF (8 mL) was added Ag$_2$CO$_3$ (1.29 g) and a solution of 6-(3-chloropropoxy)-N-(3-ethynylphenyl)-7-methoxyquinazolin-4-amine (0.45 g) in DMF (2 mL) at room temperature under stirring. The mixture was stirred at 80° C. for 36 h under N$_2$ and cooled to room temperature. To this, CH$_2$Cl$_2$ (100 mL) was added. The mixture was washed with brine (100 mL×3), dried over anhydrous Na$_2$SO$_4$ and filtered. The filtrate was concentrated in vacuo and the residue was chromatographed with a silica gel column (eluting agent: 20:1 (v/v) CH$_2$Cl$_2$/CH$_3$OH) to give the product (114 mg, 20.50%), HPLC: 90.63%. The compound was characterized by the following spectroscopic data: MS (ESI, pos. ion) m/z: 456.2 (M+1); $^1$H NMR (400 MHz, CDCl$_3$) δ: 2.03-2.10 (m, 2H), 2.68 (t, J=13.20 Hz, 2H), 3.03 (t, J=10.80 Hz, 2H), 3.75 (s, 2H), 3.89 (s, 3H), 3.99 (s, 1H), 4.03 (t, J=10.80 Hz, 2H), 4.08 (t, J=12.40 Hz, 2H), 7.03 (m, 1H), 7.24 (s, 1H), 7.32 (m, 1H), 7.38 (s, 1H), 7.81-7.84 (m, 2H), 8.46 (s, 1H), 8.70 (s, 1H) ppm.

Example 49

N-(3-ethynylphenyl)-6-(3-(hexahydrofuro[3,4-c]pyridin-5(3H)-yl)propoxy)-7-methoxyquinazolin-4-amine

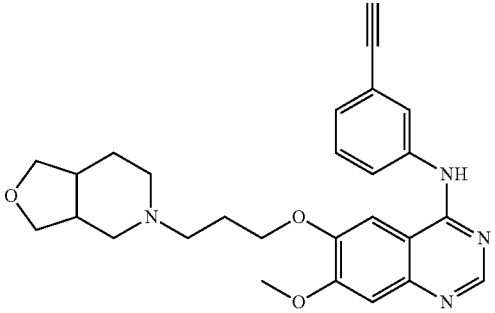

A mixture of 4-((3-ethynylphenyl)amino)-7-methoxyquinazolin-6-ol (250 mg, 0.68 mmol, 1 eq), 5-(3-chloropropyl)octahydrofuro[3,4-c]pyridine (280 mg, 0.82 mmol, 1.2 eq) and K₂CO₃ (188 mg, 1.36 mmol, 2 eq) in DMF (10 mL) was stirred at 80° C. overnight and cooled to room temperature. To this, CH₂Cl₂ (50 mL) was added. The mixture was washed with brine (20 mL×3) and water (20 mL×2), then dried over anhydrous Na₂SO₄ and filtered. The filtrate was concentrated in vacuo and the residue was purified by a silica gel column chromatography (eluting agent: 20:1 (v/v) CH₂Cl₂/CH₃OH) to give the title compound as a yellow solid (140 mg, 45.50%), HPLC: 98.47%. The compound was characterized by the following spectroscopic data: MS (ESI, pos. ion) m/z: 459.2 (M+1); ¹H NMR (400 MHz, CDCl₃) δ: 1.73-1.75 (2H, m), 2.35-2.46 (3H, m), 2.54-2.68 (2H, m), 2.65-2.70 (3H, m), 2.72-2.76 (2H, m), 2.96-3.03 (3H, m), 3.05-3.10 (2H, m), 3.71-3.90 (2H, m), 4.03 (1H, s), 4.22-4.27 (2H, m), 7.06-7.12 (1H, m), 7.13 (1H, s), 7.76-7.82 (2H, m), 7.85 (1H, s), 8.06-8.11 (1H, m), 8.55 (1H, s) ppm.

Example 50

N-(4-bromo-2-fluorophenyl)-6-(3-(hexahydropyrrolo [3,4-c]pyrrol-2(1H)-yl)propoxy)-7-methoxyquinazolin-4-amine

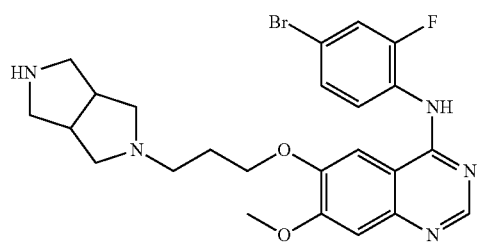

Step 1) tert-butyl 5-(3-((4-((4-bromo-2-fluorophenyl) amino)-7-methoxyquinazolin-6-yl)oxy)propyl) hexahydropyrrolo[3,4-c]pyrrole-2(1H)-carboxylate

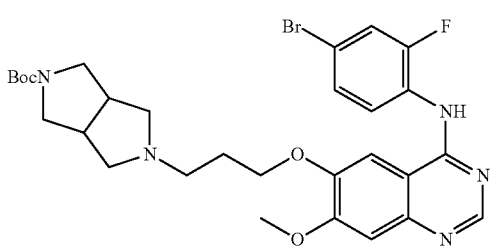 [SMILES: COc1cc2ncnc(Nc3ccc(Br)cc3F)c2cc1OCCCN1CC2CN(C(=O)OC(C)(C)C)CC2C1]

To a mixture of N-(4-bromo-2-fluorophenyl)-6-(3-chloropropoxy)-7-methoxyquinazolin-4-amine (1.25 g), K₂CO₃ (0.78 g) and a catalytic amount of KI in DMF (20 mL) was added tert-butyl hexahydropyrrolo[3,4-c]pyrrole-2(1H)-carboxylate (0.78 g) at room temperature. The reaction mixture was heated to 80° C. and stirred for 8 h, then diluted with water and extracted with CH₂Cl₂. The organic layer was dried over anhydrous Na₂SO₄ for 1 h and filtered. The filtrate was concentrated in vacuo and the residue was chromatographed with a silica gel column (eluting agent: 30:1 (v/v) DCM/MeOH) to give the title compound as a white solid (1.16 g, 66.50%).

Step 2) N-(4-bromo-2-fluorophenyl)-6-(3-(hexahydropyrrolo[3,4-c]pyrrol-2(1H)-yl)propoxy)-7-methoxyquinazolin-4-amine

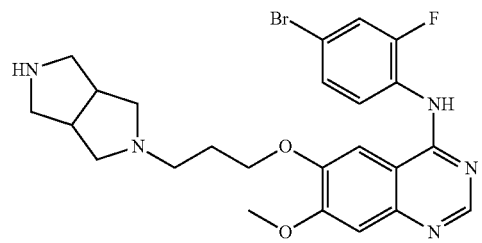 [SMILES: COc1cc2ncnc(Nc3ccc(Br)cc3F)c2cc1OCCCN1CC2CNCC2C1]

To a solution of tert-butyl 5-(3-((4-((4-bromo-2-fluorophenyl)amino)-7-methoxyquinazolin-6-yl)oxy)propyl) hexahydropyrrolo[3,4-c]pyrrole-2(1H)-carboxylate (1.16 g) in DCM (30 mL) was added a solution of HCl in EtOAc at room temperature. The reaction mixture was stirred for 6 h at room temperature and filtered to give crude product. The crude product was recrystallized from a mixture of MeOH and EA to give the title compound as a white solid (0.90 g, 92.60%), HPLC: 95.57%. The compound was characterized by the following spectroscopic data: MS (ESI, pos. ion) m/z: 516.1 (M+1); ¹H NMR (400 MHz, CDCl₃) δ: 1.80-1.85 (m, 4H), 2.40-2.44 (m, 5H), 2.70-2.76 (m, 4H), 3.98 (s, 3H), 4.03 (s, 1H), 4.14 (t, J=7.2 Hz, 2H), 7.13 (s, 1H), 7.25 (s, 1H), 7.43 (s, 1H), 7.55-7.60 (m, 1H), 7.90-7.93 (m, 1H), 8.68 (s, 1H) ppm.

Example 51

N-(4-bromo-2-fluorophenyl)-6-(3-(5,6-dihydro-[1,2,4]triazolo[4,3-a]pyrazin-7(8H)-yl)propoxy)-7-methoxyquinazolin-4-amine

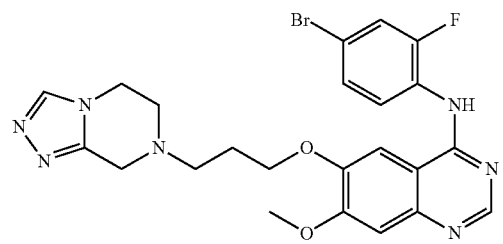 [SMILES: COc1cc2ncnc(Nc3ccc(Br)cc3F)c2cc1OCCCN1CCn2cnnc2C1]

To a solution of 5,6,7,8-tetrahydro-[1,2,4]triazolo[4,3-a]pyrazine (0.15 g) in DMF (8 mL) was added Ag₂CO₃ (1.00 g) and a solution of N-(4-bromo-2-fluorophenyl)-6-(3-chloropropoxy)-7-methoxy quinazolin-4-amine (0.40 g) in DMF (2 mL) at room temperature under stirring. The mixture was stirred at 80° C. for 36 h under N₂ and cooled to room temperature. To this, CH₂Cl₂ (100 mL) was added. The mixture was washed with brine (100 mL×3), dried over anhydrous Na₂SO₄ and filtered. The filtrate was concentrated in vacuo and the residue was chromatographed with a silica gel column (eluting agent: 20:1 (v/v) CH₂Cl₂/CH₃OH) to give the product (89 mg, 18.50%), HPLC: 91.13%. The compound was characterized by the following spectroscopic data: MS (ESI, pos. ion) m/z: 528.1 (M+1); $^1$H NMR (400 MHz, CDCl$_3$) δ: 2.03-2.10 (m, 2H), 2.68 (t, J=13.20 Hz, 2H), 3.03 (t, J=10.80 Hz, 2H), 3.75 (s, 2H), 3.89 (s, 3H), 4.03 (t, J=10.80 Hz, 2H), 4.08 (t, J=12.40 Hz, 2H), 7.03 (m, 1H), 7.24 (s, 1H), 7.32 (m, 1H), 7.38 (s, 1H), 7.81-7.84 (m, 2H), 8.46 (s, 1H), 8.70 (s, 1H) ppm.

Example 52

N-(4-bromo-2-fluorophenyl)-6-(3-(hexahydrofuro[3,4-c]pyridin-5(3H)-yl)propoxy)-7-methoxyquinazolin-4-amine

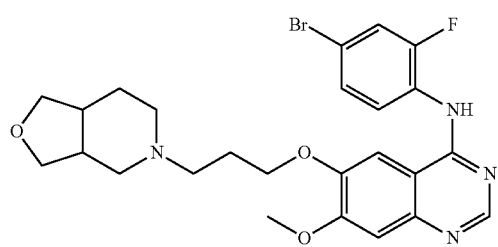 [SMILES: COc1cc2ncnc(Nc3ccc(Br)cc3F)c2cc1OCCCN1CCC2COCC2C1]

A mixture of 4-((4-bromo-2-fluorophenyl)amino)-7-methoxyquinazolin-6-ol (225 mg, 0.62 mmol, 1 eq), 5-(3-chloropropyl)octahydrofuro[3,4-c]pyridine (151 mg, 0.74 mmol, 1.2 eq) and K$_2$CO$_3$ (171 mg, 1.24 mmol, 2 eq) in DMF (10 mL) was stirred at 80° C. overnight and cooled to room temperature. To this, CH$_2$Cl$_2$ (50 mL) was added. The mixture was washed with brine (20 mL×3) and water (20 mL×2), then dried over anhydrous Na$_2$SO$_4$ and filtered. The filtrate was concentrated in vacuo and the residue was purified by a silica gel column chromatography (eluting agent: 20:1 (v/v) CH$_2$Cl$_2$/CH$_3$OH) to give the title compound as a yellow solid (199 mg, 60.50%), HPLC: 98.32%. The compound was characterized by the following spectroscopic data: MS (ESI, pos. ion) m/z: 531.1 (M+1); $^1$H NMR (400 MHz, CDCl$_3$) δ: 1.69-1.73 (2H, m), 2.41-2.46 (3H, m), 2.64-2.66 (2H, m), 2.68-2.70 (3H, m), 2.75-2.82 (2H, m), 3.00-3.03 (3H, m), 3.06-3.10 (2H, m), 3.81-3.85 (2H, m), 4.23-4.27 (2H, m), 7.06-7.12 (1H, m), 7.21 (1H, s), 7.68-7.79 (2H, m), 7.87 (1H, s), 8.06-8.11 (1H, m), 8.65 (1H, s) ppm.

Example 53

2-(3-((4-((4-fluorophenyl)amino)-7-methoxyquinazolin-6-yl)oxy)propyl)hexahydropyrano[3,4-c]pyrrol-4(2H)-one

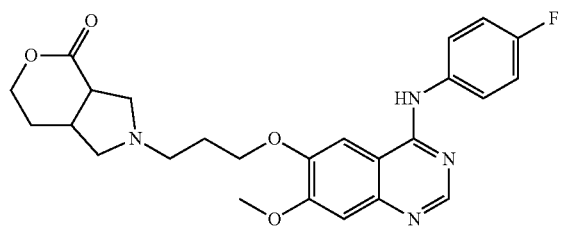 [SMILES: COc1cc2ncnc(Nc3ccc(F)cc3)c2cc1OCCCN1CC2CCOC(=O)C2C1]

To a solution of 2-(3-chloropropyl)hexahydropyrano[3,4-c]pyrrol-4(2H)-one (0.25 g) in DMF (8 mL) was added K$_2$CO$_3$ (3.0 eq), 4-((4-fluorophenyl)amino)-7-methoxyquinazolin-6-ol (0.38 g) and tetrabutylammonium iodide (0.1 eq). The reaction mixture was heated to 90° C. and stirred for 10 h. To the mixture was added CH$_2$Cl$_2$ (100 mL). The mixture was washed with water and brine. The organic layer was dried over anhydrous Na$_2$SO$_4$ and filtered. The filtrate was concentrated in vacuo and the residue was chromatographed with a silica gel column (eluting agent: 20:1 (v/v) CH$_2$Cl$_2$/CH$_3$OH) to give the product (0.20 g, 32.50%), HPLC: 97.35%. The compound was characterized by the following spectroscopic data: MS (ESI, pos. ion) m/z: 467.2 (M+1); $^1$H NMR (400 MHz, CDCl$_3$) δ: 2.06-2.12 (m, 4H), 2.35 (d, J=2.92 Hz, 1H), 2.51-2.58 (m, 3H), 2.76-2.79 (m, 2H), 2.97-3.02 (m, 1H), 3.49-3.50 (m, 1H), 3.52 (s, 1H), 4.00 (s, 3H), 4.18 (d, J=1.80 Hz, 1H), 4.21-4.24 (m, 1H), 4.35-4.40 (m, 1H), 7.13 (t, J=8.80 Hz, 1H), 7.24 (d, J=9.48 Hz, 1H), 7.41 (s, 1H), 7.68 (m, 2H), 7.95-7.98 (m, 1H), 8.28 (s, 1H), 8.63 (s, 1H) ppm.

Example A

Human Liver Microsomal Stability Test

General LC/MS/MS Analysis Method

An Agilent 6430 series LC/MS/MS spectrometer equipped with G4220A binary pumps, a G1367A autosampler and a G1315C UV detector were used in the analysis. An ESI source was done in positive ion mode as appropriate and the MRM transition for each analyte was optimized using standard solution. An XBradge™-C18 50×2.1 mm I.D., 3.5 μm column (Waters, USA) was used during the analysis. The mobile phase was 2 mM ammonium formate, 0.1% formic acid in water (A); 2 mM ammonium formate, 0.1% formic acid in acetonitrile (B) (70:30, v/v). The flow rate was 0.4 mL/min, column was maintained at 40° C. 5 μL of the sample were injected.

The gradient condition was shown in Table 1:

TABLE 1

| t (min) | A (%) | B (%) |
|---|---|---|
| 0.5 | 90 | 10 |
| 1.2 | 10 | 90 |
| 2.5 | 10 | 90 |
| 2.6 | 90 | 10 |
| 4 | 90 | 10 |

Methods for Determination of Stability in Human Liver Microsomes

Human liver microsomes incubations were conducted in duplication in polypropylene tubes. The typical incubation mixtures consisted of human liver microsomes (0.75 mg protein/mL), compounds of interest (1.5 μM) and NADPH (6.0 mM) in total volume of 200 μL potassium phosphate buffer (PBS, 100 mM, pH7.4). Compounds were dissolved in DMSO and diluted with PBS such that the final concentration of DMSO was 0.05%. The enzymatic reactions were commenced with the addition of protein after a 10-min preincubation and incubated in a water bath open to the air at 37° C. Reactions were terminated at various time points (0, 15 and 30 min) by adding equal volume of ice-cold acetonitrile. The samples were stored at −80° C. until LC/MS/MS assays.

The concentrations of compounds in the incubation mixtures of human live microsomes were determined by a LC/MS/MS method.

A parallel incubation was performed using denatured microsomes as the negative control, and reactions were terminated at various time points (0, 15 and 30 min) after incubation at 37° C.

Ketanserin (1.5 µM) was selected as the positive control, and reaction were terminated at various time points (0, 15 and 30 min) after incubation at 37° C. Both positive and negative control sample were included in each assay to ensure the integrity of the microsomal incubation system.

Data Analysis

The concentrations of compounds in human liver microsome incubations were plotted as a percentage of the relevant zero time point control for each reaction. The in vivo CLint were extrapolated (ref.: Naritomi Y, Terashita S, Kimura S, Suzuki A, Kagayama A, Sugiyama Y. Prediction of human hepatic clearance from in vivo animal experiments and in vitro metabolic studies with liver microsomes from animals and humans. Drug Metabolism and Disposition 2001, 29: 1316-1324.). The compounds disclosed herein generally exhibited high clearance values (Clint>58.95 mL/min/Kg).

Example B

Preclinical Pharmacokinetics Evaluation

Compounds were assessed in pharmacokinetic studies in mice, rats, dogs or monkeys. The compounds were administered as 5% DMSO+5% solutol-15 in water solution. For the intravenous administration, rats, dogs and monkeys were given at 2 mg/Kg dose, mice were given 10 mg/Kg dose. For the oral (p.o.) dosing, mice were given 10 mg/Kg dose and rats, dogs and monkeys were given 5 mg/Kg dose. The blood samples (0.3 mL) were drawn at 0.083, 0.25, 0.5, 1.0, 2.0, 4.0, 6.0, 8.0 and 24 h time points and centrifuged at 3,000 rpm for 10 min, the plasma solution were collected, stored at −20° C. until analyzed by LC/MS/MS as described above.

Compounds demonstrated high bioavailability in mice and rats, and medium bioavailability in dogs and monkeys when administrated orally.

Biological Activity

The following representative assays were performed in assessing the biological activities of compounds disclosed herein. They are given to illustrate the invention in a non-limiting fashion.

Example C

EGFR Inhibitory Activity Test

In a pilot study, the compounds disclosed herein were screened for their EGFR inhibitory activity. The Cisbio Research Product HTRF kinEASE STK S1 kinase assay/inhibitor screening Kit, can detect the generation of the phosphorylated substrate. Kinase, biotinylated substrate and ATP were first added into buffer solution, and the phosphorylated biotinylated substrates were formed by enzyme reaction. Then, to the above solution was added europium-labeled anti-phospho-site specific antibodies and XL665-labeled avidin. The Specific combinations of antibody with antigen, and biotin with avidin, bring the europium and XL665 closer together and resonance energy transferred. The signals at 620 nm and 665 nm were detected, and the activity of the kinase was evaluated by the ratio of the two signals value. Specific procedures were shown in FIG. 1.

Made replicate wells detection to all samples and standards, and most of the compounds showed high inhibitory activity on EGFR. (Specific data were shown in Table 2).

TABLE 2

Inhibitory Activity of Compounds on EGFR Kinase

| Examples | $IC_{50}$(nM) |
|---|---|
| 1 | C |
| 2 | D |
| 3 | B |
| 4 | A |
| 5 | B |
| 6 | A |
| 7 | C |
| 8 | A |
| 9 | C |
| 10 | D |
| 11 | A |
| 12 | B |
| 13 | A |
| 14 | C |
| 15 | B |
| 16 | C |
| 17 | A |
| 18 | A |
| 19 | A |
| 20 | A |
| 21 | A |
| 22 | A |
| 23 | C |
| 24 | A |
| 25 | A |
| 26 | A |
| 27 | A |
| 28 | A |
| 29 | A |
| 31 | A |
| 32 | C |
| 33 | A |
| 34 | A |
| 35 | A |
| 36 | C |
| 37 | C |
| 38 | B |
| 39 | C |
| 40 | A |
| 41 | A |
| 42 | C |
| 43 | B |
| 44 | B |
| 45 | B |

$IC_{50}$: A = 0.001 nM-0.100 nM; B = 0.101 nM-1.000 nM; C = 1.001 nM-10.000 nM; D > 10 nM.

Example D

Human Xenograft Tumor Models Assays

Human A549 Non-small Cell Lung Cancer Xenograft Tumor Model

In a pilot study, the efficacy of compounds disclosed herein was evaluated in a nude mice model of subcutaneous xenografts. A549 cells (ATCC) were grown as subcutaneous tumors in 6-7 weeks old female nude mice (BALB/cA nu/nu, Shanghai SLAC Laboratory Animal. Co.). When tumors reached a volume of 100-250 mm³, animals were randomly divided into vehicle control (citric acid (0.362 g)+propylene glycol (30 mL)+water (70 mL)+polyoxyethylene 35 castor oil solution (6.6 mL)) and compound groups. Subsequent administration of compound by oral gavage (40 mg/kg, dissolved in a solution of citric acid (0.362 g)+propylene glycol (30 mL)+water (70 mL)+polyoxyethylene 35 castor oil solution (6.6 mL)) for three weeks. Tumor volumes and body weights were recorded 2-3 times a week.

Human Calu-3 Non-Small Cell Lung Cancer Xenograft Tumor Model

Calu-3 cells (ATCC) were grown as subcutaneous tumors in 6-7 weeks old female nude mice (BALB/cA nu/nu, Shanghai SLAC Laboratory Animal. Co.). When tumors reached a volume of 100-250 mm³, animals were randomly divided into vehicle control (citric acid (0.362 g)+propylene glycol (30 mL)+water (70 mL)+polyoxyethylene 35 castor oil solution (6.6 mL)) and compound groups. Subsequent administration of compound by oral gavage (40 mg/kg, dissolved in a solution of citric acid (0.362 g)+propylene glycol (30 mL)+water (70 mL)+polyoxyethylene 35 castor oil solution (6.6 mL)) for three weeks. Tumor volumes and body weights were recorded 2-3 times a week.

Human BT474 Breast Cancer Xenograft Tumor Model

BT474 cells (ATCC) were grown as subcutaneous tumors in 6-7 weeks old female nude mice (BALB/cA nu/nu, Shanghai SLAC Laboratory Animal. Co.). When tumors reached a volume of 100-250 mm³, animals were randomly divided into vehicle control (citric acid (0.362 g)+propylene glycol (30 mL)+water (70 mL)+polyoxyethylene 35 castor oil solution (6.6 mL)) and compound groups. Subsequent administration of compound by oral gavage (40 mg/kg, dissolved in a solution of citric acid (0.362 g)+propylene glycol (30 mL)+water (70 mL)+polyoxyethylene 35 castor oil solution (6.6 mL)) for three weeks. Tumor volumes and body weights were recorded 2-3 times a week.

Human MDA-MB-231 Breast Cancer Xenograft Tumor Model

MDA-MB-231 cells (ATCC) were grown as subcutaneous tumors in 6-7 weeks old female nude mice (BALB/cA nu/nu, Shanghai SLAC Laboratory Animal. Co.). When tumors reached a volume of 100-250 mm³, animals were randomly divided into vehicle control (citric acid (0.362 g)+propylene glycol (30 mL)+water (70 mL)+polyoxyethylene 35 castor oil solution (6.6 mL)) and compound groups. Subsequent administration of compound by oral gavage (40 mg/kg, dissolved in a solution of citric acid (0.362 g)+propylene glycol (30 mL)+water (70 mL)+polyoxyethylene 35 castor oil solution (6.6 mL)) for three weeks. Tumor volumes and body weights were recorded 2-3 times a week.

Human BxPC-3 Pancreatic Cancer Xenograft Tumor Model

BxPC-3 cells (ATCC) were grown as subcutaneous tumors in 6-7 weeks old female nude mice (BALB/cA nu/nu, Shanghai SLAC Laboratory Animal. Co.). When tumors reached a volume of 100-250 mm³, animals were randomly divided into vehicle control (citric acid (0.362 g)+propylene glycol (30 mL)+water (70 mL)+polyoxyethylene 35 castor oil solution (6.6 mL)) and compound groups. Subsequent administration of compound by oral gavage (40 mg/kg, dissolved in a solution of citric acid (0.362 g)+propylene glycol (30 mL)+water (70 mL)+polyoxyethylene 35 castor oil solution (6.6 mL)) for three weeks. Tumor volumes and body weights were recorded 2-3 times a week.

Human A431 Epidermoid Carcinoma Xenograft Tumor Model

Xenografts were also generated with human epidermoid tumor cells (A431 cells, ATCC) and grown as subcutaneous tumors in 6-7 weeks old female nude mice (BALB/cA nu/nu, Shanghai SLAC Laboratory Animal. Co.) (n=10 for each vehicle group, n=6 for each dosing group). When tumors reached a volume of 100-200 mm³, animals were randomly divided into vehicle control (citric acid (0.362 g)+propylene glycol (30 mL)+water (70 mL)+polyoxyethylene 35 castor oil solution (6.6 mL)) and compound groups. Subsequent administration of compound by oral gavage (2.5, 5 and 10 mg/kg, dissolved in a solution of citric acid (0.362 g)+propylene glycol (30 mL)+water (70 mL)+polyoxyethylene 35 castor oil solution (6.6 mL)) for three weeks. Tumor volumes and body weights were recorded 2-3 times a week.

Tumor Growth Inhibition (TGI) Analysis

Progression of tumor growth is assessed by tumor volumes and recorded as a function of time. The long (L) and short (S) axes of the subcutaneous tumors were measured with calipers twice weekly, and the tumor volume (TV) calculated as (L×W2)/2. TGI was calculated from the difference between the median tumor volumes of vehicle-treated and drug-treated mice, expressed as a percentage of the median tumor volume of the vehicle-treated control group, by the following relation:

$$\% \ TGI = \left( \frac{\text{Median Tumor } Volume_{control} - \text{Median Tumor } Volume_{drug\text{-}treated}}{\text{Median Tumor } Volume_{control}} \right) \times 100$$

Results of xenografted tumor assays indicated that compounds disclosed herein can inhibit the growth of various human cancer cells in a nude mice model of subcutaneous xenografts, including human non-small cell lung cancer (A549 and Calu-3), human breast cancer (BT474 and MDA-MB-231), human pancreatic cancer (BxPC-3), human epidermoid carcinoma (A431). The effective dose ranged from 5 mg/kg to 40 mg/kg, and the animals were well tolerated during administration. In a certain range of dose, tumor inhibition rate of A431 and BxPC-3 (≥60%) was superior to those of Iressa. Additionally, general conditions and life quality of nude mice were improved.

Finally, it should be noted that there are alternative ways of implementing the present invention. Accordingly, the present embodiments are to be considered as illustrative and not restrictive and the invention is not be limited to the details given herein, but may be modified within the scope and equivalents of the appended claims. All publications and patents cited herein are incorporated by reference.

What is claimed is:

1. A compound having formula (III)

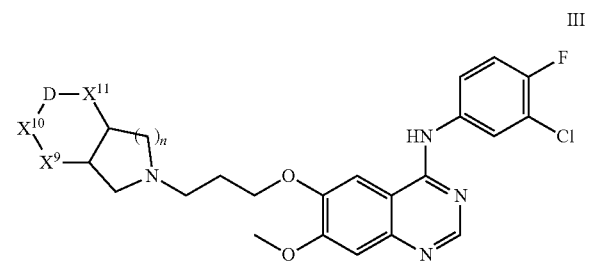

wherein each of $X^9$, $X^{10}$ and $X^{11}$ is independently $CR^eR^f$, $NR^e$, O or S, with the proviso that at least one of $X^9$, $X^{10}$ and $X^{11}$ is $CR^eR^f$;

D is a bond, methylene or ethylene;

each of $R^e$ and $R^f$ is independently H, $C_{1-6}$ alkyl, $C_{1-6}$ alkylacyl, $C_{3-8}$ cycloalkyl, $C_{6-10}$ aryl-$C_{1-6}$-alkyl, or $C_{1-6}$ haloalkyl; and n is 1 or 2.

2. A compound having one of the following structures:
(1)
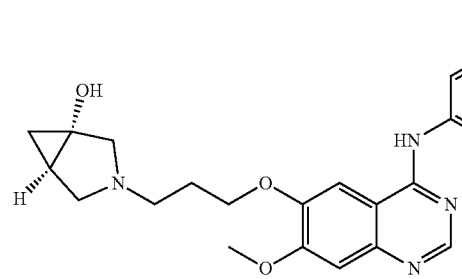
(2)
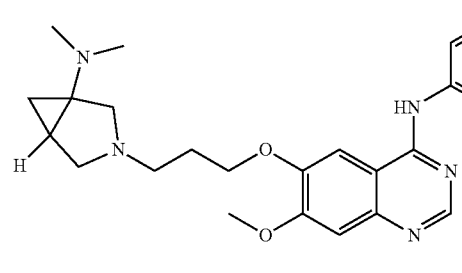
(3)
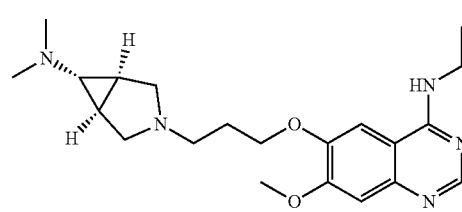
(4)
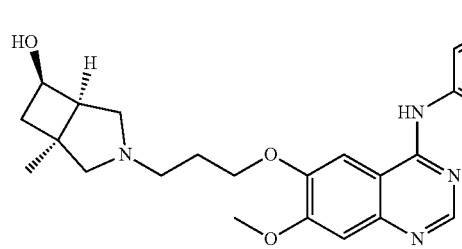
(5)
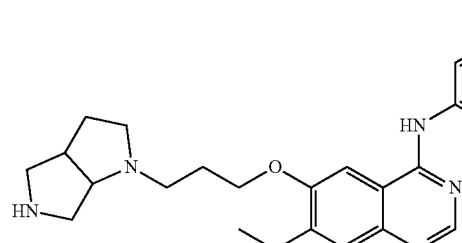
(6)
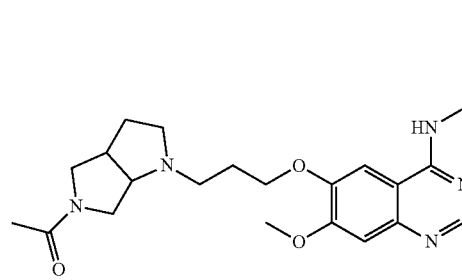
(7)
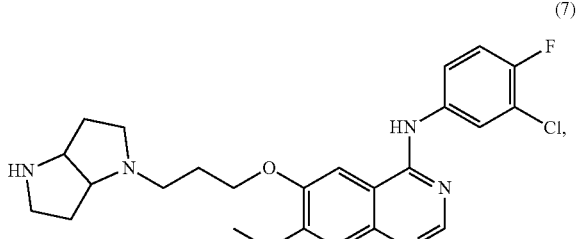
(8)
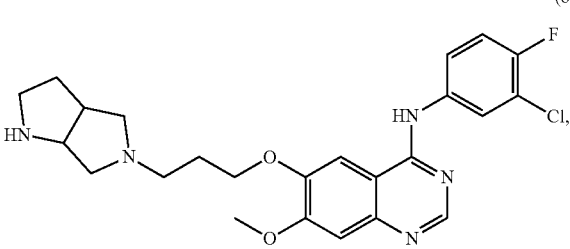
(9)
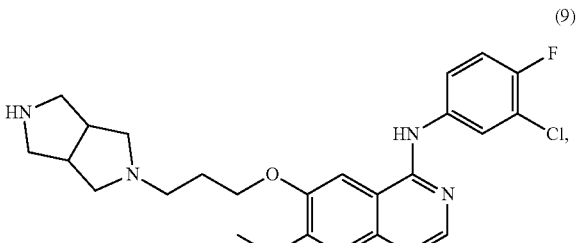
(10)
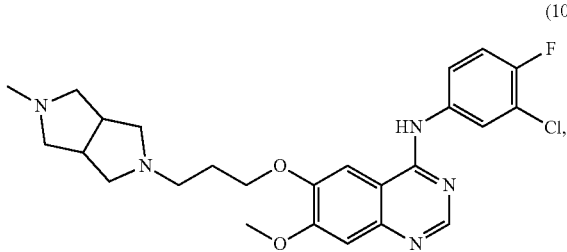
(11)
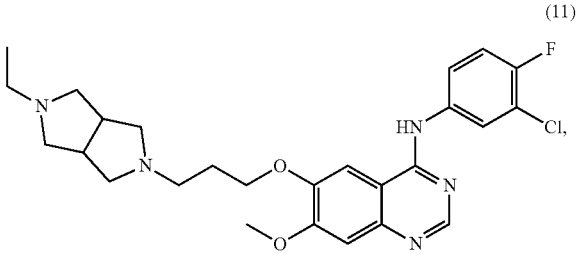
(12)
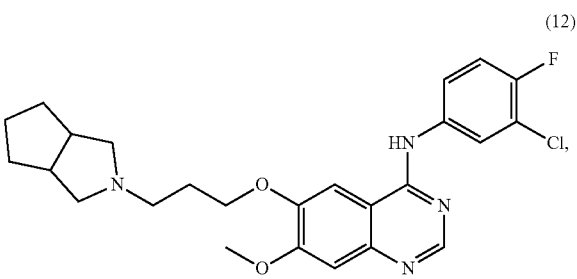

(13)
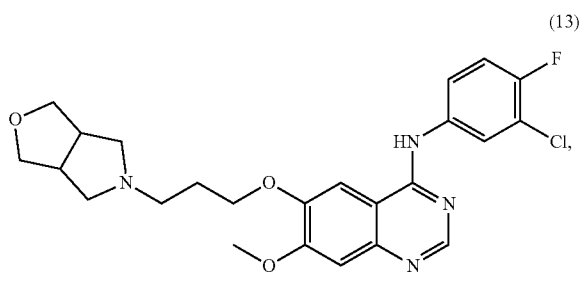
(14)
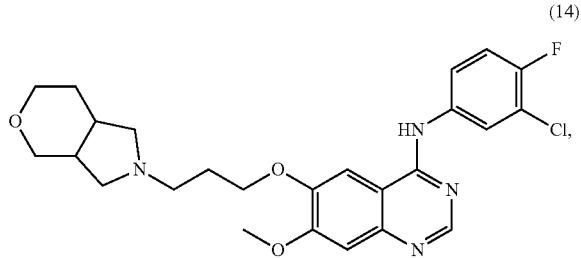
(15)
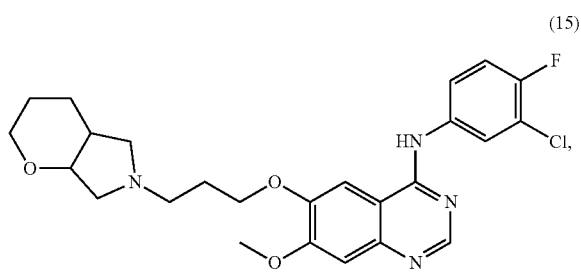
(16)
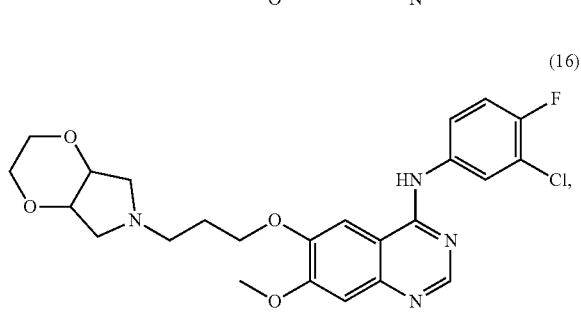
(17)
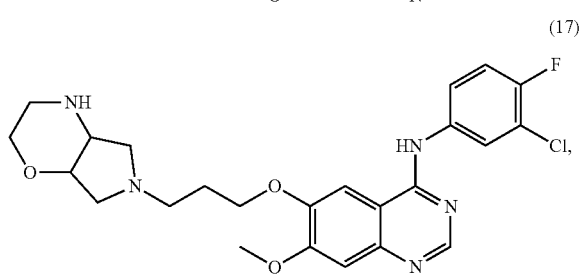
(18)
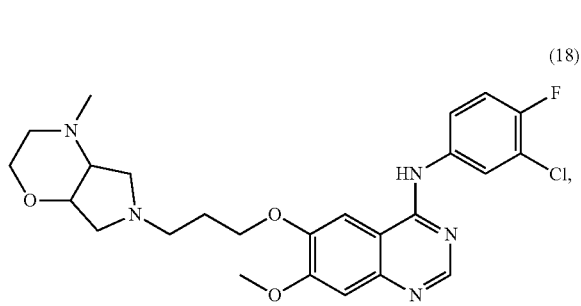
(19)
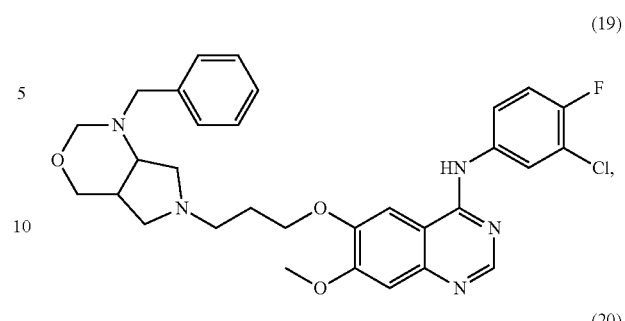
(20)
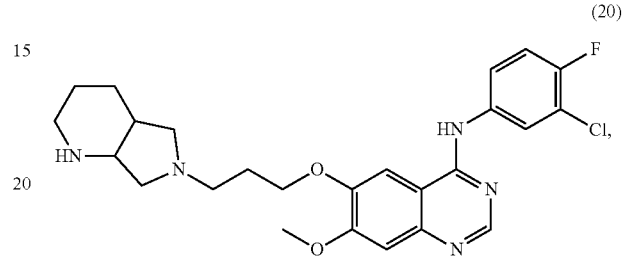
(21)
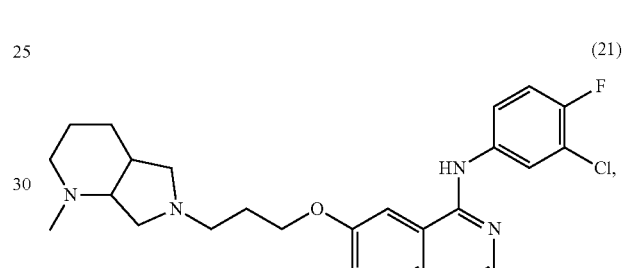
(22)
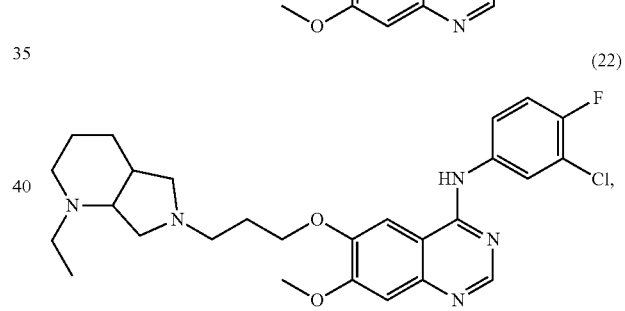
(23)
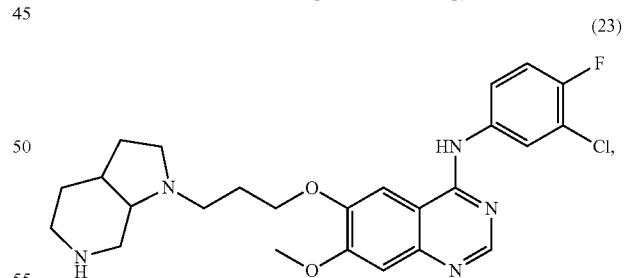
(24)
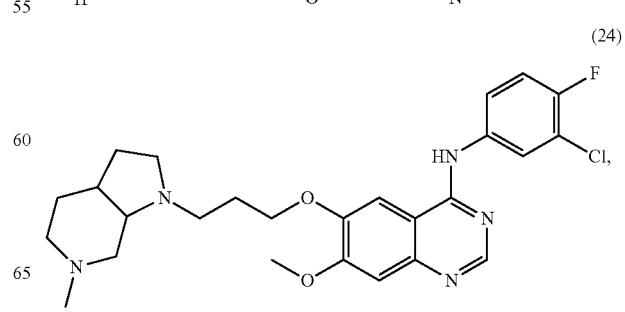

(25)
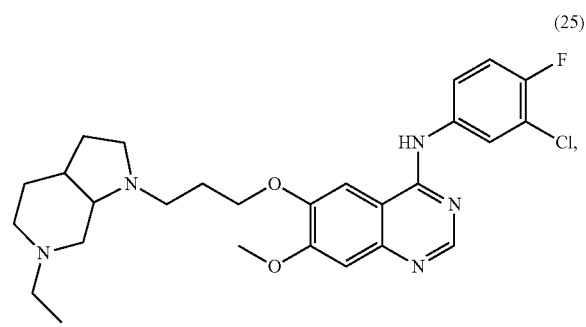
(31)
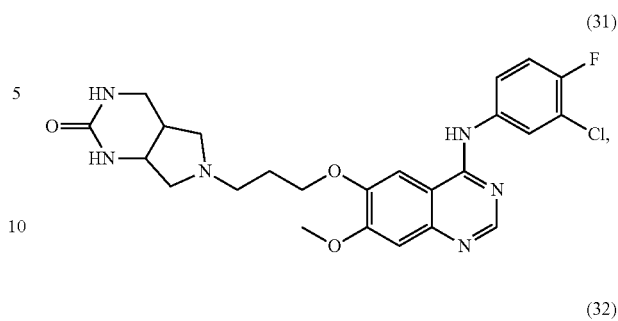
(26)
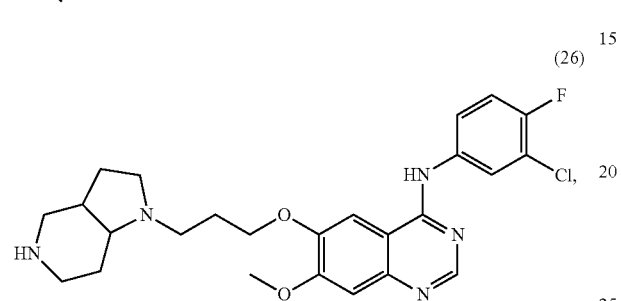
(32)
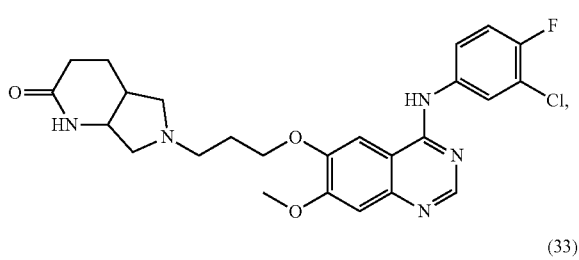
(27)
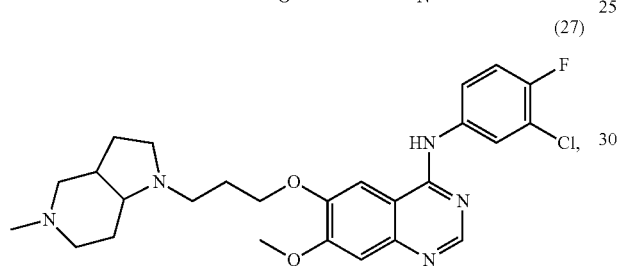
(33)
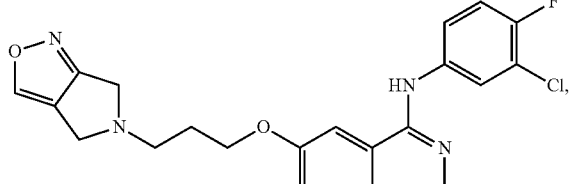
(28)
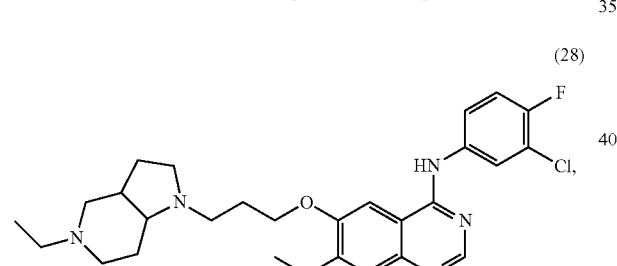
(34)
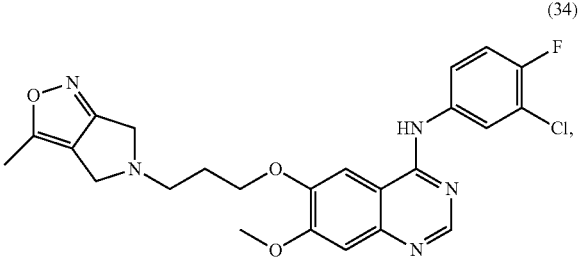
(29)
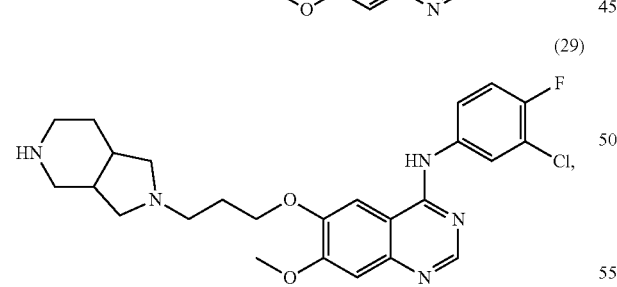
(35)
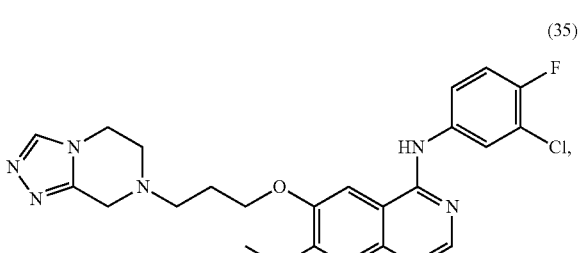
(30)
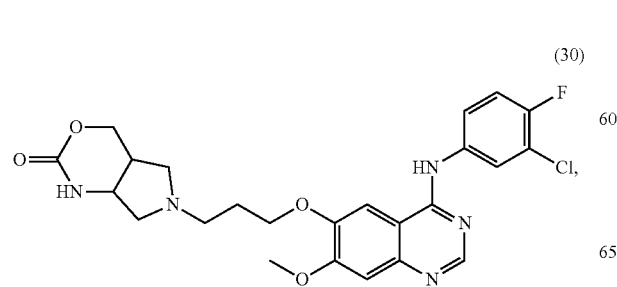
(36)
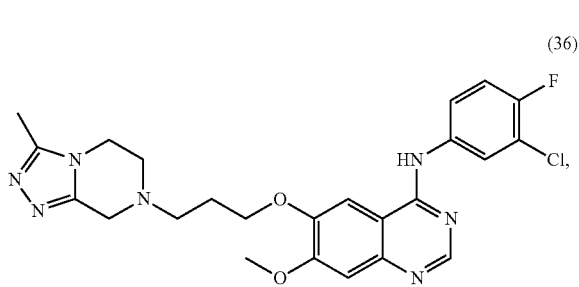

(37)
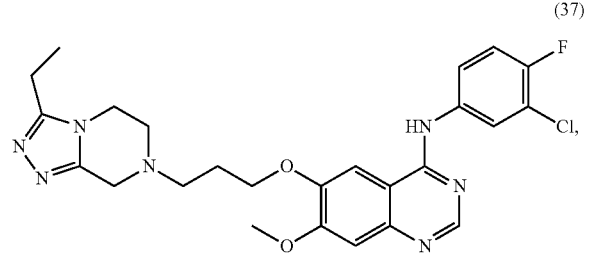
(38)
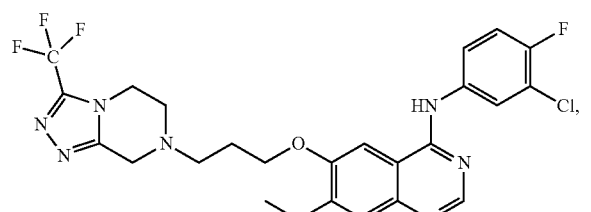
(39)
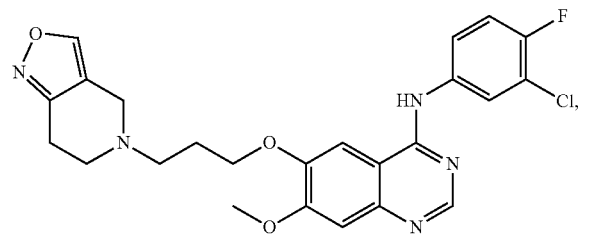
(40)
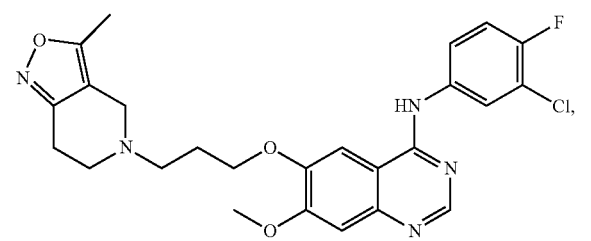
(41)
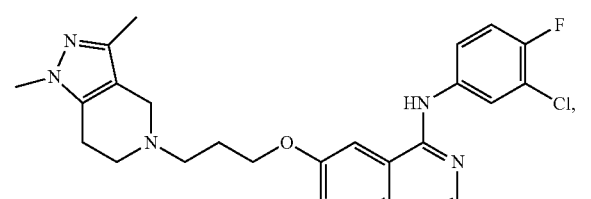
(42)
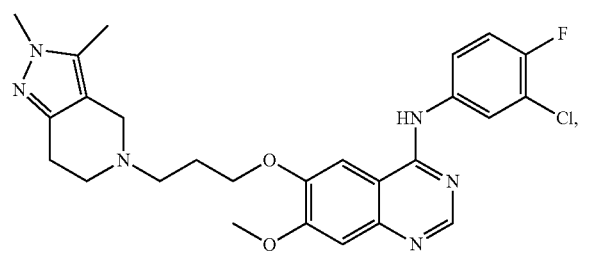
(43)
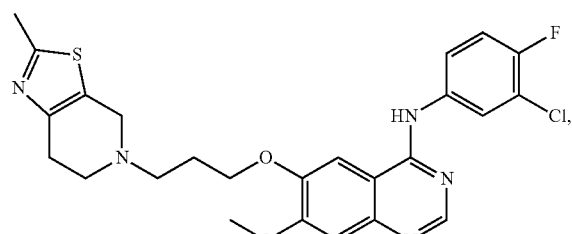
(44)
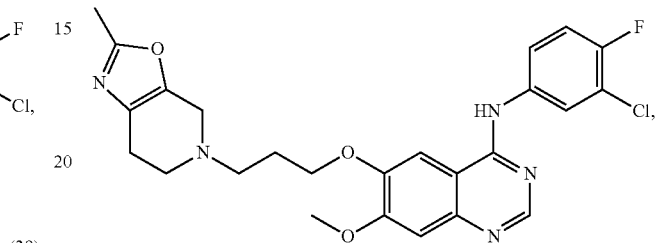
(45)
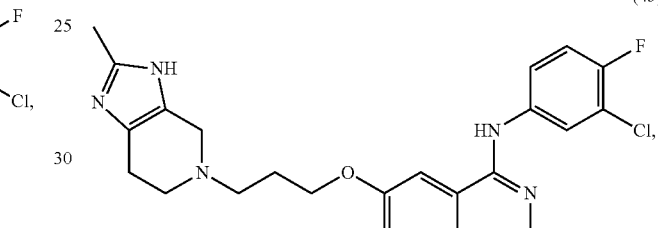
(46)
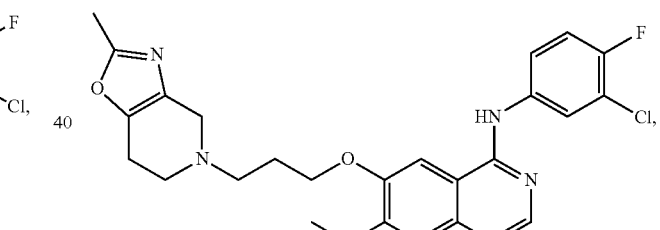
(47)
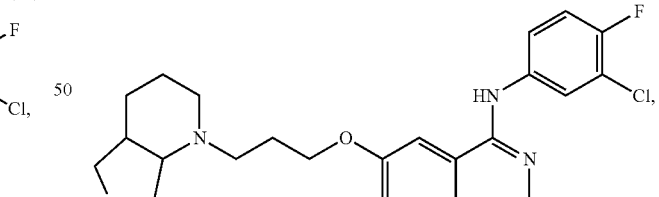
(48)
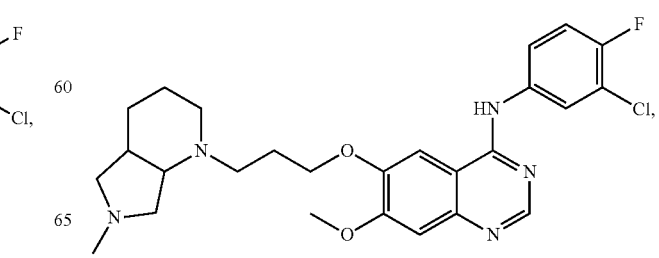

(49)
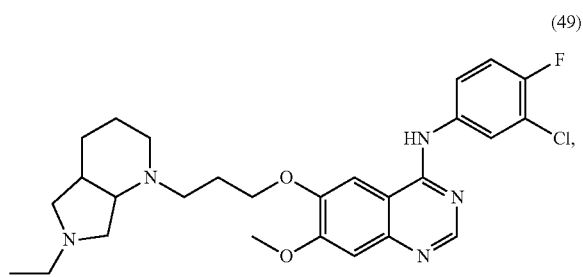
(50)
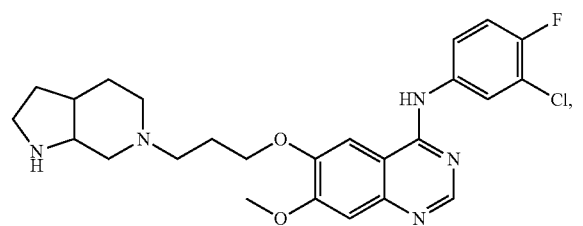
(51)
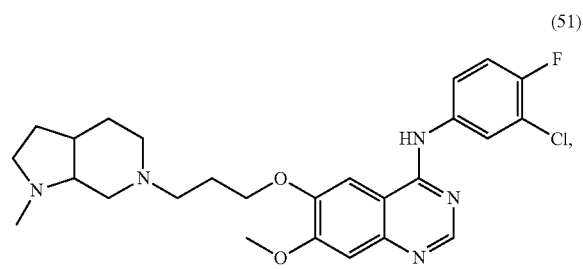
(52)
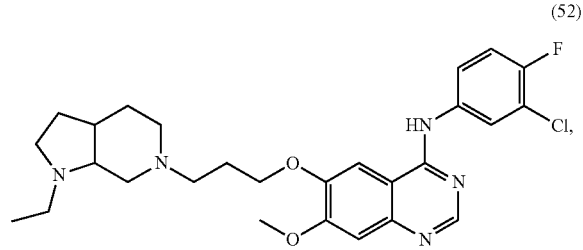
(53)
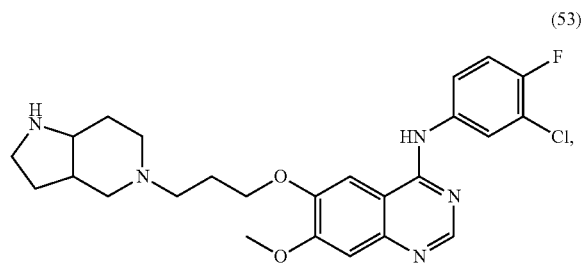
(54)
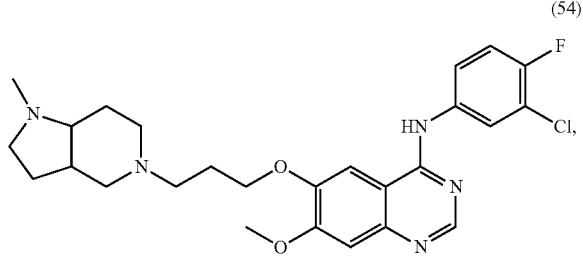
(55)
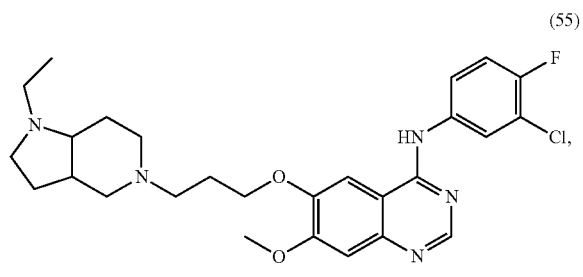
(56)
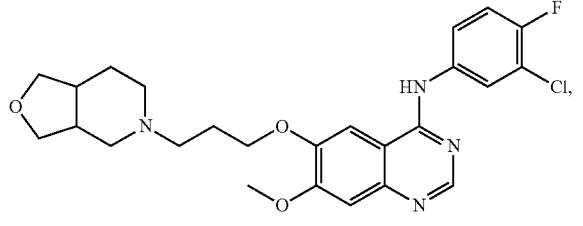
(57)
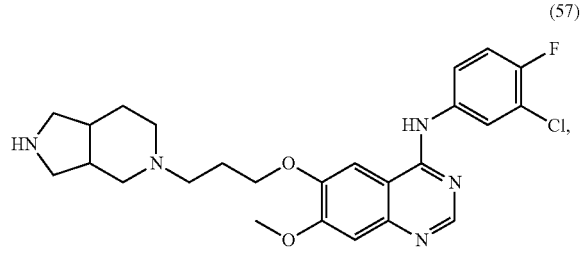
(58)
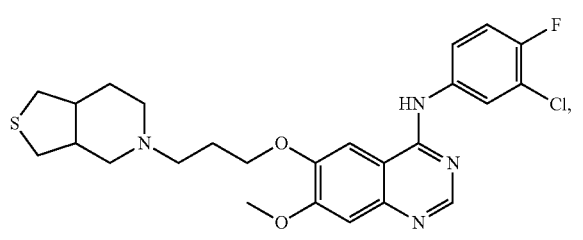
(59)
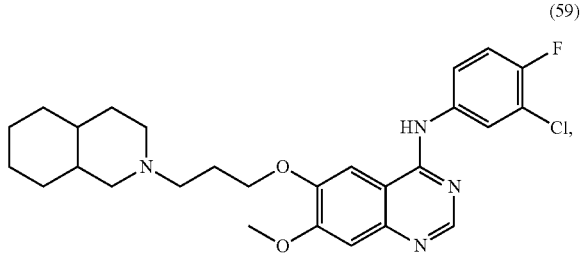
(60)
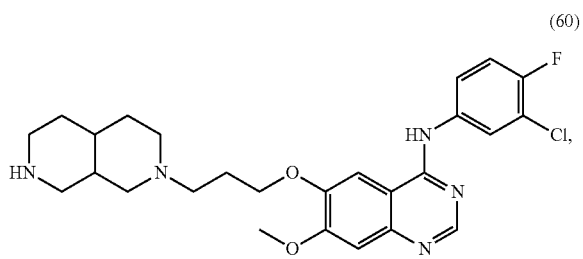

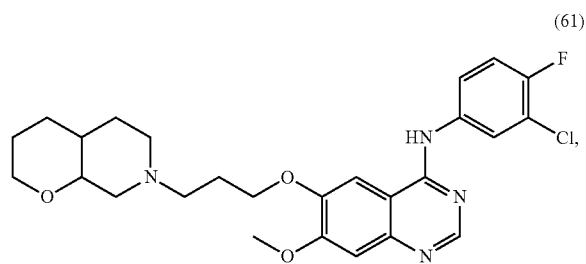
(61)
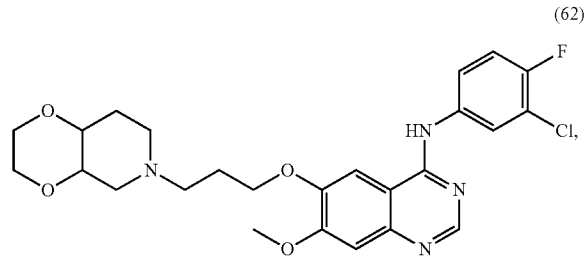
(62)
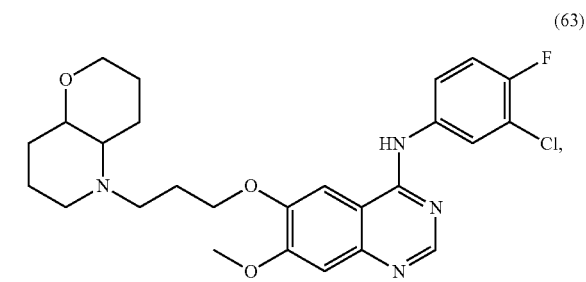
(63)
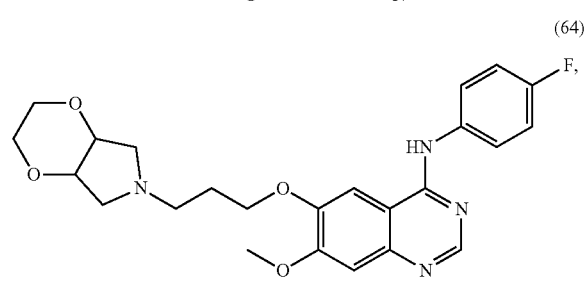
(64)
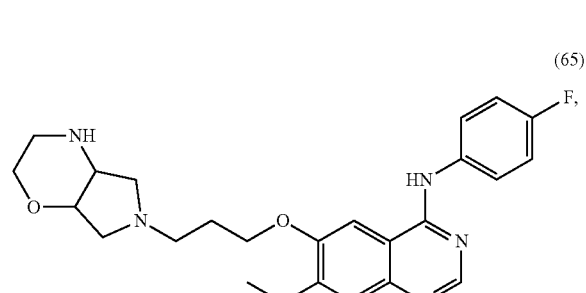
(65)
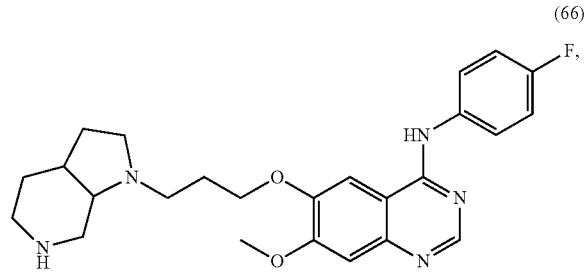
(66)
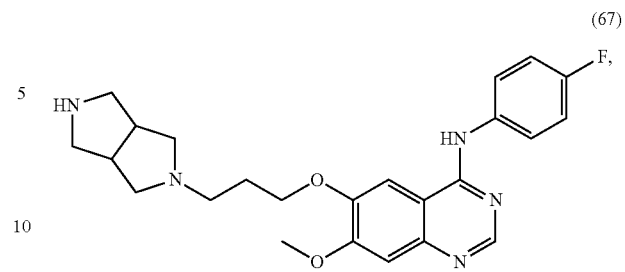
(67)
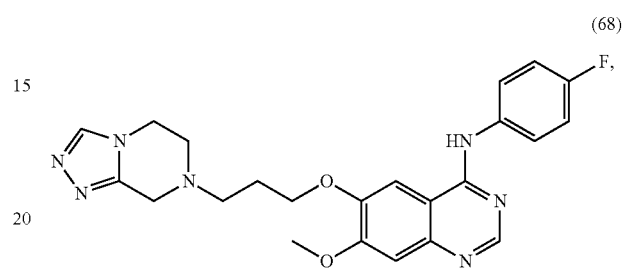
(68)
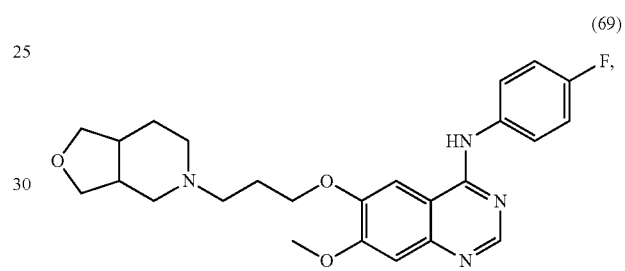
(69)
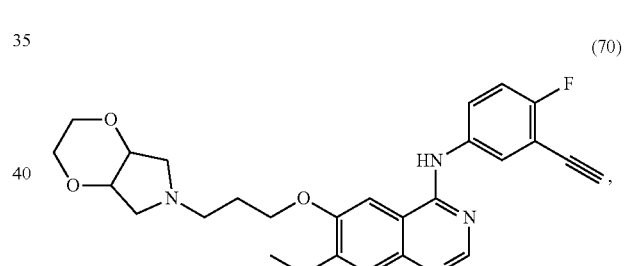
(70)
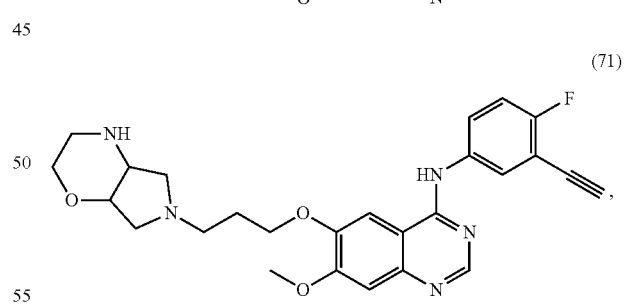
(71)
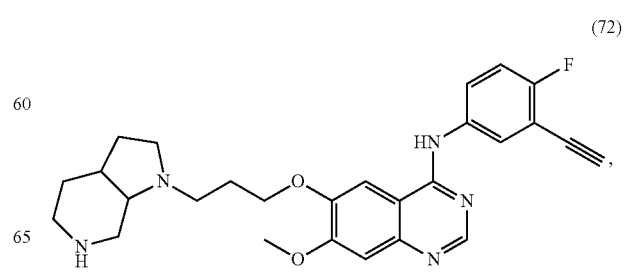
(72)

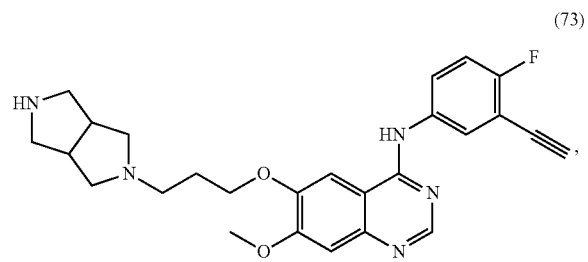
(73)
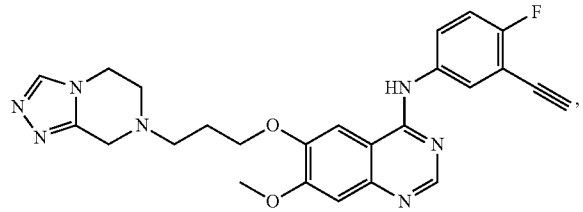
(74)
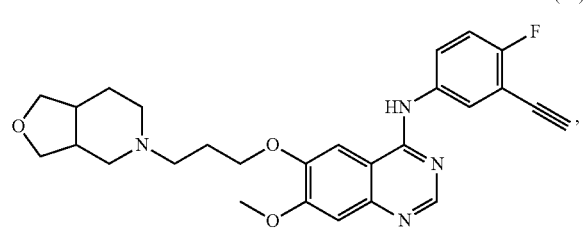
(75)
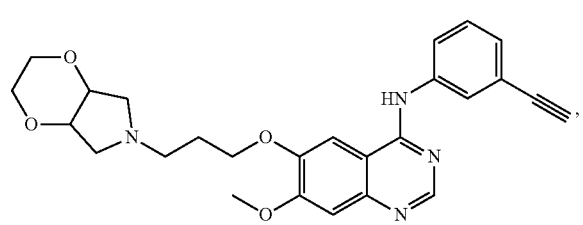
(76)
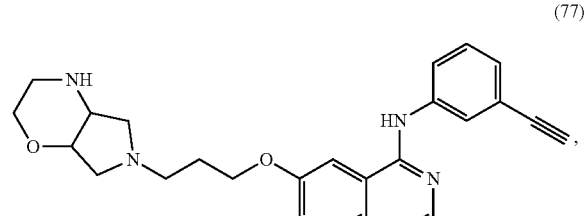
(77)
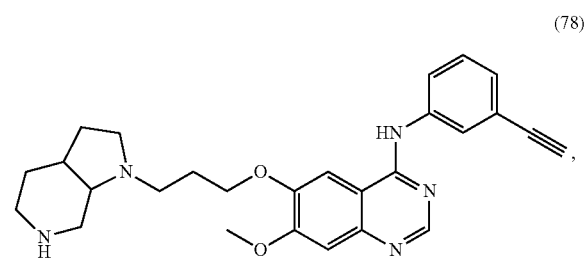
(78)
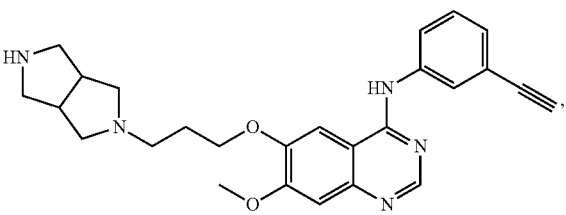
(79)
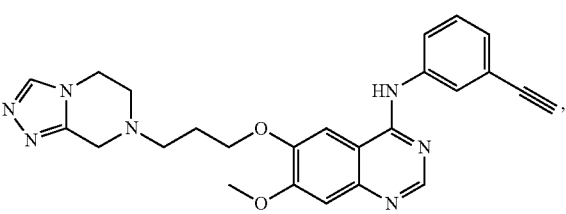
(80)
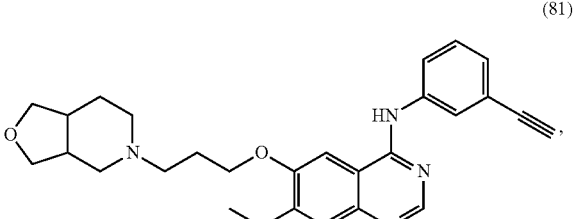
(81)
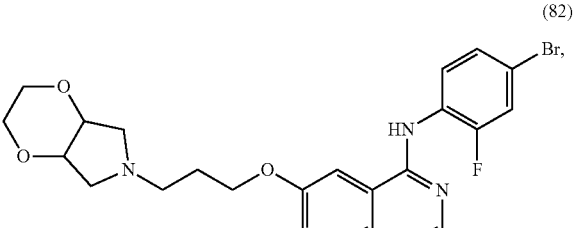
(82)
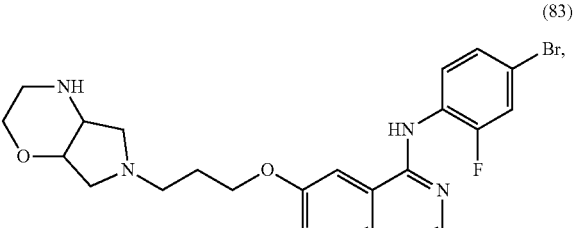
(83)
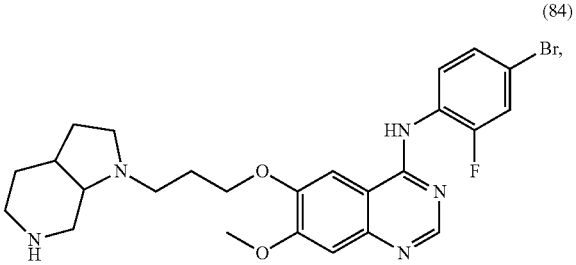
(84)

(85) 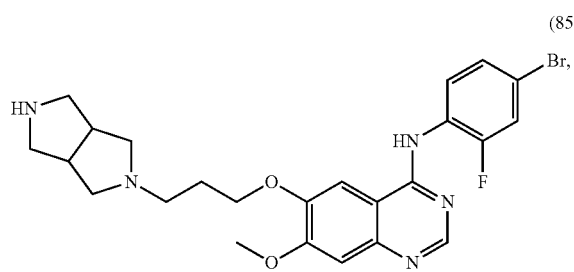
(86) 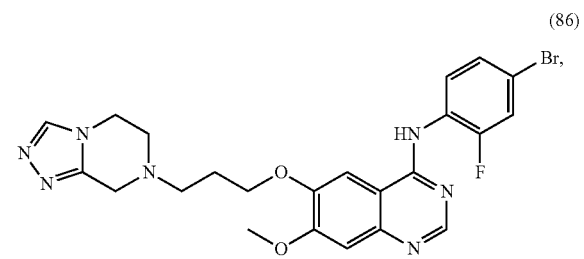
(87) 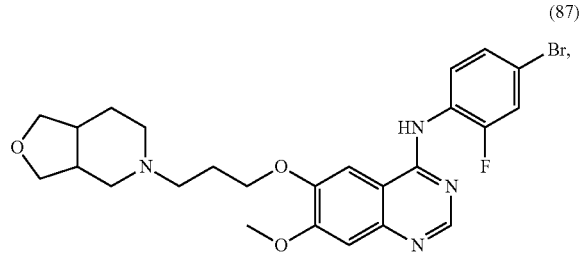
(88) 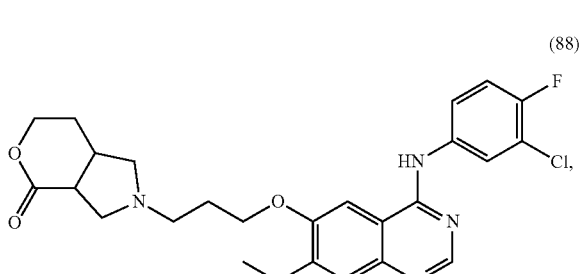
(89) 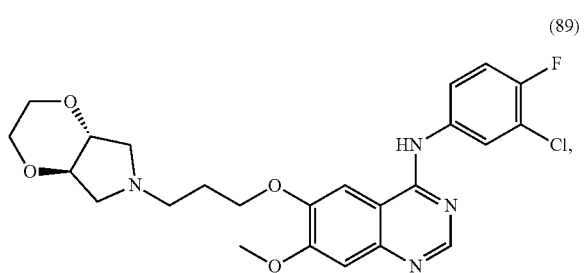
(90) 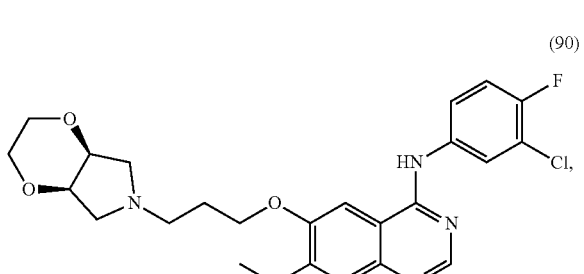
(91) 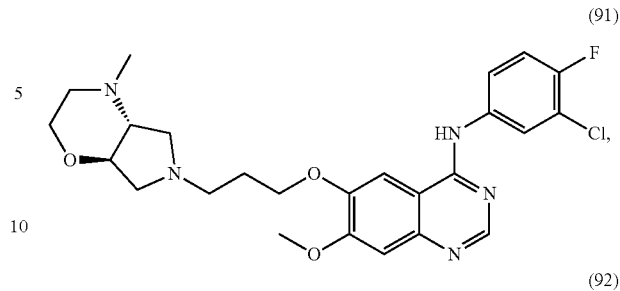
(92) 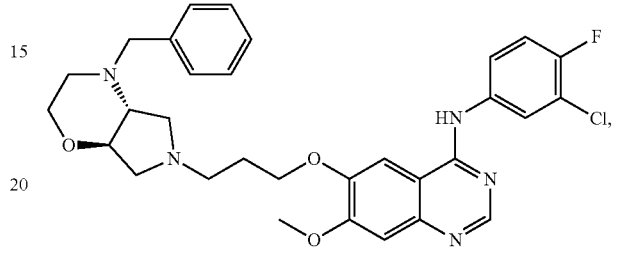
(93) 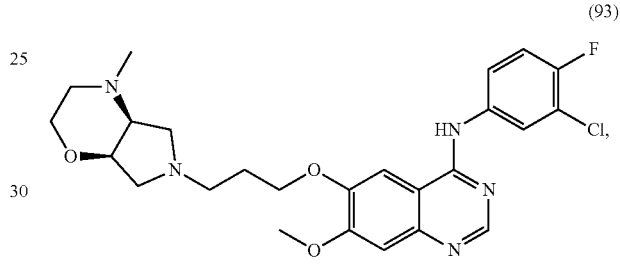
(94) 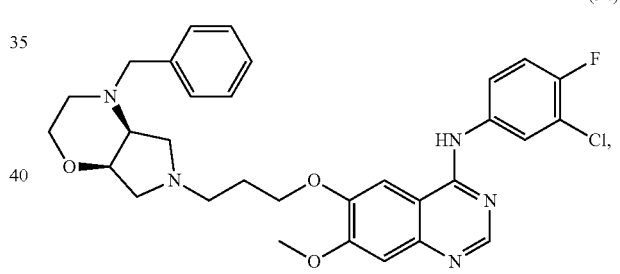
(95) 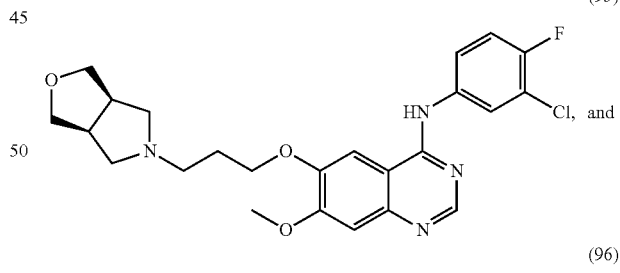
(96) 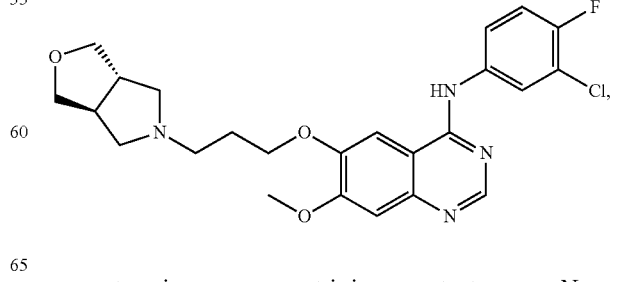
or a stereoisomer, a geometric isomer, a tautomer, an N-oxide, or a pharmaceutically acceptable salt thereof.

3. A pharmaceutical composition comprising the compound according to claim 1 and a pharmaceutically acceptable carrier, excipient, diluent, adjuvant, vehicle or a combination thereof.

4. The pharmaceutical composition according to claim 3 further comprising a therapeutic agent selected from a chemotherapeutic agent, an anti-proliferative agent, an agent for treating non-small cell lung cancer or epidermoid carcinoma, or a combination thereof.

5. The pharmaceutical composition according to claim 4, wherein the therapeutic agent is adriamycin, rapamycin, temsirolimus, everolimus, ixabepilone, gemcitabine, cyclophosphamide, dexamethasone, etoposide, fluorouracil, imatinib-mesylate, dasatinib, nilotinib, erlotinib, lapatinib, gefitinib, sorafenib, sunitinib, an interferon, carboplatin, topotecan, taxol, vinblastine, vincristine, temozolomide, tositumomab, trabectedin, bevacizumab, trastuzumab, cetuximab, panitumumab or a combination thereof.

6. A pharmaceutical composition comprising the compound according to claim 2 and a pharmaceutically acceptable carrier, excipient, diluent, adjuvant, vehicle or a combination thereof.

7. The pharmaceutical composition according to claim 6 further comprising a therapeutic agent selected from a chemotherapeutic agent, an anti-proliferative agent, an agent for treating non-small cell lung cancer or epidermoid carcinoma, or a combination thereof.

8. The pharmaceutical composition according to claim 7, wherein the therapeutic agent is adriamycin, rapamycin, temsirolimus, everolimus, ixabepilone, gemcitabine, cyclophosphamide, dexamethasone, etoposide, fluorouracil, imatinib-mesylate, dasatinib, nilotinib, erlotinib, lapatinib, gefitinib, sorafenib, sunitinib, an interferon, carboplatin, topotecan, taxol, vinblastine, vincristine, temozolomide, tositumomab, trabectedin, bevacizumab, trastuzumab, cetuximab, panitumumab or a combination thereof.

* * * * *